(12) United States Patent
Nakayama et al.

(10) Patent No.: US 11,697,797 B2
(45) Date of Patent: Jul. 11, 2023

(54) MANUFACTURING METHOD OF A CELL STRUCTURE

(71) Applicant: NATIONAL CEREBRAL AND CARDIOVASCULAR CENTER, Suita (JP)

(72) Inventors: Yasuhide Nakayama, Suita (JP); Ryosuke Iwai, Suita (JP); Yasushi Nemoto, Yokohama (JP)

(73) Assignee: NATIONAL CEREBRAL AND CARDIOVASCULAR CENTER, Suita (JP)

( * ) Notice: Subject to any disclaimer, the term of this patent is extended or adjusted under 35 U.S.C. 154(b) by 40 days.

(21) Appl. No.: 17/447,004

(22) Filed: Sep. 7, 2021

(65) Prior Publication Data

US 2021/0395687 A1     Dec. 23, 2021

Related U.S. Application Data

(63) Continuation of application No. 16/073,879, filed as application No. PCT/JP2017/003879 on Jan. 27, 2017, now Pat. No. 11,149,252.

(30) Foreign Application Priority Data

Jan. 29, 2016  (JP) .................................. 2016-016459
Feb. 15, 2016  (JP) .................................. 2016-026293
(Continued)

(51) Int. Cl.
*C12N 5/071*     (2010.01)
*C12N 5/077*     (2010.01)
(Continued)

(52) U.S. Cl.
CPC ............ *C12N 5/0655* (2013.01); *A61L 27/36* (2013.01); *A61L 27/3813* (2013.01);
(Continued)

(58) Field of Classification Search
CPC .............. C12N 5/0602; C12N 2533/30; C12N 2535/00
See application file for complete search history.

(56) References Cited

U.S. PATENT DOCUMENTS

2008/0293139 A1   11/2008  Watanabe
2011/0229962 A1   9/2011   Mizutani et al.

FOREIGN PATENT DOCUMENTS

EP    1857126 A1   11/2007
EP    2330182 A1   6/2011
(Continued)

OTHER PUBLICATIONS

Mar. 23, 2022, Office Action issued by the China National Intellectual Property Administration in the corresponding Chinese Patent Application No. 201780008925.2.
(Continued)

*Primary Examiner* — Kara D Johnson
(74) *Attorney, Agent, or Firm* — Kenja IP Law PC

(57) ABSTRACT

The present disclosure aims to provide a manufacturing method of a cell structure. The manufacturing method comprises producing a coated region in which a culturing surface is coated with a temperature-responsive polymer or a temperature-responsive polymer composition, forming a droplet of a cell suspension in the coated region, and performing cell culturing in the droplet. A surface zeta potential of the coated region is 0 mV to 50 mV.

8 Claims, 37 Drawing Sheets

(30) Foreign Application Priority Data

| Mar. | 16, 2016 | (JP) | 2016-053081 |
|---|---|---|---|
| Mar. | 16, 2016 | (JP) | 2016-053082 |
| Mar. | 16, 2016 | (JP) | 2016-053084 |
| Mar. | 16, 2016 | (JP) | 2016-053086 |
| Jun. | 23, 2016 | (JP) | 2016-124458 |
| Jul. | 28, 2016 | (JP) | 2016-148977 |
| Aug. | 23, 2016 | (JP) | 2016-162950 |

(51) Int. Cl.
    *A61L 27/36*     (2006.01)
    *A61L 27/38*     (2006.01)
    *C12M 1/00*     (2006.01)
    *C12M 1/34*     (2006.01)

(52) U.S. Cl.
    CPC ......... *A61L 27/3817* (2013.01); *C12M 23/20* (2013.01); *C12M 41/12* (2013.01); *C12N 5/0602* (2013.01); *C12N 2533/30* (2013.01); *C12N 2535/00* (2013.01)

(56) References Cited

FOREIGN PATENT DOCUMENTS

| EP | 3315596 | A1 | | 5/2018 |
|---|---|---|---|---|
| JP | H05260950 | A | | 10/1993 |
| JP | H0614764 | A | | 1/1994 |
| JP | H08173144 | A | | 7/1996 |
| JP | 2003010309 | A | | 1/2003 |
| JP | 2009050194 | A | | 3/2009 |
| JP | 2010524458 | A | | 7/2010 |
| JP | 2014027918 | A | | 2/2014 |
| JP | 2014027919 | A | * | 2/2014 |
| JP | 2014027919 | A | | 2/2014 |
| JP | 2015097481 | A | | 5/2015 |
| JP | 5746240 | B2 | | 7/2015 |
| JP | 2015192640 | A | | 11/2015 |
| JP | 2018029505 | A | | 3/2018 |
| WO | 0168799 | A1 | | 9/2001 |
| WO | 2004092359 | A1 | | 10/2004 |
| WO | 2006093151 | A1 | | 9/2006 |
| WO | 2013005780 | A1 | | 1/2013 |
| WO | 2013073707 | A1 | | 5/2013 |
| WO | 2015029707 | A1 | | 3/2015 |

OTHER PUBLICATIONS

Alison Abbott, Biology's new dimension, Nature, Aug. 21, 2003, pp. 870-872, vol. 424.

Corning Cell Culture Product Selection Guide. Datasheet [online]. Coming Inc., 2005-2020 [retrieved Dec. 10, 2020]. Retrieved from the Internet: [URL: https://mpep.uspto.gov/RDMS/MPEP/current#/current/d0e73852.html&scrollTo=KSAZCJCGRHEI1457175119817]. (Year: 2005).

Michiya Matsusaki et al., Three-Dimensional Human Tissue Chips Fabricated by Rapid and Automatic Inkjet Cell Printing, Adv. Healthcare Mater., 2013, pp. 534-539, vol. 2, Issue 4.

Nov. 26, 2019, Notification of Reasons for Refusal issued by the Japan Patent Office in the corresponding Japanese Patent Application No. 2016-148977.

Oct. 29, 2019, Notification of Reasons for Refusal issued by the Japan Patent Office in the corresponding Japanese Patent Application No. 2016-026293.

Ryosuke Iwai et al., O-14-2 Production of angioid double-layer structure body via phased cell seeding to self-assembly inducing surface, The Journal of the Japanese Society for Regenarative Medicine special extra issue, Feb. 1, 2015, p. 203, vol. 14, Suppl. 2015.

Ryosuke Iwai et al., O-36-2 Development of One-Day-Aggregated Spheroids (ODAS) technique: production of spheroid aiming regenerative medicine and drug discovery, The Journal of the Japanese Society for Regenerative Medicine special extra issue, Feb. 1, 2016, p. 251, vol. 15, Suppl. 2016.

Ryosuke Iwai et al., The effect of electrically charged polyion complex nanoparticle-coated surfaces on adipose-derived stromal progenitor cell behaviour, Biomaterials, 2013, pp. 9096-9102, vol. 34.

Sep. 26, 2019, Extended European Search Report issued by the European Patent Office in the corresponding European Patent Application No. 17744470.0.

Tetsuo Tomonaga et al., Rat hepatocyte spheroids formed on temperature-responsive PIPAAm polymer-grafted surface maintain long-term differentiated hepatocyte function, Acta Medica Nagasakiensia, 2014, pp. 1-6, vol. 59.

Yongzhong Wang et al., Charge-selective fractions of naturally occurring nanoparticles as bioactive nanocarriers for cancer therapy, Acta Biomaterialia, 2014, pp. 4269-4284, vol. 10, Issue 10, Elsevier Ltd.

Dec. 9, 2021, Office Action issued by the China National Intellectual Property Administration in the corresponding Chinese Patent Application No. 201780008925.2.

Apr. 18, 2017, International Search Report issued in the International Patent Application No. PCT/JP2017/003879.

Apr. 21, 2020, Notification of Reasons for Refusal issued by the Japan Patent Office in the corresponding Japanese Patent Application No. 2016-026293.

Bridgestone Corp. et al., The 42nd Annual Meeting of the Japanese Society of Toxicology, Kigyo Booth Pamphlet, Jun. 29, 2015, pp. 1-7.

Corning Cell Culture Product Selection Guide. Datasheet [online]. Corning Inc., 2005-2020 [retrieved Dec. 10, 2020], Retrieved from the Internet. (Year: 2005).

Gordon M Keller, In vitro differentiation of embryonic stem cells, Current Opinion in Cell Biology, 1995, pp. 862-869, vol. 7, Issue 6.

Jul. 31, 2018, International Preliminary Report on Patentability issued in the International Patent Application No. PCT/JP2017/003879.

Mar. 19, 2020, Communication pursuant to Article 94(3) EPC issued by the European Patent Office in the corresponding European Patent Application No. 17744470.0.

Mar. 25, 2021, Communication pursuant to Article 94(3) EPC issued by the European Patent Office in the corresponding European Patent Application No. 17744470.0.

May 12, 2020, Official Decision of Refusal issued by the Japan Patent Office in the corresponding Japanese Patent Application No. 2016-148977.

May 20, 2021, Office Action issued by the China National Intellectual Property Administration in the corresponding Chinese Patent Application No. 201780008925.2.

Michiya Matsusaki et al., 3D-fibroblast tissues constructed by a cell-coat technology enhance tight-junction formation of human colon epithelial cells, Biochemical and Biophysical Research Communications, 2015, pp. 363-369, vol. 457, Issue 3.

\* cited by examiner

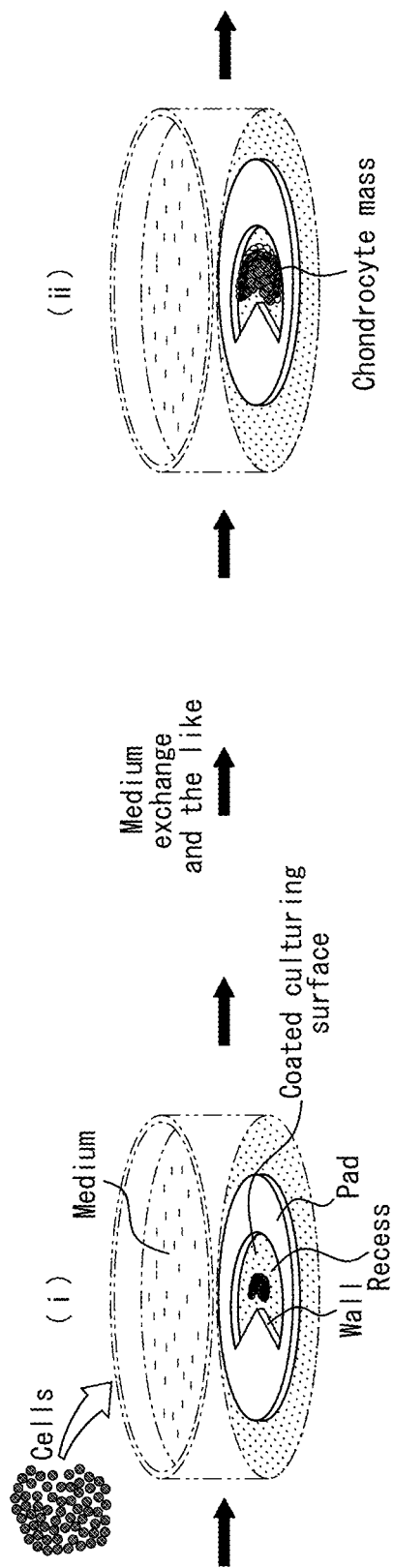

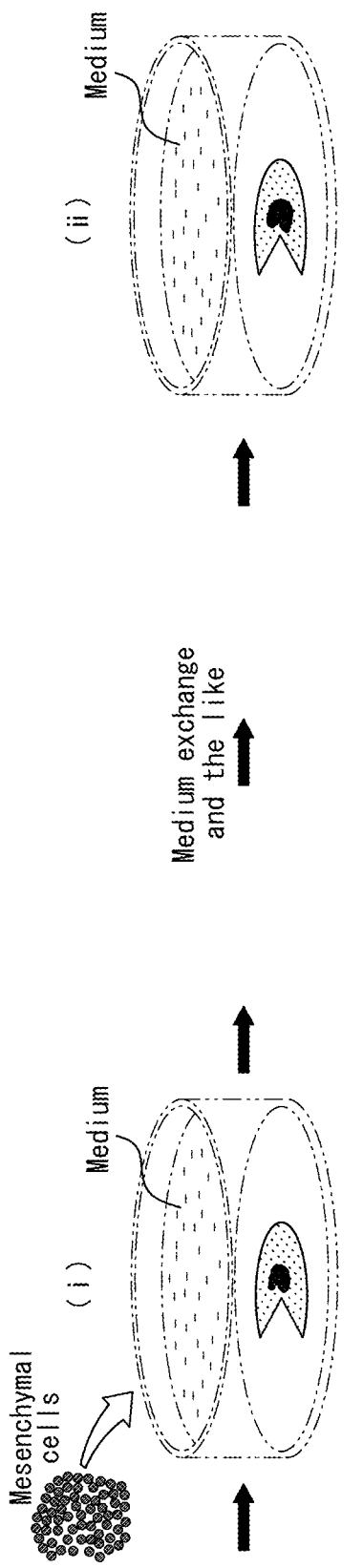

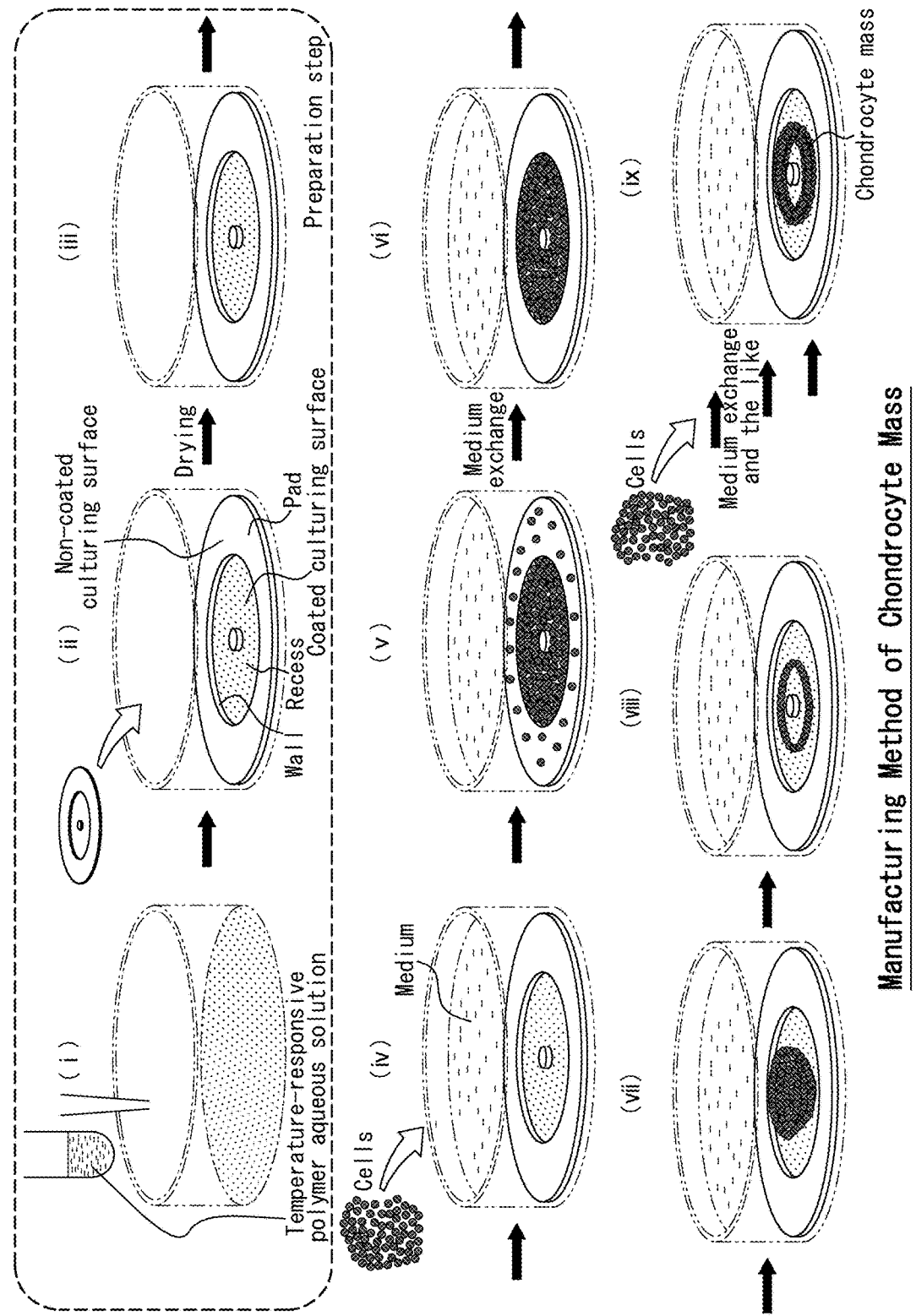

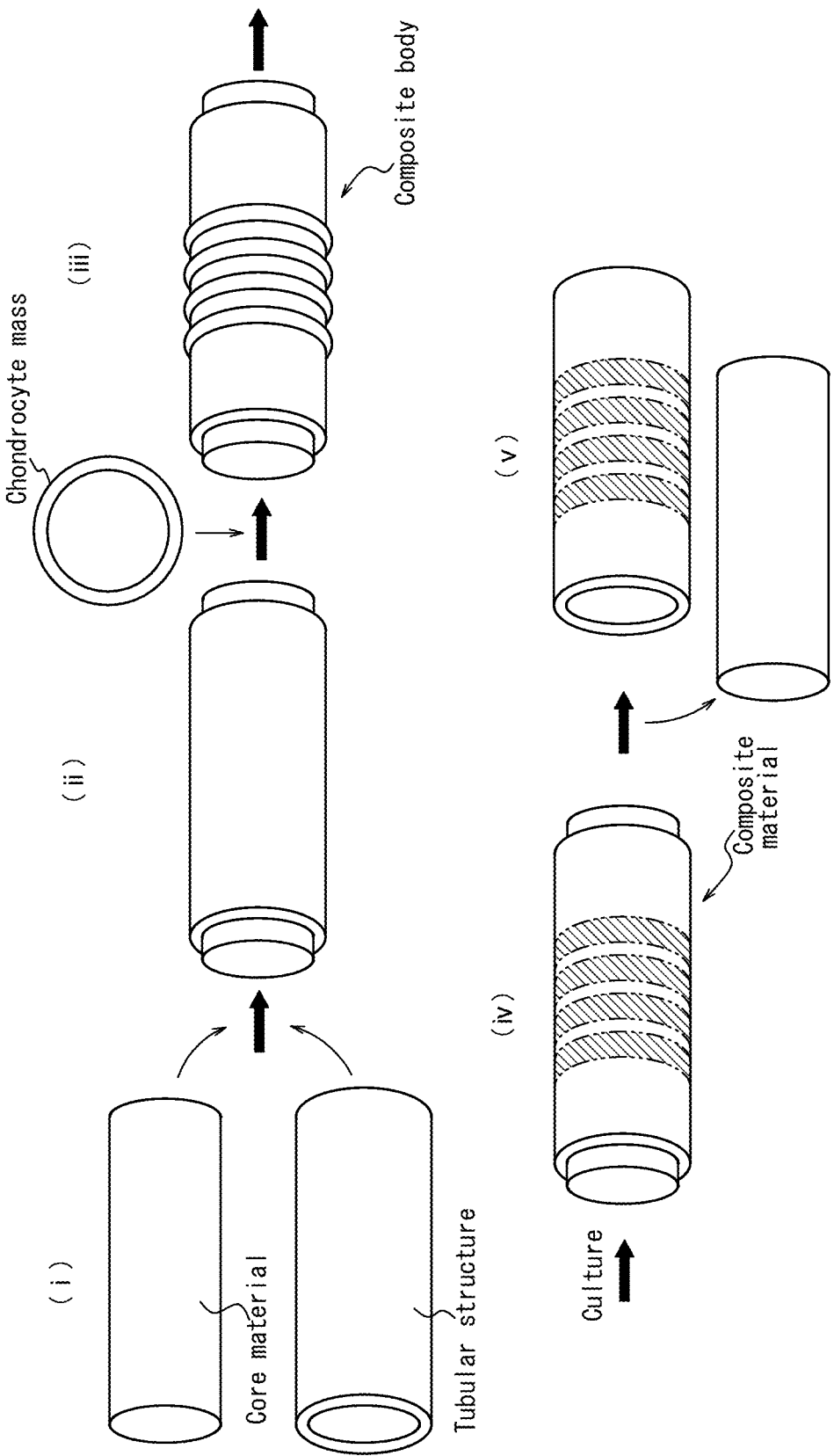

After 6 days of culturing

After 21 days of culturing

FIG. 16
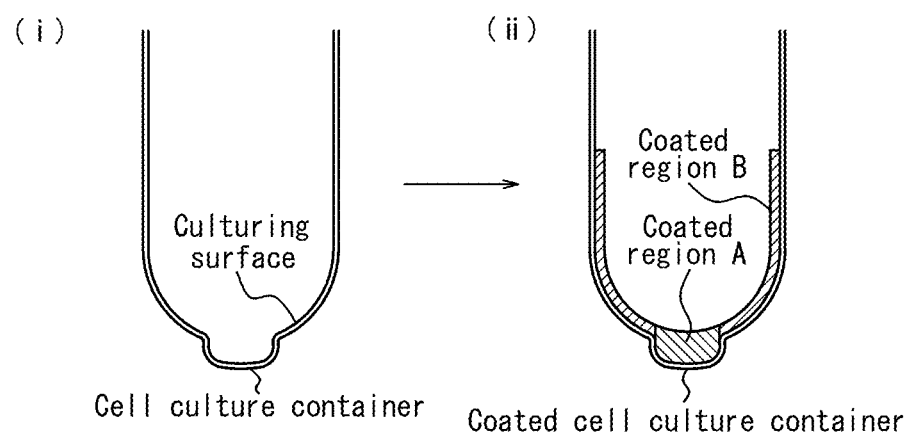
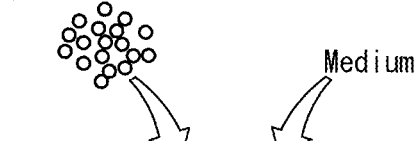
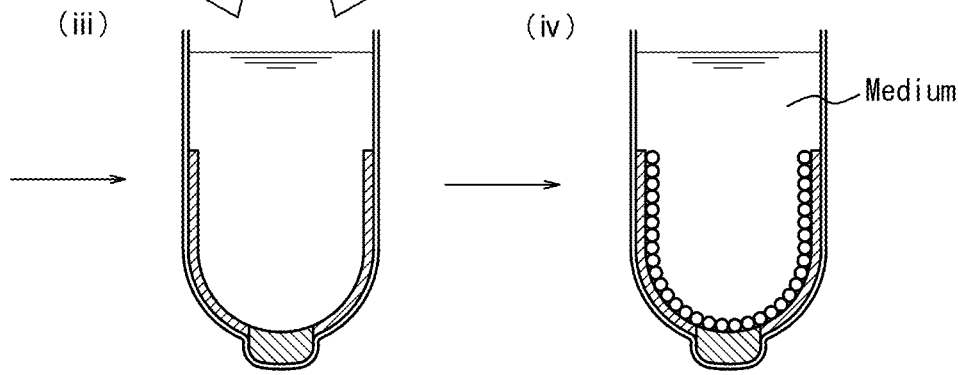
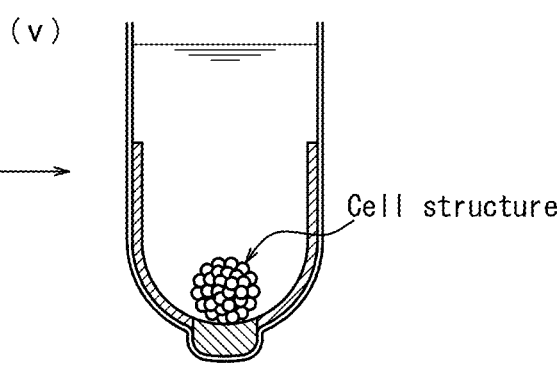

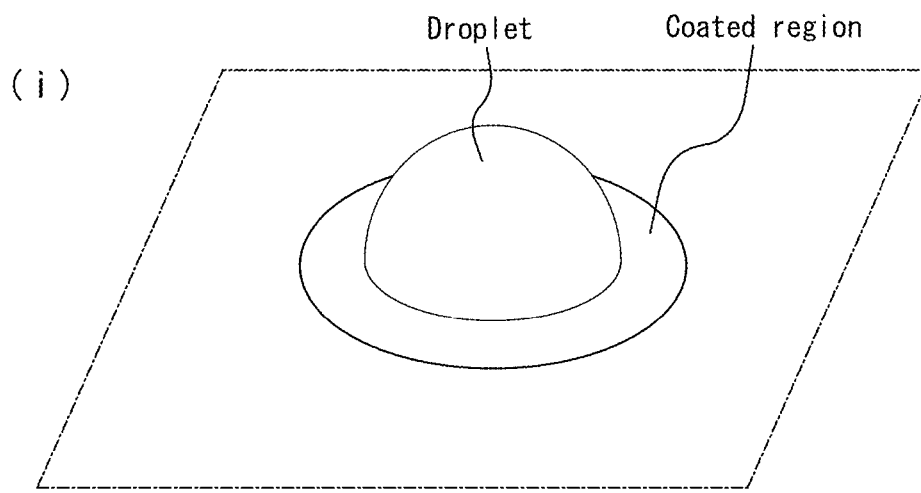
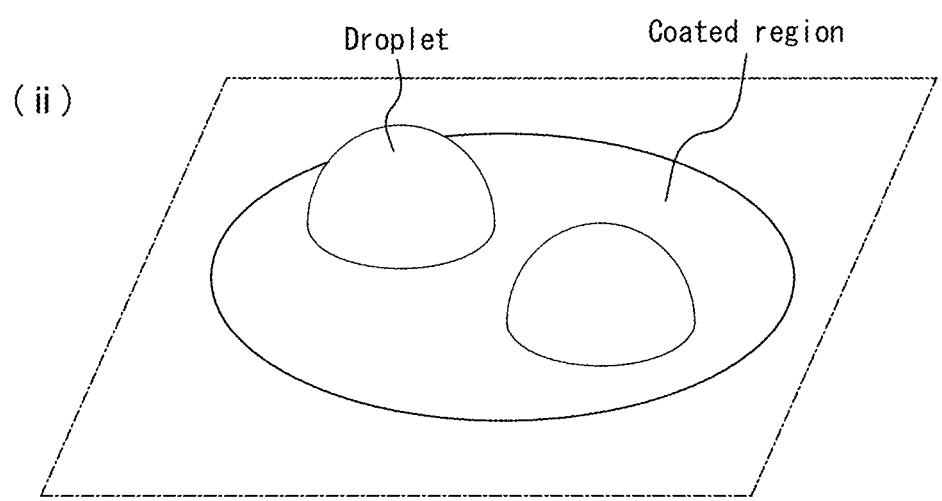
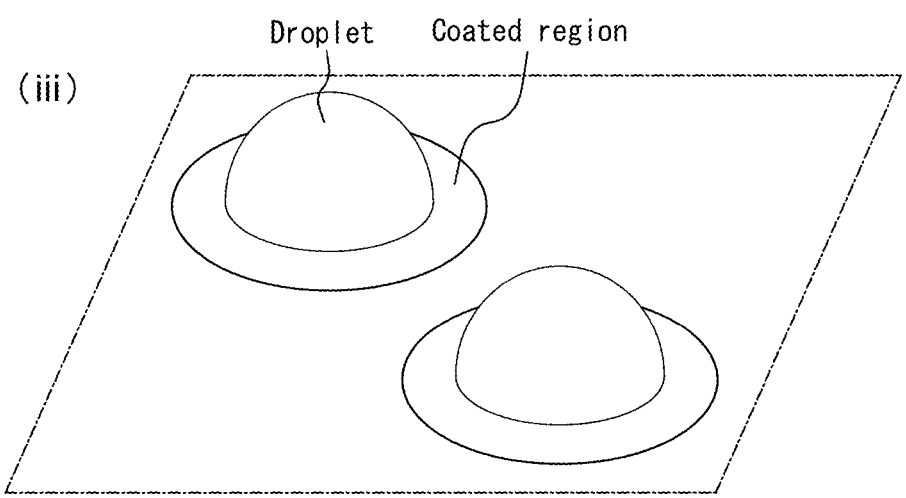
FIG. 32 y = 0.581x + 0.9201
R² = 0.9634 y = 0.078x + 4.06
R² = 0.9974

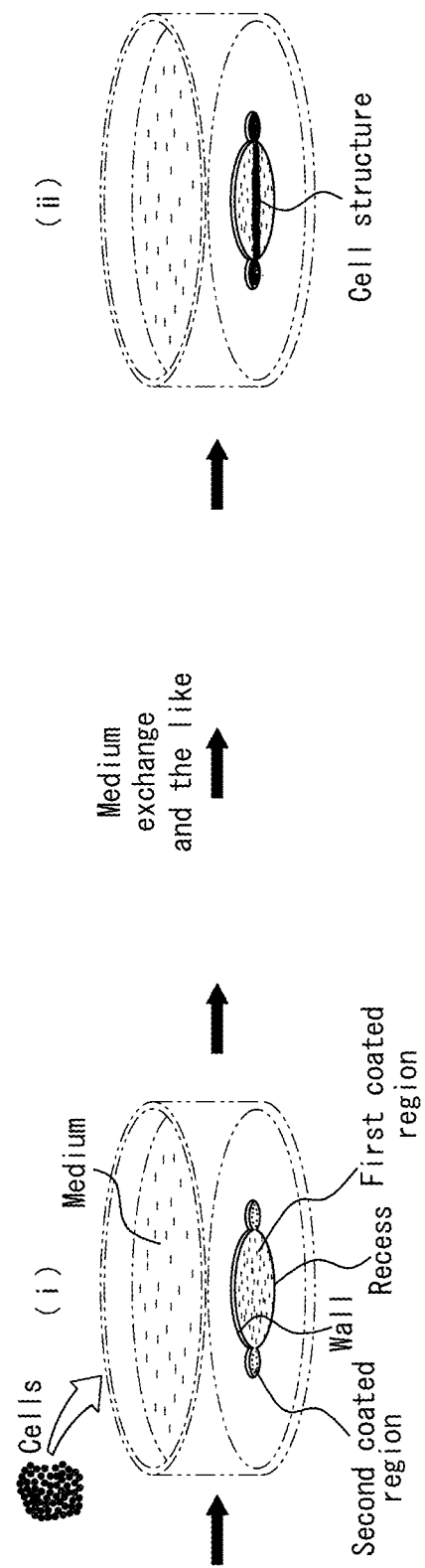

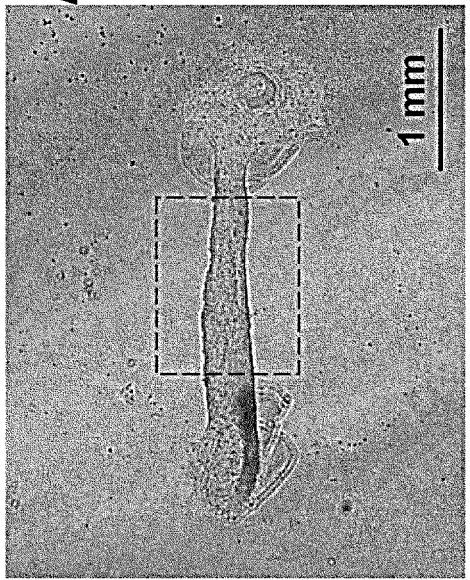
FIG. 37B
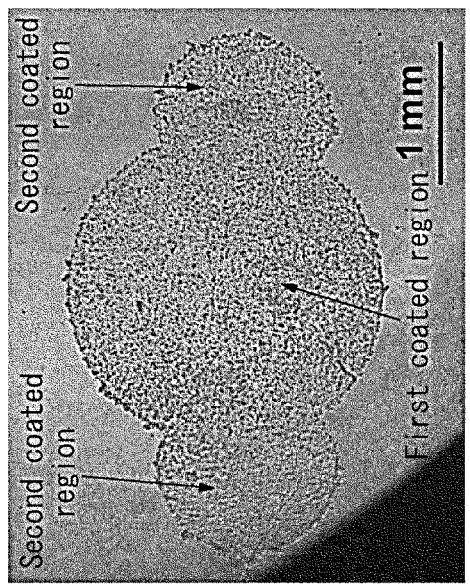
FIG. 37A
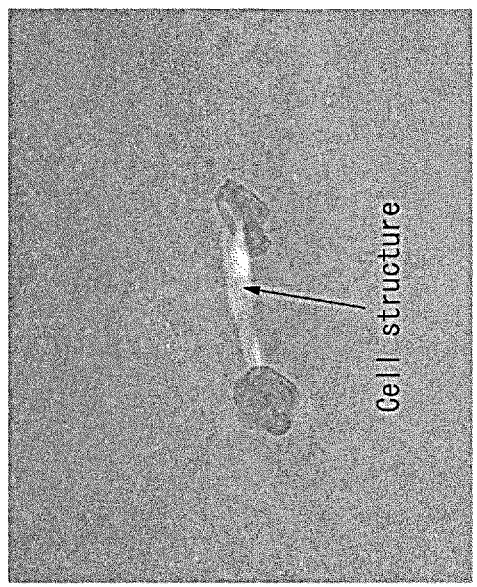
FIG. 37D
FIG. 37C

MANUFACTURING METHOD OF A CELL STRUCTURE

CROSS-REFERENCE TO RELATED APPLICATION

The present application is a continuation application of U.S. patent application Ser. No. 16/073,879 filed Jul. 30, 2018, which is a National Stage Application of PCT/JP2017/003879 filed Jan. 27, 2017, which claims priorities based on Japanese Patent Application No. 2016-016459 filed Jan. 29, 2016, Japanese Patent Application No. 2016-124458 filed Jun. 23, 2016, Japanese Patent Application No. 2016-162950 filed Aug. 23, 2016, Japanese Patent Application No. 2016-148977 filed Jul. 28, 2016, Japanese Patent Application No. 2016-026293 filed Feb. 15, 2016, Japanese Patent Application No. 2016-053081 filed Mar. 16, 2016, Japanese Patent Application No. 2016-053082 filed Mar. 16, 2016, Japanese Patent Application No. 2016-053084 filed Mar. 16, 2016, Japanese Patent Application No. 2016-053086 filed Mar. 16, 2016. The disclosures of the prior applications are hereby incorporated by reference herein in their entirety.

TECHNICAL FIELD

The present disclosure relates to a method of efficiently manufacturing a cell mass, a cell structure, or a three-dimensional tissue body using a culturing surface coated with a temperature-responsive polymer or a temperature-responsive polymer composition, and to a cell mass, a cell structure, or a three-dimensional tissue body obtainable using this method.

In particular, Aspect (I) of the present disclosure relates to a manufacturing method of a chondrocyte mass and a graft material, and to a chondrocyte mass, a graft material, and a composite material. Aspect (II) of the present disclosure relates to a culture method of epithelial cells, a manufacturing method of a cell structure, and a cell culture container for epithelial cells. Aspect (III) of the present disclosure relates to a production apparatus of a three-dimensional tissue body and a production method of a three-dimensional tissue body. Aspect (IV) of the present disclosure relates to a manufacturing method of a cell structure. Aspect (V) of the present disclosure relates to a manufacturing method of a cell structure, a cell structure, and a cell culture container. Aspect (VI) of the present disclosure relates to a manufacturing method of a cell structure. Aspect (VII) of the present disclosure relates to a manufacturing method of a cell structure.

BACKGROUND

With regard to Aspect (I), demand has increased for customized medical treatment to improve the quality of life (QOL) of patients. Regenerative medicine, which aims to regenerate tissues and organs with impaired or lost functions using a patient's own cells, plays a leading role in customized medical treatment.

Regenerative medicine requires operations to culture cells collected from a patient's tissue in a cell culture container, to form tissue, and then to graft the tissue onto the patient. For this reason, a technique for culturing cells to form a cell structure such as tissue and a technique for collecting the cell structure without altering its state are desired.

In general, cells extracted from a living organism suffer various stresses that disturb gene regulation, often provoking dedifferentiation. Dedifferentiation is also often necessary to grow cells. Consequently, the initial gene expression state of the cells often cannot be maintained by culturing cells collected from a patient under simple culture conditions. This prevents formation of cell structures, and therefore of tissue. Furthermore, advanced functions of the cells cannot be achieved. For example, when cells are cultured in a typical polystyrene cell culture dish, the cells merely form a single layer structure, making it difficult to form a cell structure similar to the structure seen in highly differentiated cells, such as the pellet structure adopted by chondrocytes in a living organism. Many specific functions of chondrocytes are also lost.

To address these problems, cell culture methods to construct a three-dimensional structure that imitates the structure of tissue have been developed, such as methods for a spheroid culture, cluster culture, pellet culture, three-dimensional carrier culture, and the like. A cell culture method of producing cells that have a three-dimensional structure by using an extracellular matrix with a three-dimensional structure as a cell culture scaffold is known.

In the field of biological tissue regeneration, related techniques are being perfected, such as an unattended, automated cell culture method, drug discovery for differentiation control, and methods of testing for virus infection. In light of this, the free design of high-order physical structures that imitate the structures in living organisms has become an active area of research (see Non-patent Literature (NPL) 1, 2).

With regard to three-dimensional culturing of cartilage, an example of successfully producing a cartilage disk measuring 10 mm in diameter and 1 mm thick by injecting dedifferentiated chondrocytes into a shaped mold and inducing differentiation by chemically stimulating the cells with BMP2, b-FGF, or the like has been reported in particular.

With regard to Aspect (II), epithelial cells have weak adhesiveness to cell culture containers, which has made it extremely difficult to culture epithelial cells using a regular cell culture container. Cell culture containers that improve the adhesiveness of cells by being coated with a cell adhesion factor, such as a collagen-coated cell culture container (see Patent Literature (PTL) 1), a fibronectin-coated cell culture container (see PTL 2), a laminin-coated cell culture container (see PTL 3), and the like are known. A method using a cell adhesion factor that is a chemical synthetic substance, however, is desired to conserve animal resources and to avoid the unknown substances or pathogenic substances that might be included when using a cell adhesion factor derived from natural products.

Furthermore, the adhesiveness between the epithelial cells and the culturing surface is insufficient with a method using a known cell adhesion factor, such as collagen, fibronectin, laminin, or the like. A cell culture container with excellent adhesiveness of epithelial cells thus is currently in demand.

With regard to Aspect (III), a hanging drop method (see NPL 3), a low-adhesion U-shaped bottom culture dish (see PTL 4), and the like for simple cell structures such as spheres and sheets are known as production methods of cell structures and synthetic tissue bodies with a three-dimensional structure.

Cell structures formed using a 3D printer are also known as cell structures with a complex three-dimensional shape.

With regard to Aspect (IV), important experimental techniques in the field of biology include cell culture techniques developed around the year 1900. Initial development of these techniques focused only on conditioning cells, such as optimizing the medium components, and techniques for single layer cultures and suspension cultures were mainly studied.

In recent years, it has become clear that various properties, stimulus responsiveness, cell functions, and the like differ between single layer cultured cells and cells in living tissue. Instead of single layer cultures that form a single layer structure, demand is increasing for 3D cultures, in particular spheroid cultures, that form a 3D structure resembling the tissue structure in a living organism (see NPL 4).

Traditional techniques that have been actively developed include a technique for embedding cells in a 3D gel formed by suspending cells in a protein solution and causing the cell suspension to gel in reaction to a certain trigger (heat, light, a chemical crosslinking agent, or the like), a technique for grafting cells onto a porous scaffold, and a technique for producing a laminate of a cell sheet using a culture dish with hardened NIPAM.

Techniques developed in recent years include a technique of causing cells to precipitate on a non-adhesive round bottom, as with PrimeSurface by Sumitomo Bakelite Co. or the like; a technique of heightening the migration property of cells adhered to a culturing surface by providing a smooth surface with a regular pattern of unevenness by laser processing, thereby inducing self-assembly of cells on the culturing surface, as with Nano Culture Plate by JSR Co., Nano Pillar Plate by Hitachi, or the like; and a technique of using a culture dish with countless holes approximately 100 µm to 500 µm in diameter and 500 µm deep to precipitate cells seeded in each hole onto the bottom of the hole, as with Elplasia by Kuraray Co., EZSPHERE by Iwaki & Co., or the like.

A hanging drop method to manufacture a spheroidal cell structure in a droplet by producing a droplet of a cell suspension at the tip of a tubular member and holding the droplet for a predetermined time period (such as approximately 2 weeks) while maintaining the spherical shape of the droplet using the surface tension of the droplet has also been developed recently.

With regard to Aspect (V), demand has increased for customized healthcare to improve the QOL of patients. Regenerative medicine, which aims to regenerate tissues and organs with impaired or lost functions using a patient's own cells, plays a leading role in customized medical treatment.

Regenerative medicine requires operations to culture cells collected from a patient's tissue in a cell culture container, to form tissue, and then to transplant the tissue into the patient. For this reason, a technique for culturing cells to form a cell structure such as tissue and a technique for collecting the cell structure without altering its state are desired.

In general, cells extracted from a living organism suffer various stresses that disturb gene regulation, often provoking dedifferentiation. Dedifferentiation is also often necessary to grow cells. Consequently, the initial gene expression state of the cells often cannot be maintained by culturing cells collected from a patient under simple culture conditions. This prevents formation of cell structures, and therefore of tissue. Furthermore, advanced functions of the cells cannot be achieved. For example, when cells are cultured in a typical polystyrene cell culture dish, the cells merely form a single layer structure, making it difficult to form a cell structure similar to the structure seen in highly differentiated cells, such as the pellet structure adopted by chondrocytes in a living organism. Many specific functions of chondrocytes are also lost.

To address these problems, cell culture methods to construct a three-dimensional structure that imitates the structure of tissue have been developed, such as methods for a spheroid culture, cluster culture, pellet culture, three-dimensional carrier culture, and the like. A cell culture method of producing cell structures that have a three-dimensional structure by using an extracellular matrix with a three-dimensional structure as a cell culture scaffold is known (see PTL 5).

Other techniques that have been developed to produce three-dimensional cell structures include a technique of using a low-adhesion culture dish with a U-shaped bottom and a hanging drop method.

In recent years, a method of easily manufacturing three-dimensional cell structures by seeding and culturing cells on a culturing surface coated with a special temperature-responsive polymer and/or temperature-responsive polymer composition has been reported (see PTL 6).

With regard to Aspect (VI), research on cardiac dysfunction has led to a heart disease model that places an animal's biological heart in a state such as cardiac failure. A widely known example is a model animal produced with a method such as provoking autoimmune myocarditis by occluding coronary arteries, administering drugs, or injecting cardiac myosin intramuscularly into a lower extremity.

The heart is an extremely important organ for maintaining life and also affects the state of other organs, making production of a reproducible heart disease model with reduced cardiac function difficult. In the case of coronary artery occlusion, for example, a minor occlusion yields little difference from a healthy state, whereas the animal is lost quickly with an even slightly significant occlusion. The difference between these two extremes is small, making adjustment extremely difficult. In a model of myocarditis due to an autoimmune reaction upon administration of myosin, the medical state of cardiac tissue differs greatly depending on the degree of the immune reaction. Moreover, the cardiac function itself is greatly affected by the state of other organs separate from the heart. Hence, it is extremely difficult to perform stable experiments or construct a reproducible experiment system.

When a produced heart disease model organ is extracted from a living organism, it is also difficult to maintain the cardiomyocytes, which require much oxygen.

The use of laboratory animals also raises issues regarding animal welfare and ethics.

Typically, in tissue that has suffered cardiac failure or the like, it is known that cardiomyocytes necrotize due to partial obstruction of tubular arteries, viral or bacterial infection, an autoimmune reaction, or the like, and that the necrotic cardiomyocytes are replaced by excessive growth of fibroblasts.

Attempts are thus being made to reproduce heart disease tissue that has suffered cardiac failure or the like in a test tube. To do so, it is necessary to form a cell structure by coculturing cardiomyocytes with rapid-growing fibroblasts while protecting the cardiomyocytes, which are susceptible to hypoxia. This is difficult with a known hanging drop method or low-adhesion culture dish, which require 1 to 2 weeks to produce cell structures.

A known method of manufacturing a cell mass efficiently and rapidly uses a cell culture container coated with a particular temperature-responsive polymer (see PTL 6).

With regard to Aspect (VII), a hepatic failure model animal is used in research on liver regeneration therapy, a representative example of which is the transplanting of Muse cells (pluripotent stem cells). Known production methods of hepatic failure model animals include, for example, methods for partial excision of the liver, printing of portal veins and upstream blood vessels, and repeated administration of liver-damaging drugs such as carbon tetrachloride. In many cases, a diseased liver is used in an in vivo experiment, without being extracted from the animal's body.

Experiments using animals raise issues regarding animal welfare and ethics, and the balance between the purpose of the experiment, the success rate, and the value of the obtained findings is important.

In methods for partial excision of the liver, the degree of hepatic failure and the individual animal's state greatly depend on the operator's technique. In methods using liver-damaging drugs, well-known standard protocols exist, but repeated administration is often necessary, and it is difficult to control the degree of progress of symptoms. It is thus difficult to stably construct a reproducible experiment system using a hepatic failure model animal.

Hepatocytes are actively being cultured, but fibroblasts or the like must be cocultured to reproduce a hepatic failure model. However, the adhesiveness to the culture dish and the culture method differ between hepatocytes, which are epithelial cells, and fibroblasts, which are mesenchymal cells, making it difficult to produce a three-dimensional cell structure that includes hepatocytes and fibroblasts with a known hanging drop method or low-adhesion culture dish, which require 1 to 2 weeks for production.

A known method of manufacturing a cell mass efficiently and rapidly uses a cell culture container coated with a particular temperature-responsive polymer (see PTL 6).

CITATION LIST

Patent Literature

PTL 1: JPH05260950A
PTL 2: JPH06014764A
PTL 3: JPH08173144
PTL 4: JP2009050194
PTL 5: JP2010524458
PTL 6: JP5746240B2

Non-Patent Literature

NPL 1: M. Matsusaki et al, Adv. Healthcare Mater., 2, 534 (2013)
NPL 2: M. Matsusaki et al, Biochem. Biophys. Res. Commun., 457, 363 (2015)
NPL 3: Keller G. M. et al., Curr. Opin. Cell Biol., 7, 862-869 (1995)
NPL 4: Nature, Vol 424, P870-872, 21 Aug. 2003.

SUMMARY

Technical Problem

The present disclosure aims to provide a method of efficiently manufacturing a cell mass, a cell structure, or a three-dimensional tissue body using a culturing surface coated with a temperature-responsive polymer or a temperature-responsive polymer composition.

With regard to Aspect (I), it has been reported that use of the aforementioned known methods to produce cultured cartilage with a larger size and/or a complex structure leads to necrosis of cells inside the structure, causing death.

Therefore, Aspect (I) aims to easily manufacture a chondrocyte mass and a graft material, along with a composite material, that are useful for treatment of joints, the trachea, the nose, and the like.

Aspect (II) aims to provide a culture method of epithelial cells that tend not to adhere to a cell culture container, a manufacturing method of a cell structure that includes epithelial cells that tend not to adhere to a cell culture container, and a cell culture container that allows culturing of epithelial cells and manufacturing of a cell structure thereof.

With regard to Aspect (III), the provision of oxygen and nutrients to cells inside the cell structure depends on the concentration gradient diffusion in a hanging drop method or a method using a low-adhesion U-shaped bottom culture dish or the like. Hence, the size is restricted, with a diameter of approximately 0.1 mm typically being considered the maximum. The shape is also limited to being spherical.

A production method of a cell structure using a 3D printer uses a cell suspension, in which cells are individually dispersed using an enzyme such as trypsin, and ejects the cells from a nozzle to produce a cell structure. With this method, an adhesion factor or the like needs to be ejected simultaneously from the outside to the area surrounding the individually ejected cells for the ejected cells to cohere. This adhesion factor was not secreted by the cells, however, and the resulting three-dimensional cell structure does not have sufficient cohesion between cells or sufficient cell activity.

In recent years, the importance of techniques for culturing cells in a cell culture container to form a three-dimensional cell structure imitating a tissue structure, such as a ringed shape or a luminal shape, has increased from the perspective of regenerative medicine, which aims to regenerate tissues and organs with impaired or lost functions. Apart from cell structures with cells as the principal component, a method is also now in demand for producing a cell structure with a principal component of extracellular matrix as a three-dimensional cell structure imitating a tissue structure.

No method, however, for easily forming a three-dimensional tissue body that imitates a tissue structure with a ringed shape, a luminal shape, or the like is currently known.

Accordingly, Aspect (III) aims to provide a production apparatus of a three-dimensional tissue body that can easily yield a three-dimensional tissue body with a ringed shape, a luminal shape, or the like, and to provide a production method of a three-dimensional tissue body that can easily yield a three-dimensional tissue body with a ringed shape, a luminal shape, or the like.

With respect to Aspect (IV), manufacturing of spheroidal cell structures using the aforementioned known methods has the problem of low vitality of the cell structures, a difficulty in achieving the desired size, and trouble adjusting the shape. In particular, if the size and shape of the cell structures are not uniform, it becomes necessary to sort the manufactured cell structures, complicating the manufacturing process and increasing costs.

Therefore, Aspect (IV) aims to easily manufacture cell structures having a desired size and a well-defined spheroidal shape.

With respect to Aspect (V), the aforementioned spheroid culture method and the like have the problems of a small diameter of approximately 10 μm and the ability only to produce spheroids (aggregates of multiple cells) with a weak intercellular network.

The aforementioned hanging drop method and technique using a low-adhesion culture dish with a U-shaped bottom can only yield spheroids that are substantially a true sphere and cannot yield spheroids with a cell-specific form, such as a cobblestone or spindle form.

The cell structures obtainable with a method using the aforementioned special polymer and/or polymer composition developed in recent years do not always reach the desired form, and the conditions for this method have room for optimization and improvement.

Therefore, Aspect (V) aims to manufacture a cell structure with the desired form by controlling the aggregation mode of cells.

With regard to Aspect (VI), the method disclosed in PTL 6 does not consider reproduction of heart disease tissue that has suffered cardiac failure or the like. A method of reproducing heart disease in a test tube is currently in demand.

Accordingly, Aspect (VI) aims to provide a manufacturing method of a cell structure for easy formation of a cell structure that includes cardiomyocytes and fibroblasts and is useful as a heart disease model.

With regard to Aspect (VII), the method disclosed in PTL 6 does not consider reproduction of hepatic failure tissue. A method of reproducing hepatic failure in a test tube is currently in demand.

Accordingly, Aspect (VII) aims to provide a manufacturing method of a cell structure for easy formation of a cell structure that includes cardiomyocytes and fibroblasts and is useful as a hepatic failure model.

Solution to Problem

The following is a summary of Aspects (I) to (VII) of the present disclosure.

A manufacturing method of a chondrocyte mass of Aspect (I) includes a seeding and culturing step of seeding, in the presence of a cell mass, cells capable of differentiating into chondrocytes onto a coated culturing surface coated with a temperature-responsive polymer or a temperature-responsive polymer composition and culturing the cell mass and the cells capable of differentiating into chondrocytes to produce a chondrocyte mass.

In the manufacturing method of a chondrocyte mass of Aspect (I), the cell mass is preferably produced by seeding and culturing the cells capable of differentiating into chondrocytes.

In the manufacturing method of a chondrocyte mass of Aspect (I), the seeding and culturing step is preferably performed a plurality of times.

In the manufacturing method of a chondrocyte mass of Aspect (I), the coated culturing surface is preferably surrounded by a cell non-adhesive wall.

In the manufacturing method of a chondrocyte mass of Aspect (I), the coated culturing surface preferably has a width of 3 mm or less, and the wall preferably has a height of 3 mm or less.

In the manufacturing method of a chondrocyte mass of Aspect (I), an amount of the temperature-responsive polymer and the temperature-responsive polymer composition that the coated culturing surface has per unit area is preferably 0.1 μg/cm$^2$ to 3.0 μg/cm$^2$.

In the manufacturing method of a chondrocyte mass of Aspect (I), the cells capable of differentiating into chondrocytes are preferably seeded at a cell density of $0.3 \times 10^4$ cells/cm$^2$ to $10.0 \times 10^5$ cells/cm$^2$ in the seeding and culturing step.

A chondrocyte mass of Aspect (I) is manufactured using the above-described manufacturing method of a chondrocyte mass of the present disclosure.

The chondrocyte mass of Aspect (I) preferably has a donut shape.

A manufacturing method of a graft material of Aspect (I) includes seeding mesenchymal cells in the presence of the chondrocyte mass of the present disclosure and culturing the chondrocyte mass and the mesenchymal cells to produce a graft material.

A graft material of Aspect (I) is manufactured using the manufacturing method of a graft material of the present disclosure.

A composite material of Aspect (I) includes the chondrocyte mass of the present disclosure on an outer surface of a tubular structure.

The composite material of Aspect (I) preferably further includes a core material inside the tubular structure.

Aspect (II) provides a culture method of epithelial cells, the culture method including a production step of producing a temperature-responsive polymer or a temperature-responsive polymer composition, a culture container preparation step of forming a coated region A by coating at least a portion of a culturing surface of a cell culture container with the temperature-responsive polymer or the temperature-responsive polymer composition to prepare a coated cell culture container including the coated region A, a seeding step of seeding epithelial cells in the coated cell culture container, and a culturing step of culturing the epithelial cells adhered to the coated region A. The concentration of the temperature-responsive polymer or the temperature-responsive polymer composition in the coated region A is 0.3 pg/mm$^2$ or more.

In the culture method of epithelial cells of Aspect (II), at least a portion of the culturing surface of the cell culture container preferably includes a depression located within the coated region A.

Aspect (II) also provides a manufacturing method of a cell structure, the manufacturing method including a production step of producing a temperature-responsive polymer or a temperature-responsive polymer composition, a culture container preparation step of forming a coated region A by coating at least a portion of a culturing surface of a cell culture container with the temperature-responsive polymer or the temperature-responsive polymer composition to prepare a coated cell culture container including the coated region A, a seeding step of seeding epithelial cells in the coated cell culture container, and a culturing step of forming an aggregated cell structure from the epithelial cells to obtain a cell structure adhered to the coated region A. The concentration of the temperature-responsive polymer or the temperature-responsive polymer composition in the coated region A is 0.3 pg/mm$^2$ or more.

In the manufacturing method of a cell structure of Embodiment (II), in the culture container preparation step, a coated region B coated with the temperature-responsive polymer or the temperature-responsive polymer composition is preferably formed on at least a portion of the culturing surface of the cell culture container at a different position than the coated region A, and the concentration of the temperature-responsive polymer or the temperature-responsive polymer composition in the coated region B is preferably less than 200 pg/mm$^2$.

In the manufacturing method of a cell structure of Embodiment (II), at least a portion of the culturing surface of the cell culture container preferably includes a depression located within the coated region A.

Aspect (II) also provides a cell culture container for epithelial cells, the cell culture container including a coated region A, coated with a temperature-responsive polymer or a temperature-responsive polymer composition, on at least a portion of a culturing surface. The concentration of the temperature-responsive polymer or the temperature-responsive polymer composition in the coated region A is 0.3 pg/mm$^2$ or more.

The cell culture container for epithelial cells of Embodiment (II) preferably further includes a coated region B, coated with a temperature-responsive polymer or a temperature-responsive polymer composition, on at least a portion of the culturing surface at a different position than the coated region A, and the concentration of the temperature-responsive polymer or the temperature-responsive polymer composition in the coated region B is preferably less than 200 pg/mm$^2$.

In the cell culture container for epithelial cells of Embodiment (II), at least a portion of the culturing surface of the cell culture container preferably includes a depression located within the coated region A.

Aspect (III) provides a production apparatus of a three-dimensional tissue body, the production apparatus including a culturing surface having one or more through holes, a shaft inserted through the one or more through holes, and one or more coated culturing surfaces where the culturing surface is coated with a temperature-responsive polymer or a temperature-responsive polymer composition. At least one of the one or more through holes is located within one of the one or more coated culturing surfaces, and the culturing surface is movable in an extending direction of the shaft.

The production apparatus of a three-dimensional tissue body preferably includes a plurality of the culturing surfaces, and the shaft is preferably inserted through the through holes of the plurality of the culturing surfaces.

Aspect (III) also provides a production method of a three-dimensional tissue body using the production apparatus of a three-dimensional tissue body, the production method including a seeding step of seeding at least one type of cells on the coated culturing surface, and a culturing step of culturing the seeded cells to obtain a ringed three-dimensional tissue body wound around the shaft.

The production method of a three-dimensional tissue body preferably further includes repetition of a culturing surface moving step of moving the culturing surface in the extending direction of the shaft after obtaining the ringed three-dimensional tissue body wound around the shaft, a seeding step of seeding at least one type of cells on the coated culturing surface after the culturing surface is moved, and a culturing step of culturing the seeded cells to obtain another ringed three-dimensional tissue body wound around the shaft adjacent to the ringed three-dimensional tissue body wound around the shaft.

In the production method of a three-dimensional tissue body, the cells are preferably seeded on all of the coated culturing surfaces, and the seeded cells are preferably cultured to obtain a three-dimensional tissue body.

The production method of a three-dimensional tissue body preferably includes obtaining a three-dimensional tissue body including the cells seeded in the seeding step.

The production method of a three-dimensional tissue body preferably includes removing the cells after the culturing step, and obtaining a three-dimensional tissue body including a substance secreted by the cells.

In the production method of a three-dimensional tissue body, the substance is preferably a protein.

A manufacturing method of a cell structure of Aspect (IV) includes producing a coated region in which a culturing surface is coated with a temperature-responsive polymer or a temperature-responsive polymer composition, forming a droplet of a cell suspension in the coated region, and performing cell culturing in the droplet. The surface zeta potential of the coated region is 0 mV to 50 mV.

In the manufacturing method of a cell structure of Aspect (IV), the contact angle of water relative to the coated region is preferably 50° to 90°.

The manufacturing method of a cell structure of Aspect (IV) preferably includes producing a plurality of the coated regions on the culturing surface.

The manufacturing method of a cell structure of Aspect (IV) preferably includes forming a plurality of the droplets on the coated region.

In the manufacturing method of a cell structure of Aspect (IV), in each coated region, the bottom area of the droplet is preferably smaller than the area of the coated region.

In the manufacturing method of a cell structure of Aspect (IV), the number of cells included in the droplet is preferably $3.0 \times 10^5$ cells/mL or less.

In the manufacturing method of a cell structure of Aspect (IV), the droplet preferably has a diameter of 1 µm to 8 mm.

In the manufacturing method of a cell structure of Aspect (IV), the amount of the droplet is preferably 0.5 µL to 50 µL.

The following is a summary of Aspect (V).

A manufacturing method of a cell structure of Aspect (V) includes a preparation step of preparing, on a culturing surface of a cell culture container, a first coated region coated with a temperature-responsive polymer and/or a temperature-responsive polymer composition, and a plurality of second coated regions located at an edge of the first coated region and coated with a cell adhesive substance, and a seeding and culturing step of seeding cells in the first coated region and the second coated regions and culturing the cells to produce a cell structure.

In the manufacturing method of a cell structure of Aspect (V), the culturing surface is preferably cell non-adhesive.

In the manufacturing method of a cell structure of Aspect (V), the cell adhesive substance is preferably at least one selected from the group consisting of laminin, collagen, and fibronectin.

In the manufacturing method of a cell structure of Aspect (V), the region occupied by the first coated region and the second coated regions is preferably surrounded by a cell non-adhesive wall.

In the manufacturing method of a cell structure of Aspect (V), the first coated region preferably has a shape extending in a predetermined direction, and the edge of the first coated region preferably lies in the predetermined direction.

A cell structure of Aspect (V) is manufactured using any of the aforementioned manufacturing methods of a cell structure.

A cell of Aspect (V) includes, on a culturing surface, a first coated region coated with a temperature-responsive polymer and/or a temperature-responsive polymer composition, and a plurality of second coated regions located at an edge of the first coated region and coated with a cell adhesive substance.

Aspect (VI) provides a manufacturing method of a cell structure, the manufacturing method including a production step of producing a temperature-responsive polymer or a temperature-responsive polymer composition, a culture container preparation step of coating a culturing surface of a cell culture container with the temperature-responsive polymer or the temperature-responsive polymer composition to prepare a coated cell culture container, a seeding step of seeding cardiomyocytes and fibroblasts in the coated cell culture container at a ratio of 200 to 300 fibroblasts per 100 cardiomyocytes, and a culturing step of culturing the seeded cells to obtain an aggregated cell structure.

In the seeding step, vascular endothelial cells are preferably further seeded.

Immune system cells are preferably added to the coated cell culture container during or after the seeding step and before obtaining the cell structure.

The immune system cells are preferably macrophages and/or T cells.

The area of the portion coated with the temperature-responsive polymer or the temperature-responsive polymer composition is preferably 200 mm$^2$ or less.

Aspect (VII) provides a manufacturing method of a cell structure, the manufacturing method including a production step of producing a temperature-responsive polymer or a temperature-responsive polymer composition, a culture container preparation step of coating a culturing surface of a cell culture container with the temperature-responsive polymer or the temperature-responsive polymer composition to prepare a coated cell culture container, a seeding step of seeding hepatocytes and fibroblasts in the coated cell culture container at a ratio of 10 to 50 fibroblasts per 100 hepatocytes, and a culturing step of culturing the seeded cells to obtain an aggregated cell structure.

In the seeding step, vascular endothelial cells are preferably further seeded.

In the seeding step, adipocytes are preferably further seeded.

In the seeding step, the adipocytes are preferably seeded in a ratio of 50 adipocytes per 100 hepatocytes and 100 to 500 adipocytes per 100 fibroblasts.

Immune system cells are preferably added to the coated cell culture container during or after the seeding step and before obtaining the cell structure.

The immune system cells are preferably at least one selected from the group consisting of monocytes, granulocytes, lymphocytes, and macrophages.

Advantageous Effect

The present disclosure can provide a method of efficiently manufacturing a cell mass, a cell structure, or a three-dimensional tissue body.

In particular, Aspect (I) allows easy manufacturing of a chondrocyte mass and a graft material, along with a composite material, that are useful for treatment of joints, the trachea, the nose, and the like.

The culture method of epithelial cells in Aspect (II) has the aforementioned configuration, thereby allowing epithelial cells that tend not to adhere to a cell culture container to be cultured easily. The manufacturing method of a cell structure in Aspect (II) has the aforementioned configuration, thereby allowing a cell structure including epithelial cells that tend not to adhere to a cell culture container to be manufactured easily. The cell culture container for epithelial cells in Aspect (II) has the aforementioned structure, thereby allowing the culturing of epithelial cells and the manufacturing of a cell structure thereof.

The production apparatus of a three-dimensional tissue body in Aspect (III) has the aforementioned configuration, thereby allowing easy production of a three-dimensional tissue body with a ringed shape, a luminal shape, or the like. The production method of a three-dimensional tissue body in Aspect (III) has the aforementioned configuration, thereby allowing easy production of a three-dimensional tissue body with a ringed shape, a luminal shape, or the like.

Furthermore, Aspect (IV) allows easy manufacturing of cell structures having a desired size and a well-defined spheroidal shape.

Aspect (V) can control the aggregation mode of cells to manufacture cell structures with a desired form.

The manufacturing method of a cell structure in Aspect (VI) has the aforementioned configuration, thereby allowing easy formation of a cell structure that includes cardiomyocytes and fibroblasts and is useful as a heart disease model.

The manufacturing method of a cell structure in Aspect (VII) has the aforementioned configuration, thereby allowing easy formation of a cell structure that includes hepatocytes and fibroblasts and is useful as a hepatic failure model.

BRIEF DESCRIPTION OF THE DRAWINGS

In the accompanying drawings:

FIGS. 3A and 3B are an outline of a modification to the preparation step in Embodiment (I), with the subsequent seeding and culturing step, where FIG. 3A illustrates a first modification to the preparation step, and FIG. 3B illustrates a second modification to the preparation step;

FIG. 4 is an overview of a manufacturing method of a graft material in Embodiment (I);

FIG. 5 is an overview of another example manufacturing method of a chondrocyte mass in Embodiment (I);

FIG. 6 is an overview, in (i) to (v), of an example manufacturing method of a composite material in Embodiment (I);

Figure 12:
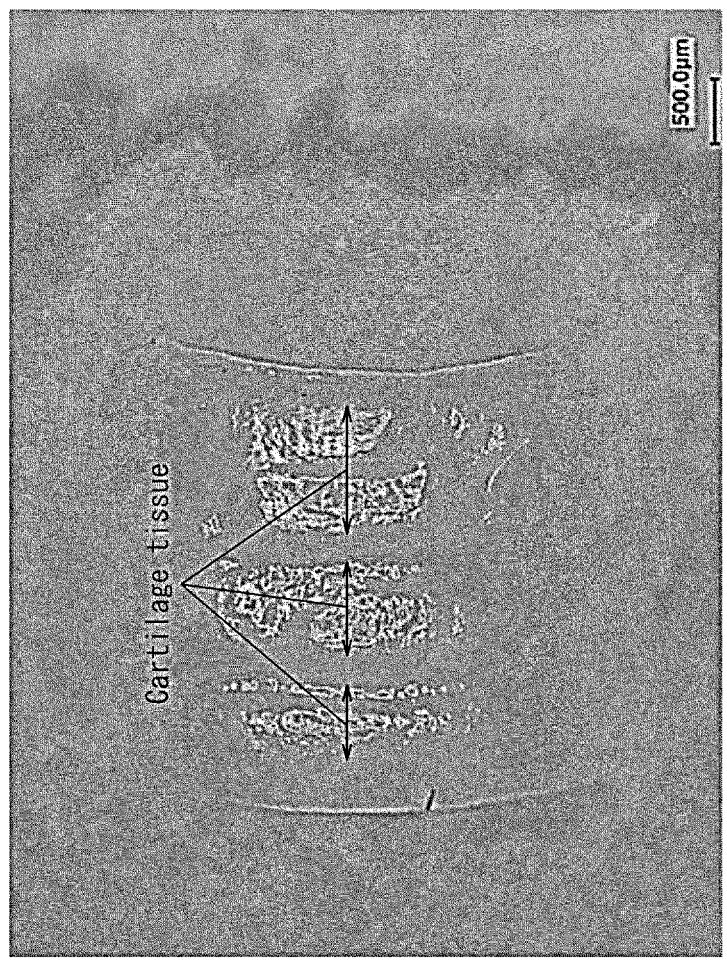
Figure 13B:
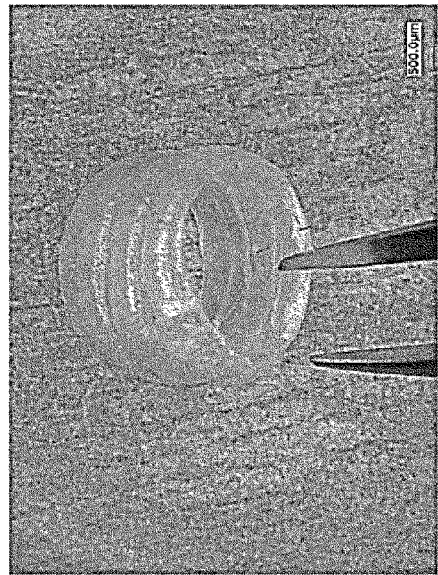
Figure 13D:
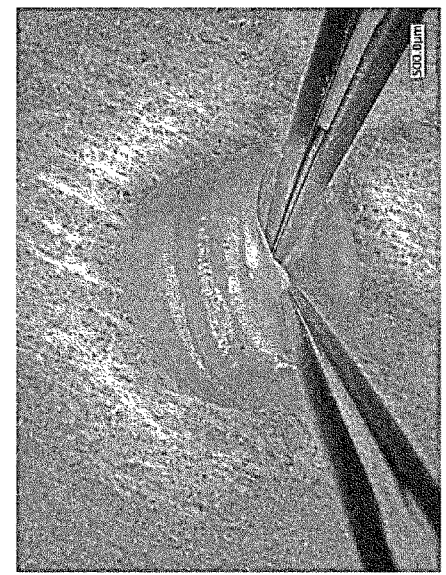
Figure 13A:
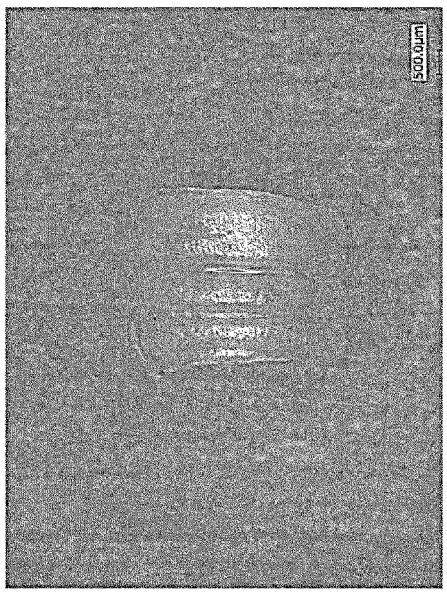
Figure 13C:
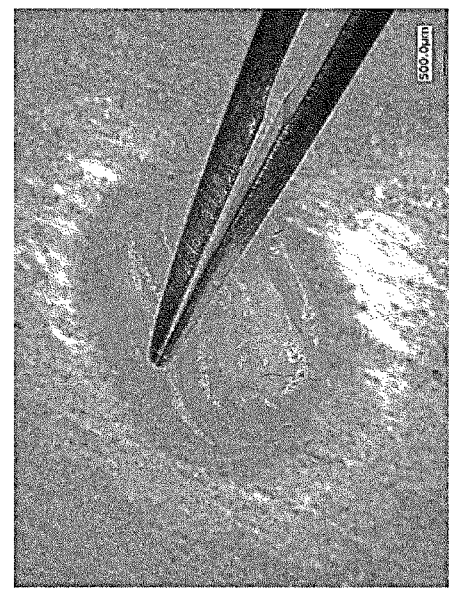
Figure 14A:
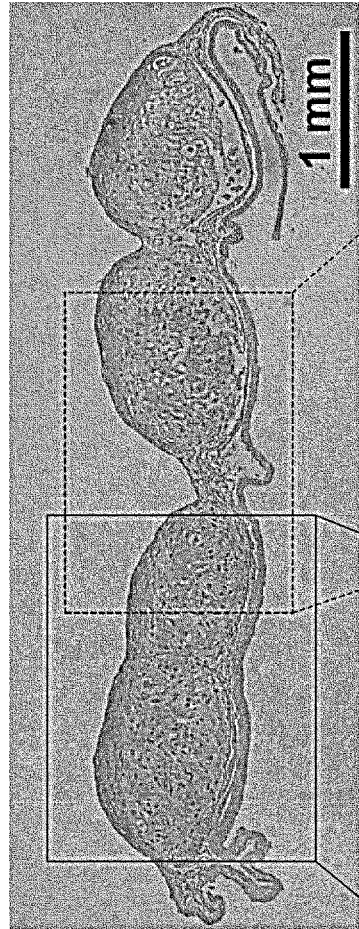
Figure 14B:
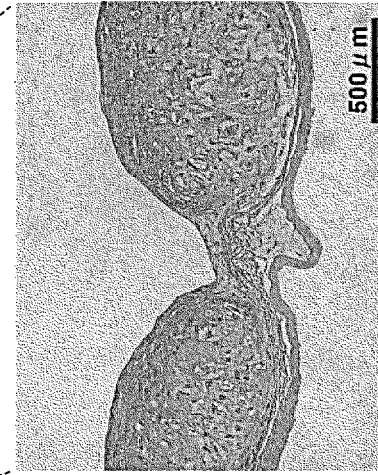
Figure 14C:
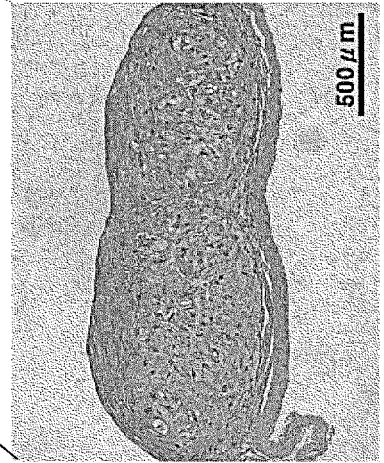
Figure 14D:
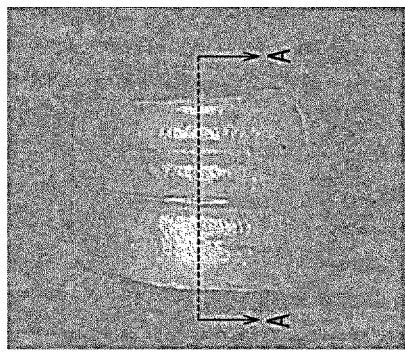
Figure 15:
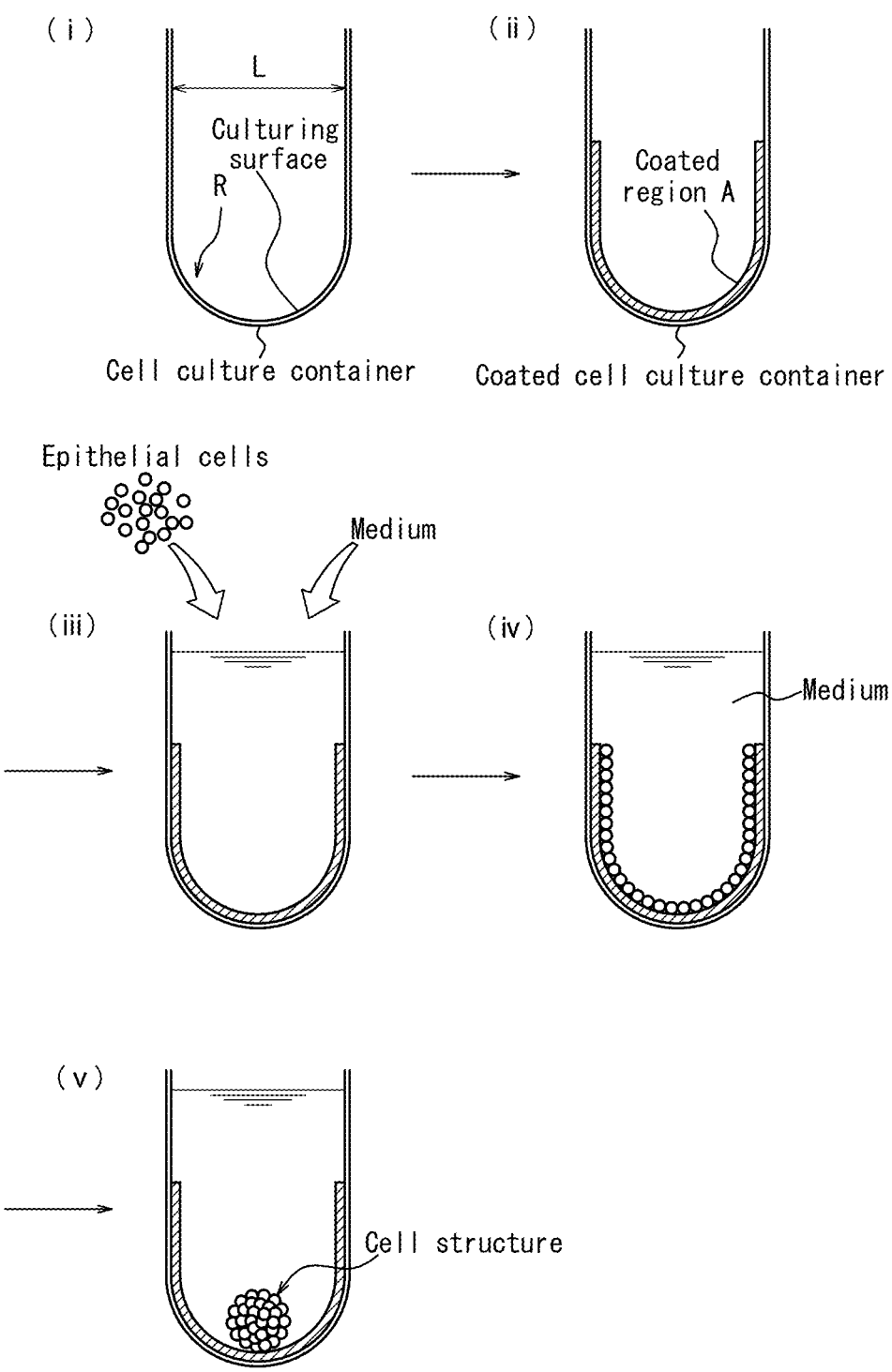
Figure 17:
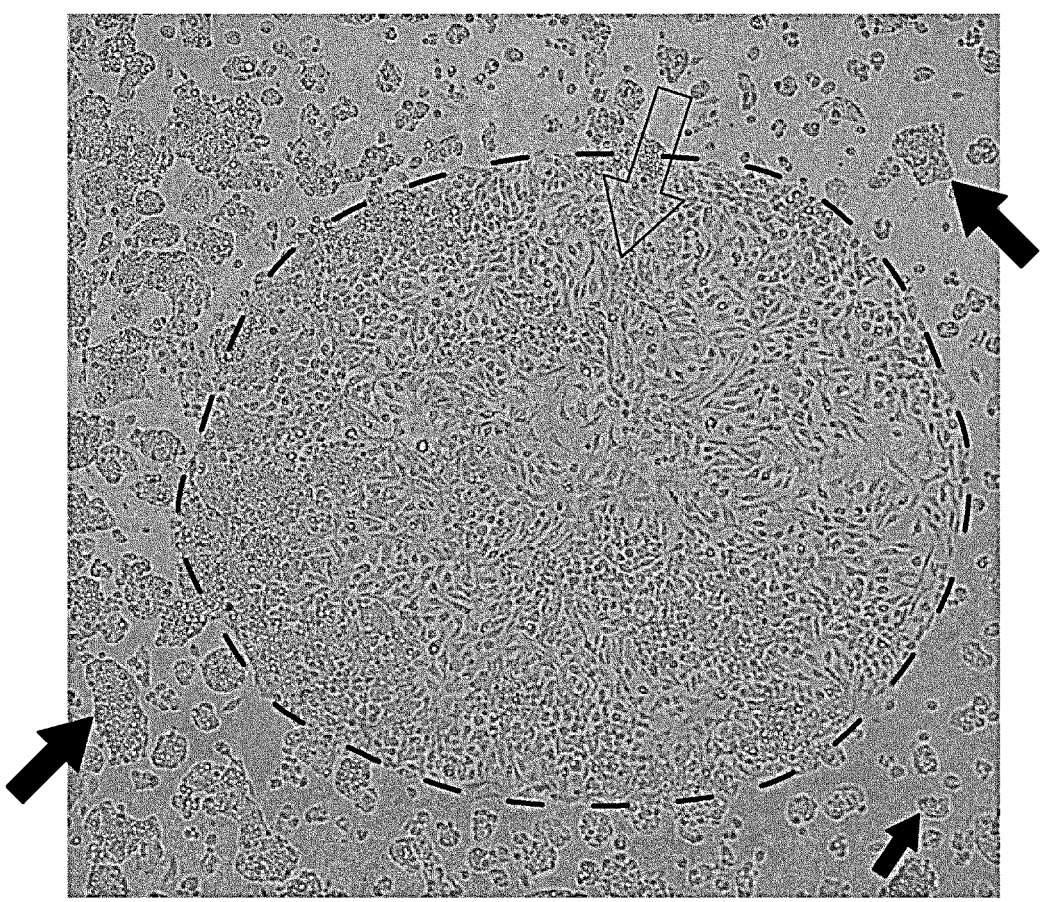
Figure 18:
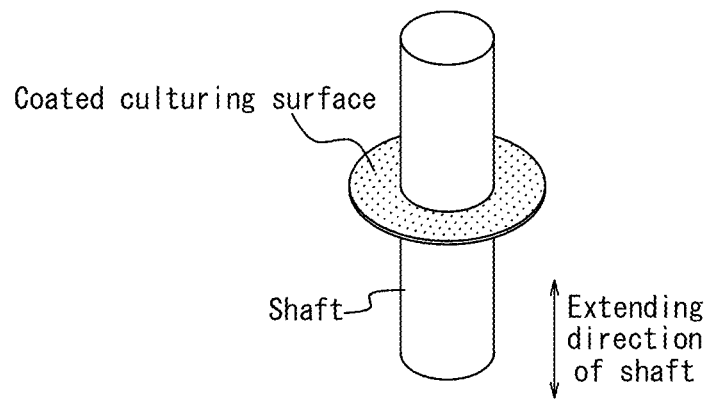
Figure 19:
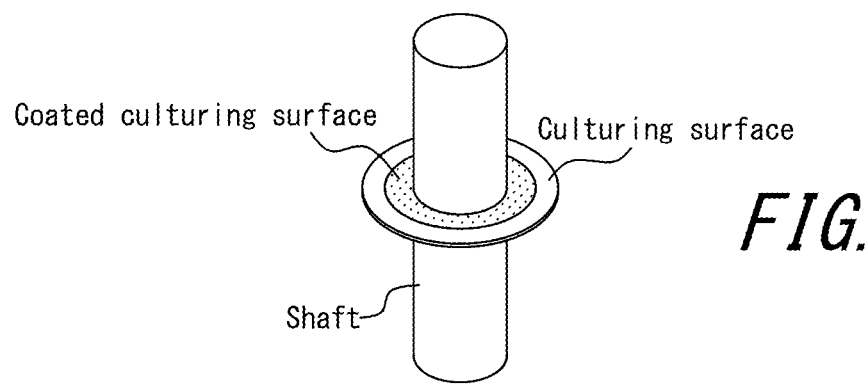
Figure 20:
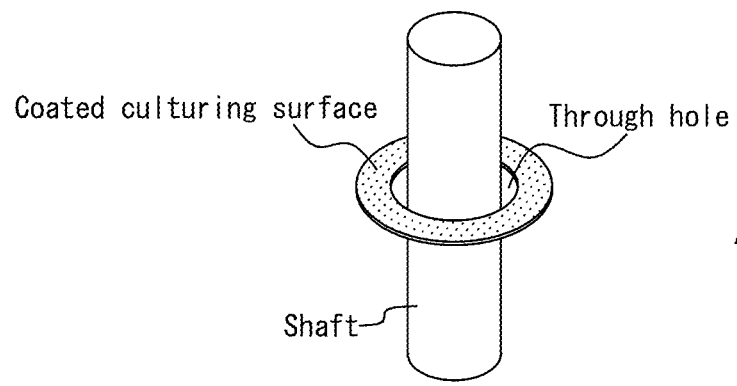
Figure 21:
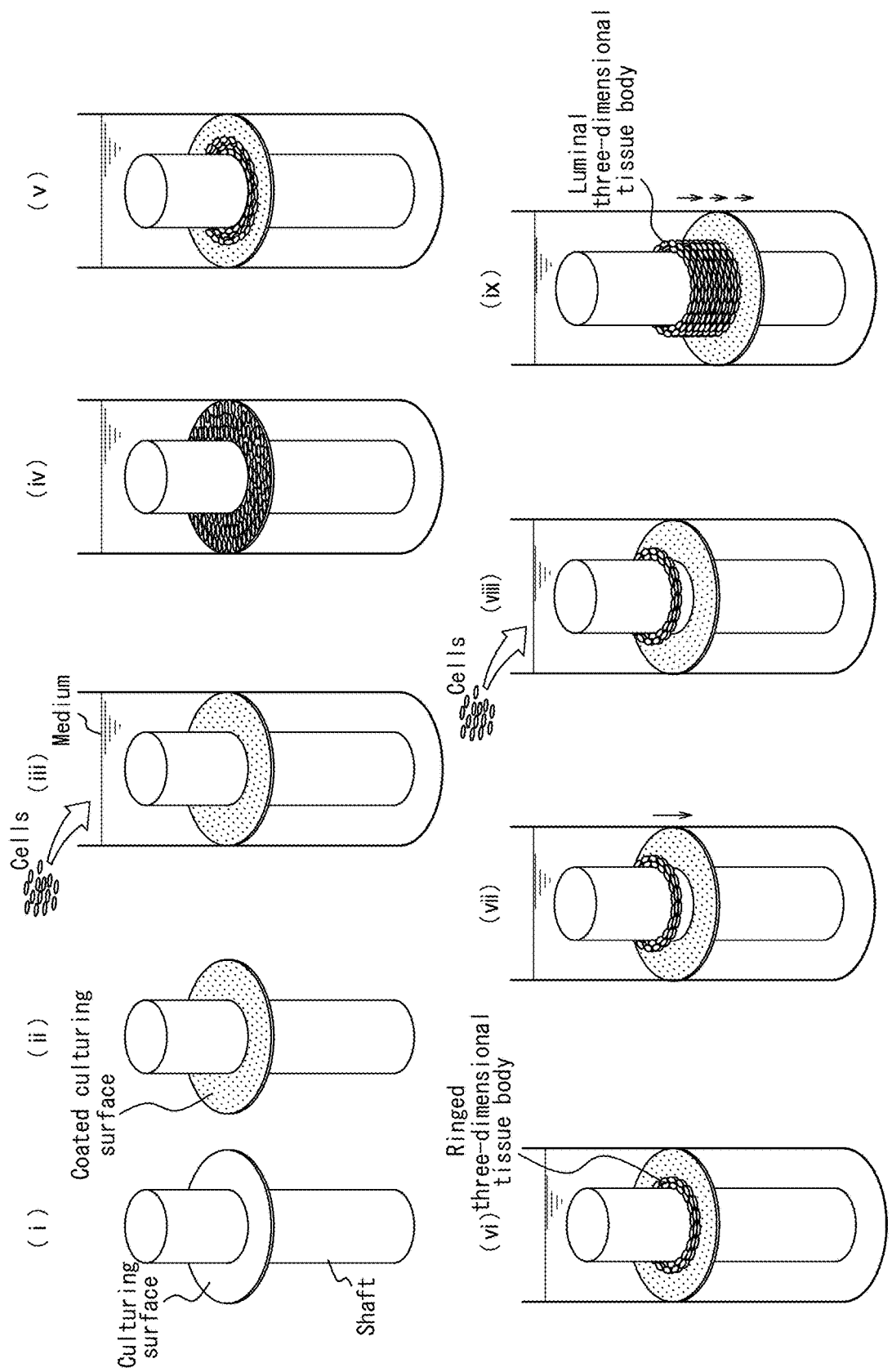
Figure 22:
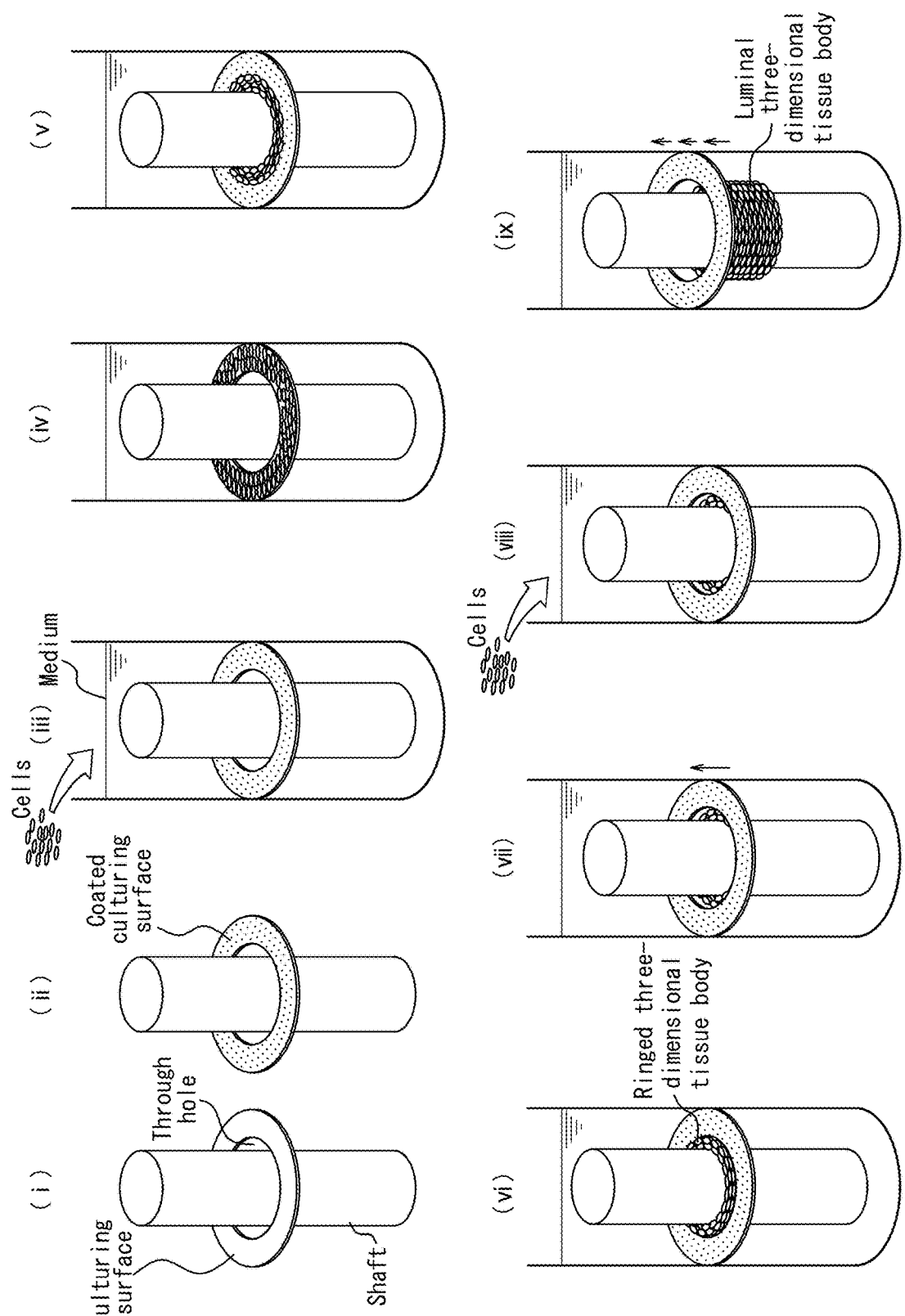
Figure 23:
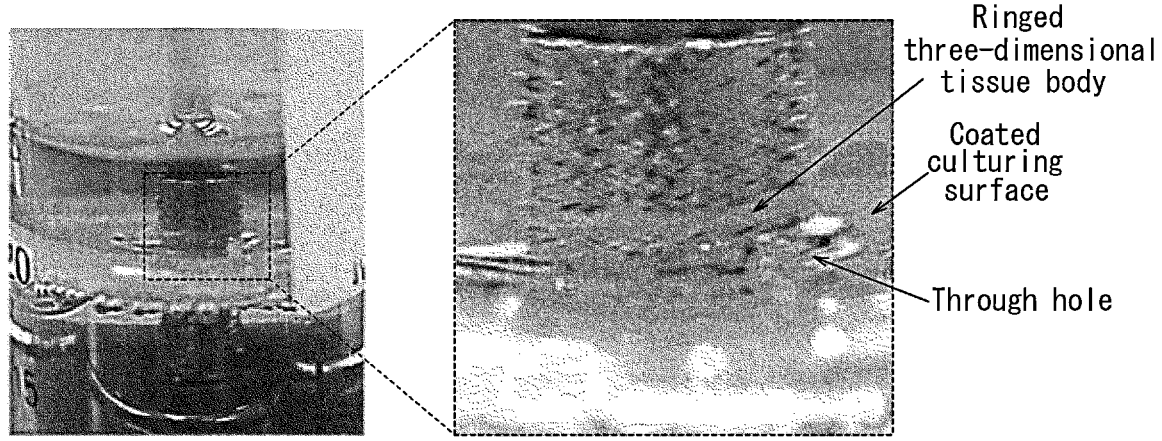
Figure 24:
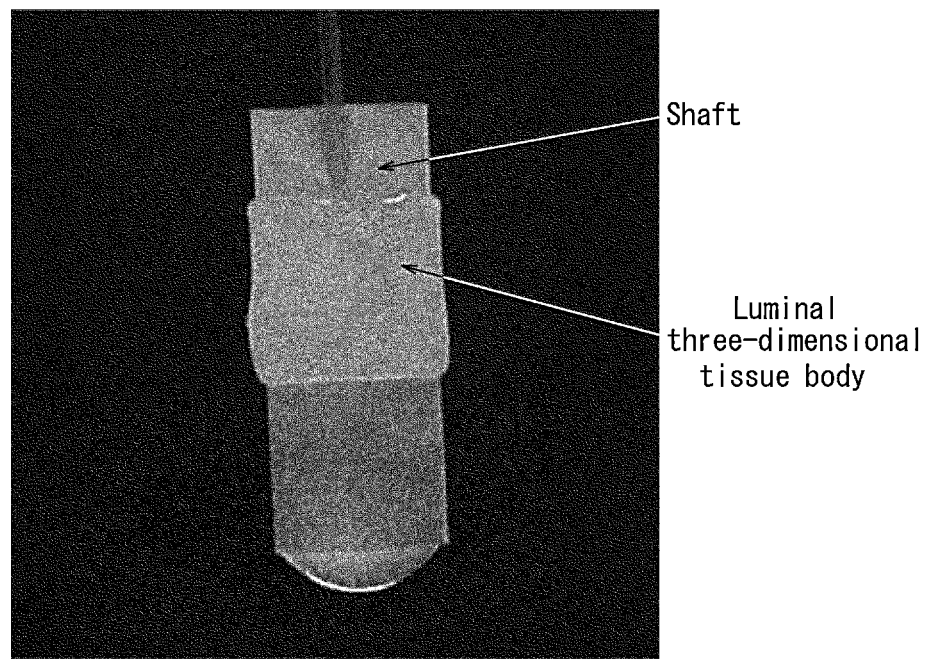
Figure 25:
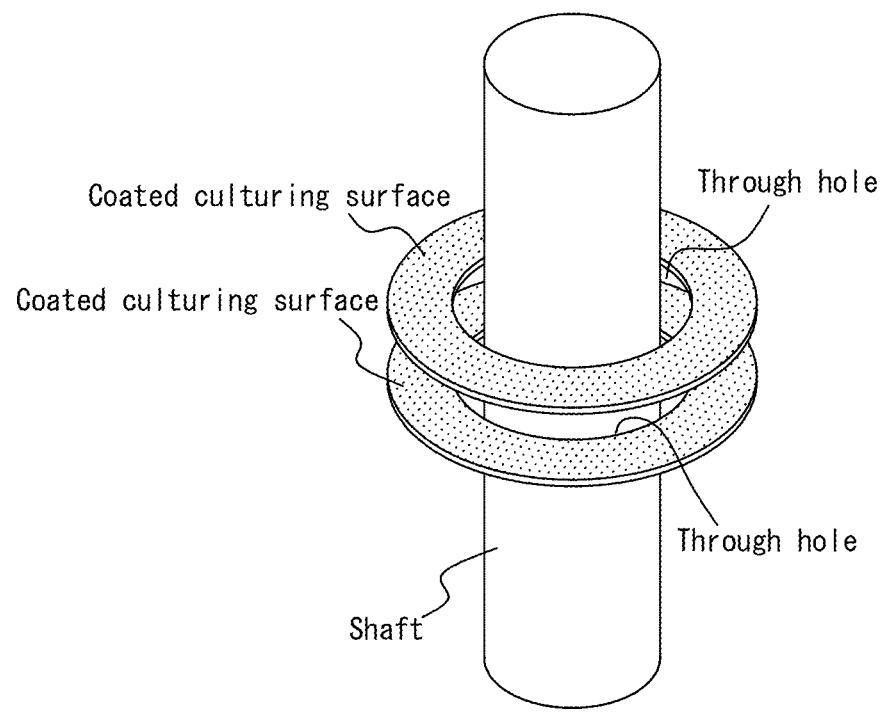
Figure 26:
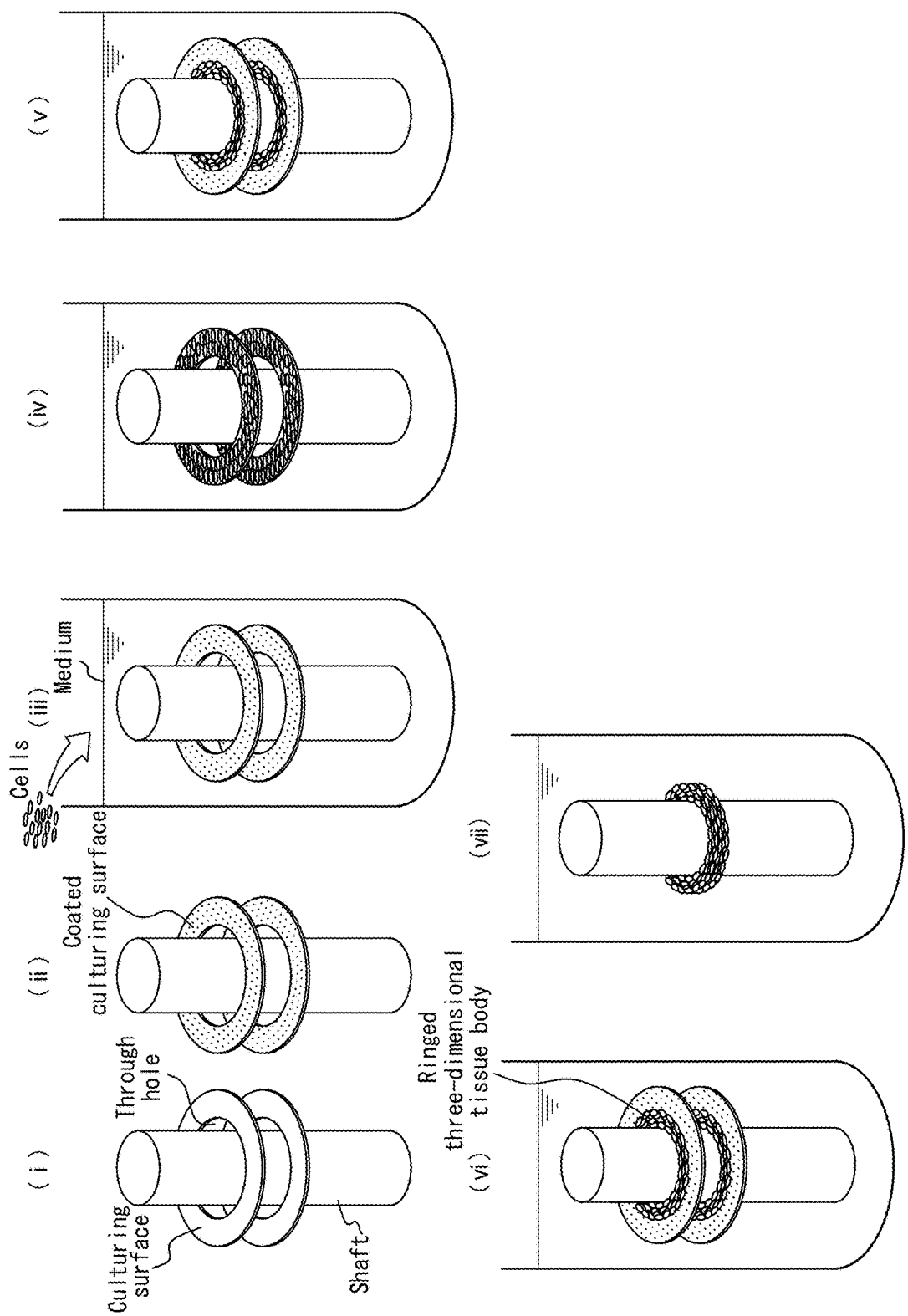
Figure 27A:
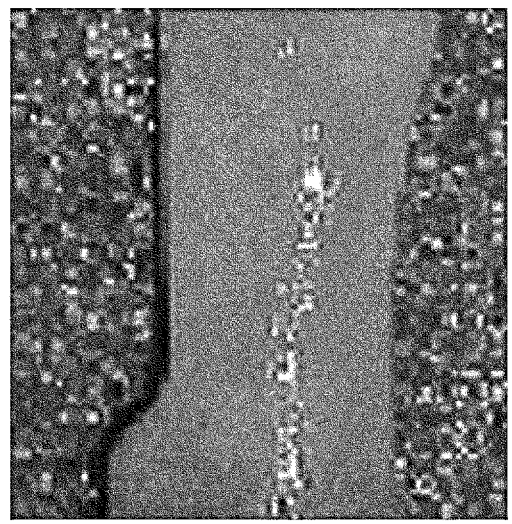
Figure 27B:
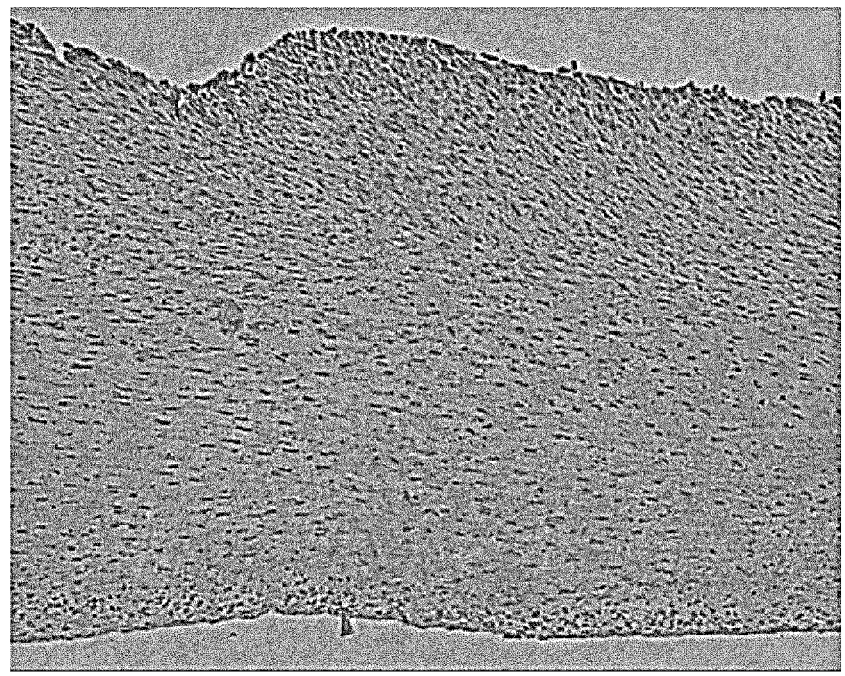
Figure 28:
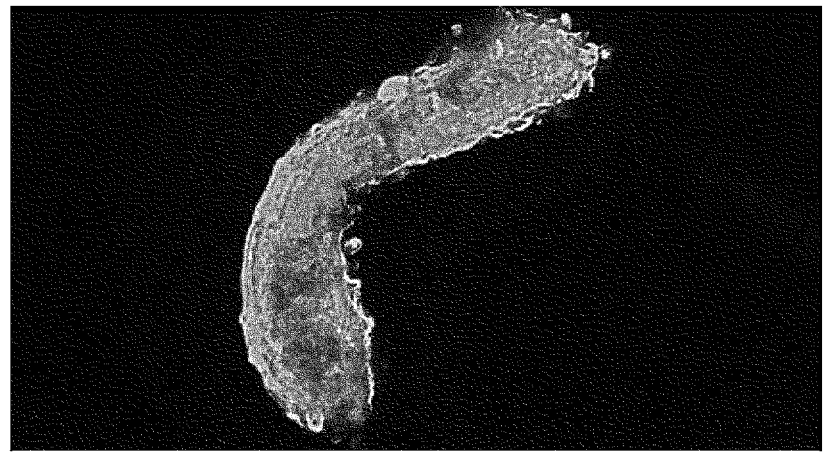
Figure 29:
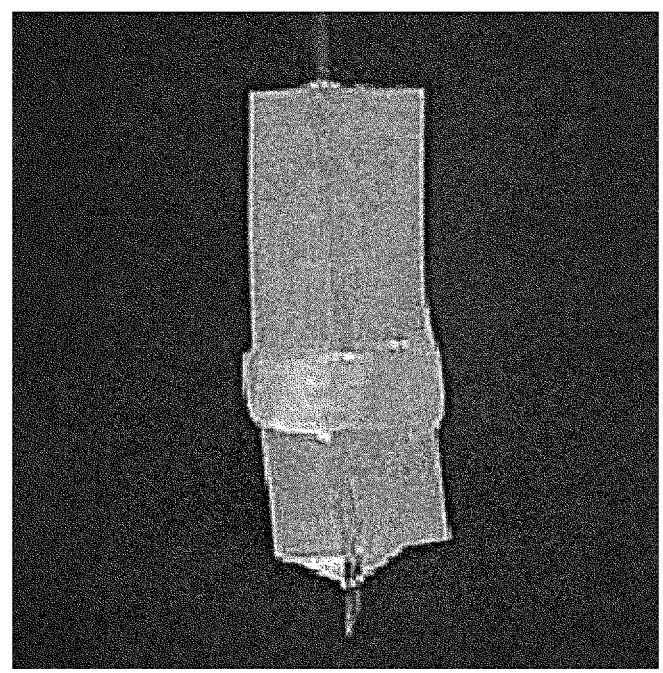
Figure 30:
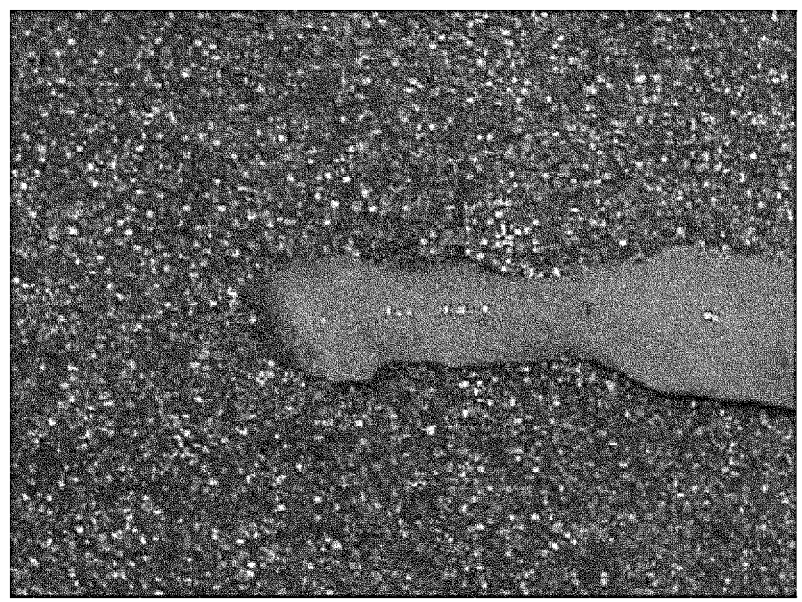
Figure 31:
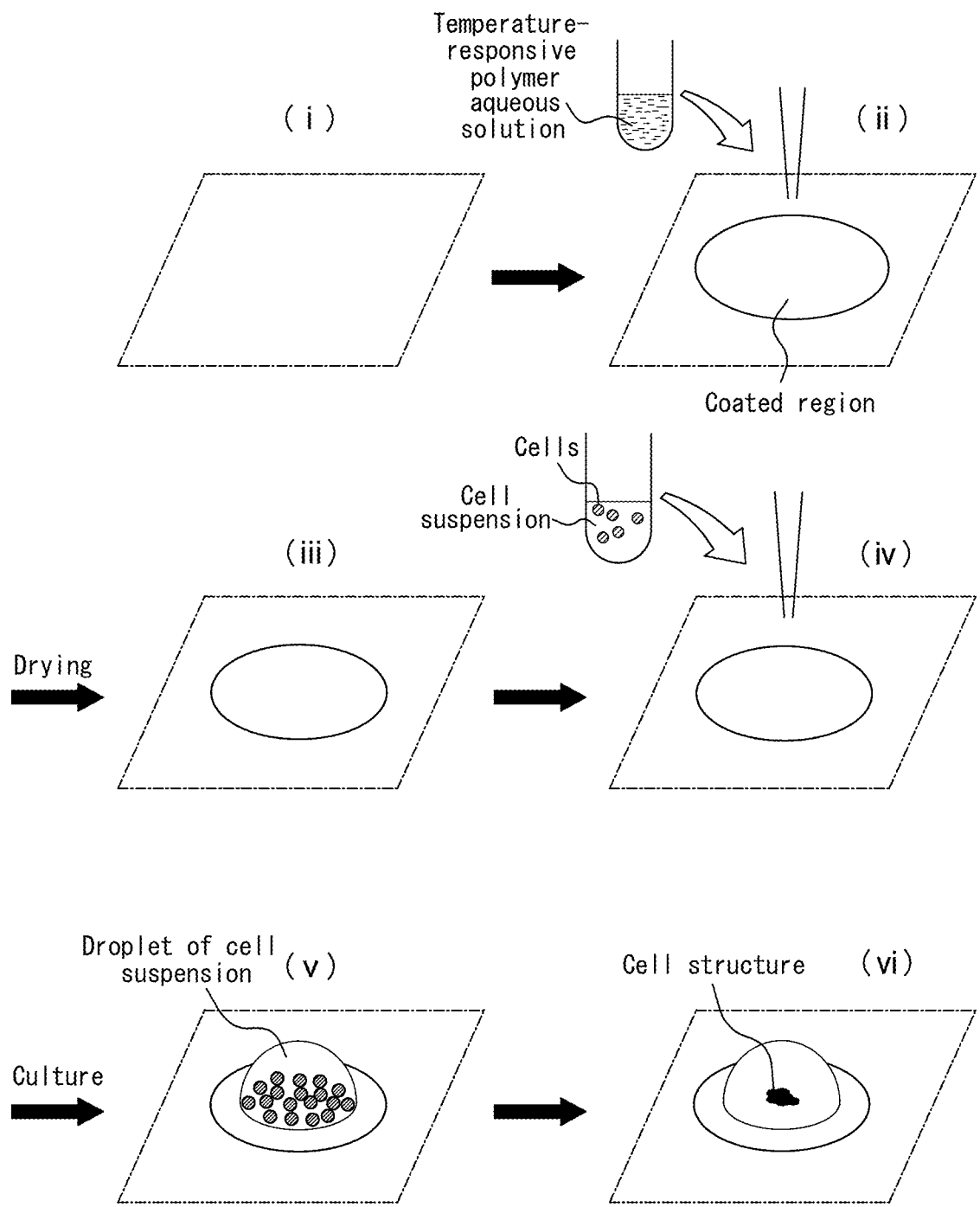
Figure 33A:
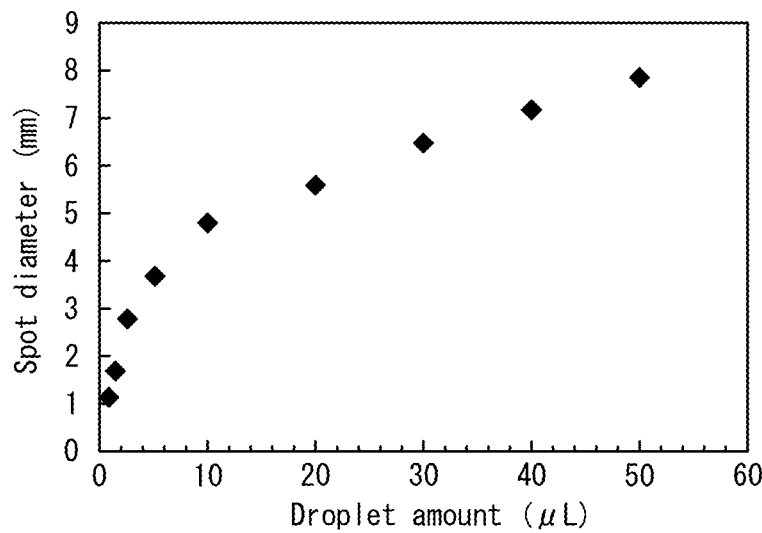
Figure 33B:
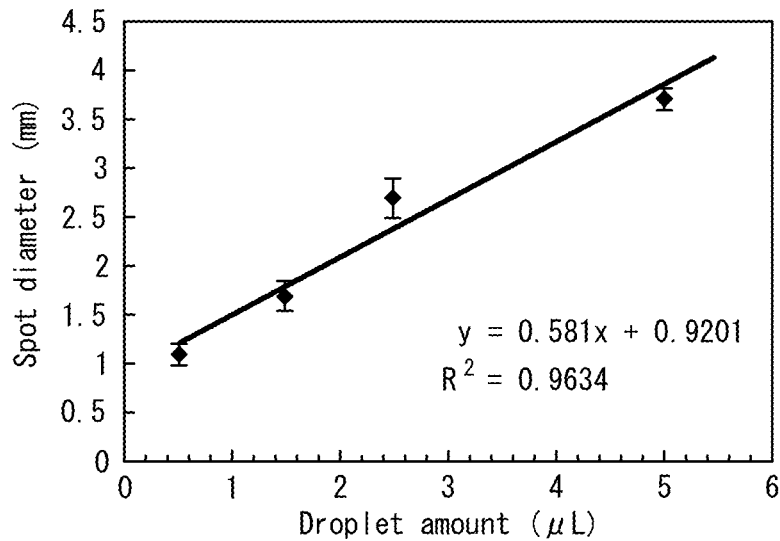
Figure 33C:
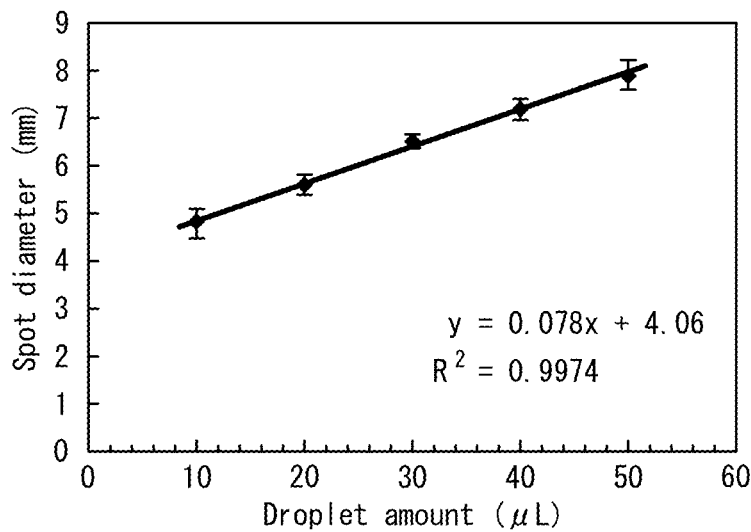
Figure 34:
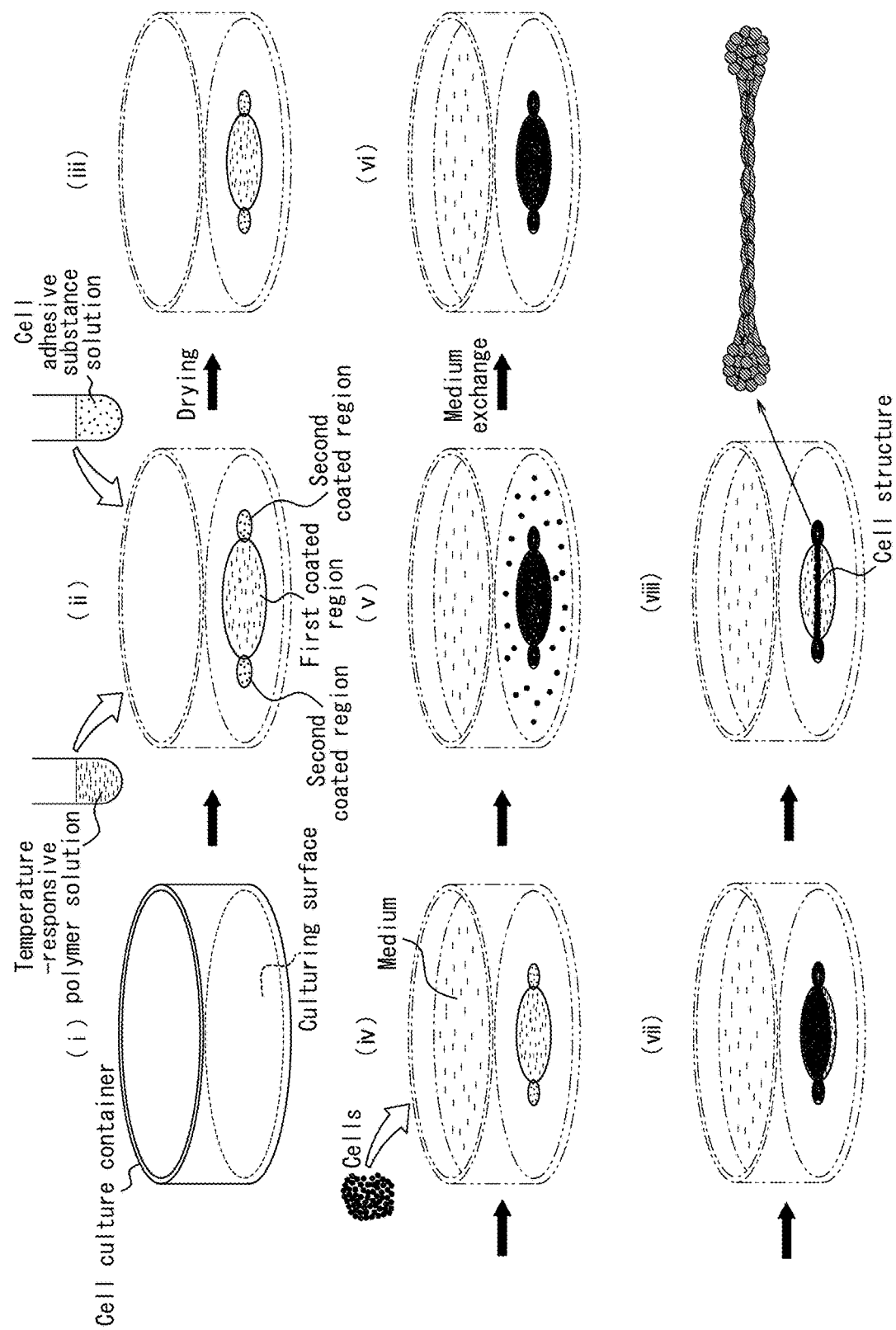
Figure 35A:
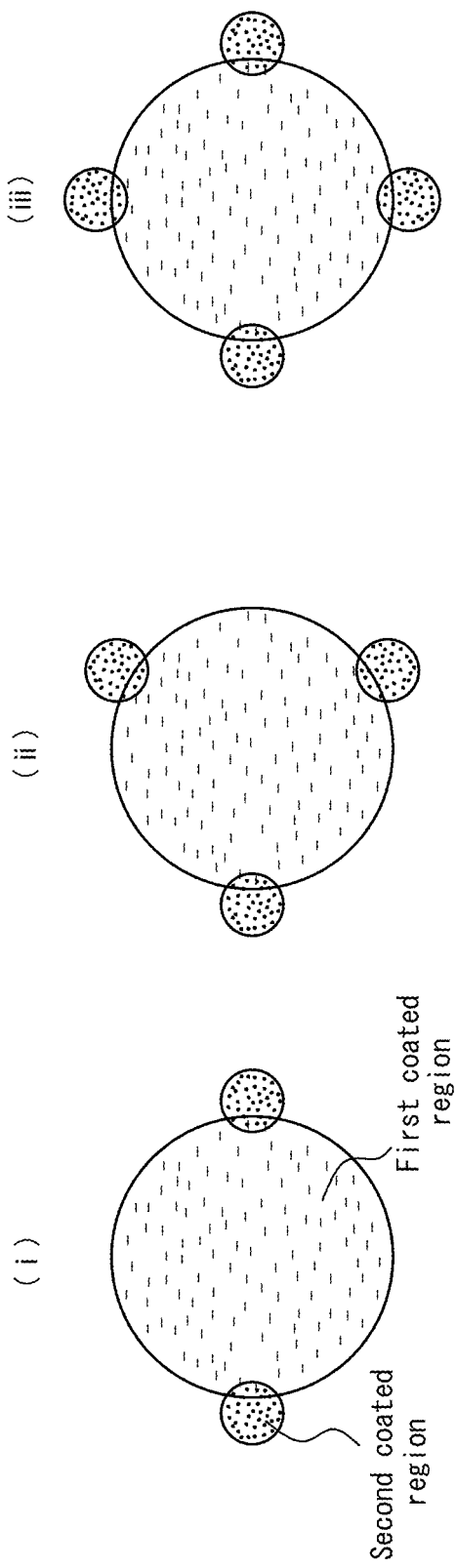
Figure 35C:
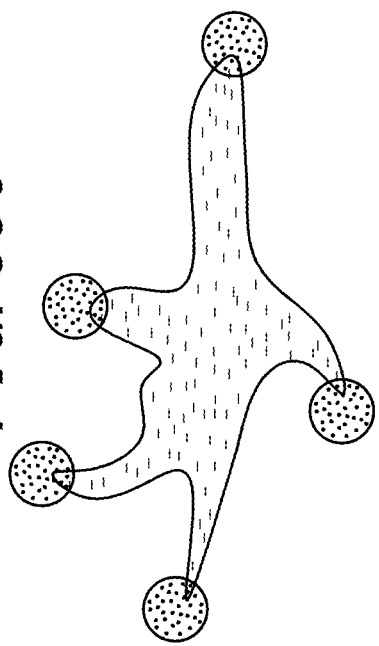
Figure 35B:
Figure 38:
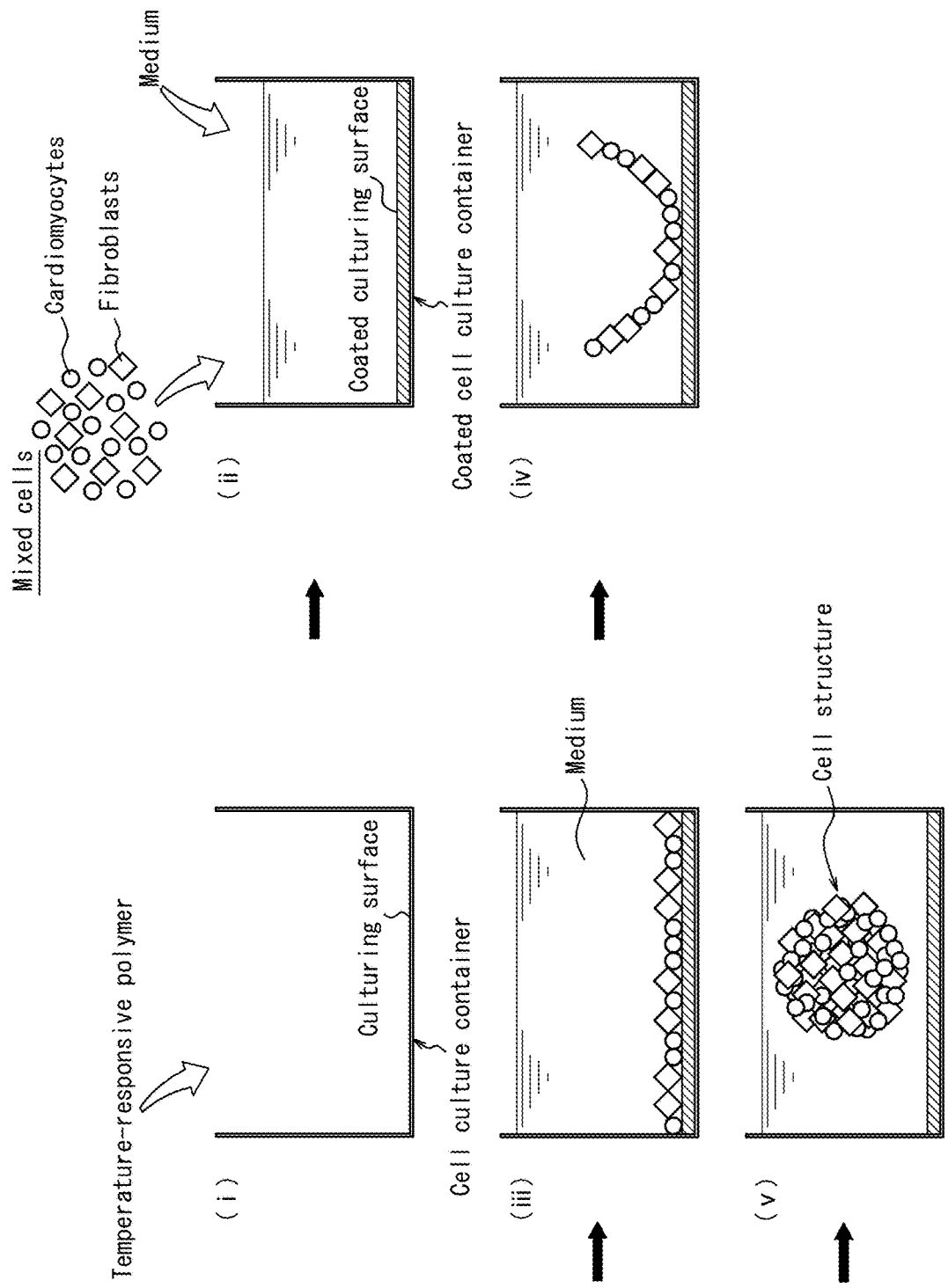
Figure 39:
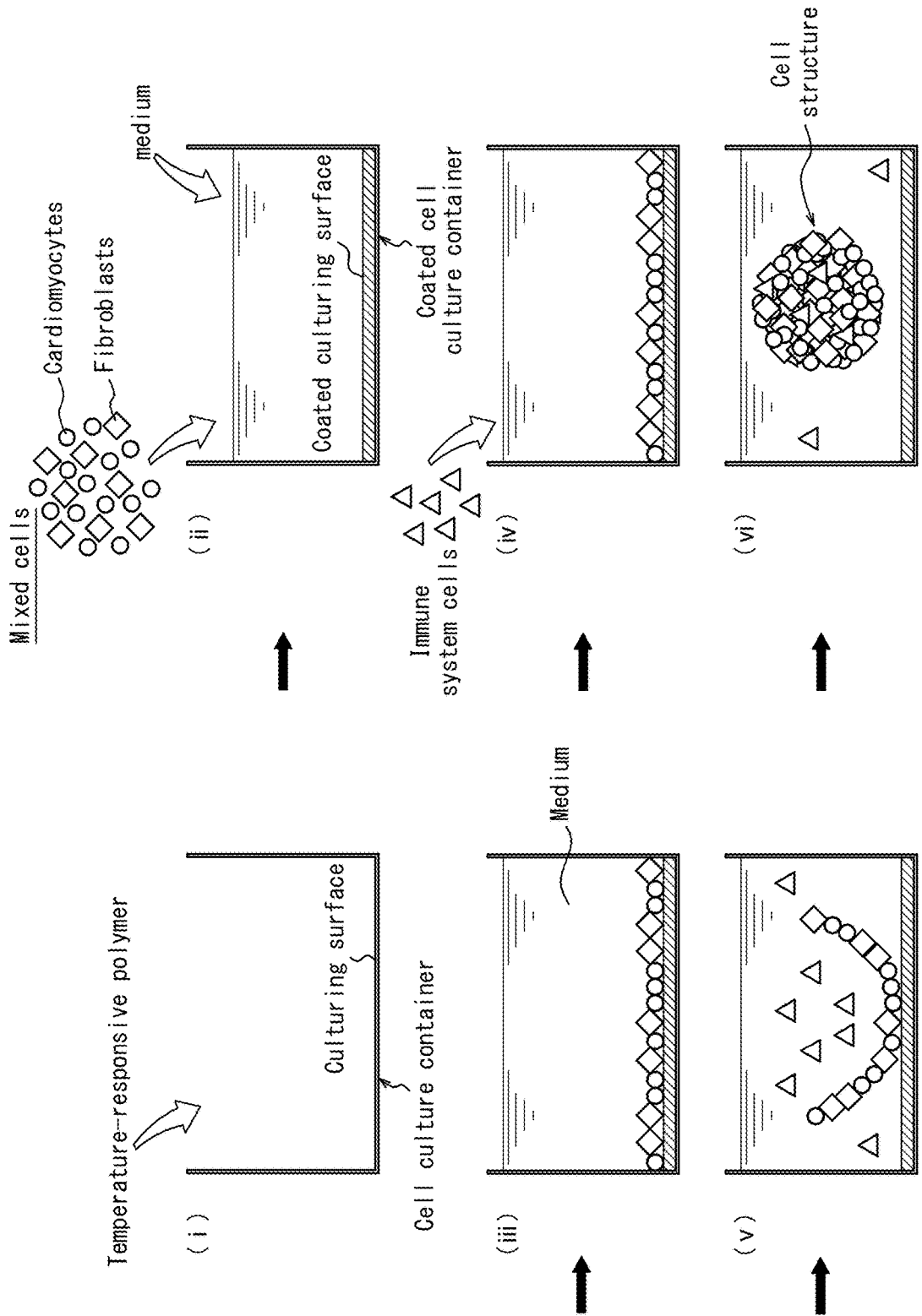
Figure 40:
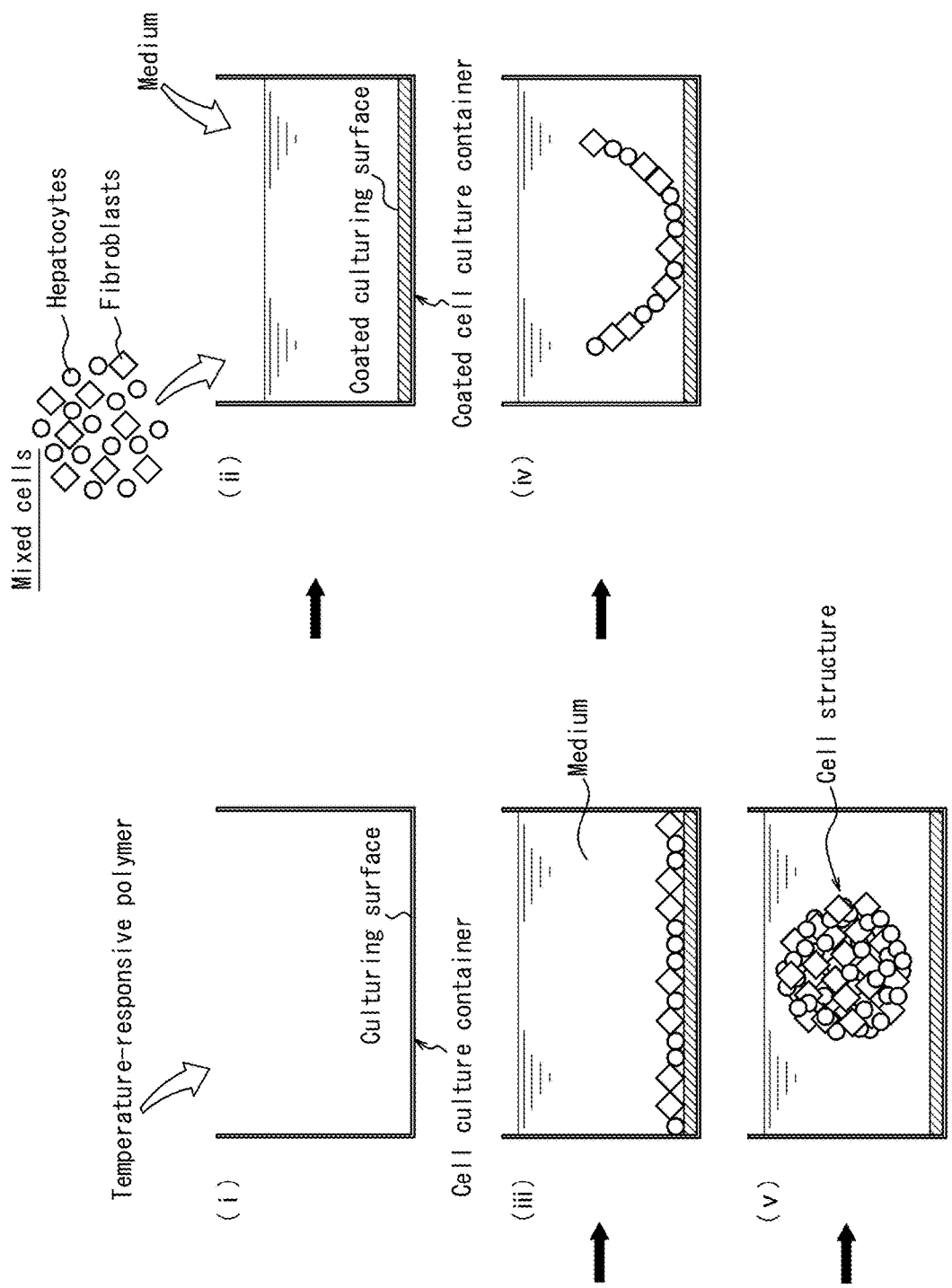
Figure 41:
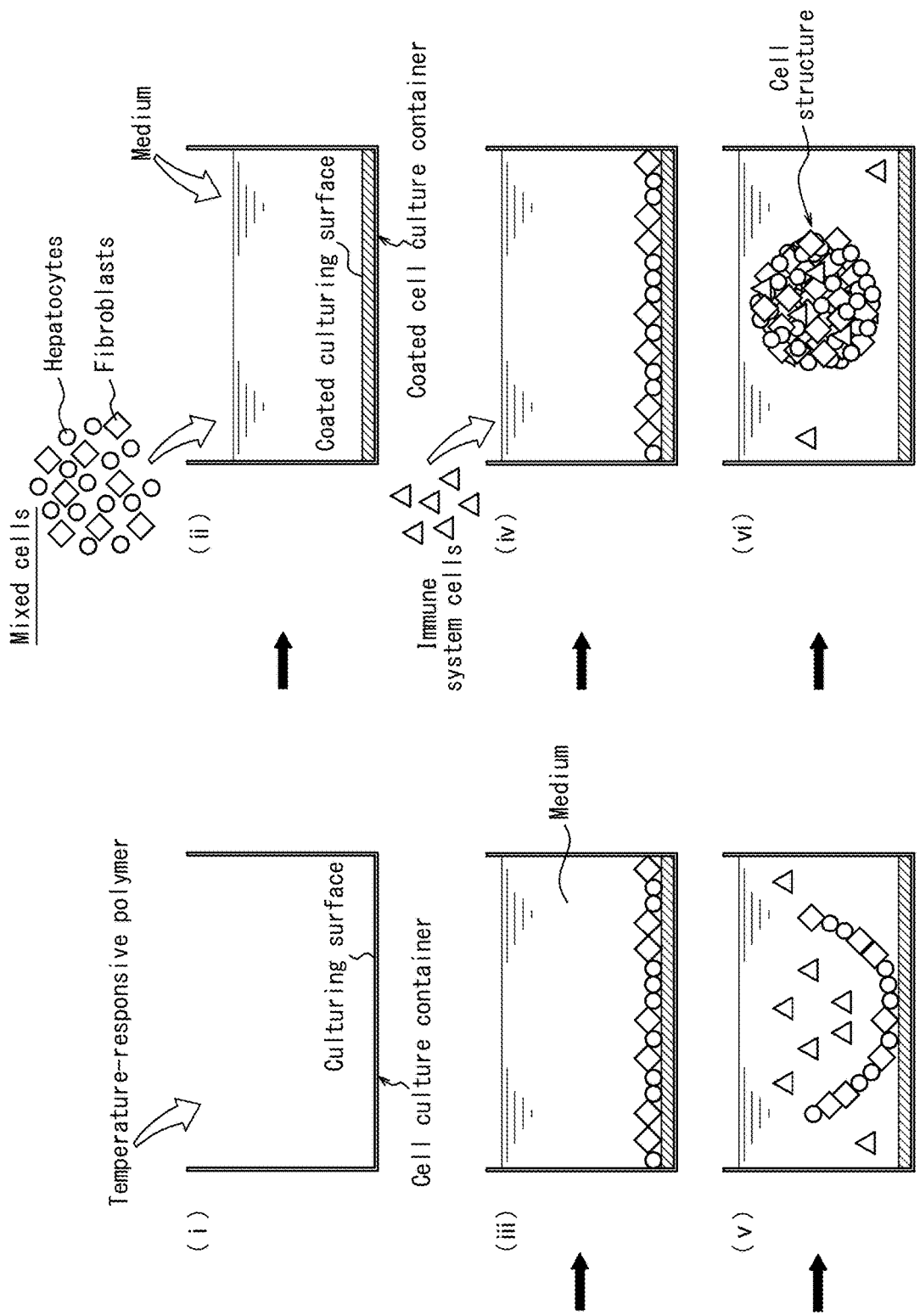

11B is a photograph taken when observing the state of a composite material with the naked eye 21 days after the start of culturing in Test I-D of Embodiment (I);

FIG. 12 is an enlargement of a photograph taken when observing the state of a portion of a composite material with the naked eye 21 days after the start of culturing in Test I-D of Embodiment (I);

FIGS. 13A to 13D are photographs taken when observing, with the naked eye, the state of a composite material produced in Test I-D of Embodiment (I) when manipulating the composite material with tweezers, where FIG. 13A illustrates the outer peripheral surface without manipulation, FIG. 13B illustrates the luminal surface without manipulation, FIG. 13C illustrates the state when the entire material is crushed, and FIG. 13D illustrates the state when pulling towards a portion of the side surface;

FIGS. 14A to 14D are photographs taken when using a microscope to observe the state of a composite material produced in Test I-D of Embodiment (I) when subjecting the composite material to a hematoxylin and eosin stain (H&E stain), where FIG. 14A is an exterior photograph of the composite material, FIG. 14B is a cross-sectional view of the composite material in a plane along the A-A line in FIG. 14A, and FIGS. 14C and 14D are partial enlargements of the photograph in FIG. 14B;

FIG. 15 is an outline illustrating a manufacturing method of a cell structure in an embodiment of Aspect (II);

FIG. 16 is an outline illustrating a manufacturing method of a cell structure in an embodiment of Aspect (II);

FIG. 17 is a photograph illustrating the state when culturing epithelial cells for 96 hours on a temperature-responsive polymer or a temperature-responsive polymer composition used in Aspect (II); the portion surrounded by the dashed line indicates a coated region A, the arrow with a black outline indicates cells adhered to and growing in the coated region A, and the solid black arrows indicate cells adhered to and growing in the non-coated region;

FIG. 18 is an outline (perspective view) illustrating a production apparatus of a three-dimensional tissue body in an embodiment of Aspect (III);

FIG. 19 is an outline (perspective view) illustrating a production apparatus of a three-dimensional tissue body in an embodiment of Aspect (III);

FIG. 20 is an outline (perspective view) illustrating a production apparatus of a three-dimensional tissue body in an embodiment of Aspect (III);

FIG. 21 is an outline illustrating a production method of a three-dimensional tissue body in an embodiment of Aspect (III);

FIG. 22 is an outline illustrating a production method of a three-dimensional tissue body in an embodiment of Aspect (III);

FIG. 23 is a photograph of a ringed three-dimensional tissue body obtained in Example III-4 of Aspect (III);

FIG. 24 is a photograph of a luminal three-dimensional tissue body obtained in Example III-5 of Aspect (III);

FIG. 25 is an outline (perspective view) illustrating a production apparatus of a three-dimensional tissue body in an embodiment of Aspect (III);

FIG. 26 is an outline illustrating a production method of a three-dimensional tissue body in an embodiment of Aspect (III);

FIG. 27A is a photograph of a luminal three-dimensional tissue body obtained in Example III-8 of Aspect (III), and FIG. 27B is an HE stain section image of a luminal three-dimensional tissue body obtained in Example III-8 of Aspect (III);

FIG. 28 is a photograph of a synthetic blood vessel obtained in Example III-9 of Aspect (III);

FIG. 29 is a photograph of a synthetic trachea obtained in Example III-10 of Aspect (III);

FIG. 30 is a photograph of a three-dimensional tissue body, having protein as the principal component, obtained in Example III-11 of Aspect (III);

FIG. 31 is an outline of an example manufacturing method of a cell culture body in an embodiment of Aspect (IV);

FIG. 32 illustrates a modification, in (i) to (iii), to the manufacturing method of a cell culture body in an embodiment of Aspect (IV);

FIGS. 33A to 33C illustrate the results of investigating the correlation between the amount of a droplet and the diameter of the droplet on the culturing surface in an example of Aspect (IV);

FIG. 34 is an overview, in (i) to (viii), of an example manufacturing method of a cell structure in Embodiment (V);

FIGS. 35A to 35C illustrate arrangements of a first coated region and a first coated region in Embodiment (V);

FIG. 36 is an outline of a modification to the preparation step in Embodiment (V), with the subsequent seeding and culturing step;

FIG. 37A is a photograph when using a microscope, in Test V-C in Embodiment (V), to observe the state after 2 hours of culturing ADSC of a GFP recombinant Lewis rat in the first coated region and the second coated regions prepared in Test V-B; FIG. 37B is a photograph when using a microscope, in Test V-C, to observe the state after 20 hours of culturing ADSC of a GFP recombinant Lewis rat in the first coated region and the second coated regions prepared in Test V-B; FIG. 37C is a photograph when observing the cell structure in FIG. 37B at lower magnification; and FIG. 37D is a photograph when using a fluorescence microscope to observe the state of the cell structure indicated by the dashed line in FIG. 37B;

FIG. 38 is an outline illustrating a manufacturing method of a cell structure in an embodiment of Aspect (VI);

FIG. 39 is an outline illustrating a manufacturing method of a cell structure in an embodiment of Aspect (VI);

FIG. 40 is an outline illustrating a manufacturing method of a cell structure in an embodiment of Aspect (VII); and FIG. 41 is an outline illustrating a manufacturing method of a cell structure in an embodiment of Aspect (VII).

DETAILED DESCRIPTION

In the present disclosure, cells are seeded and cultured on a culturing surface coated with a temperature-responsive polymer or a temperature-responsive polymer composition. Specifically, the present disclosure encompasses Aspects (I) to (VII) below.

[[Aspect (I)]]

With regard to Aspect (I), we have previously developed a temperature-responsive polymer and a temperature-responsive polymer composition that have particular properties and are extremely useful for manufacturing cell structures. When a culturing surface of a cell culture container is coated with this polymer and/or polymer composition and cells corresponding in number to a confluency of approximately 100% are seeded and cultured, the cells adhere to the coating and subsequently aggregate at once on the coated culturing surface to form a cell mass in the central portion of the coated culturing surface. This phenomenon is thought to be due to contraction by the inter-cell network exceeding adhesion of the cells to the coated culturing surface, causing the cells to separate from the coated culturing surface.

The manufacturing method of a chondrocyte mass and a graft material in Aspect (I) uses this temperature-responsive polymer or temperature-responsive polymer composition.

With reference to the drawings, embodiments of the manufacturing method of a chondrocyte mass and a graft material in Aspect (I) and of the chondrocyte mass and graft material in Aspect (I) are described in detail with examples.

(Manufacturing Method of Chondrocyte Mass)

A manufacturing method of a chondrocyte mass in an embodiment (Embodiment (I)) of Aspect (I) includes a seeding and culturing step of seeding, in the presence of a cell mass, cells capable of differentiating into chondrocytes onto a coated culturing surface coated with a temperature-responsive polymer or a temperature-responsive polymer composition and coculturing the cell mass and the cells capable of differentiating into chondrocytes to produce a chondrocyte mass.

The manufacturing method of Embodiment (I) preferably includes a production step of producing a temperature-responsive polymer and/or a temperature-responsive polymer composition, a preparation step of coating a portion of a culturing surface with the temperature-responsive polymer and/or the temperature-responsive polymer composition to prepare a coated culturing surface, and a seeding and culturing step of seeding, in the presence of a cell mass, cells capable of differentiating into chondrocytes onto the coated culturing surface and coculturing the cell mass and the cells capable of differentiating into chondrocytes to produce a chondrocyte mass.

Figure 1:
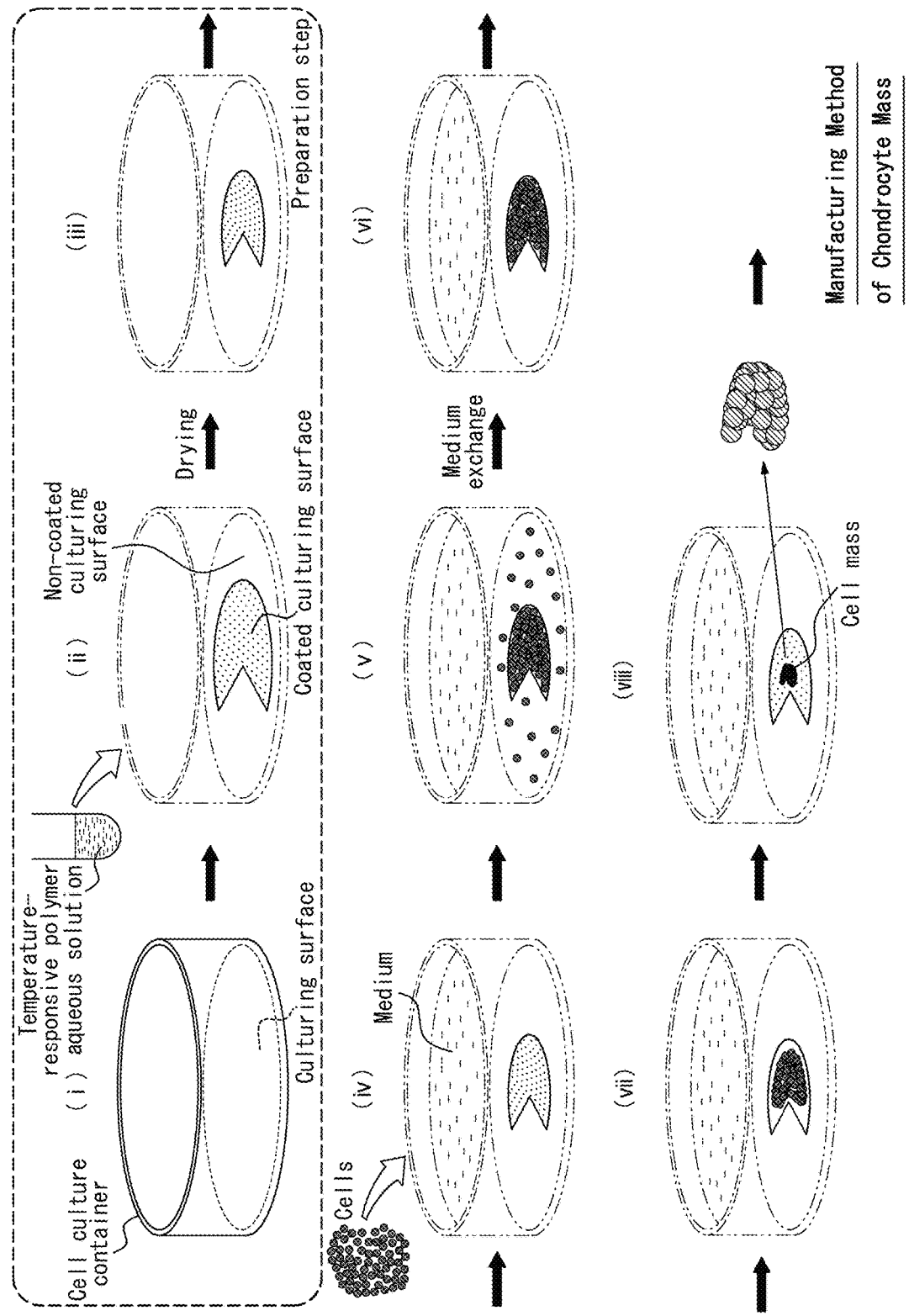
FIG. 1 is an overview, in (i) to (viii), of an example manufacturing method of a chondrocyte mass in Embodiment (I)
Figure 2:
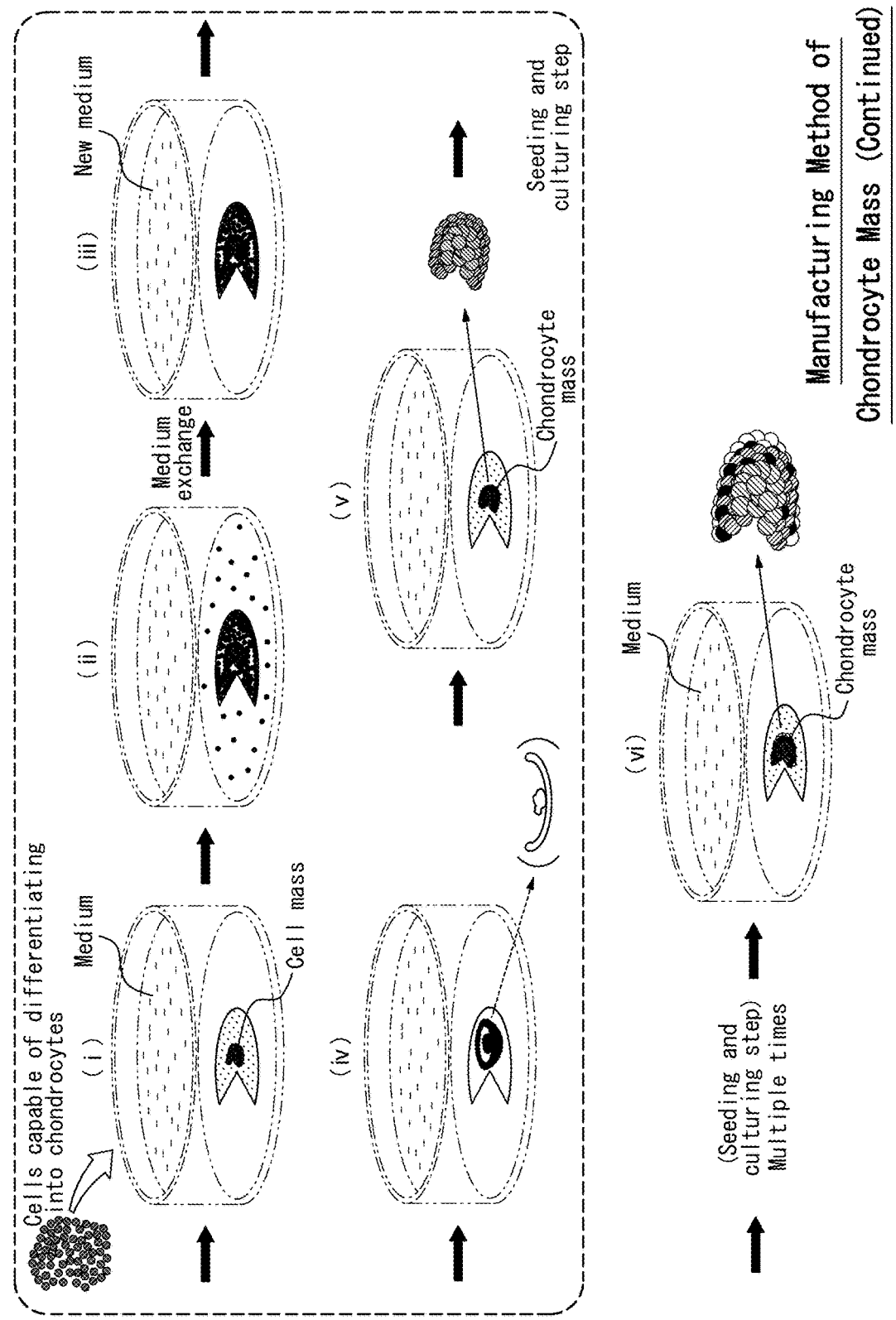
FIG. 2 is an overview, in (i) to (vi), of an example manufacturing method of a chondrocyte mass in Embodiment (I), and includes a cross-sectional view of the structure in parentheses in (iv)

An example manufacturing method of a chondrocyte mass in Embodiment (I) is outlined in (i) to (viii) of FIG. 1 and (i) to (vi) of FIG. 2.

Details of each step in an example manufacturing method of a chondrocyte mass in Embodiment (I) are provided below.

(Production Step)

In an example manufacturing method, a temperature-responsive polymer and/or a temperature-responsive polymer composition is first produced (production step).

Examples of the temperature-responsive polymer and temperature-responsive polymer composition include (A) a temperature-responsive polymer containing 2-N,N-dimethylaminoethyl methacrylate (DMAEMA) units and anionic monomer units, (B) a temperature-responsive polymer containing N-isopropyl acrylamide (NIPAM) units, cationic monomer units, and anionic monomer units, and (C) a temperature-responsive polymer composition containing a polymer of 2-N,N-dimethylaminoethyl methacrylate (DMAEMA) and/or a derivative thereof, 2-amino-2-hydroxymethyl-1,3-propanediol (tris), and one or more anionic substances selected from the group consisting of nucleic acids, heparin, hyaluronic acid, dextran sulfate, polystyrene sulfonic acid, polyacrylic acid, polymethacrylic acid, polyphosphoric acid, sulfated polysaccharide, curdlan, polyarginic acid, and alkali metal salts thereof. Examples of (A) include (A-1) a temperature-responsive polymer obtained by a method of polymerizing DMAEMA in the presence of water and (A-2) a temperature-responsive polymer containing a polymer block principally containing DMAEMA (polymer chain α terminal) and a copolymer block principally containing DMAEMA and an anionic monomer (polymer chain ω terminal).

One type of these polymers and polymer compositions may be used alone, or a combination of two or more types may be used in Embodiment (I).

The temperature-responsive polymer of (A-1) and a manufacturing method thereof are described below.

(Manufacturing Method of Temperature-Responsive Polymer)

A manufacturing method of the temperature-responsive polymer of (A-1) includes a production step of producing a mixture containing 2-N,N-dimethylaminoethyl methacrylate (DMAEMA) and an irradiation step of irradiating the mixture with ultraviolet light, where in the production step, the mixture further contains a polymerization inhibitor and water, and in the irradiation step, the mixture is irradiated with ultraviolet light under an inert atmosphere.

In a manufacturing method of the temperature-responsive polymer of (A-1), a mixture containing 2-N,N-dimethylaminoethyl methacrylate (DMAEMA) is first produced (production step). The mixture further includes a polymerization inhibitor and water.

A commercial product may be used as the 2-N,N-dimethylaminoethyl methacrylate (DMAEMA). Examples of the polymerization inhibitor include methylhydroquinone (MEHQ), hydroquinone, p-benzoquinoline, N,N-diethylhydroxylamine, N-nitroso-N-phenylhydroxylamine (Cupferron), and t-butylhydroquinone. MEHQ or the like included in commercially available DMAEMA may be used as is. Examples of water include ultrapure water.

The mass ratio of the polymerization inhibitor to the mixture is preferably 0.01% to 1.5% and more preferably 0.1% to 0.5%. Adopting these ranges suppresses a runaway radical polymerization reaction and reduces the occurrence of uncontrollable crosslinking, while also providing the manufactured temperature-responsive polymer with solubility in a solvent.

The mass ratio of the water to the mixture is preferably 1.0% to 50% and more preferably 9.0% to 33%. Adopting these ranges achieves a good balance between the reaction rate of the hydrolysis reaction of the side chain and the reaction rate of the growth reaction of the polymer chain being polymerized. It is thus possible to obtain a temperature-responsive polymer having a ratio of DMAEMA in which the side chain is not hydrolyzed to DMAEMA in which the side chain is hydrolyzed (the copolymerization ratio) of approximately 1.0 to 20.

Next, in the manufacturing method of the temperature-responsive polymer of (A-1), the mixture is irradiated with ultraviolet light (irradiation step). Here, the irradiation with ultraviolet light takes place under an inert atmosphere. The DMAEMA undergoes radical polymerization by irradiation with ultraviolet light to become a polymer.

In this step, the aforementioned mixture is added to a transparent, sealed vial, for example, and an inert atmosphere is formed inside the vial by bubbling an inert gas. Subsequently, the mixture is irradiated with ultraviolet light from outside the vial using an ultraviolet light irradiation apparatus.

The wavelength of the ultraviolet light is preferably 210 nm to 600 nm and more preferably 360 nm to 380 nm. These wavelength ranges can cause the polymerization reaction to progress efficiently and stably yield polymer material with the desired copolymerization ratio. These wavelength ranges can also prevent coloring of the manufactured polymer material.

Examples of the inert gas include nitrogen, argon, helium, and neon.

Among reaction conditions, the temperature condition is preferably from 15° C. to 50° C., more preferably from 20° C. to 30° C. These temperature ranges suppress a heat initiated reaction, giving preference instead to a reaction initiated by irradiation with light. Furthermore, the reaction rate of the hydrolysis reaction can be balanced well against the reaction rate of the growth reaction of the polymer chain.

The reaction time is preferably from 7 hours to 24 hours, more preferably from 17 hours to 21 hours. These time ranges can obtain a high yield of the temperature sensitive polymer of (A-1) and allow radical polymerization while suppressing a photolytic reaction and an unnecessary crosslinking reaction.

The time from when production of the mixture in the production step is finished until the start of irradiation with ultraviolet light in the irradiation step is preferably from 10 minutes to 1 hour.

It takes approximately 10 minutes to replace the gas inside the vial to which the mixture is added and to form an inert atmosphere inside the vial. Setting the aforementioned time to less than 10 minutes may therefore not result in the inert atmosphere necessary for radical polymerization. On the other hand, the hydrolysis reaction of DMAEMA in the mixture starts before the start of irradiation with ultraviolet light. Setting the aforementioned time to longer than one hour therefore yields a large amount of methacrylic acid, which is inactive in the radical polymerization reaction, in the mixture.

In the manufacturing method of the temperature-responsive polymer of (A-1), water is included in the mixture. The radical polymerization reaction of DMAEMA and the hydrolysis reaction of the ester bond in the side chain of the poly(2-N,N-dimethylaminoethyl methacrylate) (PDMAEMA) can therefore be caused to compete.

The product yielded by this competition is a polymer including the repeating unit (A) represented by formula (I),

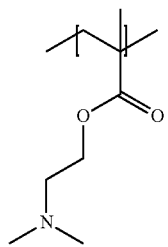

(I)

and the repeating unit (B) represented by formula (II).

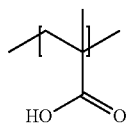

(II)

Therefore, a good balance of both the cationic functional group included in the polymer, i.e. a dimethylamino group, and the anionic functional group included in the polymer, i.e. a carboxyl group formed by hydrolysis of the ester bond in a side chain, can be provided. The manufacturing method of the temperature-responsive polymer of (A-1) can then easily manufacture, with few steps, a polymer derived from poly (2-N,N-dimethylaminoethyl methacrylate) and including a cationic functional group and an anionic functional group.

Even without using the same manufacturing method as the manufacturing method of the temperature-responsive polymer of (A-1), the same effects as those of the manufacturing method of a temperature-responsive polymer of Aspect (I) may be obtained if DMAEMA, a polymerization inhibitor, and water are present together in the reaction system at the time of irradiating with ultraviolet light.

For example, the following manufacturing method of a temperature-responsive polymer can also be used for the temperature-responsive polymer of (A-1): water and a mixture containing DMAEMA and a polymerization inhibitor are prepared separately, an inert gas is then bubbled in the mixture and the water, and subsequently, the mixture and the water are mixed under an inert atmosphere while simultaneously being irradiated with ultraviolet light.

(Temperature-Responsive Polymer)

The temperature-responsive polymer of (A-1) is manufactured by the aforementioned manufacturing method of (A-1).

The temperature-responsive polymer of (A-1) is preferably a molecule with a number-average molecular weight (Mn) of 10 kDa to 500 kDa. The temperature-responsive polymer of (A-1) is also preferably a molecule for which the ratio (Mw/Mn) of the weight-average molecular weight (Mw) to the number-average molecular weight (Mn) is from 1.1 to 10.0.

The molecular weight of the temperature-responsive polymer of (A-1) can be appropriately adjusted by the irradiation time and irradiation intensity of the ultraviolet light.

The temperature-responsive polymer of (A-1) can reduce the cloud point, for example to room temperature (25° C.) or below.

Insoluble matter of the temperature-responsive polymer (A-1) formed at a temperature at or above the cloud point exhibits an extremely long delay until becoming soluble again at room temperature (approximately 25° C.). The reason is thought to be that the resulting temperature-responsive polymer of (A-1) has high self-cohesion due to the presence of a cationic functional group and an anionic functional group in the molecule.

As described below, the temperature-responsive polymer of (A-1) can be used to produce a cell culture container having a culturing surface coated with this temperature-responsive polymer.

Furthermore, as described below, the temperature-responsive polymer of (A-1) allows formation of cell structures that have a luminal (tube-like), aggregated (pellet-like), or other structure by culturing cells under appropriate culture conditions.

The ratio (C/A ratio) of the number of cationic functional groups (2-N,N-dimethylamino groups) to the number of anionic functional groups (carboxyl groups) in the temperature-responsive polymer of (A-1) is preferably from 0.5 to 32 and more preferably from 4 to 16.

Setting the C/A ratio in these ranges facilitates achievement of the aforementioned effect of reducing the cloud point. The reason is thought to be that in a temperature-responsive polymer with the aforementioned C/A ratio, the cationic functional group and the anionic functional group affect inter- and/or intra-molecular aggregation by ionic bonding throughout the temperature-responsive polymer, thereby increasing the aggregation strength of the temperature-responsive polymer.

Another reason is thought to be that setting the C/A ratio within the aforementioned ranges can suppress cytotoxicity due to positive charges by achieving a particularly preferable balance between positive and negative charges in the temperature-responsive polymer and can also facilitate cell migration and orientation by achieving a particularly preferable balance between hydrophilicity and hydrophobicity of the temperature-responsive polymer.

The temperature-responsive polymer of (A-2) and a manufacturing method thereof are described below.

(Manufacturing Method of Temperature-Responsive Polymer)

A manufacturing method of the temperature-responsive polymer of (A-2) includes a first polymerization step of irradiating a first mixture containing 2-N,N-dimethylaminoethyl methacrylate (DMAEMA) with ultraviolet light, an adding step of adding an anionic monomer to the first mixture at the point when the number-average molecular weight of the polymer in the first polymerization step reaches at least a predetermined value to produce a second mixture, and a second polymerization step of irradiating the second mixture with ultraviolet light.

In a manufacturing method of the temperature-responsive polymer of (A-2), the first mixture containing 2-N,N-dimethylaminoethyl methacrylate (DMAEMA) is first irradiated with ultraviolet light (first polymerization step).

Other than DMAEMA, the first mixture may, for example, optionally include another monomer, solvent, or the like.

The irradiation with ultraviolet light may take place under an inert atmosphere.

A commercially available product may be used for the DMAEMA.

Examples of the other monomers that may be included in the first mixture include N,N-dimethyl acrylamide, esters of acrylic acid or methacrylic acid having polyethylene glycol side chains, N-isopropyl acrylamide, 3-N,N-dimethylaminopropyl acrylamide, and 2-N,N-dimethylaminoethyl methacrylamide. In particular, N,N-dimethyl acrylamide, esters of acrylic acid or methacrylic acid having polyethylene glycol side chains, and N-isopropyl acrylamide are preferable for allowing the ion balance to be adjusted stably. One type of these monomers may be used alone, or a combination of two or more types may be used. The ratio (mole ratio) of the amount of other monomers used to the amount of DMAEMA used is preferably from 0.001 to 1 and more preferably from 0.01 to 0.5.

Examples of the solvent include toluene, benzene, chloroform, methanol, and ethanol. In particular, toluene and benzene are preferable by virtue of being inert relative to the ester bond of the DMAEMA. One type of these solvents may be used alone, or a combination of two or more types may be used.

In this step, the aforementioned first mixture is added to a transparent, sealed vial, for example, and an inert atmosphere is formed inside the vial by bubbling an inert gas. Subsequently, the first mixture is irradiated with ultraviolet light from outside the vial using an ultraviolet light irradiation apparatus.

The wavelength of the ultraviolet light is preferably 210 nm to 600 nm and more preferably 360 nm to 380 nm. These wavelength ranges can cause the polymerization reaction to progress efficiently and stably yield polymer material with the desired copolymerization ratio. These wavelength ranges can also prevent coloring of the manufactured polymer material.

The irradiation intensity of the ultraviolet light is preferably from 0.01 mW/cm$^2$ to 50 mW/cm$^2$ and more preferably from 0.1 mW/cm$^2$ to 5 mW/cm$^2$. These ranges can suppress decomposition due to unnecessary cutting of chemical bonds or the like while stably allowing the polymerization reaction to proceed at an appropriate rate (time).

Examples of the inert gas include nitrogen, argon, helium, and neon.

The temperature condition is preferably from 10° C. to 40° C., more preferably from 20° C. to 30° C. These temperature ranges allow the reaction to take place at room temperature in a typical laboratory while suppressing a reaction due to means other than light (such as heat).

The reaction time is preferably from 10 minutes to 48 hours, more preferably from 60 minutes to 24 hours.

In this step, the DMAEMA undergoes radical polymerization by irradiation with the ultraviolet light and becomes a polymer (poly(2-N,N-dimethylaminoethyl methacrylate), i.e. PDMAEMA), thereby forming a homopolymer block containing 2-N,N-dimethylaminoethyl methacrylate. In the case of also using another monomer, a polymer block containing DMAEMA and the other monomer is formed.

Next, in the manufacturing method of the temperature-responsive polymer of (A-2), at the point when the number-average molecular weight of the polymer (specifically, polymerized 2-N,N-dimethylaminoethyl methacrylate) reaches at least a predetermined value in the first polymerization step, an anionic monomer is added to the first mixture to produce a second mixture (adding step).

Other than the first mixture after the first polymerization step and the anionic monomer, the second mixture may, for example, include another monomer, the above-described solvents that can be included in the first mixture (such as toluene, benzene, or methanol), and the like.

The anionic monomer may be added under an inert atmosphere.

Examples of the anionic monomer include acrylic acid, methacrylic acid, and vinyl derivatives containing at least one group selected from the group consisting of a carboxyl group, a sulfonic acid group, and a phosphoric acid group in a side chain. In particular, acrylic acid and methacrylic acid are preferable in terms of chemical stability.

One type of these anionic monomers may be used alone, or a combination of two or more types may be used.

Examples of the other monomers that may be included in the second mixture include N,N-dimethyl acrylamide, esters of acrylic acid or methacrylic acid having polyethylene glycol side chains, N-isopropyl acrylamide, 3-N,N-dimethylaminopropyl acrylamide, and 2-N,N-dimethylaminoethyl methacrylamide. N,N-dimethyl acrylamide, which is electrically neutral and hydrophilic, is particularly preferable. One type of these monomers may be used alone, or a combination of two or more types may be used. The ratio (in moles) of the amount of other monomers used to the amount of DMAEMA used is preferably from 0.01 to 10 and more preferably from 0.1 to 5.

In this step, the second mixture is added while, for example, maintaining an inert atmosphere in the vial by causing an inert gas to flow into the vial.

The predetermined value of the number-average molecular weight is preferably 5,000, more preferably 20,000, and particularly preferably 100,000 to sufficiently obtain the effect of reducing the cloud point.

The number-average molecular weight of the polymerized PDMAEMA in the first mixture after the first polymerization step can be measured by sampling a small amount of the reaction mixture from the polymerization system at a predetermined point in time and using a method known to a person skilled in the art, such as gel permeation chromatography (GPC) or static light scattering (SLS).

In this step, an anionic monomer is included in the polymerization system in addition to the homopolymer containing DMAEMA that is being polymerized. The polymerization system in the vial thereby changes from a homopolymerization system of DMAEMA to a copolymerization system of DMAEMA and an anionic monomer.

In the manufacturing method of the temperature-responsive polymer of (A-2), the second mixture is then irradiated with ultraviolet light (second polymerization step).

Here, the irradiation with ultraviolet light may take place under an inert atmosphere.

During this step, the vial to which the second mixture has been added is, for example, irradiated with ultraviolet light from outside the vial using an ultraviolet light irradiation apparatus.

The conditions in the second polymerization step, such as the wavelength of the ultraviolet light, the radiation intensity of the ultraviolet light, the inert gas that is used, the reaction temperature, and the reaction time may be the same as the conditions in the first polymerization step.

In this step, the DMAEMA and the anionic monomer undergo radical polymerization by irradiation with the ultraviolet light, and a copolymer block containing DMAEMA and the anionic monomer is formed to be continuous with the polymer chain α terminal of the homopolymer block, which contains DMAEMA, formed in the first polymerization step. In the case of also using another monomer, a copolymer block containing DMAEMA, an anionic monomer, and the other monomer is formed.

As described above, a temperature-responsive polymer containing a homopolymer block containing DMAEMA and a copolymer block of DMAEMA and an anionic monomer is obtained.

As will be understood by a person skilled in the art, while mixtures of polymers having various molecular weights and molecular structures are generated with the manufacturing method of (A-2), polymerization is preferably carried out under identical conditions throughout the first polymerization step, the adding step, and the second polymerization step to obtain, as the principal component, a temperature-responsive polymer containing a homopolymer block containing DMAEMA and a copolymer block of DMAEMA and an anionic monomer.

(Temperature-Responsive Polymer)

The temperature-responsive polymer of (A-2) is manufactured by the aforementioned manufacturing method of (A-2).

The temperature-responsive polymer of (A-2) contains a polymer block (polymer chain α terminal) principally containing 2-N,N-dimethylaminoethyl methacrylate and optionally containing other monomer units such as dimethyl acrylamide, acrylic acid or methacrylic acid having polyethylene glycol side chains, or another such hydrophilic monomer; and contains a copolymer block principally containing 2-N,N-dimethylaminoethyl methacrylate and an anionic monomer (polymer chain ω terminal) and optionally containing other monomer units.

The temperature-responsive polymer of (A-2) preferably contains a homopolymer block of DMAEMA and a copolymer block of DMAEMA and an anionic monomer, and the temperature-responsive polymer of (A-2) is more preferably composed of these blocks.

As the temperature-responsive polymer of (A-2), the number-average molecular weight of the polymer block of the polymer chain α terminal (for example, the homopolymer block of DMAEMA) is preferably 5,000 Da or greater and more preferably 20,000 Da or greater.

The temperature-responsive polymer of (A-2) is preferably a molecule with a number-average molecular weight (Mn) of 10 kDa to 500 kDa. The temperature-responsive polymer of (A-2) is also preferably a molecule for which the ratio (Mw/Mn) of the weight-average molecular weight (Mw) to the number-average molecular weight (Mn) is 1.1 to 10.0.

The molecular weight of the temperature-responsive polymer can be appropriately adjusted by the irradiation time and irradiation intensity of the ultraviolet light.

The temperature-responsive polymer of (A-2) can reduce the cloud point, for example to room temperature (25° C.) or below.

Insoluble matter of the temperature-responsive polymer (A-2) formed at a temperature at or above the cloud point exhibits an extremely long delay until becoming soluble again at room temperature (approximately 25° C.). The reason is thought to be that the resulting temperature-responsive polymer has high self-cohesion due to the presence of a cationic functional group and an anionic functional group in the molecule.

In particular, it is thought that since the temperature-responsive polymer of (A-2) includes a homopolymer block of DMAEMA having a high molecular weight (such as 5,000 Da or greater) at the polymer chain α terminal, temperature dependent globule transition of the side chain of DMAEMA occurs more easily, effectively reducing the cloud point.

As described below, this temperature-responsive polymer can be used to produce a cell culture container having a culturing surface coated with this temperature-responsive polymer.

Furthermore, as described below, the temperature-responsive polymer of (A-2) allows formation of cell structures that have a luminal (tube-like), aggregated (pellet-like), or other structure by culturing cells under appropriate culture conditions.

The ratio (C/A ratio) of the number of cationic functional groups (2-N,N-dimethylamino groups) to the number of anionic functional groups (carboxyl groups) in the temperature-responsive polymer of (A-2) is preferably from 0.5 to 32 and more preferably from 4 to 16.

Setting the C/A ratio in these ranges facilitates achievement of the aforementioned effect of reducing the cloud point. The reason is thought to be that in a temperature-responsive polymer with the aforementioned C/A ratio, the cationic functional group and the anionic functional group affect inter- and/or intra-molecular aggregation by ionic bonding throughout the temperature-responsive polymer, thereby increasing the aggregation strength of the temperature-responsive polymer.

Another reason is thought to be that setting the C/A ratio within the aforementioned ranges can suppress cytotoxicity due to positive charges by achieving a particularly preferable balance between positive and negative charges in the temperature-responsive polymer and can also facilitate cell migration and orientation by achieving a particularly preferable balance between hydrophilicity and hydrophobicity of the temperature-responsive polymer.

The temperature-responsive polymer of (B) and a manufacturing method thereof are described below.

(Manufacturing Method of Temperature-Responsive Polymer)

A manufacturing method of the temperature-responsive polymer of (B) polymerizes N-isopropyl acrylamide (NIPAM) (monomer (A)), a cationic monomer (monomer (B)), and an anionic monomer (monomer (C)). Another monomer, other than the aforementioned 3 types of monomers, may optionally be added and polymerized.

A commercially available product may be used for the N-isopropyl acrylamide (NIPAM).

Examples of cationic monomers include monomers having a cationic functional group. Examples of cationic functional groups include amino groups, such as primary to quaternary amino groups, and guanidine groups. In particular, tertiary amino groups are preferable for chemical stability, low cytotoxicity, sterilization stability, and a strong positive charge.

More specifically, the cationic monomer is preferably highly stable even when supporting a physiologically active substance or under alkaline conditions. Examples include 3-(N,N-dimethylaminopropyl)-(meth)acrylamide, 3-(N,N-dimethylaminopropyl)-(meth)acrylate, aminostyrene, 2-(N,N-dimethylaminoethyl)-(meth)acrylamide, and 2-(N,N-dimethylaminoethyl)-(meth)acrylate.

Among these, 3-(N,N-dimethylaminopropyl)acrylamide is particularly preferable for easily supporting an anionic substance by virtue of having a strong positive charge.

Aminostyrene is also preferable for easily supporting an anionic substance by virtue of having a strong positive charge while also increasing the number of variations of supportable anionic substances through interaction between an aromatic ring in the molecule and a hydrophobic structure of another substance in the aqueous solution.

Furthermore, 2-(N,N-dimethylaminoethyl)-methacrylamide is preferable for having a weak positive charge at a neutral pH and for its solubility in water not being affected by temperature, thereby allowing easy ejection of an anionic substance that has been supported once.

One type of these cationic monomers may be used alone, or a combination of two or more types may be used.

Examples of anionic monomers include monomers having an anionic functional group. Examples of anionic functional groups include a carboxylic acid group, a sulfonic acid group, a sulfuric acid group, a phosphoric acid group, and a boronic acid group. In particular, a carboxylic acid group, a sulfonic acid group, and a phosphoric acid group are preferable for chemical stability, cell affinity, and a high degree of purification.

More specifically, examples include acrylic acid, methacrylic acid, and vinylbenzoic acid. In particular, methacrylic acid and vinylbenzoic acid are preferable for chemical stability and cell affinity.

One type of these anionic monomers may be used alone, or a combination of two or more types may be used.

Examples of other monomers include dimethyl acrylamide, acrylic acid or methacrylic acid having a polyethylene glycol side chain, or another such neutral hydrophilic monomer.

One type of these monomers may be used alone, or a combination of two or more types may be used.

The other monomers can be used to adjust the hydrophilic/hydrophobic balance apart from charge and can increase the number of variations.

Taking into consideration the reactivity in the polymerization reaction of the monomers, a person skilled in the art can appropriately adjust the ratio (moles) of the amount of NIPAM used, the amount of cationic monomers used, and the amount of other monomers used relative to the total amount of monomers (A) to (C) used in the manufacturing method of the temperature-responsive polymer of (B) so that the desired ratio of monomer components is obtained.

Examples of polymerization methods include radical polymerization and ionic polymerization.

Living radical polymerization is preferable as a type of radical polymerization. Examples of living radical polymerization include reversible addition fragmentation chain transfer (RAFT) polymerization, atom transfer radical polymerization (ATRP), and iniferter polymerization, with iniferter polymerization being preferable.

Living anionic polymerization is preferable as ionic polymerization.

An example of the manufacturing method of the temperature-responsive polymer of (B) is a method using radical polymerization.

An example of this manufacturing method includes a first polymerization step of irradiating a first mixture containing N-isopropyl acrylamide (NIPAM) with ultraviolet light, an adding step of adding a cationic monomer and an anionic monomer to the first mixture to produce a second mixture, and a second polymerization step of irradiating the second mixture with ultraviolet light.

In an example of this manufacturing method, a first mixture containing N-isopropyl acrylamide (NIPAM) is first irradiated with ultraviolet light (first polymerization step).

Other than NIPAM, the first mixture may, for example, optionally include another monomer, a solvent, a chain transfer agent, a stabilizer, a surfactant, or the like.

The irradiation with ultraviolet light may take place under an inert atmosphere.

In this step, the aforementioned first mixture is added to a transparent, sealed vial, for example, and an inert atmosphere is formed inside the vial by bubbling an inert gas. Subsequently, the first mixture is irradiated with ultraviolet light from outside the vial using an ultraviolet light irradiation apparatus.

Examples of the solvent include benzene, toluene, chloroform, methanol, and water. In particular, benzene and toluene are preferable in terms of solubility and for being inert during polymerization. One type of these solvents may be used alone, or a combination of two or more types may be used.

In this step, the aforementioned first mixture is added to a transparent, sealed vial, for example, and an inert atmosphere is formed inside the vial by bubbling an inert gas. Subsequently, the first mixture is irradiated with ultraviolet light from outside the vial using an ultraviolet light irradiation apparatus.

The wavelength of the ultraviolet light is preferably 210 nm to 600 nm and more preferably 360 nm to 380 nm. These wavelength ranges can cause the polymerization reaction to progress efficiently and stably yield polymer material with the desired copolymerization ratio. These wavelength ranges can also prevent coloring of the manufactured polymer material.

The irradiation intensity of the ultraviolet light is preferably from 0.01 mW/cm$^2$ to 50 mW/cm$^2$ and more preferably from 0.1 mW/cm$^2$ to 5 mW/cm$^2$.

Examples of the inert gas include nitrogen, argon, helium, and neon.

The temperature condition is preferably from 10° C. to 40° C., more preferably from 20° C. to 30° C. These temperature ranges allow the polymerization reaction to take place at room temperature in a typical laboratory while suppressing a reaction due to means, such as heat, differing from the light irradiation means.

The reaction time is preferably from 10 minutes to 48 hours, more preferably from 60 minutes to 24 hours.

During this step, the NIPAM undergoes radical polymerization by irradiation with the ultraviolet light and becomes a polymer (poly(N-isopropyl acrylamide), i.e. PNIPAM), thereby forming a homopolymer block containing N-isopropyl acrylamide. In the case of also using another monomer, a polymer block containing NIPAM and the other monomer is formed.

Next, in the manufacturing method of the temperature-responsive polymer of (B), a second mixture is produced by adding a cationic monomer and an anionic monomer to the first mixture after the first polymerization step (adding step).

Other than the first mixture after the first polymerization step, the cationic monomer, and the anionic monomer, the second mixture may, for example, include another monomer, a solvent, a chain transfer agent, a stabilizer, a surfactant, or the like.

The cationic monomer and the anionic monomer may be added under an inert atmosphere.

In this step, the cationic monomer and the anionic monomer are added while, for example, maintaining an inert atmosphere in the vial by causing an inert gas to flow into the vial.

In this step, a cationic monomer and an anionic monomer are included in the polymerization system in addition to the homopolymer containing NIPAM that is being polymerized. The polymerization system in the vial thereby changes from a homopolymerization system of NIPAM to a copolymerization system of NIPAM, a cationic monomer, and an anionic monomer.

In the manufacturing method of the temperature-responsive polymer of (B), the second mixture is then irradiated with ultraviolet light (second polymerization step).

Here, the irradiation with ultraviolet light may take place under an inert atmosphere.

During this step, the vial to which the cationic monomer and the anionic monomer have been added is, for example, irradiated with ultraviolet light from outside using an ultraviolet light irradiation device.

The wavelength of the ultraviolet light is preferably 210 nm to 600 nm and more preferably 360 nm to 380 nm. These wavelength ranges can cause the polymerization reaction to progress efficiently and stably yield polymer material with the desired copolymerization ratio. These wavelength ranges can also prevent coloring of the manufactured polymer material.

The irradiation intensity of the ultraviolet light is preferably from 0.01 mW/cm$^2$ to 50 mW/cm$^2$ and more preferably from 0.1 mW/cm$^2$ to 5 mW/cm$^2$.

Examples of the inert gas include nitrogen, argon, helium, and neon.

The temperature condition is preferably from 10° C. to 40° C., more preferably from 20° C. to 30° C. These temperature ranges allow the polymerization reaction to take place at room temperature in a typical laboratory while suppressing a reaction due to means, such as heat, differing from the light irradiation means.

The reaction time is preferably from 10 minutes to 48 hours, more preferably from 60 minutes to 24 hours.

In this step, the NIPAM, the cationic monomer, and the anionic monomer undergo radical polymerization by irradiation with the ultraviolet light, and a copolymer block containing NIPAM, the cationic monomer, and the anionic monomer is formed to be continuous with the polymer chain α terminal of the homopolymer block, which includes NIPAM, formed in the first polymerization step. In the case of also using another monomer, a polymer block containing NIPAM and the other monomer, and/or a copolymer block containing NIPAM, the cationic monomer, the anionic monomer, and the other monomer is formed.

As described above, a temperature-responsive polymer containing a homopolymer block containing NIPAM and a copolymer block of NIPAM, a cationic monomer, and an anionic monomer is obtained.

In an example of this manufacturing method, irradiation with ultraviolet light is preferably performed throughout the first polymerization step, the adding step, and the second polymerization step to achieve an efficient reaction.

Another example manufacturing method of the temperature-responsive polymer of (B) is a method using radical polymerization. A mixture containing N-isopropyl acrylamide (NIPAM), a cationic monomer, and an anionic monomer, and optionally containing another monomer, is irradiated with ultraviolet light.

This mixture may, for example, include a solvent, a chain transfer agent, a stabilizer, a surfactant, or the like.

The irradiation with ultraviolet light may take place under an inert atmosphere.

Other conditions may be the same as in the above-described example manufacturing method.

Furthermore, in the case of using iniferter polymerization, benzyl-(N,N-diethyl)dithiocarbamate may be used as an iniferter and toluene or the like used as a solvent. Living polymerization may then be carried out by irradiation with near ultraviolet light. Here, after polymerization by a first monomer, polymerization by a second monomer can be performed after an isolation operation, thereby yielding a block copolymer.

Furthermore, in the case of using ionic polymerization, an NaOH powder may be used as the catalyst, and a solvent for reprecipitation used for purification may be used along with an aprotic solvent as the solvent. After polymerization by a first monomer, polymerization by a second monomer can be performed after a reprecipitation operation (with an ionic species remaining on the (o terminal after this operation), thereby yielding a block copolymer.

(Temperature-Responsive Polymer)

The temperature-responsive polymer of (B) is manufactured by the aforementioned manufacturing method of (B).

The temperature-responsive polymer of (B) contains N-isopropyl acrylamide (NIPAM) units, cationic monomer units, and anionic monomer units, and optionally contains other monomer units. This polymer can be manufactured by the above-described example and other example of a manufacturing method.

The temperature-responsive polymer of (B) preferably contains a polymer block (polymer chain α terminal) principally containing N-isopropyl acrylamide (NIPAM) units and optionally containing other monomer units and a copolymer block principally containing cationic monomer units and anionic monomer units and optionally containing other monomer units. The temperature-responsive polymer of (B) more preferably contains a homopolymer block of NIPAM and a copolymer block of NIPAM, a cationic monomer, and an anionic monomer. The temperature-responsive polymer of (B) is particularly preferably composed of these blocks. This polymer can be manufactured by the above-described example manufacturing method.

In one known temperature-responsive polymer (see JP2014162865A), the DMAEMA that provides the polymer with temperature responsiveness is, at the same time, a cationic monomer that is necessary for forming a cell structure (along with an anionic monomer), and the DMAEMA involved in temperature responsiveness is included in the polymer chain α terminal as a polymer block.

Since a cationic monomer always exists in the polymer chain α terminal in this temperature-responsive polymer, the degree of freedom for adjusting the position of the cationic sites in the polymer chain is not high, and the cationic monomer is mainly limited to DMAEMA. For these reasons, it is not necessarily easy to adjust the positive charge strength of the cationic site or the pH of the temperature-responsive polymer aqueous solution.

For example, in the case of using the aforementioned temperature-responsive polymer in a drug delivery system (DDS), the type and amount of the supportable drug may be restricted. Examples of DDS techniques include a technique of sustained release of a drug from a coated material to cells or tissue by applying a temperature-responsive polymer supporting a drug on a cell culture container, and then culturing cells or tissue in the cell culture container after the application. Since the aforementioned known temperature-responsive polymer includes DMAEMA with a small positive charge strength, a drug that is an anionic substance cannot always be supported easily. Hence, the type and amount of supportable drugs may be restricted.

By contrast, in the temperature-responsive polymer of (B), the NIPAM that provides the polymer with temperature responsiveness is a neutral monomer, and the cationic monomer that is necessary for forming a cell structure (along with an anionic monomer) is a different monomer than NIPAM.

In the temperature-responsive polymer of (B), a cationic monomer does not necessarily need to be present at the polymer chain α terminal, and the position of the cationic site in the polymer chain can be adjusted freely. A wide range of cationic monomers can also be used, allowing the positive charge strength of the cationic site and the pH of the temperature-responsive polymer aqueous solution to be adjusted easily.

When used in a drug delivery system (DDS), for example, the temperature-responsive polymer of (B) can expand the variety of supportable drugs while also increasing the amount thereof. The range of applications of the temperature-responsive polymer can thus be increased.

In the temperature-responsive polymer of (B), the ratio (moles) of NIPAM units to the total of NIPAM units, cationic monomer units, and anionic monomer units is preferably from 0.6 to 0.9, more preferably from 0.7 to 0.9, and particularly preferably 0.9.

When also using another monomer, the ratio (moles) of the other monomer units to the total of NIPAM units, cationic monomer units, and anionic monomer units is preferably from 0.001 to 0.2 and is more preferably from 0.01 to 0.1.

As the temperature-responsive polymer of (B), the number-average molecular weight of the polymer block of the polymer chain α terminal (for example, the homopolymer block of NIPAM) is preferably 5,000 Da or greater and more preferably 20,000 Da or greater.

The temperature-responsive polymer of (B) is preferably a molecule with a number-average molecular weight (Mn) of 10 kDa to 500 kDa. The temperature-responsive polymer of (B) is also preferably a molecule for which the ratio (Mw/Mn) of the weight-average molecular weight (Mw) to the number-average molecular weight (Mn) is 1.1 to 10.0.

The molecular weight of the temperature-responsive polymer can be appropriately adjusted by the polymerization conditions.

The temperature-responsive polymer of (B) can reduce the cloud point, for example to room temperature (25° C.) or below.

Insoluble matter of the temperature-responsive polymer formed at a temperature at or above the cloud point exhibits an extremely long delay until becoming soluble again at room temperature (approximately 25° C.). The reason is thought to be that the resulting temperature-responsive polymer has high self-cohesion due to the presence of a cationic functional group and an anionic functional group in the molecule.

In particular, it is thought that since the temperature-responsive polymer of (B) includes a homopolymer block of NIPAM having a high molecular weight at the polymer chain α terminal, temperature dependent globule transition of the side chain of NIPAM occurs more easily, effectively reducing the cloud point.

As described below, this temperature-responsive polymer can be used to produce a cell culture container having a culturing surface coated with this temperature-responsive polymer.

Furthermore, as described below, the temperature-responsive polymer of (B) allows formation of cell structures that have a luminal (tube-like), aggregated (pellet-like), or other structure by culturing cells under appropriate culture conditions.

The ratio (C/A ratio) of the number of cationic functional groups to the number of anionic functional groups in the temperature-responsive polymer of (B) is preferably from 0.5 to 32 and more preferably from 4 to 16.

Setting the C/A ratio in these ranges facilitates achievement of the aforementioned effect of reducing the cloud point. The reason is thought to be that in a temperature-responsive polymer with the aforementioned C/A ratio, the cationic functional group and the anionic functional group affect inter- and/or intra-molecular aggregation by ionic bonding throughout the temperature-responsive polymer, thereby increasing the aggregation strength of the temperature-responsive polymer.

Another reason is thought to be that setting the C/A ratio within the aforementioned ranges can suppress cytotoxicity due to positive charges by achieving a particularly preferable balance between positive and negative charges in the temperature-responsive polymer and can also facilitate cell migration and orientation by achieving a particularly preferable balance between hydrophilicity and hydrophobicity of the temperature-responsive polymer.

The temperature-responsive polymer of (C) and a manufacturing method thereof are described below.

(Manufacturing Method of Temperature-Responsive Polymer Composition)

In a manufacturing method of a temperature-responsive polymer composition of (C), a mixed-type temperature-responsive polymer composition is first produced (mixture production step). Specifically, (C1) a polymer of 2-N,N-dimethylaminoethyl methacrylate (DMAEMA) and/or a derivative thereof, (C2) 2-amino-2-hydroxymethyl-1,3-propanediol (tris), and (C3) one or more anionic substances selected from the group consisting of nucleic acids, heparin, hyaluronic acid, dextran sulfate, polystyrene sulfonic acid, polyacrylic acid, polymethacrylic acid, polyphosphoric acid, sulfated polysaccharide, curdlan, polyarginic acid, and alkali metal salts thereof are mixed. Note that (C2) tris is an optional component.

(Temperature-Responsive Polymer Composition)

As described above, the temperature-responsive polymer composition of (C) includes a polymer of 2-N,N-dimethylaminoethyl methacrylate (DMAEMA) and/or a derivative thereof; 2-amino-2-hydroxymethyl-1,3-propanediol; and one or more anionic substances selected from the group consisting of nucleic acids, heparin, hyaluronic acid, dextran sulfate, polystyrene sulfonic acid, polyacrylic acid, polymethacrylic acid, polyphosphoric acid, sulfated polysaccharide, curdlan, polyarginic acid, and alkali metal salts thereof.

The (C1) polymer of DMAEMA and/or a derivative thereof is a temperature-responsive polymer with a cloud point of 32° C. It is inferred that the (C2) tris has the function of slightly reducing the cloud point and/or reducing the speed at which a polymer formed at a higher temperature than the cloud point becomes soluble again when cooled to the cloud point or lower. It is also inferred that the (C2) tris has the function of stimulating cells by a positive charge derived from an amino group while maintaining hydrophilicity even in a hydrophobized polymer layer. It is inferred that the (C3) anionic substance has the function of allowing migration and orientation of the cultured cells and of suppressing cytotoxicity.

This mixed-type temperature-responsive polymer composition can reduce the cloud point to room temperature (25° C.) or below.

In the aforementioned composition, it is inferred that the side chain of the polymer of DMAEMA and/or a derivative thereof and the tris interact with each other (for example, by crosslinking), making it easier for the polymer to aggregate.

In (C1), the polymer of DMAEMA and/or a derivative thereof is preferably a molecule with a number-average molecular weight (Mn) of 10 kDa to 500 kDa. The temperature-responsive polymer of (C1) is also preferably a molecule for which the ratio (Mw/Mn) of the weight-average molecular weight (Mw) to the number-average molecular weight (Mn) is 1.1 to 6.0.

Examples of the (C1) derivative of DMAEMA include a derivative in which a hydrogen atom of the methyl group of methacrylate is replaced by a halogen atom, a derivative in which the methyl group of methacrylate is replaced by a lower alkyl group, a derivative in which the hydrogen atom of the methyl group of a dimethylamino group is replaced by a halogen atom, and a derivative in which the methyl group of a dimethylamino group is replaced by a lower alkyl group.

The (C2) tris is preferably is a pure substance with a 99.9% or higher purity or is a tris aqueous solution that is made neutral or basic at the time of use, for example by addition of an alkaline substance. When using tris in its commercially available state of hydrochloride, the pH of the tris aqueous solution lowers, and the cloud point of the composition ends up rising to approximately 70° C. Therefore, a tris aqueous solution is not preferred.

Among the examples of anionic substances listed above in (C3), examples of the nucleic acids include DNA, RNA, and synthetic nucleic acids such as single-stranded, double-stranded, oligomer, and hairpin nucleic acids.

The anionic substances listed above in (C3) preferably have a certain size, such as a molecular weight (M) of 1 kDa to 5,000 kDa.

Setting the molecular weight in this range allows the anionic substance to undergo ionic bonding with the cationic substance and fulfill the role of trapping the cationic substance for an extended period of time. Stable microparticles of an ion complex can thus be formed. The cytotoxicity of a typical cationic substance, caused by electrostatic interaction with the membrane surface of a cell, can also be mitigated.

In addition to the anionic substances listed in (C3), it is also possible to use a polymer derivative, for example, that substantially functions as an anionic substance by introducing an anionic functional group into an amino group in the 4-position of poly(4-aminostyrene), which is a cationic polymer, by dehydration synthesis of a dicarboxylic acid such as oxalic acid.

Two or more types of the anionic substances listed above in (C3) may be included.

Here, a mixed-type temperature-responsive polymer composition in which the ratio ((C2)/(C1)) of (C2) 2-amino-2-hydroxymethyl-1,3-propanediol (tris) to (C1) a polymer of 2-N,N-dimethylaminoethyl methacrylate (DMAEMA) and/or a derivative thereof is 1.0 or less is preferably used.

The ratio ((C2)/(C1)) is designated as the mass ratio.

When using a mixed-type temperature-responsive polymer composition with the above ratio, the cell structure can be formed more easily in the below-described culturing step.

This composition can further improve the balance between hydrophilicity and hydrophobicity of the composition. It is inferred that this suitable balance favorably adjusts the adhesiveness of cells to the culturing surface and activates migration and orientation of the cells.

The above ratio ((C2)/(C1)) is preferably 0.1 or greater.

Setting the above ratio to 0.1 or greater facilitates achievement of the aforementioned effect of reducing the cloud point and also facilitates achievement of the aforementioned effect of easier formation of cell structures.

For the same reasons as above, the above ratio ((C2)/(C1)) is more preferably 0.1 to 0.5.

The C/A ratio (positive/negative charge) in the mixed-type temperature-responsive polymer composition is preferably 0.5 to 16.

In the present disclosure, the C/A ratio refers to the ratio of the positive charge of substances included in the composition to the negative charge of substances included in the composition. Specifically, the C/A ratio is represented by the expression ((positive charge per polymer molecule)×N1)/((negative charge per molecule of anionic substance)×N3), where N1 is the number of moles of (C1) the polymer of DMAEMA and/or a derivative thereof, and N3 is the number of moles of (C3) the anionic substance.

Furthermore, when the anionic substance is DNA in the present disclosure, the number of negative charges per molecule of the anionic substance is calculated as the number of base pairs (bp number) of DNA×2, and the molecular weight (Da) is calculated as the bp number×660 (the average molecular weight of an AT pair and a CG pair).

Setting the C/A ratio to be 0.5 to 16 facilitates achievement of the aforementioned effect of easier formation of tubular cell structures.

It is inferred that this range makes the balance between negative charge and positive charge in the composition suitable and can suppress cytotoxicity due to positive charge. It is also inferred that this range further improves the balance between hydrophilicity and hydrophobicity of the composition and can facilitate cell migration and orientation.

For the same reasons as above, the above ratio C/A is more preferably 2 to 10 and most preferably near 8.

(Preparation Step)

In an example manufacturing method, a portion of a culturing surface is coated with the temperature-responsive polymer and/or the temperature-responsive polymer composition to prepare a coated culturing surface (preparation step) (see FIG. 1, (i) to (iii)).

Here, the culturing surface apart from the coated culturing surface may be either cell adhesive or cell non-adhesive, but a cell non-adhesive culturing surface is preferable to facilitate obtaining a cell mass of the desired shape. The production method of the cell non-adhesive culturing surface is not restricted. For example, a cell culture container provided with a cell non-adhesive culturing surface, such as Prime-Surface® (PrimeSurface is a registered trademark in Japan, other countries, or both) by SUMILON; a cell culture container not subjected to surface treatment for cell adhesion, such as a cell culture container for culturing *Escherichia coli*; or a cell non-adhesive sheet, pad, or the like may be used.

As illustrated in FIG. 1, the coated culturing surface is preferably surrounded by a non-coated culturing surface to inhibit contact between cells and the wall and to adjust the shape of the cell mass (see (ii), (iii) of FIG. 1).

The shape of the coated culturing surface may be appropriately adjusted in conjunction with the desired shape of the chondrocyte mass. Examples include a circle, a rectangle, and a donut (ringed) shape in plan view.

The preparation step may, for example, be a step of dissolving a temperature-responsive polymer or a temperature-responsive polymer composition in a solvent to form a temperature-responsive polymer solution, applying the solution onto the culturing surface of a cell culture container, and drying to prepare a coated cell culture container (preparation step I). The preparation step may also be a step of cooling an aqueous solution including a temperature-responsive polymer or a temperature-responsive polymer composition (temperature-responsive polymer aqueous solution) to the cloud point of the temperature-responsive polymer or below, casting the cooled temperature-responsive polymer aqueous solution onto the culturing surface of a cell culture container, and heating to a temperature above the cloud point to prepare a coated cell culture container (preparation step II).

Examples of the solvent in the temperature-responsive polymer solution in preparation step I include water; physiological saline; buffer solutions; alcohols such as methanol, ethanol, n-propyl alcohol, isopropyl alcohol, 1-butanol, isobutyl alcohol, 2-butanol, t-butyl alcohol, 1-pentanol, 2-pentanol, 3-pentanol, 2-methyl-1-butanol, 3-methyl-1-butanol, 2-methyl-2-butanol, 3-methyl-2-butanol, 2,2-dimethyl-1-propanol, 1-pentanol, 2-pentanol, 3-pentanol, 2-methyl-1-butanol, 3-methyl-1-butanol, 2-methyl-2-butanol, 3-methyl-2-butanol, 2,2-dimethyl-1-propanol, 1-hexanol, 2-methyl-2-pentanol, allyl alcohol, benzyl alcohol, and salicyl alcohol; ketones such as acetone, ethyl methyl ketone, diethyl ketone, methyl propyl ketone, methyl isobutyl ketone, methyl vinyl ketone, cyclohexanone, 2-methyl cyclopentanone, acetophenone, benzophenone, and isophorone; esters such as methyl acetate, ethyl acetate, propyl acetate, isopropyl acetate, n-butyl acetate, isobutyl acetate, sec-butyl acetate, tert-butyl acetate, vinyl acetate, methyl formate, ethyl formate, propyl formate, esters of the aforementioned alcohols and phosphoric acid, and esters of the aforementioned alcohols and carbonic acid; chloroform; benzene; toluene; diethyl ether; and dichloromethane.

Among these, alcohols such as methanol, ethanol, n-propyl alcohol, isopropyl alcohol, 2-butanol, t-butyl alcohol, and allyl alcohol; ketones such as acetone, ethyl methyl ketone, diethyl ketone, and methyl vinyl ketone; esters such as methyl acetate, ethyl acetate, isopropyl acetate, tert-butyl acetate, and vinyl acetate; chloroform; benzene; toluene; diethyl ether; and dichloromethane are preferred for facilitating uniform coating of the culturing surface and for having excellent solubility of temperature-responsive polymers. An organic solvent with a low boiling point (such as at least one selected from the group consisting of a low-molecular alcohol with 1 to 4 carbon atoms, a low-molecular ketone with 3 to 5 carbon atoms, and an acetic acid alkyl ester having an alkyl group with 1 to 4 carbon atoms; in particular, at least one selected from the group consisting of a low-molecular alcohol with 1 to 4 carbon atoms, a low-molecular ketone with 3 to 5 carbon atoms, and an acetic acid alkyl ester having an alkyl group with 1 to 4 carbon atoms, the low-molecular alcohol, low-molecular ketone, and acetic acid alkyl ester having a boiling point lower than that of water) is more preferable for allowing drying in a short time and facilitating even more uniform application on the culturing surface. Methanol and ethanol are particularly preferable for their low cost and excellent operability.

One type of these solvents may be used alone, or a combination of two or more types may be used.

Since the solvent has excellent solubility with respect to a temperature-responsive polymer, the temperature-responsive polymer tends not to become insoluble and precipitate even at a temperature equal to or greater than the cloud point (such as room temperature or 37° C.). This eliminates the need to manage the temperature of the temperature-responsive polymer during application of the temperature-responsive polymer, allowing easy preparation of a coated cell culture container.

In the preparation step I, a hydrophilic molecule is preferably included in the temperature-responsive polymer to facilitate self-aggregation of cells. Examples of the hydrophilic molecule include non-ionic, hydrophilic molecules that do not affect the C/A ratio of the temperature-responsive polymer, such as polyethylene glycol (PEG), dimethyl acrylamide (DMAA), glycerin, Triton X, polypropylene glycol, and the like.

In the preparation step I, the content of the temperature-responsive polymer in the temperature-responsive polymer solution is preferably 0.00075 to 0.015 weight %, more preferably 0.001 to 0.01 weight %, relative to the temperature-responsive polymer solution (100 weight %) to facilitate uniform coating of the culturing surface by the temperature-responsive polymer.

In the preparation step I, the content of the hydrophilic molecule in the temperature-responsive polymer solution is preferably 0.00001 to 0.00015 weight %, more preferably 0.00003 to 0.0001 weight %, relative to the temperature-responsive polymer (100 weight %) to facilitate self-aggregation of cells.

To facilitate uniform coating of the culturing surface by the temperature-responsive polymer or the temperature-responsive polymer composition, the temperature-responsive polymer solution in the preparation step I preferably does not include water, and the weight ratio of water in the temperature-responsive polymer solution (100 weight %) is more preferably 0.5 weight % or less and even more preferably 0.1 weight % or less.

The weight ratio of water can be measured by a method known to a person skilled in the art, such as gas chromatography or the Karl Fischer method.

In the preparation step I, the temperature-responsive polymer solution may be applied to the entire culturing surface or to a portion of the culturing surface, but application to the entire culturing surface is preferable to facilitate obtaining a cell structure.

In the preparation step I, preferred conditions for drying the applied temperature-responsive polymer solution are drying under atmospheric pressure at a temperature of 10° C. to 70° C. for 1 to 3,000 minutes to uniformly coat the culturing surface with the temperature-responsive polymer or the temperature-responsive polymer composition. Quick drying of the applied temperature-responsive polymer solution facilitates uniform coating on the culturing surface with an even distribution of the temperature-responsive polymer or the temperature-responsive polymer composition.

The applied temperature-responsive polymer solution may, for example, be dried by letting the cell culture container stand in an incubator at 37° C.

In the preparation step II, examples of the solvent for dissolving the temperature-responsive polymer or the temperature-responsive polymer composition include water; physiological saline; and buffer solutions such as a phosphate buffer solution, phosphate buffered saline (PBS), and a tris buffer solution.

In the preparation step II, examples of the method of cooling the temperature-responsive polymer aqueous solution include placing the temperature-responsive polymer aqueous solution in a refrigerator at approximately 4° C. and cooling to a temperature at or below the cloud point.

In the preparation step II, examples of the method of casting the temperature-responsive polymer aqueous solution onto the culturing surface include a method of tilting the culturing surface of the cell culture container to spread the temperature-responsive polymer aqueous solution that has a temperature at or below the cloud point and a method of spreading the temperature-responsive polymer aqueous solution using a spatula.

In the preparation step II, examples of the method of heating the cast temperature-responsive polymer aqueous solution to above the cloud point include a method of letting the cell culture container after the casting step stand in an incubator at 37° C.

In an example, illustrated in FIG. 1, of a manufacturing method of a chondrocyte mass, the preparation step is performed by applying the temperature-responsive polymer and/or the temperature-responsive polymer composition to the central portion of the culturing surface of a cell culture container (see (i) of FIG. 1) while drawing a desired shape (see (ii) of FIG. 1) and then drying the applied region (see (iii) of FIG. 1).

The preparation step in Embodiment (I) may also be performed by laying a masking sheet (not illustrated) with a hole (cutout) of a desired shape on the culturing surface of the cell culture container, arranging the temperature-responsive polymer and/or the temperature-responsive polymer composition on the sheet, and then removing the sheet.

A material known to a person skilled in the art may be used for the masking sheet, such as a material with a contact angle of 700 or less. Specific examples include polyethylene terephthalate, polystyrene, polycarbonate, glass, polypropylene, and the like modified with a hydrophilic group. In particular, polystyrene or the like with N,N-dimethylacrylylamide introduced and fixed therein by radiation graft polymerization is preferred to reduce eluates for use in cell culturing.

The shape, size, thickness, and the like of the sheet are not restricted, but a thickness of 0.05 mm to 2.0 mm is preferred.

The area of the coated culturing surface is not restricted and may, for example, be 0.5 $mm^2$ to 300 $mm^2$ when using a φ35 mm cell culture container to manufacture a donut-shaped chondrocyte mass with an outer diameter of 1 mm to 20 mm and an inner diameter of 0.1 mm to 19 mm.

The amount of temperature-responsive polymer and temperature-responsive polymer composition that the coated culturing surface has per unit area is preferably 0.1 μg/$cm^2$ to 3.0 μg/$cm^2$ and more preferably 0.5 μg/$cm^2$ to 2.5 μg/$cm^2$.

The zeta potential of the coated culturing surface is preferably 0 mV to 50 mV, more preferably 0 mV to 35 mV, and even more preferably 10 mV to 25 mV. A zeta potential of 0 mV or more facilitates adhesion of negatively charged cells. A zeta potential of 50 mV or less can reduce cytotoxicity.

Furthermore, setting the zeta potential in the aforementioned ranges further facilitates production of cell structures having an aggregated (pellet-like) shape by simply culturing cells under appropriate culture conditions. The reason is that setting the surface zeta potential within the aforementioned ranges is inferred to provide the coated culturing surface with a weak positive charge that does not trigger cytotoxicity, to ensure rapid adhesion of the seeded cells, to improve cell activity and encourage secretion of extracellular matrix, and also to appropriately inhibit cell migration, strengthening the bond between cells.

The zeta potential refers to the value calculated with the Smoluchowski equation by measurement using a zeta potential meter (for example, model "ELSZ" by Otsuka Electronics Co.) with a particle (zeta potential: −5 mV to +5 mV) in which polystyrene latex is coated with hydroxypropyl cellulose as a reference monitor particle.

The contact angle of water relative to the coated culturing surface is preferably 50° to 90°, more preferably 60° to 80°, and even more preferably 62° to 78° to increase the effects of Aspect (I).

The contact angle of water relative to the coated culturing surface refers to the average contact angle measured in accordance with JIS R3257 at any number of points on the coated culturing surface.

FIGS. 3A and 3B are an outline of a modification to the preparation step, with the subsequent seeding and culturing step.

FIG. 3A illustrates a first modification to the preparation step.

The first modification to the preparation step uses a cell non-adhesive pad that has a planar shape fitting within the culturing surface of the cell culture container, has a predetermined thickness, and has the central portion thereof cut out into a desired planar shape (see (i) of FIG. 3A).

Cell non-adhesive refers to cells not adhering or tending not to adhere.

In the preparation step of the first modification, the temperature-responsive polymer and/or the temperature-responsive polymer composition is first arranged on the entire culturing surface of the cell culture container, and the cell non-adhesive sheet is then laid on the polymer and/or polymer composition. As a result, the coated culturing surface is surrounded by walls, i.e. the coated culturing surface is provided on the bottom of the recess.

This first modification allows three-dimensional control of the shape of the cell mass during the below-described seeding and culturing step and allows more precise manufacturing of a chondrocyte mass having a desired shape.

A material known to a person skilled in the art may be used for the cell non-adhesive pad usable in the first modification, such as a material with a contact angle of 70° C. or less. Specific examples include polyethylene terephthalate, polystyrene, polycarbonate, glass, polypropylene, and the like modified with a hydrophilic group. In particular, polystyrene or the like with N,N-dimethylacrylylamide introduced and fixed therein by radiation graft polymerization is preferred to reduce eluates for use in cell culturing.

The shape, size, thickness, and the like of the pad are not restricted, but a diameter (maximum diameter) of 0.1 mm to 10 mm is preferable when using a φ35 mm cell culture container.

In the first modification, a cell non-adhesive pad with a size fitting within the culturing surface of the cell culture container and provided with a recess of a desired planar shape in the central portion thereof may be used (not illustrated).

In the preparation step in this case, the temperature-responsive polymer and/or the temperature-responsive polymer composition is arranged only on the bottom of the recess in the pad (not illustrated). The polymer and/or polymer composition is not arranged on the surface other than the bottom of the recess, i.e. the surface of the walls of the recess and the pad apart from the recess.

In this example as well, a chondrocyte mass having a desired shape can be manufactured more precisely in the recess during the below-described seeding and culturing step.

In Embodiment (I), cell non-adhesive pads of different sizes may be used, for example by allowing a chondrocyte mass to expand in the seeding and culturing step, transferring the chondrocyte mass to the recess of a larger-sized cell non-adhesive pad, and performing the next seeding and culturing step.

This technique allows the size of the coated culturing surface relative to the size of the chondrocyte mass to be kept constant in each seeding and culturing step, thus bringing the shape of the chondrocyte mass closer to the desired shape.

FIG. 3B illustrates a second modification to the preparation step.

In the second modification to the preparation step, a recess with a desired planar shape is carved into the culturing surface of the cell culture container (see FIG. 3B).

In the preparation step of the second modification, the temperature-responsive polymer and/or temperature-responsive polymer composition is arranged only on the bottom of the carved-out recess (see (i) of FIG. 3B). The polymer and/or polymer composition is not arranged on the surface other than the bottom of the recess, i.e. the surface of the walls of the recess and the sheet apart from the recess.

This second modification allows three-dimensional control of the shape of the cell mass during the below-described seeding and culturing step and allows more precise manufacturing of a chondrocyte mass having a desired shape.

In the above-described first and second modifications to the preparation step, the walls of the recess in particular are preferably cell non-adhesive to inhibit adhesion between the seeded cells and the walls of the recess and to adjust the shape of the obtainable cell mass.

(Seeding and Culturing Step)

Next in an example manufacturing method in Embodiment (I), cells capable of differentiating into chondrocytes are seeded onto a coated culturing surface in the presence of a cell mass, and the cell mass and the cells capable of differentiating into chondrocytes are cocultured to produce a chondrocyte mass (seeding and culturing step).

As illustrated in FIG. 1, after the above-described preparation step and before the below-described seeding and culturing step in an example manufacturing method of Embodiment (I), cells capable of differentiating into chondrocytes are seeded onto the coated culturing surface prepared in the above-described preparation step, and the seeded cells are cultured to produce a cell mass used in the below-described seeding and culturing step (see (iv) to (viii) of FIG. 1).

The manufacturing method of Embodiment (I), however, is not limited to this example, and the cell mass used in the seeding and culturing step may be produced separately (not illustrated), for example in a different cell culture container.

In the example in FIG. 1, the seeding and culturing step is performed by providing a cell mass on the coated culturing surface, adding cells and a cell culture medium to the cell culture container (see (i) of FIG. 2), subsequently placing the cell culture container in a typical 37° C. cell incubator (see (ii) of FIG. 2), adding new cell culture medium by medium exchange (see (iii) of FIG. 2), and placing the cell culture container again in the cell incubator (see (iv) and (v) of FIG. 2). The parentheses in (iv) of FIG. 2 contain a cross-sectional view of the structure.

In this step, the cell mass is preferably present in the central portion of the coated culturing surface, as illustrated in (i) of FIG. 2, to adjust the overall shape of the chondrocyte mass.

The cell culture medium used before medium exchange and the cell culture medium used after medium exchange may be selected appropriately in accordance with purpose or use. For example, the medium before exchange may be a growth medium, and the medium after exchange may be a differentiation medium or a redifferentiation medium.

Examples of the cells capable of differentiating into chondrocytes include chondrocytes, adipose, synovium, fascia, periosteum, periodontal membrane, dental pulp, mesenchymal stem cells derived from bone marrow, and iPS cells.

One type of these cells capable of differentiating into chondrocytes may be used alone, or a combination of two or more types may be used.

The cell density when seeding cells in the seeding and culturing step is $0.3 \times 10^4$ cells/cm$^2$ or more, preferably $0.3 \times 10^5$ cells/cm$^2$ or more, and more preferably $0.5 \times 10^5$ cells/cm$^2$ or more. Furthermore, to prevent problems related to the cell cycle, such as growth arrest due to contact between cells during culturing, the cell density is preferably $10.0 \times 10^5$ cells/cm$^2$ or less and more preferably $4.5 \times 10^5$ cells/cm$^2$ or less.

A person skilled in the art can appropriately determine the culture conditions on the basis of the type of cells being used and the purpose of the experiment. Example conditions are 37° C. and a 5% $CO_2$ atmosphere.

The phenomenon that occurs in the seeding and culturing step is described below with reference to FIG. 2.

In this step, the seeded cells first precipitate onto the coated culturing surface, on which a cell mass is present in the central portion, and onto the non-coated culturing surface. At this time, the cells that precipitate on the coated culturing surface adhere to the coated culturing surface and survive, whereas the cells that precipitate on the non-coated culturing surface survive without adhering to the non-coated culturing surface (see (ii) of FIG. 2). The cells that do not adhere, however, are removed by suction during the first medium exchange after seeding (see (iii) of FIG. 2). These cells are preferably removed rapidly to inhibit the release of harmful components, such as heat shock proteins and inflammatory cytokines that accompany apoptosis.

Upon further culturing of the cells adhered to the coated culturing surface, the cells located near the boundary between the coated culturing surface and the non-coated culturing surface start to aggregate from the coated culturing surface, along with the cells positioned closer to the central portion of the coated culturing surface, so as to surround the cell mass in the central portion (see (iv) of FIG. 2). In other words, the cells that were adhered peel off towards the central portion of the coated culturing surface, separating from the culturing surface, so that periphery of the entire sheet of cells warps. Ultimately, the cell mass provided in advance and the seeded cells integrate to form a layered structure in a cross-sectional view (see (v) of FIG. 2).

The cells, used in the seeding and culturing step of Aspect (I), capable of differentiating into cartilage pass through the aforementioned aggregation process, differentiate into chondrocytes, and mature. As is known by a person skilled in the art, however, chondrocytes are cells with a special property allowing a hypoxic state upon maturing. Accordingly, the chondrocytes in the cell mass obtained through the aggregation process can survive even in a hypoxic state, and these chondrocytes can continue to survive even when surrounded by new cells capable of differentiating into cartilage and placed in a hypoxic state in the next seeding and culturing step.

Apart from the coated culturing surface, the seeded cells also precipitate on the cell mass, and these cells are integrated together during cell aggregation.

In an example manufacturing method in Embodiment (I), the above-described seeding and culturing step is performed multiple times (see (vi) of FIG. 2).

A large chondrocyte mass can be obtained by performing the seeding and culturing step multiple times, and the size can be adjusted in accordance with purpose and use.

This embodiment allows a cell mass constituted by mature cells formed in a previous seeding and culturing step to be successively surrounded by immature cells in subsequent seeding and culturing steps, thereby making maturation of cells capable of differentiating into cartilage compatible with growth of a cell mass.

Immature cells (cells that grow but have insufficient cartilage properties) and mature cells (cells that do not grow but have acquired the properties of chondrocytes, such as the characteristics of survival in a hypoxic environment and highly elastic flexibility) can be controlled by appropriately selecting the medium. For example, mixing a differentiation inducing factor such as TGF-β1 into the medium that is used can encourage cell differentiation.

The length of time from when the cell mass is formed in the central portion of the coated culturing surface in the previous seeding and culturing step until cells are seeded in the next seeding and culturing step is not restricted. This length of time may be set appropriately by a person skilled in the art in view of maturing the formed cell mass into a chondrocyte mass and inhibiting a reduction in activity of the chondrocyte mass, and comprehensively considering the type, concentration, and the like of the redifferentiation medium being used.

(Chondrocyte Mass)

The chondrocyte mass of Embodiment (I) is manufactured by the manufacturing method of a chondrocyte mass of Embodiment (I).

The size of the chondrocyte mass is not restricted. The diameter (maximum diameter) may be 1 mm to 100 mm, and particularly in the case of a donut-shaped chondrocyte mass, the outer diameter may be 3 mm to 50 mm, and the inner diameter may be 0.3 mm to 49 mm.

(Manufacturing Method of Graft Material)

The manufacturing method of a graft material of Embodiment (I) includes the step of seeding mesenchymal cells in the presence of the chondrocyte mass manufactured with the manufacturing method of a chondrocyte mass of Embodiment (I) and coculturing the chondrocyte mass and the mesenchymal cells to produce a graft material.

FIG. 4 is an overview of the manufacturing method of a graft material of Embodiment (I).

Apart from using mesenchymal cells, the aforementioned step in the manufacturing method of a graft material in Embodiment 1 may be performed in the same way as the above-described seeding and culturing step in the manufacturing method of a chondrocyte mass of Embodiment (I).

Examples of mesenchymal cells include chondrocytes, fibroblasts, and ADSC.

(Graft Material) The graft material of Embodiment (I) is manufactured by the manufacturing method of a graft material of Embodiment (I).

Mesenchymal cells, in particular fibroblasts, are present on the outermost side of a chondrocyte mass in the graft material of Embodiment (I). The graft material therefore tends to adhere firmly to the tissue surrounding the graft site during grafting onto a living organism. This can increase the curative effects at the graft site and yield a better prognosis.

FIG. 5 is an overview of another example manufacturing method of a chondrocyte mass in Embodiment (I).

The other example manufacturing method of a chondrocyte mass in Embodiment (I) includes the above-described first modification to the preparation step.

Specifically, the other example manufacturing method uses a cell non-adhesive pad (with a thickness of 1 mm, for example) provided at the central portion with a cutout that is donut-shaped in plan view (for example, outer diameter (φo) of 8 mm, inner diameter (φi) of 4 mm, and width of 2 mm).

Here, the outer contour line of the coated culturing surface and the inner contour line of the coated culturing surface preferably form concentric circles to improve the donut shape of the chondrocyte mass.

The details of each step in the other example manufacturing method of a chondrocyte mass in Embodiment (I) may be similar to the steps in the above-described example manufacturing method of the chondrocyte mass in Embodiment (I) (see (i) to (ix) of FIG. 5).

When using a φ35 mm plate as the cell culture container, for example, in the other example manufacturing method, the width of the coated culturing surface is preferably 3 mm or less, more preferably 2.5 mm or less, and the height of the wall is preferably 3 mm or less, more preferably 2.5 mm or less, to obtain a chondrocyte mass with a better donut shape (ringed shape).

(Manufacturing Method of Composite Material)

A manufacturing method of a composite material of Embodiment (I) includes a composite body production step of fitting a donut-shaped chondrocyte mass in particular, among the chondrocyte masses of Embodiment (I), onto a tubular structure to produce a composite body and a culturing step of culturing the composite body to produce a composite material.

The manufacturing method of a composite material of Embodiment (I) preferably includes a step of preparing a tubular structure and a core material (see (i) of FIG. 6) and then inserting the core material into a hollow portion of the tubular structure from one end to the other (see (ii) of FIG. 6), a composite body production step of fitting a donut-shaped chondrocyte mass of Embodiment (I) onto the tubular structure to produce a composite body (see (iii) of FIG. 6), a culturing step of culturing the composite body to produce a composite material (see (iv) of FIG. 6), and a step of removing the core material from the composite material (see (v) of FIG. 6).

FIG. 6 is an overview, in (i) to (v), of an example manufacturing method of a composite material in Embodiment (I).

Details of each step in an example manufacturing method of a chondrocyte mass in Embodiment (I) are provided below.

The tubular structure may have a hollow portion and may be a biotube (synthetic blood vessel), a collagen tube, an elastin tube, a polygluconic acid tube, a polylactic acid tube, or the like.

A biotube may have collagen as the principal component and may, for example, be produced with the method disclosed in the Examples of JP2004261260A.

The outer diameter of the tubular structure may be similar to the inner diameter of the donut-shaped cell structure of Embodiment (I), such as 1 mm to 100 mm. The inner diameter of the tubular structure is not restricted and may, for example, be 0.1 mm to 50 mm. The length of the tubular structure may be appropriately set in accordance with the purpose or use and is not restricted. The length may, for example, be from 1 mm to 300 mm.

A solid body or a porous body may be used as the core material. Specific examples include a silicon rod-like structure, an acrylic rod-like structure, a metallic rod-like structure, bisque, and a metal mesh compressed structure. When using a porous body, medium and oxygen can also expand from the luminal side of the composite body.

The outer diameter of the core material may be similar to the inner diameter of the tubular structure, such as 0.1 mm to 50 mm.

The core material may be similar to the tubular structure in length or may be longer or shorter than the tubular structure by, for example, 0.1 mm to 10 mm.

The composite body production step may, for example, be performed by passing the tubular structure (with the core material provided on the inside) produced in the above-described step through the circle of the donut-shaped chondrocyte mass of Embodiment (I) while securing the chondrocyte mass in place with tweezers.

The number of donut-shaped chondrocyte masses per tubular structure may be determined appropriately in accordance with purpose or use and is not restricted. The number may, for example, be from 1 to 1,000.

When using a plurality of chondrocyte masses, the distance between adjacent chondrocyte masses may be set appropriately in accordance with purpose or use and is not restricted. The distance may, for example, be from 0.1 mm to 100 mm before the below-described subsequent culturing step.

The time from when the tubular structure is completely fitted in the above-described composite body production step until culturing of the composite body starts in the below-described culturing step is preferably 1 min to 180 min, more preferably 1 min to 120 min, to maintain cell activity.

The culturing step may, for example, be performed by placing the composite body produced in the above-described composite body production step under appropriate conditions (such as 37° C., 5% $CO_2$ atmosphere) for a predetermined length of time (such as from 12 hours to 150 days).

The culturing step can also be performed inside a living organism, for example by embedding the above-described composite body inside the living organism and leaving the composite body inside for a predetermined length of time to allow the composite body to integrate with biological tissue forming around the outer surface of the composite body.

The core material can be removed from the composite material appropriately by using tweezers or the like.

The operations in the above step are not restricted and may be performed by hand or by using machines or apparatuses.

(Composite Material)

In the composite material of Embodiment (I), donut-shaped chondrocyte masses in particular among the chondrocyte masses of Embodiment (I) are provided on the outer surface of a tubular structure (see (v) of FIG. 6).

The material, outer diameter, inner diameter, length, and the like of the tubular structure, along with the number of donut-shaped chondrocyte masses per tubular structure, may be as described above in the manufacturing method of a composite material of Embodiment (I).

When using a plurality of chondrocyte masses, the distance between adjacent chondrocyte masses (cartilage tissue) may be determined appropriately in accordance with purpose or use and is not restricted. For example, the distance may be from 0.1 mm to 100 mm, or adjacent chondrocyte masses (cartilage tissue) may overlap (i.e. a distance of 0 mm).

In the composite material of Embodiment (I), a core material may be provided inside the tubular structure (see (v) of FIG. 6).

The material, outer diameter, length, and the like of the core material may be as described above in the manufacturing method of a composite material of Embodiment (I).

The composite material of Embodiment (I) may be manufactured with the manufacturing method of a composite material of the present embodiment.

The chondrocyte mass, graft material, and composite material of Embodiment (I) are useful for treatment of joints, the trachea, the nose, and the like and more specifically are useable in treatment of a meniscus, tracheal cartilage, nasal cartilage, ear cartilage, intervertebral discs, articular cartilage, ligaments, the Achilles tendon, and the like.

For example, the manufacturing method of a chondrocyte mass, graft material, and composite material of Embodiment (I) allows a chondrocyte mass and graft material to be shaped in accordance with a CAD drawing based on a CT image of the affected area of a patient. The manufacturing method of a chondrocyte mass, graft material, and composite material of the present embodiment therefore has the potential of contributing greatly to achieving customized medical treatment.

[[Aspect (II)]]

Epithelial cells do not adhere easily to a cell culture container. Insufficient adhesion to the culture container leads to problems such as an unstable cell form after growth, making stable cell culturing difficult with known methods. Furthermore, actin filaments are undeveloped in epithelial cells, and the binding between cells is weak. Weak adhesion to the cell culture container then tends to cause the epithelial cells to peel from the cell culturing surface. A spheroid formed from epithelial cells also tends not to adhere to a cell culture container but rather to float in the cell culture container and therefore has an extremely high risk of accidentally being suctioned during medium exchange or the like.

With regard to Aspect (II), we discovered that a cell culture container coated with a temperature-responsive polymer has excellent adhesiveness for epithelial cells. In particular, we discovered that cells other than epithelial cells adhere to the cell culture container coated with a temperature-responsive polymer with an appropriate force and often have the property of self-aggregation when the density reaches a certain level, whereas when placing epithelial cells in a cell culture container coated with a temperature-responsive polymer, the epithelial cells adhere strongly to the culturing surface, unlike other cells. We also discovered that using a cell culture container coated with a temperature-responsive polymer facilitates culturing of epithelial cells and achieves an excellent cell form during growth. Furthermore, we discovered a method allowing efficient formation of a cell structure of epithelial cells in which the cell structure tends not to peel from the coated cell culturing surface and tends not to be accidentally suctioned during medium exchange or the like.

[Culture Method of Epithelial Cells] A culture method of epithelial cells of Aspect (II) includes a production step of producing a temperature-responsive polymer or a temperature-responsive polymer composition, a culture container preparation step of forming a coated region A by coating at least a portion of a culturing surface of a cell culture container with the temperature-responsive polymer or the temperature-responsive polymer composition to prepare a coated cell culture container including the coated region A, a seeding step of seeding epithelial cells in the coated cell culture container, and a culturing step of culturing the epithelial cells adhered to the coated region A. The concentration of the temperature-responsive polymer or the temperature-responsive polymer composition in the coated region A is 0.3 pg/mm$^2$ or more.

The culture method of epithelial cells of Aspect (II) prevents epithelial cells from unintentionally peeling during culturing, allowing epithelial cells to be cultured easily.

The entire culturing surface of the coated cell culture container may be the coated region A, or a portion of the culturing surface may be the coated region A. The culturing surface may have one coated region A or a plurality of coated regions A.

(Production Step)

Examples of the production step in Embodiment (II) include a step similar to the production step in Aspect (I), and a similar step is preferred.

The temperature-responsive polymer and temperature-responsive polymer composition used in the culture method in Embodiment (II) are preferably (A) for having better adhesiveness of the epithelial cells.

The production step of producing a mixture containing 2-N,N-dimethylaminoethyl methacrylate (DMAEMA) in Embodiment (II) is also referred to as a mixture production step.

(Culture Container Preparation Step)

In the culture method of an embodiment of Aspect (II) (Embodiment (II)), the culture container preparation step is a step of forming a coated region A by coating at least a portion of a culturing surface of a cell culture container with the temperature-responsive polymer or the temperature-responsive polymer composition to prepare a coated cell culture container including the coated region A.

The culture container preparation step may, for example, be a step of dissolving a temperature-responsive polymer or a temperature-responsive polymer composition in a solvent to form a temperature-responsive polymer solution, applying the solution onto the culturing surface of a cell culture container, and drying to prepare a coated cell culture container (culture container preparation step I). The culture container preparation step may instead be a step of cooling an aqueous solution including a temperature-responsive polymer or a temperature-responsive polymer composition (temperature-responsive polymer aqueous solution) to the cloud point of the temperature-responsive polymer or below, casting the cooled temperature-responsive polymer aqueous solution onto the culturing surface of a cell culture container, and heating to a temperature above the cloud point to prepare a coated cell culture container (culture container preparation step II).

Here, the temperature-responsive polymer solution used when forming the coated region A is also referred to as temperature-responsive polymer solution A, and the temperature-responsive polymer aqueous solution used when forming the coated region A is also referred to as temperature-responsive polymer aqueous solution A.

Examples of the solvent in the temperature-responsive polymer solution in the culture container preparation step I include water; physiological saline; buffer solutions; alcohols such as methanol, ethanol, n-propyl alcohol, isopropyl alcohol, 1-butanol, isobutyl alcohol, 2-butanol, t-butyl alcohol, 1-pentanol, 2-pentanol, 3-pentanol, 2-methyl-1-butanol, 3-methyl-1-butanol, 2-methyl-2-butanol, 3-methyl-2-butanol, 2,2-dimethyl-1-propanol, 1-pentanol, 2-pentanol, 3-pentanol, 2-methyl-1-butanol, 3-methyl-1-butanol, 2-methyl-2-butanol, 3-methyl-2-butanol, 2,2-dimethyl-1-propanol, 1-hexanol, 2-methyl-2-pentanol, allyl alcohol, benzyl alcohol, and salicyl alcohol; ketones such as acetone, ethyl methyl ketone, diethyl ketone, methyl propyl ketone, methyl isobutyl ketone, methyl vinyl ketone, cyclohexanone, 2-methyl cyclopentanone, acetophenone, benzophenone, and isophorone; esters such as methyl acetate, ethyl acetate, propyl acetate, isopropyl acetate, n-butyl acetate, isobutyl acetate, sec-butyl acetate, tert-butyl acetate, vinyl acetate, methyl formate, ethyl formate, propyl formate, esters of the aforementioned alcohols and phosphoric acid, and esters of the aforementioned alcohols and carbonic acid; chloroform; benzene; toluene; diethyl ether; and dichloromethane.

Among these, water; alcohols such as methanol, ethanol, n-propyl alcohol, isopropyl alcohol, 2-butanol, t-butyl alcohol, and allyl alcohol; ketones such as acetone, ethyl methyl ketone, diethyl ketone, and methyl vinyl ketone; esters such as methyl acetate, ethyl acetate, isopropyl acetate, tert-butyl acetate, and vinyl acetate; chloroform; benzene; toluene; diethyl ether; and dichloromethane are preferred for facilitating uniform coating of the culturing surface and for having excellent solubility of temperature-responsive polymers. An organic solvent with a low boiling point (such as at least one selected from the group consisting of a low-molecular alcohol with 1 to 4 carbon atoms, a low-molecular ketone with 3 to 5 carbon atoms, and an acetic acid alkyl ester having an alkyl group with 1 to 4 carbon atoms; in particular, at least one selected from the group consisting of a low-molecular alcohol with 1 to 4 carbon atoms, a low-molecular ketone with 3 to 5 carbon atoms, and an acetic acid alkyl ester having an alkyl group with 1 to 4 carbon atoms, the low-molecular alcohol, low-molecular ketone, and acetic acid alkyl ester having a boiling point lower than that of water) is more preferable for allowing drying in a short time and facilitating even more uniform application on the culturing surface. Methanol and ethanol are particularly preferable for their low cost and excellent operability.

One type of these solvents may be used alone, or a combination of two or more types may be used.

Since the solvent has excellent solubility with respect to a temperature-responsive polymer, the temperature-responsive polymer tends not to become insoluble and precipitate even at a temperature equal to or greater than the cloud point (such as room temperature or 37° C.). This eliminates the need to manage the temperature of the temperature-responsive polymer during application of the temperature-responsive polymer, allowing easy preparation of a coated cell culture container.

In the culture container preparation step I, a hydrophilic molecule may be added to the temperature-responsive polymer solution as appropriate to adjust the adhesiveness of the epithelial cells. Examples of the hydrophilic molecule include non-ionic, hydrophilic molecules that do not affect the C/A ratio of the temperature-responsive polymer, such as polyethylene glycol (PEG), dimethyl acrylamide (DMAA), glycerin, Triton X, polypropylene glycol, and the like.

In the culture container preparation step I, the content of the temperature-responsive polymer in the temperature-responsive polymer solution A is preferably 0.00000009 mass % to 0.01 mass %, more preferably 0.0000009 mass % to 0.01 mass %, relative to the temperature-responsive polymer solution (100 mass %) to facilitate uniform coating of the culturing surface by the temperature-responsive polymer.

In the culture container preparation step I, the content of the hydrophilic molecule in the temperature-responsive polymer solution A is preferably 0.00001 mass % to 0.00015 mass %, more preferably 0.00003 mass % to 0.0001 mass %, relative to the temperature-responsive polymer (100 mass %) to facilitate self-aggregation of cells.

In the culture container preparation step I, the temperature-responsive polymer solution A may be applied to the entire culturing surface or to a portion of the culturing surface.

When the temperature-responsive polymer solution is applied to a portion of the culturing surface, one coated region or a plurality of coated regions may be provided on the culturing surface. A cell culture container with a cell non-adhesive culturing surface is preferably used when the temperature-responsive polymer solution is applied to a portion of the culturing surface.

The temperature-responsive polymer solution may be applied to have a uniform concentration over the entire coated region A or applied thickly to one portion and thinly to other portions.

"Cell non-adhesive" refers to adherent cells (for example, fibroblasts, cardiomyocytes, vascular endothelial cells, and the like) either not adhering or tending not to adhere under normal culture conditions. "Cell non-adhesive" thus also includes the case of "low-adhesive".

In the culture container preparation step I, preferred conditions for drying the applied temperature-responsive polymer solution are drying under atmospheric pressure at a temperature of 10° C. to 70° C. for 1 to 3,000 minutes to uniformly coat the culturing surface with the temperature-responsive polymer or the temperature-responsive polymer composition. Quick drying of the applied temperature-responsive polymer solution facilitates uniform coating on the culturing surface with an even distribution of the temperature-responsive polymer or the temperature-responsive polymer composition.

The applied temperature-responsive polymer solution may, for example, be dried by letting the cell culture container stand in an incubator at 37° C.

In the culture container preparation step II, examples of the solvent for dissolving the temperature-responsive polymer or the temperature-responsive polymer composition include water; physiological saline; and buffer solutions such as a phosphate buffer solution, phosphate buffered saline (PBS), and a tris buffer solution.

In the culture container preparation step II, examples of the method of cooling the temperature-responsive polymer aqueous solution include placing the temperature-responsive polymer aqueous solution in a refrigerator at approximately 4° C. and cooling to a temperature at or below the cloud point.

In the culture container preparation step II, examples of the method of casting the temperature-responsive polymer aqueous solution onto the culturing surface include a method of tilting the culturing surface of the cell culture container to spread the temperature-responsive polymer aqueous solution that has a temperature at or below the cloud point and a method of spreading the temperature-responsive polymer aqueous solution using a spatula.

In the culture container preparation step II, examples of the method of heating the cast temperature-responsive polymer aqueous solution to above the cloud point include a method of letting the cell culture container after the casting step stand in an incubator at 37° C.

Examples of the cell culture container include commercially available multiwell plates, dishes, flasks, and the like. Examples of the material of the cell culture container include polystyrene, polyethylene terephthalate (PET), polypropylene, polybutene, polyethylene, polycarbonate, and glass. Among these, polystyrene and polyethylene terephthalate (PET) are preferable for being easy to mold precisely, for allowing adoption of various sterilization methods, and for being suitable for microscope observation by virtue of being transparent.

Cell adhesion treatment or the like may be applied to the culturing surface of the cell culture container, or the surface may be untreated. The culturing surface may be coated, processed, or the like to adjust the cell adhesiveness.

The planar shape of the culturing surface is not restricted and may, for example, be a substantially rectangular shape or other substantially polygonal shape, a substantially circular shape, or the like. Among these, a substantially circular shape is preferred to facilitate obtaining a more homogeneous cell structure.

The bottom shape of the culturing surface (the cross-sectional shape of the bottom) is not restricted, and examples include a flat bottom, round bottom (U-bottom), V-bottom, and uneven bottom. In particular, in the culture method of epithelial cells and the below-described culturing step of a cell structure, the epithelial cells are a spheroidal cell structure.

At least a portion of the culturing surface may have a depression. In this case, the depression is preferably provided within the coated region A and is preferably located in the central portion of the coated region A.

The depth of the depression is, for example, preferably 0.001 mm to 10.0 mm and more preferably 0.01 mm to 1 mm.

The area of the depression in plan view is, for example, preferably 0.01 $mm^2$ to 10.0 $mm^2$ and more preferably 0.1 $mm^2$ to 1 $mm^2$.

The area of the culturing surface of the cell culture container is preferably 150 $cm^2$ or less, more preferably 21 $cm^2$ or less, and even more preferably 200 $mm^2$ or less. The lower limit on the area of the culturing surface of the cell culture container is not restricted, and any commercially available size may be used.

The area of the coated region A is preferably 150 $cm^2$ or less, more preferably 21 $cm^2$ or less, and even more preferably 200 $mm^2$ or less.

The area of the coated region A relative to the entire area (100%) of the culturing surface of the cell culture container is preferably from 50% to 100% and more preferably from 80% to 100%.

The amount of temperature-responsive polymer per unit area in the coated region A is 0.3 $pg/mm^2$ or more, preferably 3.0 $pg/mm^2$ or more, more preferably 30 $pg/mm^2$ or more, and preferably 200 $ng/mm^2$ or less. These ranges allow the epithelial cells to adhere to the culturing surface and facilitate culturing.

The zeta potential of the coated region A in the coated cell culture container is preferably 0 mV to 50 mV, more preferably 0 mV to 35 mV, and even more preferably 10 mV to 25 mV. A zeta potential of 0 mV or more facilitates adhesion of negatively charged cells. A zeta potential of 50 mV or less can reduce cytotoxicity.

Furthermore, setting the zeta potential in the aforementioned ranges further improves the adhesiveness between epithelial cells and the coated region A. The reason is that setting the surface zeta potential within the aforementioned ranges is inferred to provide the coated region A with a weak positive charge that does not trigger cytotoxicity, to ensure rapid adhesion of the seeded cells, to improve cell activity and encourage secretion of extracellular matrix, and also to appropriately inhibit cell migration, strengthening the bond between cells.

The zeta potential refers to the value calculated with the Smoluchowski equation by measurement using a zeta potential meter (for example, model "ELSZ" by Otsuka Electronics Co.) with a particle (zeta potential: −5 mV to +5 mV) in which polystyrene latex is coated with hydroxypropyl cellulose as a reference monitor particle.

The contact angle of water relative to the coated region A is preferably 50° to 90°, more preferably 60° to 80°, and even more preferably 620 to 780 to increase the effects of Aspect (II). The contact angle of water relative to the coated region A refers to the average contact angle measured in accordance with JIS R3257 at any number of points on the coated region A.

(Seeding Step)

The seeding step is a step of seeding epithelial cells on the coated cell culture container. Cells may be seeded a portion at a time.

Examples of epithelial cells include cultured cells derived from liver cancer, such as HepG2, HepaRG, and HepaRA frequently used in drug discovery tests; hepatocytes; cells derived from pancreatic cancer such as BxPC-3; and primary cultured cells of these types collected from a living organism. Among these, cultured cells derived from liver cancer, such as HepaRG and HepaRA, in which all of the inherent cell properties are average and which are well known to a person skilled in the art, are preferable for drug discovery tests. Primary cells are suitable for anticancer drug development and laboratory testing.

One type of the aforementioned epithelial cells may be used alone, or a combination of two or more types may be used.

In the seeding step, cells other than the aforementioned epithelial cells may be included, such as mesenchymal stem cells or stromal cells.

In the seeding step, the density of seeded epithelial cells on the coated region A is not restricted, as long as the density is not so low that the epithelial cells die out. For example, a confluency relative to the surface area of the coated region A of 5% to 100% is preferable, a confluency of 50% to 100% is more preferable, and a confluency of 80% to 100% is even more preferable. Epithelial cells can more easily be cultured if the seeded cell density is within the aforementioned ranges.

The density of seeded cells on the coated region A is not restricted, as long as the density is not so low that the epithelial cells die out. The density is preferably 20 cells/$mm^2$ to 15,000 cells/$mm^2$, for example, and more preferably 50 cells/$mm^2$ to 1,500 cells/$mm^2$. For example, when seeding by adding 25 μL of cell fluid to a 384 well cell culture plate with a culturing surface area of 8.4 $mm^2$, the number of cells in the cell fluid is preferably 7 cells/μL to 5040 cells/μL. Live cells are seeded.

The coated cell culture container may be left to stand in an incubator at 37° C. and subsequently removed and placed on a clean bench at room temperature, for example, with cell seeding then being performed.

Cells are preferably seeded after being diluted in a medium. The medium for dilution may be any medium in which epithelial cells can be cultured.

(Culturing Step)

The culturing step is a step of culturing the epithelial cells adhered to the coated region A.

The epithelial cells may be cultured by, for example, using a typical cell incubator at 37° C.

The cultured epithelial cells can be washed with PBS or the like, then peeled off using trypsin, trypsin-EDTA, commercially available cell peeling solution, or the like, and subsequently diluted and passaged.

[Epithelial-Mesenchymal Transition Inducer]

We discovered that the temperature-responsive polymer and temperature-responsive polymer composition used in the above-described culture method of an embodiment of Aspect (II) are effective for inducing transition of epithelial cells to mesenchymal cells, i.e. epithelial-mesenchymal transition (EMT).

In other words, an epithelial-mesenchymal transition inducer of Aspect (II) includes the temperature-responsive polymer and temperature-responsive polymer composition used in the above-described culture method of an embodiment of Aspect (II) and is preferably composed of the temperature-responsive polymer and temperature-responsive polymer composition.

Known techniques for inducing epithelial-mesenchymal transition include techniques for inducing EMT using growth factors such as transforming growth factor (TGF)-β, epidermal growth factor (EGF), and the like, and techniques for inducing EMT by culturing epithelial cancer cells on type IV collagen.

However, when using substances derived from natural products as the growth factor, such as TGF-β or EGF, in the above-described known techniques, unknown substances or pathogenic substances might be included in the growth factor. Variation between lots might also adversely affect the reproducibility of experiments. Use of a growth factor produced with a genetic modification technique also leads to problems such as endotoxins derived from *Escherichia coli* contaminating the growth factor, or the resulting protein undergoing host-specific *Escherichia coli* glycosylation and having a structure and properties different from growth factors derived from natural products.

While the mechanism is unclear, the epithelial-mesenchymal transition inducer of Aspect (II) allows induction of mesenchymal transition by simply culturing epithelial cells on a culturing surface coated with a 100% chemically synthesized temperature-responsive polymer and temperature-responsive polymer composition, without requiring a growth factor. This yields a low risk of contamination by substances that could adversely affect transition and yields low variation between lots. The strict temperature control required when using a growth factor is also unnecessary, and animal resources can also be conserved. The epithelial-mesenchymal transition inducer of Aspect (II) can inexpensively and simply achieve epithelial-mesenchymal transition.

Examples of the temperature-responsive polymer and temperature-responsive polymer composition in Embodiment (II) include (A) a temperature-responsive polymer containing 2-N,N-dimethylaminoethyl methacrylate (DMAEMA) units and anionic monomer units, (B) a temperature-responsive polymer containing N-isopropyl acrylamide (NIPAM) units, cationic monomer units, and anionic monomer units, and (C) a temperature-responsive polymer composition containing a polymer of 2-N,N-dimethylaminoethyl methacrylate (DMAEMA) and/or a derivative thereof, 2-amino-2-hydroxymethyl-1,3-propanediol (tris), and one or more anionic substances selected from the group consisting of nucleic acids, heparin, hyaluronic acid, dextran sulfate, polystyrene sulfonic acid, polyacrylic acid, polymethacrylic acid, polyphosphoric acid, sulfated polysaccharide, curdlan, polyarginic acid, and alkali metal salts thereof, as described above in Embodiment (II). Among these, (A) is preferred for having better adhesiveness of the epithelial cells.

Examples of (A) include (A-1) a temperature-responsive polymer obtained by a method of polymerizing DMAEMA in the presence of water and (A-2) a temperature-responsive polymer containing a polymer block principally containing DMAEMA (polymer chain α terminal) and a copolymer block principally containing DMAEMA and an anionic monomer (polymer chain ω terminal). Of these, (A-1) is preferred for better induction of epithelial-mesenchymal transition.

The details of the temperature-responsive polymer and temperature-responsive polymer composition of (A) to (C) may be as described above.

In Embodiment (II), the effect of epithelial-mesenchymal transition by an epithelial-mesenchymal transition inducer can be achieved by forming a coated region A by coating at least a portion of a culturing surface of a cell culture container with a temperature-responsive polymer or temperature-responsive polymer composition to prepare a coated cell culture container including the coated region A, next seeding epithelial cells in the coated cell culture container, and subsequently culturing the epithelial cells adhered to the coated region A.

The details of the culture container preparation, cell seeding, and cell culturing are not restricted and may be similar to those of the culture method of epithelial cells of Embodiment (II) and the manufacturing method of a cell structure of Embodiment (II).

[Manufacturing Method of a Cell Structure]

A manufacturing method of a cell structure of Aspect (II) includes a production step of producing a temperature-responsive polymer or a temperature-responsive polymer composition, a culture container preparation step of forming a coated region A by coating at least a portion of a culturing surface of a cell culture container with the temperature-responsive polymer or the temperature-responsive polymer composition to prepare a coated cell culture container including the coated region A, a seeding step of seeding epithelial cells in the coated cell culture container, and a culturing step of forming an aggregated cell structure from the epithelial cells to obtain a cell structure adhered to the coated region A. The concentration of the temperature-responsive polymer or the temperature-responsive polymer composition in the coated region A is 0.3 pg/mm$^2$ or more.

(Production Step)

Examples of the production step in the manufacturing method of a cell structure of Embodiment (II) include a step similar to the production step in the above-described culture method of epithelial cells of Embodiment (II).

(Culture Container Preparation Step)

Examples of the production step in the manufacturing method of a cell structure of Embodiment (II) include a step similar to the production step in the above-described culture method of epithelial cells of Embodiment (II).

In the culture container preparation step I of the production step in the manufacturing method of a cell structure of Embodiment (II), the content of the temperature-responsive polymer in the temperature-responsive polymer solution A is preferably 0.00000009 mass % to 0.0001 mass %, more preferably 0.00000009 mass % to 0.0000009 mass %, relative to the temperature-responsive polymer solution (100 mass %) to facilitate uniform coating of the culturing surface by the temperature-responsive polymer.

The area of the culturing surface of the cell culture container in the production step of the manufacturing method of a cell structure of Embodiment (II) is preferably 200 mm$^2$ or less, more preferably 50 mm$^2$ or less, and even more preferably 10 mm$^2$ or less, to further facilitate manufacturing of a cell structure that includes epithelial cells. The lower limit on the area of the culturing surface of the cell culture container is not restricted, and any commercially available size may be used.

The area of the coated region A in the production step of the manufacturing method of a cell structure of Embodiment (II) is preferably 10 mm$^2$ or less, more preferably 1.0 mm$^2$ or less, and even more preferably 0.1 mm$^2$ or less, so that the cell structure including epithelial cells adheres more firmly to the coated region A and so that the cell structure tends not to peel due to operations such as pipetting.

The area the coated region A relative to the entire area (100%) of the culturing surface of the cell culture container in the production step of the manufacturing method of a cell structure of Embodiment (II) is preferably from 0.1% to 50% and more preferably from 0.1% to 10%.

To facilitate formation of a cell structure, the coated region A preferably not only covers the bottom of the cell culture container but also reaches the side surface.

The amount of temperature-responsive polymer per unit area in the coated region A in the production step of the manufacturing method of a cell structure of Embodiment (II) is 0.3 pg/mm$^2$ or more, preferably 0.3 pg/mm$^2$ to 200 pg/mm$^2$, more preferably 0.3 pg/mm$^2$ to 150 pg/mm$^2$, and even more preferably 0.3 pg/mm$^2$ to 9 pg/mm$^2$. These ranges allow the cell structure to adhere to the coated region A more firmly.

In the production step of the manufacturing method of a cell structure of Embodiment (II), the temperature-responsive polymer or the temperature-responsive polymer composition is preferably applied to the entire culturing surface to obtain a cell structure with abundant secretion of extracellular matrix and high cell activity.

Cell culturing operations are often performed with an automatic incubator when culturing cells in a 384-well plate or a 1536-well plate, for which operations such as medium exchange are difficult to perform manually, or when culturing cells in numerous wells. During operations with an automatic incubator, however, it is difficult to adjust the position of the suction port that suctions the medium in each well to avoid accidentally suctioning suspended cell structures. An automatic incubator thus tends to accidentally suction suspended cell structures, yielding a low culturing efficiency of cell structures. In particular, cell structures of epithelial cells tend not to adhere to the culturing surface, causing frequent accidental suctioning.

If the concentration of the temperature-responsive polymer or the temperature-responsive polymer composition is high at the bottom of the culturing surface (for example, the coated region A) and is low or zero on the side surface, the epithelial cells temporarily adhere to the side surface but tend to peel because of gravity. The epithelial cells that peel off from the side surface and fall onto the bottom assemble to form a cell structure, which adheres firmly to the bottom. Hence, a cell structure of epithelial cells that is easy to produce and is not prone to accidental suction during medium exchange can be formed. Furthermore, if the concentration of the temperature-responsive polymer or the temperature-responsive polymer composition on the side surface is low, the epithelial cells adhere to the side surface once and secrete cell matrix but then peel off and fall to the bottom. A cell structure that includes epithelial cells with high cell activity can thus be obtained.

Examples of a cell culture container in which the concentration of a temperature-responsive polymer or a temperature-responsive polymer composition is high on the bottom of the culturing surface and low on the side surface include a cell culture container having a coated region A on at least a portion of the culturing surface and a coated region B on at least a portion of the culturing surface at a different position than the coated region A. The coated region B is preferably formed to surround the coated region A. For example, by providing the coated region A at the central portion (deepest portion) of a culturing surface with a round bottom and providing the coated region B in the portion other than the coated region A, the epithelial cells on the coated region B fall due to gravity and gather in the coated region A in the central portion to more easily form a cell structure. The formed cell structure adheres firmly to the coated region A and thus tends not to peel off due to operations such as pipetting.

The concentration of the temperature-responsive polymer or the temperature-responsive polymer composition in the coated region B is preferably lower than in the coated region A, is more preferably less than 200 pg/mm$^2$, even more preferably less than 100 pg/mm$^2$, and still more preferably 50 pg/mm$^2$ or less.

The concentration of the temperature-responsive polymer or the temperature-responsive polymer composition in the coated region B is preferably 5% to 90%, more preferably 10% to 50%, of the concentration of the temperature-responsive polymer or the temperature-responsive polymer composition in the coated region A.

The concentration of the temperature-responsive polymer or the temperature-responsive polymer composition in the coated region B may be uniform throughout the region or higher in one portion and lower in other portions. The coated region B may also include a portion without the temperature-responsive polymer or the temperature-responsive polymer composition.

In the production step of the manufacturing method of a cell structure of Embodiment (II), the bottom of the culturing surface (the cross-sectional shape of the bottom) is preferably a round bottom (U-bottom), V-bottom, or uneven bottom to facilitate gathering of the epithelial cells in the deepest portion of the culturing surface for formation of a cell structure. A round bottom (U-bottom, spindle bottom) is particularly preferable to facilitate formation of a spheroidal cell structure.

In a cell culture container having a round bottom (U-bottom, spindle bottom), the radius of curvature R of the contour line of the bottom of the culturing surface in a cross-section along the depth direction of the cell culture container is, on average over the entire round bottom (U-bottom, spindle bottom), preferably 50 mm or less, more preferably 10 mm or less, even more preferably 5 mm or less, and particularly preferably 2 mm or less, and preferably 0.1 mm or more, more preferably 0.2 mm or more, even more preferably 0.4 mm or more, and particularly preferably 0.8 mm or more.

The maximum width L of the cell culture container is preferably 100 mm or less, more preferably 50 mm or less, even more preferably 20 mm or less, and particularly preferably 10 mm or less, and preferably 1 mm or more, more preferably 2 mm or more, even more preferably 3 mm or more, and particularly preferably 4 mm or more.

The deepest portion of the round bottom (U-bottom, spindle bottom) is not limited to the shape illustrated in FIG. 15 and may have a predetermined width in plan view.

Examples of a method of setting the concentration of the temperature-responsive polymer or the temperature-responsive polymer composition to be high in the coated region A and to be lower in the coated region B than in the coated region A include using a culture container provided with a depression at the bottom of the culturing surface (see (i) of FIG. 16), adding a temperature-responsive polymer solution, and drying while the amount of temperature-responsive polymer solution is larger in the depression and smaller on the side surface.

Examples of the shape of the depression are listed above.

(Seeding Step)

Examples of the seeding step in the manufacturing method of a cell structure of Embodiment (II) include a step similar to the seeding step in the above-described culture method of epithelial cells of Embodiment (II).

In the seeding step in the manufacturing method of a cell structure of Embodiment (II), the density of seeded epithelial cells on the coated region A is not restricted, as long as the density is not so low that the epithelial cells die out. For example, a confluency relative to the surface area of the coated region A of 5% to 100% is preferable, a confluency of 50% to 100% is more preferable, and a confluency of 80% to 100% is even more preferable. A cell structure of epithelial cells can more easily be produced if the seeded cell density is within the aforementioned ranges.

In the seeding step, the number of seeded cells is preferably 20 cells/mm$^2$ or more, more preferably 50 cells/mm$^2$ or more, even more preferably 100 cells/mm$^2$ or more, and particularly preferably 500 cells/mm$^2$ or more, and preferably 15,000 cells/mm$^2$ or less, 10,000 cells/mm$^2$ or less, 5,000 cells/mm$^2$ or less, or 1,500 cells/mm$^2$ or less to facilitate formation of a cell structure. For example, when seeding by adding 25 µL of cell fluid to a 384 well cell culture plate with a culturing surface area of 8.4 mm$^2$, the number of cells in the cell fluid is preferably 7 cells/µL to 5040 cells/µL. Live cells are seeded.

(Culturing Step)

The culturing step is a step of forming an aggregated cell structure from the epithelial cells to obtain a cell structure adhered to the coated region A.

The seeded cells are preferably left to stand. The temperature at which the seeded cells are left to stand is not restricted. For example, a temperature of 30° C. or more is preferable, 35° C. to 38° C. is more preferable, and 37° C. is even more preferable.

The time for which the seeded cells are left to stand is not restricted. For example, the cells are preferably cultured for 1 hour to 240 hours and more preferably for 10 hours to 96 hours.

An example manufacturing method of a cell structure of Embodiment (II) is described below with reference to FIGS. 15 and 16.

FIG. 15 illustrates an example manufacturing method of a cell structure that includes epithelial cells.

A temperature-responsive polymer or a temperature-responsive polymer composition is applied to coat a cell culture container having a round culturing surface (for example, a 384-well plate or 1536-well plate), thereby preparing a coated cell culture container including a coated region A (see (i), (ii) of FIG. 15). Subsequently, a cell fluid diluted with medium and including epithelial cells is added to the coated cell culture container (see (iii) of FIG. 15). The seeded epithelial cells adhere to the entire coated region A (see (iv) of FIG. 15). In this example, the density of the epithelial cells is 100% confluency (see (iv) of FIG. 15). By adhering once to the coated region A, the epithelial cells can secrete an extracellular matrix component and maintain high cell activity. The epithelial cells adhered to the side surface in the coated region A peel off from the coated region A because of gravity and gather at the bottom of the culturing surface. The epithelial cells gathered at the bottom adhere to form a cell structure (see (v) of FIG. 15). The formed cell structure is adhered to the coated cell culture container at the culturing surface bottom (see (v) of FIG. 15).

In this example, the concentration of the temperature-responsive polymer or the temperature-responsive polymer composition in the coated region A is such that the epithelial cells adhered to the side surface peel off because of gravity, whereas the epithelial cells adhered to the bottom adhere strongly enough for the cells to tend not to peel off due to operations such as pipetting.

FIG. 16 illustrates an example manufacturing method of a cell structure that includes epithelial cells.

A solution containing a temperature-responsive polymer or a temperature-responsive polymer composition is added to a cell culture container with a round-bottom culturing surface having a depression (recess) on the bottom (for example, a 384-well plate or 1536-well plate). The solution gathers in the depression on the bottom, and the coated region A with a high concentration of the temperature-responsive polymer or the temperature-responsive polymer composition forms in the depression. On the other hand, the coated region B with a lower concentration of the temperature-responsive polymer or the temperature-responsive polymer composition than the coated region A forms on the side surface, because the amount of solution on the side surface is less than in the depression. A coated cell culture container including the coated region A and the coated region B is thus prepared (see (i) and (ii) of FIG. 16). In the coated region B on the side surface, epithelial cells adhere temporarily but then tend to peel because of gravity. The epithelial cells that fall after peeling off from the side surface assemble to form a cell structure that firmly adheres to the coated region A on the bottom. This helps to avoid accidental suction during medium exchange (see (ii) of FIG. 16). A cell fluid diluted with medium and including epithelial cells is added to the coated cell culture container (see (iii) of FIG. 16). The seeded epithelial cells adhere to the coated region A and the coated region B (see (iv) of FIG. 16). In this example, the density of the epithelial cells is 100% confluency (see (iv) of FIG. 16). By adhering once to the coated region A and the coated region B, the epithelial cells can secrete an extracellular matrix component and maintain high cell activity. The epithelial cells adhered to the side surface in the coated region B peel off from the coated region B because of gravity and gather at the bottom of the culturing surface. The epithelial cells gathered at the bottom adhere and form a cell structure (see (v) of FIG. 16). The formed cell structure is adhered to the coated cell culture container at the coated region A (see (v) of FIG. 16).

[Cell Culture Container for Epithelial Cells]

A cell culture container for epithelial cells of Aspect (II) includes a coated region A, coated with a temperature-responsive polymer or a temperature-responsive polymer composition, on at least a portion of the culturing surface. The concentration of the temperature-responsive polymer or the temperature-responsive polymer composition in the coated region A is 0.3 pg/mm$^2$ or more.

Epithelial cells do not easily peel off during culturing with the cell culture container for epithelial cells of Aspect (II), allowing epithelial cells to be cultured easily. A cell structure containing epithelial cells can also be manufactured easily.

Examples of the temperature-responsive polymer and the temperature-responsive polymer composition in the cell culture container for epithelial cells of Embodiment (II) include the above-described examples.

Examples of the cell culture container for epithelial cells of Embodiment (II) include the above-described coated cell culture container. The cell culture container for epithelial cells of Embodiment (II) may, for example, be manufactured by the above-described production step and culture container preparation step.

[[Aspect (III)]]

[Production Apparatus of Three-Dimensional Tissue Body]

A production apparatus of a three-dimensional tissue body of Embodiment (III) includes a culturing surface having one or more through holes, a shaft inserted through the one or more through holes, and one or more coated culturing surfaces where the culturing surface is coated by a temperature-responsive polymer or a temperature-responsive polymer composition. At least one of the one or more through holes is located within one of the one or more coated culturing surfaces, and the culturing surface is movable in an extending direction of the shaft.

In Aspect (III), the "cloud point" of the polymer does not necessary have the strict meaning of "a predetermined temperature such that the polymer dissolves below the temperature but becomes insoluble and precipitates at or above the temperature", but also refers to "a predetermined temperature such that below the temperature, 10 minutes or more are required to dissolve a polymer that has become insoluble and precipitated".

The production apparatus of a three-dimensional tissue body of Embodiment (III) has few components, is relatively easy to use as a medical product, and has a low risk of infection. The production apparatus can also be placed inside a sealed plastic container to produce a three-dimensional tissue body hygienically and aseptically. By having few components and being small, the production apparatus can also reduce the amount of waste when disposed of as a medical product.

(Shaft)

The shaft is not restricted, as long as the dimensions of the resulting three-dimensional tissue body are stable. Examples of the material for the shaft include plastics such as polystyrene, polyethylene terephthalate (PET), polypropylene, polybutene, polyethylene, acrylic resin, polyurethane resin, urea resin, and polycarbonate; rubber elastomers such as silicon rubber, chloroprene rubber (such as Neoprene®), and SBR; ceramic; glass; and metallic/inorganic material such as stainless steel, titanium, and Nitinol® (Neoprene and Nitinol are registered trademarks in Japan, other countries, or both). Among these, plastics such as polystyrene, polyurethane resin, acrylic resin, and polycarbonate; and metals such as stainless steel and Nitinol® are preferred for allowing application of various sterilization methods, producing little eluate, and having a track record as a medical material.

The surface of the shaft may be cell adhesive or cell non-adhesive. The surface of the shaft is preferably cell non-adhesive, however, to facilitate retaining the structure of the three-dimensional tissue body wound around the shaft. Proteins are preferably not included on the surface of the shaft to facilitate peeling (removal) from the shaft of a three-dimensional tissue body including substances secreted from cells.

The cell adhesiveness of the shaft surface can be adjusted by a method of coating the shaft surface with a cell adhesive substance, a method of covering the shaft surface with a film of cell adhesive substance, a method of performing radiation/plasma discharge to introduce a cell adhesive molecular group into the shaft surface, and the like.

Examples of the cell adhesive substance include laminin, collagen, fibronectin, peptides, cationic polymers, and polystyrene. Examples of the peptides include peptides containing an arginine-glycine-aspartic acid sequence and peptides containing a sequence of 8 or more consecutive arginine residual groups. Examples of the cationic polymers include aminostyrene. Among these, laminin, collagen, and fibronectin, which have high cell adhesiveness, are preferable. Reagents containing the above-listed cell adhesive substances can also be suitably used. Examples of such reagents include serum.

The ringed three-dimensional tissue body that winds around the shaft is covered by an extracellular matrix secreted by the tissue body itself. Hence, the three-dimensional tissue body can be wound around the shaft without performing a process to make the surface of the shaft cell adhesive.

"Cell adhesive" refers to adherent cells (for example, vascular endothelial cells, vascular cells, chondrocytes, fibroblasts, and the like) adhering under normal culture conditions. "Cell adhesive" thus also includes the case of "low-adhesive".

The three-dimensional tissue body with a ringed shape, a luminal shape, or the like formed to be wound around the shaft can be peeled off the shaft surface even when the shaft surface is cell adhesive. When the shaft surface is cell non-adhesive, such as Teflon® (Teflon is a registered trademark in Japan, other countries, or both), silicon rubber, or a hydrophilic coating, then by covering the shaft surface with a collagen tube, for example, the three-dimensional tissue body with a ringed shape, a luminal shape, or the like can be removed together with the collagen tube.

Examples of the cross-sectional shape of the shaft in a plane perpendicular to the extending direction (length direction) of the shaft include a substantially circular shape, a substantially polygonal shape, a half-moon shape, a crescent shape, a string shape, and a tear shape. Among these, a substantially circular shape is preferred to obtain a three-dimensional tissue body close to the shape of a cartilaginous ring, a blood vessel, the trachea, or the like. In other words, the shaft preferably has a substantially cylindrical shape.

The cross-sectional shape of the shaft may be the same or different along the extending direction in a plane perpendicular to the extending direction.

The shape of the shaft in the extending direction may be linear (see FIGS. 18 to 20) or curved, such as a C-shape, a U-shape, or a spiral.

The dimensions of the shaft are not restricted. For example, the length of the shaft is preferably 0.1 mm to 600 mm and more preferably 1 mm to 300 mm. When the cross-sectional shape of the shaft in a plane perpendicular to the extending direction is substantially circular, the maximum diameter thereof is preferably 0.01 mm to 150 mm and more preferably 0.1 mm to 50 mm.

The shaft surface may be smooth or uneven. The surface may include a hole or may be a mesh or a porous surface with multiple pores.

The shaft may also be hollow.

Among these options, the shaft is preferably hollow, and the shaft surface is preferably porous, because this configuration can maintain high cell activity by stable providing medium components and oxygen to all of the cells included in the three-dimensional tissue body wound around the shaft and can rapidly eliminate cell metabolites.

When the shaft is a porous material constituted by a sponge-like continuous foam, cells might infiltrate into the shaft, and cells that infiltrate deeply might die out, or the formed three-dimensional tissue body and the shaft might adhere stubbornly, making it difficult to peel off the three-dimensional tissue body. The maximum hole diameter on the shaft surface is therefore preferably 200 μm or less. When the shaft is constituted by a fiber assembly, such as a woven fabric of metallic fiber, the cells adhere easily to the shaft surface, and the fiber assembly might affect cell differentiation. The maximum hole diameter is therefore preferably 10 μm or more in this case.

When a plurality of shafts are used, the material, dimensions, shape, and the like of each shaft may be the same or different. The distance between shafts is not restricted, and shafts may be in contact with each other, for example.

(Culturing Surface)

At least a portion of the culturing surface includes at least one coated culturing surface that is coated by a temperature-responsive polymer or a temperature-responsive polymer composition. One coated culturing surface or a plurality of coated culturing surfaces may be provided on the culturing surface.

When one coated culturing surface is provided, the entire culturing surface may be the coated culturing surface (see FIGS. 18, 20), or a portion may be the coated culturing surface (see FIG. 19). Between these options, the entire culturing surface is preferably the coated culturing surface for greater manufacturing ease.

When the culturing surface is double sided, such as a plate or disc, either one side or both sides may be the coated culturing surface.

Examples of the material of the culturing surface include polystyrene, polyethylene terephthalate (PET), polypropylene, polybutene, polyethylene, polycarbonate, glass, silicon resin, acrylic resin, and polyurethane resin. Among these, polystyrene, polyethylene terephthalate, glass, silicon resin, and acrylic resin are preferable for being easy to mold precisely and for allowing adoption of various sterilization methods.

Cell adhesion treatment or the like may be applied to the culturing surface, or the surface may be untreated. The culturing surface may be coated, processed, or the like to adjust the cell adhesiveness.

The planar shape of the culturing surface is not restricted and may, for example, be a substantially polygonal shape (a substantially polygonal shape having a through hole) such as a substantially rectangular shape, a substantially circular shape (a substantially circular shape having a through hole, such as a ring), or the like.

The area of the culturing surface is preferably 0.1 $mm^2$ to 150 $cm^2$, more preferably 8.4 $mm^2$ to 21 $cm^2$, to further facilitate manufacturing of a three-dimensional tissue body with a ringed shape, a luminal shape, or the like.

The bottom shape of the culturing surface (the cross-sectional shape of the bottom) is not restricted, and examples include a flat bottom, round bottom, and uneven bottom.

Among these, a flat bottom is preferable to facilitate obtaining a three-dimensional tissue body with a ringed shape, a luminal shape, or the like.

A plurality (for example, 2 or more, 5 or more, 10 or more, or the like) of culturing surfaces may be provided to allow simultaneous formation of a plurality of three-dimensional tissue bodies and to allow more efficient formation of three-dimensional tissue bodies with a luminal shape in a shorter time. No upper limit is placed on the number of culturing surfaces, as long as the number is in a range allowing seeding, culturing, and the like of cells and allowing production of three-dimensional tissue bodies.

When a plurality of culturing surfaces are provided, one shaft is preferably inserted through the through hole of at least two of the culturing surfaces, and one shaft is more preferably inserted through the through hole of all of the culturing surfaces.

The production apparatus of a three-dimensional tissue body of Embodiment (III) may, for example, have one or a plurality of members in which a shaft is inserted through a plurality of culturing surfaces (i.e. a member constituted by a shaft and a plurality of culturing surfaces, with the culturing surfaces disposed like shelves in the extending direction of the shaft).

When a plurality of culturing surfaces are provided, the distances between culturing surfaces in the extending direction of the shaft may be the same or different. For example, the distance between culturing surfaces in the extending direction of the shaft is preferably 10 times or less and more preferably 7.5 times or less the length, in the extending direction of the shaft, of the cells to be used to facilitate connection between ringed or luminal three-dimensional tissue bodies produced on the culturing surfaces. Specifically, the distance between culturing surfaces in the extending direction of the shaft is preferably 0.1 mm to 10 mm, more preferably 0.2 mm to 2.0 mm.

Connection of ringed or luminal three-dimensional tissue bodies produced on the culturing surfaces includes not only adhesion between cells constituting the ringed or luminal three-dimensional tissue bodies produced on the culturing surfaces, but also connection between ringed or luminal three-dimensional tissue bodies, produced on the culturing surfaces, via proteins secreted by cells constituting the ringed or luminal three-dimensional tissue bodies produced on the culturing surfaces (such as proteins constituting the extracellular matrix).

Examples of the temperature-responsive polymer or the temperature-responsive polymer composition of the coated culturing surface include those listed below in the production step.

The content of the temperature-responsive polymer or the temperature-responsive polymer composition per unit area of the coated culturing surface is preferably 5 ng/mm$^2$ to 50 ng/mm$^2$, more preferably 15 to 40 ng/mm$^2$, to facilitate obtaining a three-dimensional tissue body with a ringed shape, a luminal shape, or the like.

When a plurality of coated culturing surfaces are provided, the content of the temperature-responsive polymer or the temperature-responsive polymer composition included per unit area of the coated culturing surfaces may be the same or different on the coated culturing surfaces.

The planar shape of the coated culturing surface is not restricted and may, for example, be a substantially polygonal shape (a substantially polygonal shape having a through hole) such as a substantially rectangular shape, a substantially circular shape (a substantially circular shape having a through hole, such as a ring), or the like. Among these, a substantially circular shape is preferred to facilitate obtaining a three-dimensional tissue body with a more homogeneous distribution of cells.

When a plurality of coated culturing surfaces are provided, the planar shape of the coated culturing surfaces may be the same or different.

The surface area of the coated culturing surface is preferably 0.1 mm$^2$ to 150 cm$^2$, more preferably 8.4 mm$^2$ to 21 cm$^2$, to facilitate obtaining a three-dimensional tissue body with a more homogeneous distribution of cells. When a plurality of coated culturing surfaces are provided, the surface areas of the coated culturing surfaces may be the same or different.

If the area of the coated culturing surface is small, the number of cells wound around the shaft decreases, facilitating formation of a three-dimensional tissue body with cell matrix as the principal component. The area of the coated culturing surface when forming a three-dimensional tissue body with cell matrix as the principal component may, for example, be 0.1 mm$^2$ to 50 mm$^2$.

The surface area of the coated culturing surface can be measured with a method well known to a person skilled in the art, such as image analysis of a photomicrograph.

The zeta potential of the coated culturing surface is preferably 0 mV to 50 mV, more preferably 0 mV to 35 mV, and even more preferably 10 mV to 25 mV. A zeta potential of 0 mV or more facilitates adhesion of negatively charged cells. A zeta potential of 50 mV or less can reduce cytotoxicity.

Furthermore, setting the zeta potential in the aforementioned ranges allows the seeded cells to be formed into a ringed three-dimensional tissue body wound around a shaft by simply culturing cells under appropriate culture conditions. The reason is that setting the surface zeta potential within the aforementioned ranges is inferred to provide the coated culturing surface with a weak positive charge that does not trigger cytotoxicity, to ensure rapid adhesion of the seeded cells, to improve cell activity and encourage secretion of extracellular matrix, and also to appropriately inhibit cell migration, strengthening the bond between cells.

When a plurality of coated culturing surfaces are provided, the zeta potential of the coated culturing surfaces may be the same or different.

The zeta potential refers to the value calculated with the Smoluchowski equation by measurement using a zeta potential meter (for example, model "ELSZ" by Otsuka Electronics Co.) with a particle (zeta potential: −5 mV to +5 mV) in which polystyrene latex is coated with hydroxypropyl cellulose as a reference monitor particle.

The contact angle of water relative to the coated culturing surface is preferably 50° to 90°, more preferably 60° to 80°, and even more preferably 620 to 780 to increase the effects of Aspect (III). When a plurality of coated culturing surfaces are provided, the contact angle of water relative to each coated culturing surface may be the same or different.

The contact angle of water relative to the coated culturing surface refers to the average contact angle measured in accordance with JIS R3257 at any number of points on the coated culturing surface.

The culturing surface includes at least one through hole. When one through hole is included, the through hole is preferably in the central portion of the culturing surface. Insertion of the shaft through the through hole yields a production apparatus of a three-dimensional tissue body in which the culturing surface and the shaft are integrated.

The planar shape of the through hole is not restricted and may, for example, be a substantially polygonal shape or a substantially circular shape. The planar shape of the through hole is preferably the same as the cross-sectional shape of the shaft in a plane perpendicular to the extending direction of the shaft to facilitate obtaining a three-dimensional tissue body with a more uniform distribution of cells. Among these options, the cross-sectional shape of the shaft in a plane perpendicular to the extending direction of the shaft and the planar shape of the through hole are preferably both substantially circular (see FIGS. 18 to 20).

As long as the shaft can be inserted through the through hole, the shape of the through hole may be the same as or different from the cross-sectional shape of the shaft in a plane perpendicular to the extending direction of the shaft. When a plurality of through holes are provided, the planar shape of each through hole may be the same or different.

At least one of the through holes is provided within the coated culturing surface, and preferably only one is provided.

The through hole is provided within the coated culturing surface, one through hole is preferably provided in the central portion of the coated culturing surface, and the one through hole is more preferably provided in a portion including the center of mass of the coated culturing surface. When the coated culturing surface is substantially circular, the through hole is preferably provided in the region within 0.75 r from the center of the coated culturing surface (where r is the radius of the coated culturing surface). If the through hole is provided in the central portion of the coated culturing surface, the direction in which cells aggregate can be concentrated towards the central portion, allowing production of a three-dimensional cell body with a more homogeneous distribution of cells. Shifting the through hole from the central portion of the coated culturing surface allows production of a three-dimensional tissue body in which the thickness of the ring is not uniform.

One through hole is preferably provided within one coated culturing surface to facilitate obtaining a three-dimensional tissue body with a good dimensional shape.

When a plurality of coated culturing surfaces are provided in the production apparatus of Embodiment (III), it suffices to provide at least one through hole within at least one coated culturing surface among all of the coated culturing surfaces. The number of coated culturing surfaces and the number of through holes may be equal, with one through hole provided within each coated culturing surface. For example, the production apparatus of Embodiment (III) may be a production apparatus that includes five coated culturing surfaces and one through hole, with five coated culturing surfaces provided on the culturing surface and the one through hole provided within one of the coated culturing surfaces; a production apparatus that includes five coated culturing surfaces and five through holes, with five coated culturing surfaces provided on the culturing surface and one through hole provided within each coated culturing surface; or the like.

The surface area of the through hole is preferably 0.1 mm$^2$ to 150 cm$^2$, more preferably 8.4 mm$^2$ to 21 cm$^2$. When the through hole is substantially circular, the maximum diameter is preferably 0.01 mm to 150 mm. When a plurality of through holes are provided, the surface area of each through hole may be the same or different.

On a coated culturing surface provided with one through hole within the coated culturing surface, the ratio of the surface area of the through hole to the surface area of the coated culturing surface (100%) is preferably 0.1% to 50%, more preferably 1% to 30%. A ratio within the aforementioned ranges further facilitates obtaining a three-dimensional tissue body wound around the shaft.

(Positional Relationship Between Shaft and Culturing Surface) It suffices for the shaft to be inserted through the through hole. The shaft and culturing surface may be in contact (see FIGS. 18, 19), or a gap may be provided between the shaft and culturing surface (see FIG. 20). The gap between the shaft and the culturing surface is preferably a distance allowing aggregated cells to jump over the gap and wind around the shaft and/or a distance at which a three-dimensional tissue body wound around the shaft does not peel off when the culturing surface is moved in the extending direction of the shaft. The gap is more preferably 5.0 mm or less and even more preferably 0.5 mm or less.

When a plurality of the culturing surfaces are provided, a gap is preferably provided between the shaft and the culturing surface to facilitate a uniform distribution of cells on each culturing surface and to facilitate connection of the ringed or luminal three-dimensional tissue bodies produced on the culturing surfaces.

The culturing surface is movable in the extending direction of the shaft and is preferably moveable in the direction from the coated culturing surface toward the culturing surface to achieve a low risk of the three-dimensional tissue body wound around the shaft suffering physical stress due to medium flow produced when the culturing surface is moved and to facilitate obtaining a three-dimensional tissue body with a ringed shape, a luminal shape, or the like. The angle between the culturing surface and the extending direction of the shaft is not restricted, but a right angle is preferable.

When a plurality of through holes are provided, a shaft may be inserted through all of the through holes or only a portion of the through holes. A shaft is preferably inserted through all of the through holes to prevent the seeded cells from falling below the culturing surface and to allow the seeded cells to adhere to the coated culturing surface.

An example of a production apparatus of a three-dimensional tissue body of Embodiment (III) is described below with reference to FIGS. 18 to 20 and FIG. 25. The production apparatuses in FIGS. 18 to 20 and FIG. 25 is preferable for having few components, being relatively easy to use as a medical product, having a low risk of infection, and allowing easy production of biotubes. Among these apparatuses, the production apparatuses of a three-dimensional tissue body in FIG. 20 and FIG. 25 are preferable to further facilitate obtaining a three-dimensional tissue body with a ringed shape, a luminal shape, or the like.

FIG. 18 is an outline of an example production apparatus of a three-dimensional tissue body of Embodiment (III).

In this example, a coated culturing surface coated by a temperature-responsive polymer or a temperature-responsive polymer composition is provided on one entire side of a disc-shaped culturing surface. The coated culturing surface has a through hole in the central portion, and a cylindrical shaft is inserted through the through hole. The coated culturing surface and the shaft are in contact, with no gap therebetween. The culturing surface is perpendicular to the extending direction of the shaft and is movable in the extending direction of the shaft. The culturing surface in FIGS. 18 to 21 is movable both in the upward direction (from the culturing surface towards the coated culturing surface) and downward direction (from the coated culturing surface towards the culturing surface) of the figures. The direction in which the culturing surface moves, the movement distance, and/or the movement timing may, for example, be controlled by a computer or the like automatically.

FIG. 19 is an outline of an example production apparatus of a three-dimensional tissue body of Embodiment (III).

In this example, a coated culturing surface coated by a temperature-responsive polymer or a temperature-responsive polymer composition is provided on a portion of one side of a disc-shaped culturing surface.

FIG. 20 is an outline of an example production apparatus of a three-dimensional tissue body of Embodiment (III).

In this example, a coated culturing surface coated by a temperature-responsive polymer or a temperature-responsive polymer composition is provided on one entire side of a disc-shaped culturing surface. A gap is provided between the coated culturing surface and the shaft. In other words, the diameter of the shaft is less than the hole diameter of the through hole.

FIG. 25 is an outline of an example production apparatus of a three-dimensional tissue body of Embodiment (III).

In this example, two disc-shaped culturing surfaces are provided, and a coated culturing surface coated by a temperature-responsive polymer or a temperature-responsive polymer composition is provided on one entire side of each culturing surface. One shaft is inserted through the through holes of the two culturing surfaces, and ringed or luminal three-dimensional tissue bodies can be formed simultaneously on the two culturing surfaces. A gap is provided between each coated culturing surface and the shaft. By adjustment of the distance between the two culturing surfaces, the ringed or luminal three-dimensional tissue bodies produced on the two culturing surfaces can easily be connected by adhesion between cells included in the three-dimensional tissue bodies or via proteins secreted by the cells included in the three-dimensional tissue bodies.

(Manufacturing Method of Production Apparatus of Three-Dimensional Tissue Body)

Examples of manufacturing methods of a production apparatus of a three-dimensional tissue body of Embodiment (III) include a method including a production step of producing a temperature-responsive polymer or a temperature-responsive polymer composition and a coated culturing surface preparation step of coating the culturing surface with the temperature-responsive polymer or the temperature-responsive polymer composition to prepare a coated culturing surface.

—Production Step—

Examples of the production step in Embodiment (III) include a step similar to the production step in Aspect (I), and a similar step is preferred.

The temperature-responsive polymer and temperature-responsive polymer composition used in the culture method in Embodiment (III) are preferably (A) to further facilitate obtaining a three-dimensional tissue body with a ringed shape, a luminal shape, or the like.

The production step of producing a mixture containing 2-N,N-dimethylaminoethyl methacrylate (DMAEMA) in Embodiment (III) is also referred to as a mixture production step.

In Embodiment (III), the temperature-responsive polymer of (A-1) allows formation of a three-dimensional tissue body with a ringed shape, a luminal shape, or the like by culturing cells under appropriate culture conditions, as described below.

In Embodiment (III), the temperature-responsive polymer of (A-2) allows formation of a three-dimensional tissue body with a ringed shape, a luminal shape, or the like by culturing cells under appropriate culture conditions, as described below.

In Embodiment (III), the temperature-responsive polymer of (B) allows formation of a three-dimensional tissue body with a ringed shape, a luminal shape, or the like by culturing cells under appropriate culture conditions, as described below.

In Embodiment (III), use of a mixed-type temperature-responsive polymer composition with the above ratio facilitates formation of a three-dimensional tissue body in the below-described culturing step.

Setting the C/A ratio to be 0.5 to 16 in Embodiment (III) facilitates achievement of the aforementioned effect of easier formation of a three-dimensional tissue body with a ringed shape, a luminal shape, or the like.

—Coated Culturing Surface Preparation Step—

The coated culturing surface preparation step is a step of coating a culturing surface with the temperature-responsive polymer or the temperature-responsive polymer composition to prepare a coated culturing surface.

The coated culturing surface preparation step may, for example, be a step of dissolving a temperature-responsive polymer or a temperature-responsive polymer composition in a solvent to form a temperature-responsive polymer solution, applying the solution onto a culturing surface, and drying to prepare a coated culturing surface (coated culturing surface preparation step I), or a step of cooling an aqueous solution including a temperature-responsive polymer or a temperature-responsive polymer composition (temperature-responsive polymer aqueous solution) to the cloud point of the temperature-responsive polymer or below, casting the cooled temperature-responsive polymer aqueous solution onto a culturing surface, and heating to a temperature above the cloud point to prepare a coated culturing surface (coated culturing surface preparation step II).

Examples of the solvent in the temperature-responsive polymer solution in the coated culturing surface preparation step I include water; physiological saline; buffer solutions; alcohols such as methanol, ethanol, n-propyl alcohol, isopropyl alcohol, 1-butanol, isobutyl alcohol, 2-butanol, t-butyl alcohol, 1-pentanol, 2-pentanol, 3-pentanol, 2-methyl-1-butanol, 3-methyl-1-butanol, 2-methyl-2-butanol, 3-methyl-2-butanol, 2,2-dimethyl-1-propanol, 1-pentanol, 2-pentanol, 3-pentanol, 2-methyl-1-butanol, 3-methyl-1-butanol, 2-methyl-2-butanol, 3-methyl-2-butanol, 2,2-dimethyl-1-propanol, 1-hexanol, 2-methyl-2-pentanol, allyl alcohol, benzyl alcohol, and salicyl alcohol; ketones such as acetone, ethyl methyl ketone, diethyl ketone, methyl propyl ketone, methyl isobutyl ketone, methyl vinyl ketone, cyclohexanone, 2-methyl cyclopentanone, acetophenone, benzophenone, and isophorone; esters such as methyl acetate, ethyl acetate, propyl acetate, isopropyl acetate, n-butyl acetate, isobutyl acetate, sec-butyl acetate, tert-butyl acetate, vinyl acetate, methyl formate, ethyl formate, propyl formate, esters of the aforementioned alcohols and phosphoric acid, and esters of the aforementioned alcohols and carbonic acid; chloroform; benzene; toluene; diethyl ether; and dichloromethane.

Among these, water; alcohols such as methanol, ethanol, n-propyl alcohol, isopropyl alcohol, 2-butanol, t-butyl alcohol, and allyl alcohol; ketones such as acetone, ethyl methyl ketone, diethyl ketone, and methyl vinyl ketone; esters such as methyl acetate, ethyl acetate, isopropyl acetate, tert-butyl acetate, and vinyl acetate; chloroform; benzene; toluene; diethyl ether; and dichloromethane are preferred for facilitating uniform coating of the culturing surface and for having excellent solubility of temperature-responsive polymers. An organic solvent with a low boiling point (such as at least one selected from the group consisting of a low-molecular alcohol with 1 to 4 carbon atoms, a low-molecular ketone with 3 to 5 carbon atoms, and an acetic acid alkyl ester having an alkyl group with 1 to 4 carbon atoms; in particular, at least one selected from the group consisting of a low-molecular alcohol with 1 to 4 carbon atoms, a low-molecular ketone with 3 to 5 carbon atoms, and an acetic acid alkyl ester having an alkyl group with 1 to 4 carbon atoms, the low-molecular alcohol, low-molecular ketone, and acetic acid alkyl ester having a boiling point lower than that of water) is more preferable for allowing drying in a short time and facilitating even more uniform application on the culturing surface. Methanol and ethanol are particularly preferable for their low cost and excellent operability.

One type of these solvents may be used alone, or a combination of two or more types may be used.

Since the solvent has excellent solubility with respect to a temperature-responsive polymer, the temperature-responsive polymer tends not to become insoluble and precipitate even at a temperature equal to or greater than the cloud point (such as room temperature or 37° C.). This eliminates the need to manage the temperature of the temperature-responsive polymer during application of the temperature-responsive polymer, allowing easy preparation of a coated culturing surface.

In the coated culturing surface preparation step I, it may be preferable to include a hydrophilic molecule in the temperature-responsive polymer solution to facilitate self-aggregation of cells depending on the type of cells to be used, such as when using highly adhesive mesenchymal cells or cancer cells with low aggregation strength. Examples of the hydrophilic molecule include non-ionic, hydrophilic molecules that do not affect the C/A ratio of the temperature-responsive polymer, such as polyethylene glycol (PEG), dimethyl acrylamide (DMAA), glycerin, Triton X, polypropylene glycol, and the like.

In the coated culturing surface preparation step I, the content of the temperature-responsive polymer in the temperature-responsive polymer solution is preferably 0.0010 mass % to 3.0 mass %, more preferably 0.0012 mass % to 2.5 mass %, relative to the temperature-responsive polymer solution (100 mass %) to facilitate uniform coating of the culturing surface by the temperature-responsive polymer.

In the coated culturing surface preparation step I, the content of the hydrophilic molecule in the temperature-responsive polymer solution is preferably 0.00001 mass % to 0.00015 mass %, more preferably 0.00003 mass % to 0.0001 mass %, relative to the temperature-responsive polymer (100 mass %) to facilitate self-aggregation of cells.

In the coated culturing surface preparation step I, the temperature-responsive polymer solution may be applied to the entire culturing surface or to a portion of the culturing surface. When the temperature-responsive polymer solution is applied to a portion of the culturing surface, one coated culturing surface or a plurality of coated culturing surfaces may be provided on the culturing surface. A cell culture container with a cell non-adhesive culturing surface is preferably used when the temperature-responsive polymer solution is applied to a portion of the culturing surface.

In the coated culturing surface preparation step I, preferred conditions for drying the applied temperature-responsive polymer solution are drying under atmospheric pressure at a temperature of 10° C. to 70° C. for 1 to 3,000 minutes to uniformly coat the culturing surface with the temperature-responsive polymer or the temperature-responsive polymer composition. Quick drying of the applied temperature-responsive polymer solution facilitates uniform coating on the culturing surface with an even distribution of the temperature-responsive polymer or the temperature-responsive polymer composition.

The applied temperature-responsive polymer solution may, for example, be dried by letting the cell culture container stand in an incubator at 37° C. or 40° C.

In the coated culturing surface preparation step II, examples of the solvent for dissolving the temperature-responsive polymer or the temperature-responsive polymer composition include water; physiological saline; and buffer solutions such as a phosphate buffer solution, phosphate buffered saline (PBS), and a tris buffer solution.

In the coated culturing surface preparation step II, examples of the method of cooling the temperature-responsive polymer aqueous solution include placing the temperature-responsive polymer aqueous solution in a refrigerator at approximately 4° C. and cooling to a temperature at or below the cloud point.

In the coated culturing surface preparation step II, examples of the method of casting the temperature-responsive polymer aqueous solution onto the culturing surface include a method of tilting the culturing surface to spread the temperature-responsive polymer aqueous solution that has a temperature at or below the cloud point and a method of spreading the temperature-responsive polymer aqueous solution using a spatula.

In the coated culturing surface preparation step II, examples of the method of heating the cast temperature-responsive polymer aqueous solution to above the cloud point include a method of letting the culturing surface after the casting step stand in an incubator at 37° C.

[Production Method of Three-Dimensional Tissue Body]

The above-described production apparatus of a three-dimensional tissue body of Embodiment (III) is used in a production method of a three-dimensional tissue body of Embodiment (III).

The production method of a three-dimensional tissue body of Embodiment (III) includes a seeding step of seeding at least one type of cells on the coated culturing surface (also referred to as the "first seeding step" in Aspect (III)) and a culturing step of culturing the seeded cells to obtain a ringed three-dimensional tissue body wound around the shaft (also referred to as the "first culturing step" in Aspect (III)).

In Aspect (III), the three-dimensional tissue body, wound around the shaft, that is obtained in the first seeding and culturing step is also referred to as a "ringed three-dimensional tissue body", and the three-dimensional tissue body in which a plurality of ringed three-dimensional tissue bodies are stacked is also referred to as a "luminal three-dimensional tissue body".

Operations of the first seeding step and the first culturing step may be controlled by a computer or the like to be performed automatically, since operations performed automatically may be more aseptic and hygienic by virtue of not being performed by hand.

(First Seeding Step)

Examples of the cells seeded in the seeding step include vascular cells such as vascular endothelial cells and vascular smooth muscle cells, cardiomyocytes, chondrocytes, nerve cells, adipocytes, adipose stem cells, hepatocytes, fibroblasts, renal cells, smooth muscle cells, iPS cells, and ES cells. When manufacturing a three-dimensional tissue body having extracellular matrix as the principal component, the cells are preferably vascular cells such as vascular endothelial cells and vascular smooth muscle cells, cardiomyocytes, chondrocytes, nerve cells, adipocytes, adipose stem cells, hepatocytes, fibroblasts, renal cells, or smooth muscle cells and are more preferably fibroblasts or mesenchymal cells. One type of these cells may be used alone, or a combination of two or more types may be used.

In particular, use of vascular endothelial cells and smooth muscle cells allows a synthetic blood vessel to be obtained. Use of chondrocytes and fibroblasts allows a synthetic trachea to be obtained. Established cells (such as COS cells) that have a promoter such as an SV40 promoter, have an introduced expression vector incorporating genes expressing proteins constituting extracellular matrix such as elastin or collagen, and express a large T antigen may be used when manufacturing a three-dimensional tissue body including material secreted by cells, such as substances constituting extracellular matrix. Use of the established cells such as COS cells allows support of a copy of the introduced genes, and a large amount of gene expression allows efficient manufacturing of a three-dimensional tissue body having extracellular matrix as the principal component.

In the seeding step, the density of all of the seeded cells on the coated culturing surface is preferably a confluency of 90% to 100% relative to the surface area of the coated culturing surface, more preferably a confluency of 95% to 100%, and even more preferably a confluency of 99% to 100%. The properties of the seeded cells may change during growth. Setting the density of seeded cells within the aforementioned ranges makes it more difficult for the seeded cells to grow and allows formation of a ringed three-dimensional tissue body wound around the shaft before cells grow, thereby allowing formation of a three-dimensional tissue body that includes cells with the same properties as at the time of seeding.

While the density of all of the seeded cells on the coated culturing surface depends on the type of cell, a density of 20 cells/mm$^2$ to 15,000 cells/mm$^2$ is preferred. Live cells are seeded.

In the seeding step, a wall surface may be provided on the outer edge of the culturing surface to prevent seeded cells from being dispersed below the culturing surface and to facilitate adhesion of the cells to the coated culturing surface. The production apparatus of a three-dimensional tissue body of Embodiment (III) may be placed inside a container with a slightly larger inner diameter than the outer diameter of the culturing surface (see FIG. 21). As a result, seeded cells tend not to fall below the culturing surface, and seeded cells can be caused to adhere to the coated culturing surface. The difference between the outer diameter of the culturing surface and the inner diameter of the container is preferably 15.0 mm or less to prevent seeded cells from falling through the gap and so as not to block expansion of the medium.

The production apparatus of a three-dimensional tissue body may be left to stand in an incubator at 37° C. and subsequently removed and placed on a clean bench at room temperature, for example, with cell seeding then being performed.

Cells are preferably seeded after being diluted in a medium. The medium for dilution may be any medium in which cells can be cultured.

(First Culturing Step)

The conditions for culturing the seeded cells may, for example, be the use of a typical cell incubator at 37° C. The cells are preferably cultured continuously until obtaining a ringed three-dimensional tissue body wound around the shaft. Specifically, the cells are preferably cultured for 10 hours to 96 hours and more preferably for 15 hours to 48 hours.

The cells adhered to and cultured on the coated culturing surface self-aggregate towards the inside of the coated culturing surface and wind around the shaft in the form of a ring. The ringed three-dimensional tissue body wound around the shaft has living cells inside the three-dimensional tissue body.

Examples of the ringed three-dimensional tissue body wound around the shaft include a three-dimensional tissue body with cells as the principal component and may be a three-dimensional tissue body composed of cells. The ringed three-dimensional tissue body wound around the shaft may be a three-dimensional tissue body with extracellular matrix as the principal component, the extracellular matrix being constructed by secretion of proteins or the like that constitute extracellular matrix. The ringed three-dimensional tissue body wound around the shaft may be a three-dimensional tissue body including substances secreted from cells (for example, proteins such as those constituting extracellular matrix), a three-dimensional tissue body having substances secreted from cells as the principal component, or a three-dimensional tissue body composed only of substances secreted from cells. Examples of the substances secreted from cells include proteins, sugars, and lipids, with proteins being preferred.

"Having as a principal component" refers to exceeding 50 mass % relative to the mass of the three-dimensional tissue body (100 mass %), with 60 mass % or more being preferable and 70 mass % or more being more preferable.

The three-dimensional tissue body is preferably obtained by seeding cells on all of the coated culturing surfaces and culturing the seeded cells.

(Culturing Surface Moving Step)

The production method of a three-dimensional tissue body of Embodiment (III) preferably further includes repeating a culturing surface moving step of moving the culturing surface in the extending direction of the shaft after obtaining the ringed three-dimensional tissue body wound around the shaft, a seeding step of seeding at least one type of cells on the coated culturing surface after the culturing surface is moved (also referred to as the "second and subsequent seeding steps" in Aspect (III)), and a culturing step of culturing the seeded cells to obtain another ringed three-dimensional tissue body wound around the shaft adjacent to the ringed three-dimensional tissue body wound around the shaft (also referred to as the "second and subsequent culturing steps" in Aspect (III)). In other words, after the first seeding step and the first culturing step are performed to obtain a ringed three-dimensional tissue body, the production method may include repetition of the culturing surface moving step, the second and subsequent seeding steps, and the second and subsequent culturing steps.

Operations of the culturing surface moving step, the second and subsequent seeding steps, and the second and subsequent culturing steps may be controlled by a computer or the like to be performed automatically, since operations performed automatically may be more aseptic and hygienic by virtue of not being performed by hand.

The culturing surface moving step is a step provided after the ringed three-dimensional tissue body wound around the shaft is obtained in the previous seeding step. The culturing surface moving step may be provided immediately after the ringed three-dimensional tissue body wound around the shaft is obtained in the previous culturing step or after an interval (such as 1 minute to 96 hours).

In the culture face moving step, the distance which the culturing surface is moved in the extending direction of the shaft is preferably 0.01 mm to 50 mm and more preferably 0.1 mm to 10 mm.

The cells of the ringed three-dimensional tissue body obtained through the first seeding step and the first culturing step and the cells of the ringed three-dimensional tissue body obtained through the second seeding step and the second culturing step may be adhered to each other or separated. The distance between two ringed three-dimensional tissue bodies that are separated may, for example, be the aforementioned distance by which the culturing surface is moved in the extending direction of the shaft. Two ringed three-dimensional tissue bodies that are separated can easily be connected as follows: by the cells in the ringed three-dimensional tissue bodies expanding and contracting, migrating, or the like so that the cells in two ringed three-dimensional tissue bodies adhere to each other and connect the two ringed three-dimensional tissue bodies; by two ringed three-dimensional tissue bodies connecting via a substance (such as proteins) secreted by the cells in the two ringed three-dimensional tissue bodies; by addition of separately produced proteins, cells, or the like between two ringed three-dimensional tissue bodies for the two ringed three-dimensional tissue bodies to connect; by connecting two ringed three-dimensional tissue bodies with a combination of these methods; and the like. The culturing surface may be moved by fixing the culturing surface and moving the shaft, by fixing the shaft and moving the culturing surface, or by moving both the culturing surface and the shaft.

One method of controlling the thickness of the three-dimensional tissue body is, for example, to provide the second and subsequent seeding steps and the second and subsequent culturing steps, or to provide repetition of the second and subsequent seeding steps and the second and subsequent culturing steps, without providing the culturing surface moving step, thereby winding another ringed three-dimensional tissue body around the ringed three-dimensional tissue body, wound around the shaft, that was obtained in the previous seeding step to make a portion of the three-dimensional tissue body thicker.

After winding another ringed three-dimensional tissue body around the ringed three-dimensional tissue body wound around the shaft, the culturing surface moving step may be provided and similar operations may be continued to increase the thickness of the entire three-dimensional tissue body. A three-dimensional tissue body with layers of different cells can be obtained by using different types of cells to form the ringed three-dimensional tissue body wound around the shaft and the ringed three-dimensional tissue body wound therearound.

(Second and Subsequent Seeding Steps)

Examples of the second and subsequent seeding steps include a step similar to the first seeding step.

The type, concentration, and the like of cells used in the second and subsequent seeding steps may be the same as or different from those of the first seeding step. The type, concentration, and the like of cells used in the second and subsequent seeding steps may be the same or different in each of the second and subsequent seeding steps.

(Second and Subsequent Culturing Steps)

Examples of conditions for culturing seeded cells include conditions similar to those of the above-described first culturing step.

The conditions and the like of the second and subsequent culturing steps may be the same as or different from those of the first culturing step. The conditions and the like of the second and subsequent culturing steps may be the same or different in each of the second and subsequent culturing steps.

By performance of the second and subsequent culturing steps, a new ringed three-dimensional tissue body wound around the shaft (new ringed three-dimensional tissue body) is formed adjacent to the ringed three-dimensional tissue body, wound around the shaft, obtained in the previous culturing step (previous ringed three-dimensional tissue body). The previous and new ringed three-dimensional tissue bodies may, for example, be adhered to each other by culturing at 37° C. for one hour to 30 days to obtain a luminal three-dimensional tissue body.

The number of repetitions of the culturing surface moving step, the second and subsequent seeding steps, and the second and subsequent culturing steps may be appropriately selected in accordance with the thickness and length of the laminal three-dimensional tissue body. For example, 1 to 20 repetitions are preferable, and 1 to 10 repetitions are more preferable.

When manufacturing a three-dimensional tissue body that includes substances (in particular proteins) secreted by cells seeded in the seeding step, such as a three-dimensional tissue body including extracellular matrix, a step of removing cells included in the three-dimensional tissue body may be provided after the culturing step. Methods of removing cells included in a three-dimensional tissue body include, for example, killing cells by treating with high-pressure treatment, alcohol treatment, surfactant treatment, or the like or culturing under conditions in which cells do not easily survive. Provision of the step of removing cells included in the three-dimensional tissue body allows at least a portion of the cells in the three-dimensional tissue body to be removed.

Furthermore, a plurality of types of cells may be used to manufacture a three-dimensional tissue body, and particular cells alone may be removed (for example, COS cells alone may be removed from a three-dimensional tissue body that includes chondrocytes and COS cells incorporating genes expressing proteins constituting extracellular matrix). Examples of methods of removing only particular cells include culturing under conditions in which only particular cells can survive or do not easily survive, such as increasing the sensitivity of cells to antibiotics and culturing in a medium including antibiotics, or providing only the cells to be maintained in the three-dimensional tissue body with resistance to antibiotics and culturing in a medium including antibiotics.

The three-dimensional tissue body obtained with the production method of a three-dimensional tissue body of Embodiment (III) may be a ringed three-dimensional tissue body or a luminal three-dimensional tissue body. The inner diameter of the three-dimensional tissue body is preferably 0.01 mm to 100 mm and more preferably 0.1 mm to 50 mm. The outer diameter of the three-dimensional tissue body is preferably 0.1 mm to 120 mm and more preferably 0.2 mm to 70 mm. The length of the luminal three-dimensional tissue body is preferably 0.1 mm to 300 mm and more preferably 1 mm to 250 mm.

The three-dimensional tissue body obtained by the production method of a three-dimensional tissue body of Embodiment (III) may be a three-dimensional tissue body with cells as the principal component or a three-dimensional tissue body including material secreted by cells, such as a three-dimensional tissue body with extracellular matrix as the principal component.

Examples of preferred conditions for producing a three-dimensional tissue body with extracellular matrix as the principal component include i) using cells highly capable of producing cell matrix such as collagen, laminin, fibronectin, elastin, or the like (for example, fibroblasts or mesenchymal cells), ii) adding ascorbic acid that promotes the production of extracellular matrix to the medium, iii) reducing the seeding density of cells to increase the ratio of extracellular matrix to cells, iv) increasing the production (secretion) amount of extracellular matrix by increasing the time for culturing the three-dimensional tissue body with a ringed shape, a luminal shape, or the like wound around the shaft (for example, culturing for 24 to 350 hours, preferably 48 to 170 hours, in the first culturing step and the second culturing step) and maturing the bonds of the extracellular matrix (for example, the bonds of collagen fibers), v) using a shaft with holes on the surface to stably provide nutrients and oxygen to cells to facilitate the diffusion of cell metabolites in the medium, thereby promoting production of extracellular matrix, and vi) increasing the movement distance of the culturing surface in the culturing surface moving step to reduce the cell density in the extending direction of the shaft.

Examples of the resulting three-dimensional tissue body with extracellular matrix as the principal component include collagenous luminal biotubes usable in synthetic blood vessels, synthetic tracheae, and the like.

Examples of the three-dimensional tissue body of Embodiment (III) include three-dimensional tissue bodies usable in a synthetic blood vessel, a synthetic trachea, and the like, such as a three-dimensional tissue body including cells seeded in the seeding step; a three-dimensional tissue body including substances secreted by cells, such as a three-dimensional tissue body having proteins secreted by cells as the principal component, a three-dimensional tissue body including extracellular matrix, and a three-dimensional tissue body having extracellular matrix as the principal component; and the like.

Examples of a three-dimensional tissue body usable in a synthetic blood vessel include a three-dimensional tissue body obtained with the following method.

After obtaining a ringed three-dimensional tissue body of vascular endothelial cells around a shaft in the first seeding step and first culturing step (such as a thick ringed three-dimensional tissue body of vascular endothelial cells obtained by continuously performing the steps of seeding and culturing vascular endothelial cells 2 to 3 times), a ringed three-dimensional tissue body of smooth muscle cells (such as a thick three-dimensional tissue body of smooth muscle cells obtained by continuously performing the steps of seeding and culturing smooth muscle cells 3 to 30 times) may be wound around the ringed three-dimensional tissue body of vascular endothelial cells in the second seeding step and second culturing step to yield a double-layered ringed three-dimensional tissue body having a layer of vascular endothelial cells around the shaft and a layer of smooth muscle cells on the outside of the layer of vascular endothelial cells. Furthermore, a culturing surface moving step may be provided and similar operations performed to yield a double-layered ringed or luminal three-dimensional tissue body having a structure similar to that of a blood vessel in a living organism, such as a blood vessel having a layer of vascular endothelial cells on the inner wall and a layer of smooth muscle cells along the periphery of the layer of vascular endothelial cells. To prevent the cells forming each layer from mixing and to adjust the strength and flexibility of the blood vessel, a layer that has collagen, elastin, or the like as the principal component (in particular, a layer having elastin as the principal component) and that functions as a barrier preventing the vascular endothelial cells and smooth muscle cells from mixing can also be provided between the layer of vascular endothelial cells and the layer of smooth muscle cells in the three-dimensional tissue body by, for example, a method such as providing a step of seeding and culturing cells that secrete collagen or elastin, e.g. mesenchymal stem cells, fibroblasts, or the like, between the step of forming the layer of vascular endothelial cells and the step of forming the layer of smooth muscle cells; or covering the layer of vascular endothelial cells with a collagen or elastin tube (such as a three-dimensional tissue body, manufactured with the manufacturing method of a three-dimensional tissue body of Embodiment (III), including proteins secreted by cells). Provision of the aforementioned layer functioning as a barrier, such as the inner elastic plate found in blood vessels of living organisms, prevents migratory cells from moving between layers after forming the three-dimensional tissue body, yielding a three-dimensional tissue body with a structure even closer to that of a blood vessel in a living organism.

Examples of a three-dimensional tissue body usable in a synthetic trachea include a three-dimensional tissue body obtained with the following method.

A culturing surface moving step is provided after obtaining a ringed three-dimensional tissue body (a) of chondrocytes by the first seeding step and first culturing step, and a new ringed three-dimensional tissue body (b) of fibroblasts is formed adjacent to the ringed three-dimensional tissue body of chondrocytes by the second seeding step and second culturing step. By appropriately repeating the above process, a luminal three-dimensional tissue body in which ringed three-dimensional tissue bodies are stacked in the order a-b-b-a-b-b or the like in the extending direction of the shaft, for example, can be obtained. A ringed three-dimensional tissue body having extracellular matrix as the principal component, a three-dimensional tissue body including substances secreted by cells, a ringed three-dimensional tissue body including cells that excrete substances such as the components constituting extracellular matrix, or the like may be provided between the ringed three-dimensional tissue bodies. To adjust strength, the resulting luminal three-dimensional tissue body may be covered with a collagen tube or an elastin tube (for example, a three-dimensional tissue body, manufactured with the manufacturing method of a three-dimensional tissue body of Embodiment (III), including proteins secreted by cells).

Even when using only ringed three-dimensional tissue bodies of chondrocytes, the ringed three-dimensional tissue bodies of chondrocytes can be connected by extracellular matrix secreted from the chondrocytes to form a synthetic trachea. To strengthen the synthetic trachea and encourage blood vessels to work themselves in after grafting, the synthetic trachea preferably includes a ringed three-dimensional tissue body of chondrocytes and a ringed three-dimensional tissue body of fibroblasts.

An example of a three-dimensional tissue body including substances secreted by cells is a three-dimensional tissue body, obtained by the following method, that includes substances such as proteins (for example, proteins constituting extracellular matrix).

COS cells that have an SV40 promoter sequence and have an introduced expression vector incorporating genes expressing proteins constituting extracellular matrix such as elastin or collagen are used to form a ringed or luminal three-dimensional tissue body, and the COS cells are caused to secrete proteins or the like. After the culturing step, the COS cells are killed with a method such as killing the cells by treating with high-pressure treatment, alcohol treatment, surfactant treatment, or the like or culturing under conditions in which COS cells do not easily survive (for example, increasing the sensitivity of the COS cells to antibiotics and culturing the COS cells in a medium including antibiotics). The COS cells are then removed. The three-dimensional tissue body of Embodiment (III) may be a three-dimensional tissue body including dead cells that have not been completely removed, surviving cells, or the like.

The resulting three-dimensional tissue body including proteins constituting extracellular matrix may, for example, be used as a coating material to strengthen the three-dimensional tissue body obtained with the manufacturing method of Embodiment (III), a synthetic blood vessel, a myocardial patch, prosthetic material, or the like.

An example of a production method of a three-dimensional tissue body of Embodiment (III) is described below with reference to FIG. 21, FIG. 22, and FIG. 26.

FIG. 21 is an outline of an example production method of a three-dimensional tissue body of Embodiment (III).

With a shaft inserted through a through hole of a culturing surface in a production apparatus of a three-dimensional tissue body (see (i) of FIG. 21), a temperature-responsive polymer is applied to the culturing surface to coat the culturing surface, thereby preparing a coated culturing surface (see (ii) of FIG. 21). In this example, the culturing surface and the shaft are in contact. Subsequently, the production apparatus of the three-dimensional tissue body is placed inside a container having an inner diameter slightly larger than the outer diameter of the culturing surface and is immersed in a medium. Cells are then seeded (first seeding step; see (iii) of FIG. 21). The seeded cells adhere to the coated culturing surface (see (iv) of FIG. 21). In this example, the density of cells is 100% confluency. Subsequently, the cells adhered to the coated culturing surface start to aggregate towards the central portion of the coated culturing surface, and the edge separates from the coated culturing surface and starts to warp, yielding a cell structure with a warped edge (see (v) of FIG. 21). The cells then further aggregate to form a ringed shape, yielding a ringed three-dimensional tissue body wound around the shaft (see (vi) of FIG. 21). The ringed three-dimensional tissue body wound around the shaft is wound around the shaft to a degree preventing the tissue body from falling off the shaft. Therefore, even when the shaft is not cell adhesive, the position at which the three-dimensional tissue body is wound during production does not change greatly. Subsequently, the culturing surface is moved downward in the extending direction of the shaft to provide a gap, adjacent to the bottom of the resulting ringed three-dimensional tissue body, for forming another ringed three-dimensional tissue body (culturing surface moving step; see (vii) of FIG. 21). Cells are then seeded again (second seeding step; see (viii) of FIG. 21) and cultured to obtain a luminal three-dimensional tissue body in which ringed three-dimensional tissue bodies are stacked. A long, luminal three-dimensional tissue body can be obtained by repeating the culturing surface moving step, the second and subsequent seeding steps, and the second and subsequent culturing steps (see (ix) of FIG. 21).

In the above example, a three-dimensional tissue body having extracellular matrix as the principal component can be obtained by, for example, reducing the number of seeded cells, leaving the ringed three-dimensional tissue body wound around the shaft to stand and waiting for secretion of proteins constituting extracellular matrix, or the like. Some or all of the above steps may be controlled by a computer or the like to be performed automatically.

FIG. 22 is an outline of an example production method of a three-dimensional tissue body of Embodiment (III) using a production apparatus of a three-dimensional tissue body having a gap between the culturing surface and the shaft.

With a shaft inserted through a through hole of a culturing surface in a production apparatus of a three-dimensional tissue body (see (i) of FIG. 22), a temperature-responsive polymer is applied to the culturing surface to coat the culturing surface, thereby preparing a coated culturing surface (see (ii) of FIG. 22). In this example, the diameter of the shaft is smaller than the hole diameter of the through hole, thus forming a gap between the culturing surface and the shaft. Subsequently, the production apparatus of the three-dimensional tissue body is placed inside a container having an inner diameter slightly larger than the outer diameter of the culturing surface and is immersed in a medium. Cells are then seeded (first seeding step; see (iii) of FIG. 22). The seeded cells adhere to the coated culturing surface (see (iv) of FIG. 22). In this example, the density of cells is 100% confluency. Subsequently, the cells adhered to the coated culturing surface start to aggregate towards the central portion of the coated culturing surface, and the edge separates from the coated culturing surface and starts to warp, yielding a cell structure with a warped edge (see (v) of FIG. 22). The cells then further aggregate to form a ringed shape, and the aggregating cell structure jumps over the gap between the culturing surface and the shaft to wind around the shaft and form a ringed three-dimensional tissue body (see (vi) of FIG. 22). Subsequently, the culturing surface is moved upward in the extending direction of the shaft to provide a gap, adjacent to the top of the resulting ringed three-dimensional tissue body, for forming another ringed three-dimensional tissue body (culturing surface moving step; see (vii) of FIG. 22). Cells are then seeded again (second seeding step; see (viii) of FIG. 22) and cultured to obtain a luminal three-dimensional tissue body in which ringed three-dimensional tissue bodies are stacked. A long, luminal three-dimensional tissue body can be obtained by repeating the culturing surface moving step, the second and subsequent seeding steps, and the second and subsequent culturing steps (see (ix) of FIG. 22).

Some or all of the above steps may be controlled by a computer or the like to be performed automatically.

FIG. 26 is an outline of an example production method of a three-dimensional tissue body of Embodiment (III) using a production apparatus of a three-dimensional tissue body having a plurality of culturing surfaces and a gap between the culturing surfaces and the shaft.

With one shaft inserted through a through hole of each of two culturing surfaces in a production apparatus of a three-dimensional tissue body (see (i) of FIG. 26), a temperature-responsive polymer is applied to the two culturing surfaces to coat the two culturing surfaces, thereby preparing coated culturing surfaces (see (ii) of FIG. 26). In this example, the diameter of the shaft is smaller than the hole diameter of the through hole, thus forming a gap between each culturing surface and the shaft. Subsequently, the production apparatus of a three-dimensional tissue body is placed inside a container having an inner diameter larger than the outer diameter of the culturing surfaces and is immersed in a medium. Cells are then seeded (first seeding step; see (iii) of FIG. 26). The seeded cells adhere to the coated culturing surfaces (see (iv) of FIG. 26). In this example, the density of cells is 100% confluency. Subsequently, the cells adhered to the coated culturing surface start to aggregate towards the central portion of the coated culturing surface, and the edge separates from the coated culturing surface and starts to warp, yielding a cell structure with a warped edge (see (v) of FIG. 26). The cells then further aggregate to form a ringed shape, and the aggregating cell structure jumps over the gap between the culturing surface and the shaft to wind around the shaft and form a ringed three-dimensional tissue body (see (vi) of FIG. 26). Subsequently, the two ringed three-dimensional tissue bodies are cultured and connect to each other to yield a luminal three-dimensional tissue body (see (vii) of FIG. 26).

In (vii) of FIG. 26, the culturing surface is omitted to illustrate the luminal three-dimensional tissue body more clearly. Since a gap exists between the culturing surfaces and the shaft in FIG. 26, the two ringed three-dimensional tissue bodies connect to yield a luminal three-dimensional tissue body whether or not the culturing surfaces are present.

Furthermore, a longer luminal three-dimensional tissue body can be obtained by methods such as increasing the number of culturing surfaces or providing a culturing surface moving step, second and subsequent seeding steps, and second and subsequent culturing steps.

Some or all of the above steps may be controlled by a computer or the like to be performed automatically.

[[Aspect (IV)]]
(Manufacturing Method of a Cell Structure)

A manufacturing method of a cell structure in an embodiment of Aspect (IV) (manufacturing method of Embodiment (IV)) is a method of producing a coated region in which a culturing surface is coated with a temperature-responsive polymer or a temperature-responsive polymer composition, forming a droplet of a cell suspension in the coated region, and performing cell culturing in the droplet.

As illustrated in greater detail in FIG. 31, an example manufacturing method of Embodiment (IV) includes preparing a culturing surface (see (i) of FIG. 31), then disposing a temperature-responsive polymer or a temperature-responsive polymer composition on the culturing surface (see (ii) of FIG. 31), coating the culturing surface with the temperature-responsive polymer or the temperature-responsive polymer composition to produce a coated region (see (iii) of FIG. 31), forming a droplet of cell suspension in the coated region (see (iv) of FIG. 31), performing cell culturing in the droplet (see (v) of FIG. 31), and forming a cell structure (see (vi) of FIG. 31).

Here, in the manufacturing method of Embodiment (IV), it is essential that the surface zeta potential of the coated region produced on the culturing surface be 0 mV to 50 mV to obtain the effect of spontaneous formation of a cell structure, as described below.

The effects of the manufacturing method of Embodiment (IV) are now described.

A hanging drop method known as a manufacturing method of a cell structure manufactures a spheroidal cell structure in a droplet by producing a droplet of a cell suspension at the tip of a tubular member and holding the droplet for a predetermined time period (such as approximately 2 weeks) while maintaining the spherical shape of the droplet using the surface tension of the droplet. The operation to hold the droplet is complicated, however, making it difficult to manufacture a spheroidal cell structure easily.

By contrast, the manufacturing method of Embodiment (IV) allows a droplet to be held in the state when placed on a culturing surface, thereby allowing a spheroidal cell structure to be manufactured easily.

Another possible method would be to use a cell culture container provided with one or a plurality of wells partitioned by a culturing surface and a wall surface to produce a coated region and a non-coated region, separated from the coated region, on the culturing surface of the well. A cell suspension is then added to the well. The manufacturing method of Embodiment (IV) has the following effects as compared to such a method.

In the above-described method, the cell suspension is added to the cell culture container so as to immerse both the coated region and the non-coated region in the cell suspension. Seeded cells may therefore adhere to the non-coated region. At this time, the cells in the non-coated region might obstruct formation of a spheroidal cell structure with a well-defined shape in the coated region. Therefore, when using a cell culture container with a wall surface, it may become necessary to treat all or a portion of the culturing surface to become cell non-adhesive. Such treatment may also cause elution of cytotoxic substances into the medium.

By contrast, the droplet of cell suspension in the coated region is isolated from the non-coated region in the manufacturing method of Embodiment (IV), making the aforementioned treatment to provide cell non-adhesiveness unnecessary and reducing the likelihood of adversely affecting cell growth.

In the above-described method, cells adhere to the coated region after addition of the cell suspension to the well, whereas cells do not adhere to the non-coated region treated to be cell non-adhesive. The cells that do not adhere to the non-coated region might adversely affect the growth of cells adhered to the coated region by provoking apoptosis or producing heat shock proteins. Therefore, with this method it may be necessary to remove the cells in the non-coated region from the well by an operation such as medium exchange.

By contrast, the need to remove cells in the non-coated region with the manufacturing method of Embodiment (IV) is small, because a droplet of cell suspension is formed in the coated region, which is provided with cell adhesiveness by being coated with a temperature-responsive polymer or a temperature-responsive polymer composition, in isolation from the non-coated region. Hence, the amount of cells used can be reduced. Furthermore, the need for operations such as medium exchange is small, allowing a reduction in the amount of medium used. Overall, the manufacturing method of Embodiment (IV) allows a reduction in manufacturing costs.

In the manufacturing method of Embodiment (IV), an automatic cell culturing apparatus used in a 384 well cell culture plate or the like may be used (for example, a droplet of cell suspension can be ejected onto a culturing surface, which is coated with a temperature-responsive polymer or a temperature-responsive polymer composition, by a program for injecting a cell suspension onto multiple plates using 16 nozzles). Devices normally used in the present technical field, such as analysis devices for cell culturing plates, may also be used. Therefore, the manufacturing method of Embodiment (IV) can reduce the manufacturing costs of cell structures while also achieving an economic effect by broadening the uses of the aforementioned apparatuses and devices.

As described above, it is essential that the surface zeta potential of the coated region be 0 mV to 50 mV in the manufacturing method of a cell structure in an embodiment of Aspect (IV). Setting the surface zeta potential to 0 mV or greater allows adhesion of negatively charged cells, while setting the surface zeta potential to 50 mV or less can reduce cytotoxicity.

For similar reasons, the surface zeta potential is preferably from 0 mV to 35 mV and more preferably from 10 mV to 25 mV.

The surface zeta potential can be adjusted by adjusting the C/A ratio in the temperature-responsive polymer or the temperature-responsive polymer composition.

A culturing surface that has a surface zeta potential in the aforementioned particular range allows a cell structure (spheroid) having an aggregated (pellet-like) structure to be formed easily by simply culturing cells under appropriate culture conditions.

The reason is that setting the surface zeta potential within the aforementioned particular range is inferred to provide the culturing surface with a weak positive charge that does not trigger cytotoxicity, to ensure rapid adhesion of the seeded cells, to improve cell activity and encourage secretion of extracellular matrix, and also to appropriately inhibit cell migration, strengthening the bond between cells.

The phenomenon of forming a cell structure on a culturing surface having a surface zeta potential in the aforementioned particular range is extremely reproducible, allowing production of homogenous cell structures.

The mass of cells produced using a known cell culture container is simply a collection of cells that cannot adhere to a culturing surface that is cell non-adhesive, leading to the problem of low viability of the cells constituting the cell mass.

A cell structure (spheroid) manufactured with the manufacturing method of Embodiment (IV), however, is formed after the process of cells rapidly adhering to the culturing surface and expanding while growing. A rich extracellular matrix is thus produced between these cells, providing the cell structure itself with an extremely high viability (activity).

With the manufacturing method of Embodiment (IV), the experimenter can appropriately determine the size of the cell structures in accordance with purpose and can either provide the size with a distribution or make the size uniform.

The cell structure can be minute in size (for example, several hundred μm or less) or may have a diameter of 50 μm to 1,500 μm, with a diameter of 50 μm to 200 μm being preferable.

Since the manufacturing method of Embodiment (IV) allows production of cell structures on a flat plate culturing surface, the culture container can be observed directly with a microscope when performing an assay on the cell structures produced using the cell culture container.

The manufacturing method of Embodiment (IV) also makes it possible for cells not to adhere to the outer edge of the culturing surface, which is the border between the culturing surface and the wall of the cell culture container, allowing the size to be kept homogeneous for an extended period of time.

Each step in the manufacturing method of a cell culture container in an embodiment of Aspect (IV) is described below in detail.

In an example manufacturing method of Embodiment (IV), a culturing surface is first prepared (see (i) of FIG. 31).

The culturing surface may be the culturing surface of a cell culture container or the culturing surface of a material other than a cell culture container. Examples include commercially available plates, dishes, flasks, glass plates, silicone sheets, and the like.

The culturing surface may be cell adhesive or cell non-adhesive.

"Cell non-adhesive" refers to adherent cells (for example, fibroblasts, hepatocytes, vascular endothelial cells, and the like) either not adhering or tending not to adhere under normal culture conditions.

Examples of the material of the culturing surface include polystyrene, polyethylene terephthalate (PET), polypropylene, polybutene, polyethylene, and polycarbonate. Polystyrene and PET are preferable for being easy to mold precisely, for allowing adoption of various sterilization methods, and for being suitable for microscope observation by virtue of being transparent.

A typical cell culture plate is made of plastic, such as polystyrene, that is surface treated (for example, plasma treated) for cells to adhere more easily to the culturing surface.

In the manufacturing method of a cell structure of Aspect (IV), it suffices to prepare a culturing surface, and a cell culture container need not be used.

Next, a temperature-responsive polymer or a temperature-responsive polymer composition is disposed on the culturing surface (see (ii) of FIG. 31).

The temperature-responsive polymer and temperature-responsive polymer composition disposed on the culturing surface in the manufacturing method of an embodiment of Aspect (IV) are now described in detail.

Examples of the temperature-responsive polymer and temperature-responsive polymer composition in Aspect (IV) include temperature-responsive polymers and temperature-responsive polymer compositions similar to those of Aspect (I), and similar polymers and polymer compositions are preferred.

In Embodiment (IV), a manufacturing method of the temperature-responsive polymer of (A-1) includes a production step of producing a mixture containing 2-N,N-dimethylaminoethyl methacrylate (DMAEMA) and an irradiation step of irradiating the mixture with ultraviolet light, wherein in the production step, the mixture further contains a polymerization inhibitor and water, and in the irradiation step, the mixture is irradiated with ultraviolet light under an inert atmosphere. However, the manufacturing method is not limited to this example and may be a different method.

In Embodiment (IV), the temperature-responsive polymer of (A-1) allows formation of cell structures that have a luminal (tube-like) and an aggregated (pellet-like) structure by culturing cells under appropriate culture conditions, as described below.

In Embodiment (IV), a manufacturing method of the temperature-responsive polymer of (A-2) includes a first polymerization step of irradiating a first mixture containing 2-N,N-dimethylaminoethyl methacrylate (DMAEMA) with ultraviolet light, an adding step of adding an anionic monomer to the first mixture at the point when the number-average molecular weight of the polymer in the first polymerization step reaches at least a predetermined value to produce a second mixture, and a second polymerization step of irradiating the second mixture with ultraviolet light. However, the manufacturing method is not limited to this example and may be a different method.

In Embodiment (IV), the temperature-responsive polymer composition of (C) may include a polymer of 2-N,N-dimethylaminoethyl methacrylate (DMAEMA) and/or a derivative thereof; 2-amino-2-hydroxymethyl-1,3-propanediol; and one or more anionic substances selected from the group consisting of nucleic acids, heparin, hyaluronic acid, dextran sulfate, polystyrene sulfonic acid, polyacrylic acid, polymethacrylic acid, polyphosphoric acid, sulfated polysaccharide, curdlan, polyarginic acid, and alkali metal salts thereof, as described above.

In Embodiment (IV), the DNA in the anionic substances listed in (C3) is preferably DNA capable of inducing differentiation into differentiated cells of stem cells such as iPS cells, ES cells, and mesenchymal stem cells, in particular cardiomyocytes, hepatocytes, nerve cells, and vascular endothelial cells.

In an example manufacturing method of Embodiment (IV), the coated region may be produced on the entire culturing surface (see (i), (ii) of FIG. 32), or a plurality of coated regions may be produced on the culturing surface (see (iii) of FIG. 32).

When producing a coated region on the entire culturing surface, a temperature-responsive polymer or a temperature-responsive polymer composition solution may be cast on the culturing surface.

When producing a plurality of coated regions on the culturing surface, the temperature-responsive polymer or the temperature-responsive polymer composition may be spotted by a technique using an eight-channel micropipettor, by spotter printing to discharge solution quantitatively, by rotating screen drum printing, or by another such technique.

In particular, when producing a plurality of coated regions on the culturing surface, the area of each coated region is preferably 0.1 mm² to 30 mm². Adopting this range makes it easier to obtain the desired minute spheroids.

The distance between coated regions is preferably from 0.1 mm to 10 mm. The "distance between coated regions" refers to the shortest distance on the culturing surface between coated regions. Setting this distance to 0.1 mm or greater can inhibit adhesion between the cells seeded in adjacent coated regions. Setting this distance to 10 mm or less allows efficient production of a large quantity of cell structures (spheroids or the like).

In particular, when producing a plurality of coated regions on the culturing surface, the number of coated regions may be set appropriately in accordance with the experimenter's purpose. The number may be 2 or more, 10 or more, or 1,000 or more.

In particular, when producing a plurality of coated regions on the culturing surface, the planar shape of each coated region is preferably a circle, an ellipse, or another shape having the center of curvature on the inside of the outer contour line.

The radius of curvature is preferably 0.1 mm to 50 mm and more preferably 1 mm to 10 mm.

The diameter of a circular coated region is preferably 10 μm to 10 mm and more preferably 30 μm to 1,500 μm.

One of these shapes may be used alone, or a combination of two or more shapes may be used.

In an example manufacturing method of Embodiment (IV), the amount of temperature-responsive polymer per unit area in the coated regions of the culturing surface is preferably 5.0 ng/mm² to 50 ng/mm² and more preferably 15 ng/mm² to 40 ng/mm². Adopting these ranges facilitates achievement of the effect of easier formation of cell structures.

In an example manufacturing method of Embodiment (IV), the culturing surface of the cell culture container may be coated with the temperature-responsive polymer by techniques such as precipitation from the state of an aqueous solution, application of a solution and drying of the solvent, exposure to radiation, exposure to low temperature plasma, corona discharge, glow discharge, ultraviolet light, or graft polymerization using a radical generator.

A method of coating the culturing surface with a temperature-responsive polymer or a temperature-responsive polymer composition and a method of spotting a temperature-responsive polymer or a temperature-responsive polymer composition at a plurality of positions on the culturing surface that become the coated regions are described below.

The culturing surface in the manufacturing method of Embodiment (IV) may be produced on the basis of a cell culture plate (for example, a 35 mm dish or the like) and can, for example, be used suitably in the field of regenerative medicine.

The culturing surface may also be produced on the basis of a microplate (for example, a 96 hole plate or the like) and can, for example, be used suitably in the field of drug discovery (particularly drug screening).

Moisture may be removed from the temperature-responsive polymer or the temperature-responsive polymer composition by heating or freeze drying, vacuum distillation, or the like, and the result may be dissolved in an organic solvent, examples of which include methanol, ethanol, and other alcohols; ketones; and esters. Among these solvents, methanol is preferable for dissolution by virtue of having a low surface tension and boiling point, allowing rapid drying, and allowing more uniform covering with the temperature-responsive polymer. In the case of dissolution in an organic solvent, hydrophilic molecules that are non-ionic and hydrophilic, such as polyethylene glycol (PEG), dimethyl acrylamide (DMAA), glycerin, Triton X, polypropylene glycol, and the like may be further added.

In an example of this manufacturing method, a coated region in which the culturing surface is coated with a temperature-responsive polymer or a temperature-responsive polymer composition is thus produced (see (iii) of FIG. 32).

In the manufacturing method of Embodiment (IV), it is essential that the surface zeta potential of the coated region be 0 mV to 50 mV, preferably 0 mV to 35 mV, and more preferably 10 mV to 25 mV, as described above.

In the manufacturing method of Embodiment (IV), the contact angle of water relative to the coated region of the culturing surface is preferably from 50° to 90°, more preferably 60° to 80°, and particularly preferably 620 to 780 to improve the effects of Aspect (IV).

The contact angle of water relative to the coated region refers to the average contact angle measured in conformity with JIS R3257 at several arbitrary points within the coated region.

As described above, the coated region is preferably a region with a predetermined degree or higher of hydrophobicity to increase the interaction with the cell surface and to increase the adhesiveness of cells relative to the coated region.

The contact angle of water relative to the coated region of the culturing surface can be adjusted by adjusting the structure or amount of hydrophobic groups in the temperature-responsive polymer or the temperature-responsive polymer composition.

In an example manufacturing method of Embodiment (IV), the bottom area of the droplet in each coated region is preferably smaller than the area of the coated region.

In the step of coating the culturing surface, the amount of the temperature-responsive polymer or the temperature-responsive polymer composition per unit area may become larger at the edge of the coated region than in the central portion of the coated region, and the edge of the coated region sometimes swells relative to the central portion. In this case, the shape of the cell structure formed by cells adhered to the coated region tends to be difficult to control. Setting the bottom area of the droplet to be smaller than the area of the coated region makes it possible to prevent cells from adhering to a portion of the coated region in which the amount of the temperature-responsive polymer or the temperature-responsive polymer composition might not be uniform, thereby facilitating production of a cell structure with a well-defined shape.

In each coated region, the upper limit on the ratio of the bottom area of the droplet to the area of the coated region may be 99% or less for the same reasons as above, and the upper limit is preferably 97%, 95% 90%, 80%, 70%, 60%, or 50%.

The lower limit on this ratio may be 10% or more, and the lower limit is preferably 20% or 30%. Setting this ratio to 10% or more allows efficient production of a sufficiently large cell structure.

In an example of a cell culture method using a cell culture container of an embodiment of Aspect (IV), a droplet of cell suspension is formed in the coated region (see (iv) of FIG. 31).

The manufacturing method of Embodiment (IV) can be suitably adopted in particular for cells for which the diameter of the manufactured cell structure is required to be highly homogeneous (such as cells used in drug discovery tests or multipotent stem cells) or cells that are expensive to culture due to precise control of the differentiation state (specifically, stem cells such as iPS cells, ES cells, mesenchymal stem cells, cancer stem cells, and differentiation induction cells thereof; mesenchymal cells such as vascular endothelial cells, adipocytes, adipose stem cells, fibroblasts, cardiomyocytes, and myoblasts; epithelial cells such as HepaRA, HepaRG, HepG2, and BxPC-3; and the like). In the case of primary cells, it suffices to select adherent cells that form colonies, which a person skilled in the art can appropriately select.

When forming the droplet of cell suspension in the coated region in an example of this manufacturing method, the cell suspension is preferably dripped so that the shape of the bottom is circular. This technique facilitates obtaining a cell structure with a well-defined spheroidal shape.

In an example manufacturing method of Embodiment (IV), the number of cells included in the droplet is preferably $3.0 \times 10^5$ cells/mL or less. In the step of seeding cells, cells may precipitate in an overlapped state if the cell density is too high, leading to cells that do not come in contact with the temperature-responsive polymer or the temperature-responsive polymer composition. In this case, the cells that are not in contact with the polymer or the polymer composition might have harmful effects, such as fusing with other cells and thereby changing the properties of the other cells. If the number of cells included in the droplet is $3.0 \times 10^5$ cells/mL or less, the cells can be caused to precipitate on the coated region nearly as a single layer, allowing the cells to be cultured under suitable conditions.

The number of cells included in the droplet is preferably $1.0 \times 10^4$ cells/mL or more to produce a sufficiently large cell structure.

For the same reasons as above, the number of cells included in the droplet is more preferably $1.0 \times 10^5$ cells/mL to $3.0 \times 10^5$ cells/mL and particularly preferably $2.0 \times 10^5$ cells/mL to $3.0 \times 10^5$ cells/mL. The number of cells can be adjusted appropriately by a person skilled in the art considering the form, size, and the like of the seeded cells. The aforementioned number of cells refers to the number of living cells.

In an example of this manufacturing method, the diameter of the droplet is preferably 1 μm to 8 mm.

If the diameter of the droplet is less than 1 μm, the amount of medium becomes too small, which might lead to conditions unfavorable for cell culturing, such as the medium drying out.

If the diameter of the droplet exceeds 8 mm, the density of cells disposed on the polymer may become uneven when the cells precipitate onto the polymer or polymer composition in the droplet, which might produce spheroidal shapes at a plurality of locations (i.e. a plurality of stress points become the nucleus of cell aggregation) and prevent the spheroid from becoming a true sphere.

For the same reasons as above, the diameter of the droplet is more preferably 100 μm to 4 mm and particularly preferably 300 μm to 3 mm.

In an example manufacturing method of Embodiment (IV), the amount of the droplet is preferably 0.5 μL to 50 μL, more preferably 1.0 μL to 40 μL, and particularly preferably 5.0 μL to 25 μL to facilitate production of a cell structure with a well-defined shape.

In an example of this manufacturing method, one droplet or a plurality of droplets may be formed in one coated region.

In particular, when forming a plurality of droplets in one coated region, the interval between droplets (nearest distance between droplets) is preferably 1 μm to 500 μm.

If the distance is less than 1 μm, the droplets may combine with each other. A distance exceeding 500 μm might prevent achievement of efficient mass production of spheroids.

For the same reasons as above, the interval between droplets is more preferably 2 μm to 250 μm and particularly preferably 5 μm to 100 μm.

In an example of this manufacturing method, cells are cultured in the droplet (see (v) of FIG. 31).

The culture conditions may be determined appropriately in accordance with the cells being used. An example is 37° C. and a 5% $CO_2$ atmosphere.

When culturing cells, a method of actively adding humidity to the culture container by spraying a mist of water or a method of inhibiting volatilization of moisture in the droplet by covering the droplet surface of the cell suspension with a film of an inert oil component with low specific gravity such as a phospholipid, a higher carboxylic acid, or liquid paraffin may be used. This method is particularly effective for maintaining the droplet of cell suspension when the amount of the droplet is less than 10 μL.

Subsequently, in an example of this manufacturing method, culturing is further continued to form a cell structure (see (vi) of FIG. 31).

The culture conditions may be determined appropriately in accordance with the cells being used. An example is 37° C. and a 5% $CO_2$ atmosphere.

At this time, a cell structure that has an aggregated (pellet-like) structure can easily be formed in the coated region that has particular characteristics.

The following describes a preferred culturing surface used in a manufacturing method of a cell structure in an embodiment of Aspect (IV).

The preferred culturing surface includes a glass culturing surface and the temperature-responsive polymer used in the above-described manufacturing method of a cell structure that starts at the culturing surface in an embodiment of Aspect (IV).

In the preferred culturing surface, the glass itself provides resistance to an organic solvent, allowing the culturing surface to be washed with an organic solvent and allowing a further reduction of cytotoxic substances. The culturing surface can also be manufactured without using a conventional graft polymerization method that involves irradiation (as described below), can reduce the amount of polymer decomposition products produced by irradiation, and can provide a good environment for cell growth.

Examples of a glass culturing surface include a culturing surface of a glass cell culture container and the surface of a glass plate.

Examples of temperature-responsive polymers include (A) a temperature-responsive polymer containing 2-N,N-dimethylaminoethyl methacrylate (DMAEMA) units and anionic monomer units and (B) a temperature-responsive polymer containing N-isopropyl acrylamide (NIPAM) units, cationic monomer units, and anionic monomer units, as described above.

In greater detail, examples of this preferred manufacturing method of a cell culture container include (a) treating a glass culturing surface with a silane coupling agent having a vinyl group and then polymerizing 2-N,N-dimethylaminoethyl methacrylate (DMAEMA) on the treated culturing surface while irradiating with ultraviolet light in the presence of water, and (b) treating a glass culturing surface with a silane coupling agent having a halogenated alkyl group or introducing a N,N-dialkyl substituted dithiocarbamoyl group by a substitution reaction of a halogenated alkyl group and N,N-dialkyl substituted dithiocarbamyl acid and then subjecting 2-N,N-dimethylaminoethyl methacrylate (DMAEMA) to iniferter polymerization, with the N,N-dialkyl substituted dithiocarbamoyl group as the starting point of radical polymerization, on the culturing surface while irradiating with ultraviolet light in the presence of water.

In method (a), examples of the silane coupling agent having a vinyl group include an agent having at least one selected from the group consisting of a vinyl group, a styryl group, a methacryl group, and an acryl group as a reactive functional group (Y) provided with the function of reacting or interacting with organic matter, and at least one selected from the group consisting of an alkoxy group and a halogen as a reactive functional group (X) provided with the function of reacting or interacting with glass.

Specific examples include vinyltrimethoxysilane, p-styryltrimethoxysilane, 3-methacryloyloxypropyltrimethoxysilane, and 3-acryloyloxypropyltriethoxysilane.

Treatment with a silane coupling agent may be performed under normal conditions.

The method of polymerizing DMAEMA on a treated culturing surface may be as listed above regarding (A) a temperature-responsive polymer containing 2-N,N-dimethylaminoethyl methacrylate (DMAEMA) units and anionic monomer units.

In particular, the following conditions are preferably adopted in method (a).

The wavelength of ultraviolet light during ultraviolet light irradiation is preferably a wavelength of near ultraviolet light, more preferably 330 nm to 400 nm, and particularly preferably 350 nm to 390 nm, to reduce the amount of polymer decomposition products.

Light is preferably irradiated from the back side of the treated culturing surface (irradiated to pass through the glass), as doing so can cut the short wavelength ultraviolet light included in the light source to selectively irradiate light with a wavelength in the near ultraviolet region and can irradiate light from the side of the silane coupling agent having a vinyl group towards the DMAEMA side to prioritize a polymerization reaction over monomer decomposition or the like.

In method (b), examples of the silane coupling agent having a halogenated alkyl group include an agent having a halogenated alkyl group, specifically at least one selected from the group consisting of a p-chloromethylbenzyl group, a 3-chloropropyl group, a p-bromomethylbenzyl group, and a 3-bromopropyl group, as a reactive functional group (Y) provided with the function of reacting or interacting with organic matter, and at least one selected from the group consisting of an alkoxy group and a halogen as a reactive functional group (X) provided with the function of reacting or interacting with glass.

Specific examples include 3-chloropropyltrimethoxysilane, p-chloromethylbenzyltrichlorosilane, and 3-chloropropyltrichlorosilane. Treatment with a silane coupling agent may be performed under normal conditions.

Iniferter polymerization of the 2-N,N-dimethylaminoethyl methacrylate (DMAEMA), having an N,N-dialkyl substituted dithiocarbamoyl group as the starting point of radical polymerization, introduced into the glass surface (culturing surface) may be performed under normal reaction conditions.

In particular, the following conditions are preferably adopted in the aforementioned method of (b).

The wavelength of ultraviolet light during ultraviolet light irradiation is preferably a wavelength of near ultraviolet light, more preferably 330 nm to 400 nm, and particularly preferably 350 nm to 390 nm, to reduce the amount of polymer decomposition products.

Light is preferably irradiated from the back side of the treated culturing surface (irradiated to pass through the glass), as doing so can cut the short wavelength ultraviolet light included in the light source to selectively irradiate light with a wavelength in the near ultraviolet region and can irradiate light from the silane coupling agent side towards the DMAEMA side to prioritize a polymerization reaction over monomer decomposition or the like.

An embodiment of a manufacturing method of a cell structure of Aspect (IV) has been described by examples with reference to the drawings, but the manufacturing method of a cell structure of Aspect (IV) is not limited to the above examples. Embodiment (IV) may be modified as appropriate.

[[Aspect (V)]]

With reference to the drawings, embodiments of a manufacturing method of a cell structure of Aspect (V), a cell structure of Aspect (V), and a cell culture container of Aspect (V) are described below in detail with examples.

A manufacturing method of a cell structure of an embodiment of Aspect (V) (Embodiment (V)) includes:

a preparation step of preparing, on a culturing surface of a cell culture container, a first coated region coated with a temperature-responsive polymer and/or a temperature-responsive polymer composition and a plurality of second coated regions located at the edge of the first coated region and coated with a cell adhesive substance; and a seeding and culturing step of seeding cells in the first coated region and the second coated regions and culturing the cells.

An example manufacturing method in Embodiment (V) includes a production step of producing a temperature-responsive polymer and/or a temperature-responsive polymer composition, the above-described preparation step, and the above-described seeding and culturing step.

FIG. 34 is an overview, in (i) to (viii), of an example manufacturing method of a cell structure in Embodiment (V).

Details of each step in an example manufacturing method of a cell structure in Embodiment (V) are provided below.

(Production Step)

Examples of the production step in Embodiment (V) include a step similar to the production step in Aspect (I), and a similar step is preferred.

(Preparation Step)

In an example manufacturing method, a first coated region coated with a temperature-responsive polymer and/or a temperature-responsive polymer composition and a plurality of second coated regions located at the edge of the first coated region and coated with a cell adhesive substance are prepared on a culturing surface of a cell culture container (preparation step) (see (i) to (iii) of FIG. 34).

Here, the culturing surface apart from the first coated region and the second coated regions may be either cell adhesive or cell non-adhesive, but a cell non-adhesive culturing surface is preferable to facilitate obtaining a cell structure of the desired shape.

The production method of the cell non-adhesive culturing surface is not restricted. For example, a cell culture container provided with a cell non-adhesive culturing surface, such as PrimeSurface® by SUMILON, or a cell non-adhesive sheet, pad, or the like may be used. A cell-culture container provided with an untreated polystyrene culturing surface may also be used.

Here, as illustrated in FIG. 34, the first coated region and the second coated regions are preferably provided to be surrounded by the non-coated region (the region of the culturing surface that is not particularly coated) to suppress contact with the wall of the cell culture container and to adjust the shape of the cell structure (see (ii), (iii) of FIG. 34).

The area of the first coated region is not restricted. When, for example, using a culturing surface of a ϕ35 mm cell culture container to manufacture a cell structure with a size of 1 mm to 30 mm, the area of the first coated region may be 1 mm$^2$ to 750 mm$^2$, preferably 10 mm$^2$ to 700 mm$^2$.

The shape of the first coated region is not restricted and may, in plan view, be circular (a circle, an ellipse, or the like), polygonal (a square, a rectangle, a triangle, or the like), or linear, and the corners of a polygon may be rounded.

Among these shapes, a shape extending in a predetermined direction is preferred to control the aggregation mode of cells. Specifically, a shape with a long axis and a short axis and a shape having a maximum and minimum distance between two points on the outer contour line are preferable, and a rectangle is more preferable.

When the first coated region is a rectangle, the aspect ratio thereof (length of long sides:length of short sides) may be 1 to 50, preferably 5 to 50, and more preferably 10 to 50.

When the first coated region is a rectangle, the width thereof is preferably 0.1 mm to 50 mm, more preferably 0.1 mm to 30 mm, and the length thereof is preferably 0.1 mm to 150 mm, more preferably 0.1 mm to 100 mm, to control the shape of the cell structure.

The zeta potential of the surface of the first coated region is preferably 0 mV to 50 mV, more preferably 0 mV to 35 mV, and even more preferably 10 mV to 25 mV. A zeta potential of 0 mV or more facilitates adhesion of negatively charged cells. A zeta potential of 50 mV or less can reduce cytotoxicity.

Furthermore, setting the zeta potential in the aforementioned ranges further facilitates production of cell structures having an aggregated (pellet-like) shape by simply culturing cells under appropriate culture conditions. The reason is that setting the surface zeta potential within the aforementioned ranges is inferred to provide the surface of the first coated region with a weak positive charge that does not trigger cytotoxicity, to ensure rapid adhesion of the seeded cells, to improve cell activity and encourage secretion of extracellular matrix, and also to appropriately inhibit cell migration, strengthening the bond between cells.

The zeta potential refers to the value calculated with the Smoluchowski equation by measurement using a zeta potential meter (for example, model "ELSZ" by Otsuka Electronics Co.) with a particle (zeta potential: −5 mV to +5 mV) in which polystyrene latex is coated with hydroxypropyl cellulose as a reference monitor particle.

The contact angle of water relative to the surface of the first coated region is preferably 50° to 90°, more preferably 60° to 80°, and even more preferably 62° to 78° to increase the effects of Aspect (V). The contact angle of water relative to the first coated region refers to the average contact angle measured in conformity with JIS R3257 at several arbitrary points within the coated region.

Examples of the cell adhesive substance coating the second coated regions include laminin, collagen, fibronectin, peptides, cationic polymers, and polystyrene. Examples of the peptides include peptides containing an arginine-glycine-aspartic acid sequence and peptides containing a sequence of 8 or more consecutive arginine residual groups. Examples of the cationic polymers include aminostyrene. Among these, laminin, collagen, and fibronectin, which have high cell adhesiveness, are preferable.

Reagents containing the above-listed cell adhesive substances can also be suitably used. Examples of such reagents include serum.

One type of these cell adhesive substances may be used alone, or a combination of two or more types may be used.

The area of the second coated region is not restricted. When, for example, using a culturing surface of a ϕ35 mm cell culture container to manufacture a cell structure with a size of 1 mm to 30 mm, the area of the second coated region may be 0.1 mm$^2$ to 75 mm$^2$, preferably 0.1 mm$^2$ to 10 mm$^2$.

The shape of the second coated region is not restricted and may, in plan view, be circular (a circle, an ellipse, or the like) or polygonal (a square, a rectangle, a triangle, or the like), and the corners of a polygon may be rounded.

Among these shapes, a circular shape is preferred to lessen the force that acts on cells adhered to the second coated region when cells aggregate.

When the second coated region is circular, the diameter thereof is preferably 0.1 mm to 50 mm, more preferably 0.1 mm to 10 mm, to control the shape of the cell structure.

The ratio (S2/S1) of the area of the second coated region (S2) to the area of the first coated region (S1) is not restricted but is preferably 0.001 to 1.0, more preferably 0.01 to 0.5, to facilitate controlling the aggregation mode of cells.

In Embodiment (V), the first coated region and the second coated regions may overlap, the outer contour lines thereof may touch, or the regions may be separated by a shortest distance of 0.1 mm to 10 mm.

The position of the first coated region on the culturing surface and the positions of the second coated regions on the culturing surface may be the center of gravity of each region.

In Embodiment (V), it suffices for the second coated regions to be provided at the edge of the first coated region. Here, the edge refers to the region 0.01 mm to 1 mm inward from the outer contour line of the first coated region.

In Embodiment (V), the number of second coated regions provided at the edge of the first coated region may be any number equal to or greater than 2, such as 3 or more, 4 or more, etc. The second coated regions may be coated with the same cell adhesive substance or with different substances.

FIGS. 35A to 35C illustrate arrangements of the first coated region and the first coated region in Embodiment (V).

In an example illustrated in (i) of FIG. 35A and (i) to (viii) of FIG. 34, the first coated region is circular in plan view, and the second coated regions are arranged to overlap the circular first coated region at either side of the first coated region.

In Embodiment (V), the second coated region may be arranged at 3 locations (see (ii) of FIG. 35A) or 4 locations (see (iii) of FIG. 35A) in overlap with the circular first coated region at the edge of the first coated region.

In Embodiment (V), the first coated region may be a rectangle with rounded corners, and the second coated regions may be arranged at either edge of the first coated region in overlap, as illustrated in FIG. 35B.

Furthermore, in Embodiment (V), the first coated region may have any desired shape, and the second coated regions may be arranged at a plurality (5 in FIG. 35C) of edges of the first coated region in overlap, as illustrated in FIG. 35C.

In an example manufacturing method of a cell structure illustrated in FIG. 34, the preparation step is performed by applying the temperature-responsive polymer and/or the temperature-responsive polymer composition to the central portion of the culturing surface of a cell culture container (see (i) of FIG. 34) while drawing a circular shape in plan view (see (ii) of FIG. 34) and then drying the applied region (see (iii) of FIG. 34) to provide the first coated region, and subsequently applying a cell adhesive substance to two locations at the edge of the first coated region along a straight line passing through the center of the circular first coated region while drawing a circular shape in plan view (see (ii) of FIG. 34) and then drying the applied region (see (iii) of FIG. 34) to provide the second coated regions.

The preparation step may, for example, be a step of dissolving a temperature-responsive polymer or a temperature-responsive polymer composition in a solvent to form a solution including a temperature-responsive polymer or a temperature-responsive polymer composition (temperature-responsive polymer solution), applying the solution onto the culturing surface of a cell culture container, and drying to prepare a coated cell culture container (preparation step I). The preparation step may also be a step of cooling an aqueous solution including a temperature-responsive polymer or a temperature-responsive polymer composition (temperature-responsive polymer aqueous solution) to the cloud point of the temperature-responsive polymer or below, casting the cooled temperature-responsive polymer aqueous solution onto the culturing surface of a cell culture container, and heating to a temperature above the cloud point to prepare a coated cell culture container (preparation step II).

Examples of the solvent in the temperature-responsive polymer solution in preparation step I include water; physiological saline; buffer solutions; alcohols such as methanol, ethanol, n-propyl alcohol, isopropyl alcohol, 1-butanol, isobutyl alcohol, 2-butanol, t-butyl alcohol, 1-pentanol, 2-pentanol, 3-pentanol, 2-methyl-1-butanol, 3-methyl-1-butanol, 2-methyl-2-butanol, 3-methyl-2-butanol, 2,2-dimethyl-1-propanol, 1-pentanol, 2-pentanol, 3-pentanol, 2-methyl-1-butanol, 3-methyl-1-butanol, 2-methyl-2-butanol, 3-methyl-2-butanol, 2,2-dimethyl-1-propanol, 1-hexanol, 2-methyl-2-pentanol, allyl alcohol, benzyl alcohol, and salicyl alcohol; ketones such as acetone, ethyl methyl ketone, diethyl ketone, methyl propyl ketone, methyl isobutyl ketone, methyl vinyl ketone, cyclohexanone, 2-methyl cyclopentanone, acetophenone, benzophenone, and isophorone; esters such as methyl acetate, ethyl acetate, propyl acetate, isopropyl acetate, n-butyl acetate, isobutyl acetate, sec-butyl acetate, tert-butyl acetate, vinyl acetate, methyl formate, ethyl formate, propyl formate, esters of the aforementioned alcohols and phosphoric acid, and esters of the aforementioned alcohols and carbonic acid; chloroform; benzene; toluene; diethyl ether; and dichloromethane. Among these, alcohols such as methanol, ethanol, n-propyl alcohol, isopropyl alcohol, 2-butanol, t-butyl alcohol, and allyl alcohol; ketones such as acetone, ethyl methyl ketone, diethyl ketone, and methyl vinyl ketone; esters such as methyl acetate, ethyl acetate, isopropyl acetate, tert-butyl acetate, and vinyl acetate; chloroform; benzene; toluene; diethyl ether; and dichloromethane are preferred for facilitating uniform coating of the culturing surface and for having excellent solubility of temperature-responsive polymers. An organic solvent with a low boiling point (such as at least one selected from the group consisting of a low-molecular alcohol with 1 to 4 carbon atoms, a low-molecular ketone with 3 to 5 carbon atoms, and an acetic acid alkyl ester having an alkyl group with 1 to 4 carbon atoms; in particular, at least one selected from the group consisting of a low-molecular alcohol with 1 to 4 carbon atoms, a low-molecular ketone with 3 to 5 carbon atoms, and an acetic acid alkyl ester having an alkyl group with 1 to 4 carbon atoms, the low-molecular alcohol, low-molecular ketone, and acetic acid alkyl ester having a boiling point lower than that of water) is more preferable for allowing drying in a short time and facilitating even more uniform application on the culturing surface. Methanol and ethanol are particularly preferable for their low cost and excellent operability.

One type of these solvents may be used alone, or a combination of two or more types may be used.

Since the solvent has excellent solubility with respect to a temperature-responsive polymer, the temperature-responsive polymer tends not to become insoluble and precipitate even at a temperature equal to or greater than the cloud point (such as room temperature or 37° C.). This eliminates the need to manage the temperature of the temperature-responsive polymer during application of the temperature-responsive polymer, allowing easy preparation of a coated cell culture container.

In the preparation step I, a hydrophilic molecule is preferably included in the temperature-responsive polymer to facilitate self-aggregation of cells. Examples of the hydrophilic molecule include non-ionic, hydrophilic molecules that do not affect the C/A ratio of the temperature-responsive polymer, such as polyethylene glycol (PEG), dimethyl acrylamide (DMAA), glycerin, Triton X, polypropylene glycol, and the like.

In the preparation step I, the content of the temperature-responsive polymer in the temperature-responsive polymer solution is preferably 0.00075 to 0.015 weight %, more preferably 0.001 to 0.01 weight %, relative to the temperature-responsive polymer solution (100 weight %) to facilitate uniform coating of the culturing surface by the temperature-responsive polymer.

In the preparation step I, the content of the hydrophilic molecule in the temperature-responsive polymer solution is preferably 0.00001 to 0.00015 weight %, more preferably 0.00003 to 0.0001 weight %, relative to the temperature-responsive polymer (100 weight %) to facilitate self-aggregation of cells.

To facilitate uniform coating of the culturing surface by the temperature-responsive polymer or the temperature-responsive polymer composition, the temperature-responsive polymer solution in the preparation step I preferably does not include water, and the weight ratio of water in the temperature-responsive polymer solution (100 weight %) is more preferably 0.5 weight % or less and even more preferably 0.1 weight % or less. The weight ratio of water can be measured by a method known to a person skilled in the art, such as gas chromatography or the Karl Fischer method.

In the preparation step I, the temperature-responsive polymer solution may be applied to the entire culturing surface or to a portion of the culturing surface, but application to the entire culturing surface is preferable to facilitate obtaining a cell structure.

In the preparation step I, preferred conditions for drying the applied temperature-responsive polymer solution are drying under atmospheric pressure at a temperature of 10° C. to 70° C. for 1 to 3,000 minutes to uniformly coat the culturing surface with the temperature-responsive polymer or the temperature-responsive polymer composition. Quick drying of the applied temperature-responsive polymer solution facilitates uniform coating on the culturing surface with an even distribution of the temperature-responsive polymer or the temperature-responsive polymer composition.

The applied temperature-responsive polymer solution may, for example, be dried by letting the cell culture container stand in an incubator at 37° C.

In the preparation step II, examples of the solvent for dissolving the temperature-responsive polymer or the temperature-responsive polymer composition include water; physiological saline; and buffer solutions such as a phosphate buffer solution, phosphate buffered saline (PBS), and a tris buffer solution.

In the preparation step II, examples of the method of cooling the temperature-responsive polymer aqueous solution include placing the temperature-responsive polymer aqueous solution in a refrigerator at approximately 4° C. and cooling to a temperature at or below the cloud point.

In the preparation step II, examples of the method of casting the temperature-responsive polymer aqueous solution onto the culturing surface include a method of tilting the culturing surface of the cell culture container to spread the temperature-responsive polymer aqueous solution that has a temperature at or below the cloud point and a method of spreading the temperature-responsive polymer aqueous solution using a spatula.

In the preparation step II, examples of the method of heating the cast temperature-responsive polymer aqueous solution to above the cloud point include a method of letting the cell culture container after the casting step stand in an incubator at 37° C.

In the cell culture method of Embodiment (V), the region occupied by the first coated region and the second coated regions in the preparation step is preferably surrounded by a cell non-adhesive wall. Specifically, the following modifications may be adopted.

Cell non-adhesive refers to adherent cells not adhering or tending not to adhere.

This embodiment inhibits adhesion between the seeded cells and the walls of the recess and facilitates control of the aggregation form of cells during the below-described seeding and culturing step and allows more precise manufacturing of a cell structure having a desired orientation.

FIG. 36 is an outline of a modification to the preparation step, with the subsequent seeding and culturing step.

In this modification to the preparation step, a recess with a planar shape forming the first coated region and the second coated regions in FIG. 34 (i.e. a large circle and two small circles arranged at the edge thereof) is carved into the culturing surface of a cell culture container (see FIG. 36).

In the preparation step of this modification, the temperature-responsive polymer and/or temperature-responsive polymer composition, along with the cell adhesive substance, are arranged only on the bottom of the carved-out recess (see (i) of FIG. 36). The polymer and/or polymer composition, along with the cell adhesive substance, are not arranged on the surface other than the bottom of the recess, i.e. the surface of the walls of the recess.

This modification allows a cell structure having a desired orientation to be manufactured more precisely (see (ii) of FIG. 36).

(Seeding and Culturing Step)

In an example manufacturing method of Embodiment (V), cells are next seeded in the first coated region and the second coated regions and are cultured to produce a cell structure (seeding and culturing step).

In an example in FIG. 34, the seeding and culturing step is performed by adding cells and a cell culture medium to the cell culture container (see (iv) of FIG. 34), subsequently placing the cell culture container in a typical 37° C. cell incubator (see (v) of FIG. 34), adding new cell culture medium by medium exchange (see (vi) of FIG. 34), and placing the cell culture container in the cell incubator again (see (vii) and (viii) of FIG. 34).

Examples of the cells that can be used in the cell culturing method of Embodiment (V) include ADSC, cardiomyocytes, myocardial fibroblasts, nerve cells, neuroblasts, fibroblasts, chondrocytes, vascular endothelial cells, vascular stromal cells, and smooth muscle cells.

One type of these cells may be used alone, or a combination of two or more types may be used.

The cell density when seeding cells in the seeding and culturing step is preferably $0.3 \times 10^4$ cells/cm$^2$ or more, and more preferably $1.0 \times 10^4$ cells/cm$^2$ or more. Furthermore, to prevent problems related to the cell cycle, such as growth arrest due to contact between cells during culturing, the cell density is preferably $5.0 \times 10^4$ cells/cm$^2$ or less and more preferably $4.5 \times 10^4$ cells/cm$^2$ or less.

The first coated region after seeding preferably has a confluency of 90% to 100%, more preferably 95% to 100%, and even more preferably 99% to 100%.

Setting the confluency within the aforementioned ranges prevents the cells from each forming colonies, allowing the cells to aggregate and form a cell structure while remaining homogeneously dispersed. Furthermore, the seeded cells do not grow easily if the cell density is high, allowing formation of an aggregated cell structure before cells grow. Since the properties of seeded cells may change when the cells grow, impeding cell growth allows formation of a cell structure including cells with the same properties as at the time of seeding.

A person skilled in the art can appropriately determine the culture conditions on the basis of the type of cells being used and the purpose of the experiment. Example conditions are 37° C. and a 5% $CO_2$ atmosphere.

The phenomenon that occurs in the seeding and culturing step is described below with reference to FIG. 34.

In this step, the seeded cells first precipitate on the first coated region and the second coated regions. At this time, the cells that precipitate on the first coated region and the second coated regions adhere to the coated regions and survive, whereas the cells that precipitate on the non-coated region die without adhering to the non-coated region (see (v) of FIG. 34).

Next, the cells that did not adhere to the culturing surface are removed from the cell culture container (see (vi) of FIG. 34).

Upon further culturing of the cells adhered to the first coated region and the second coated regions, the cells located near the boundary between the first coated region and the non-coated region start to aggregate towards the central portion of the first coated region, along with the cells positioned closer to the central portion of the first coated region (see (vii) of FIG. 34). In other words, the adhered cells peel away from the first coated region, warping towards the central portion of the first coated region.

On the other hand, the cells adhered to the second coated regions remain adhered to their initial position, without peeling off from the second coated regions (see (vii) of FIG. 34).

Ultimately, the cells adhered to the first coated region form a cell structure with a linear structure at the central portion of the first coated region, connecting the two cell groups that remain adhered to the second coated regions (see (viii) of FIG. 34).

Here, within the cell structure obtained in the seeding and culturing step, the cells in the portion formed by cells that were adhered to the first coated region are stretched in the extending direction of the linear structure and are oriented along a line connecting the two second coated regions.

A plurality of cell structures obtained in this way can be interwoven or connected appropriately to produce a cell structure with a desired shape.

In terms of vitality, the resulting cell structure is preferably used immediately after formation, insofar as possible, in an experiment or the like and is more preferably used within 24 hours.

In the manufacturing method of a cell structure of Embodiment (V), single layer cells supplied with sufficient nutrients and oxygen aggregate in a short period of time to form a cell structure, thereby avoiding problems with known techniques such as cells on the inside of the cell structure dying from lack of oxygen. This method is particularly useful for culturing a cell structure composed of cardiomyocytes, which have a particularly strong need for oxygen.

Obtaining, in a test tube, a cell structure within the same environment as a living organism is extremely important in terms of experimental technique. The manufacturing method of a cell structure of Embodiment (V) allows the orientation of cells to be matched to the orientation in a living organism (for example, a spindle form in a predetermined direction in the case of cardiomyocytes).

For example, during drug discovery tests related to cardiomyocytes, the electrocardiographic waveform of cultured cardiomyocytes is evaluated to detect cardiotoxicity, such as arrhythmogenesis. To increase the measurement accuracy (S/N ratio), the electric signal from the cells is preferably as large as possible.

As described above, the manufacturing method of a cell structure of Embodiment (V) allows a large cell structure in a state with the original orientation to be obtained. Hence, a specimen imitating living cardiomyocytes in a living organism can be obtained. This can improve the accuracy of drug discovery tests related to cardiomyocytes.

[[Aspect (VI)]]
[Manufacturing Method of a Cell Structure]

A manufacturing method of a cell structure of Aspect (VI) includes the successive steps of a production step of producing a temperature-responsive polymer or a temperature-responsive polymer composition, a culture container preparation step of coating a culturing surface of a cell culture container with the temperature-responsive polymer or the temperature-responsive polymer composition to prepare a coated cell culture container, a seeding step of seeding cardiomyocytes and fibroblasts in the coated cell culture container at a ratio of 200 to 300 fibroblasts per 100 cardiomyocytes, and a culturing step of culturing the seeded cells to obtain an aggregated cell structure.

In the present disclosure, the coated portion, on the culturing surface of the cell culture container, coated with the temperature-responsive polymer or the temperature-responsive polymer composition is also referred to as a "coated culturing surface". The coated cell culture container is a cell culture container with the coated culturing surface. The entire culturing surface of the coated cell culture container may be the coated culturing surface, or a portion of the culturing surface may be the coated culturing surface. The culturing surface may have one coated culturing surface or a plurality of coated culturing surfaces.

A cell structure including cardiomyocytes and fibroblasts can be formed into a spheroid over a long time of 1 to 2 weeks using a well-known U-shaped low-adhesion culture dish or the hanging drop method. Production is time consuming, however, leading to problems such as difficulty maintaining cardiomyocytes, which are extremely susceptible to a hypoxic state, and difficulty coculturing cells with different growth rates.

We discovered the surprising fact that seeding cardiomyocytes and fibroblasts in a coated cell culture container in which the culturing surface is coated with a temperature-responsive polymer or a temperature-responsive polymer composition allows easy formation of a cell structure imitating heart disease tissue that has suffered cardiac failure.

The manufacturing method of a cell structure of Embodiment (VI) allows cardiomyocytes and fibroblasts to aggregate while maintaining a state of homogeneous dispersion and allows reproduction of tissue, in a state close to a state of existence in a living organism, that includes cardiomyocytes and fibroblasts and that has suffered cardiac failure.

In the manufacturing method of a cell structure of Embodiment (VI), the seeded mixed cells adhere to the coated culturing surface, and upon being cultured, self-aggregate and contract so that the edge of the cells that are spread out like a sheet separates from the coated culturing surface and warps. The cells thus aggregate to form an aggregated cell structure.

In particular, in the manufacturing method of a cell structure of Embodiment (VI), the culturing surface is coated by a temperature-responsive polymer or a temperature-responsive polymer composition, and the adhesiveness between the coated culturing surface and the cells is in an appropriate range. Therefore, even mixed cells including cardiomyocytes, which do not readily aggregate, can form an aggregated cell structure. An aggregated cell structure can also be formed easily by a combination with fibroblasts, which readily aggregate.

Since cardiomyocytes and fibroblasts have different growth rates, a known method of forming a cell structure by culturing for a long time does not allow formation of a cell structure that includes many cardiomyocytes. The manufacturing method of a cell structure of Embodiment (VI) allows formation of a cell structure without growing cardiomyocytes and fibroblasts, thereby yielding a cell structure constituted by cells in nearly the same ratio as the cell ratio between cardiomyocytes and fibroblasts at the time of seeding. The mixing ratio of cells constituting the cell structure can therefore easily be adjusted. Furthermore, the manufacturing method of a cell structure of Embodiment (VI) uses a coated cell culture container in which the adhesiveness between the coated culturing surface and the cells is in an appropriate range and therefore does not require cells to be grown. For example, a mixture of cardiomyocytes and fibroblasts aggregates and rolls up in a short period of time, such as within 24 hours after seeding, thereby easily allowing formation of an aggregated cell structure that is constituted by two or more types of cells with different growth rates, that includes living cardiomyocytes, and that is beating.

(Production Step)

Examples of the production step of producing the temperature-responsive polymer and the temperature-responsive polymer composition used in a cell culture container of Embodiment (VI) include a step similar to the production step in Aspect (I), and a similar step is preferred.

In Embodiment (VI), the temperature-responsive polymer and the temperature-responsive polymer composition used in the manufacturing method are preferably (A) to further facilitate obtaining an aggregated cell structure that includes cardiomyocytes and fibroblasts.

The production step of producing a mixture containing 2-N,N-dimethylaminoethyl methacrylate (DMAEMA) in Embodiment (VI) is also referred to as a mixture production step.

(Culture Container Preparation Step)

In the manufacturing method of an embodiment of Aspect (VI), the culture container preparation step is a step of coating a culturing surface of a cell culture container with the temperature-responsive polymer or the temperature-responsive polymer composition to prepare a coated cell culture container.

The culture container preparation step may, for example, be a step of dissolving a temperature-responsive polymer or a temperature-responsive polymer composition in a solvent to form a temperature-responsive polymer solution, applying the solution onto the culturing surface of a cell culture container, and drying to prepare a coated cell culture container (culture container preparation step I). The culture container preparation step may instead be a step of cooling an aqueous solution including a temperature-responsive polymer or a temperature-responsive polymer composition (temperature-responsive polymer aqueous solution) to the cloud point of the temperature-responsive polymer or below, casting the cooled temperature-responsive polymer aqueous solution onto the culturing surface of a cell culture container, and heating to a temperature above the cloud point to prepare a coated cell culture container (culture container preparation step II).

Examples of the solvent in the temperature-responsive polymer solution in the culture container preparation step I include water; physiological saline; buffer solutions; alcohols such as methanol, ethanol, n-propyl alcohol, isopropyl alcohol, 1-butanol, isobutyl alcohol, 2-butanol, t-butyl alcohol, 1-pentanol, 2-pentanol, 3-pentanol, 2-methyl-1-butanol, 3-methyl-1-butanol, 2-methyl-2-butanol, 3-methyl-2-butanol, 2,2-dimethyl-1-propanol, 1-pentanol, 2-pentanol, 3-pentanol, 2-methyl-1-butanol, 3-methyl-1-butanol, 2-methyl-2-butanol, 3-methyl-2-butanol, 2,2-dimethyl-1-propanol, 1-hexanol, 2-methyl-2-pentanol, allyl alcohol, benzyl alcohol, and salicyl alcohol; ketones such as acetone, ethyl methyl ketone, diethyl ketone, methyl propyl ketone, methyl isobutyl ketone, methyl vinyl ketone, cyclohexanone, 2-methyl cyclopentanone, acetophenone, benzophenone, and isophorone; esters such as methyl acetate, ethyl acetate, propyl acetate, isopropyl acetate, n-butyl acetate, isobutyl acetate, sec-butyl acetate, tert-butyl acetate, vinyl acetate, methyl formate, ethyl formate, propyl formate, esters of the aforementioned alcohols and phosphoric acid, and esters of the aforementioned alcohols and carbonic acid; chloroform; benzene; toluene; diethyl ether; and dichloromethane.

Among these, water; alcohols such as methanol, ethanol, n-propyl alcohol, isopropyl alcohol, 2-butanol, t-butyl alcohol, and allyl alcohol; ketones such as acetone, ethyl methyl ketone, diethyl ketone, and methyl vinyl ketone; esters such as methyl acetate, ethyl acetate, isopropyl acetate, tert-butyl acetate, and vinyl acetate; chloroform; benzene; toluene; diethyl ether; and dichloromethane are preferred for facilitating uniform coating of the culturing surface and for having excellent solubility of temperature-responsive polymers. An organic solvent with a low boiling point (such as at least one selected from the group consisting of a low-molecular alcohol with 1 to 4 carbon atoms, a low-molecular ketone with 3 to 5 carbon atoms, and an acetic acid alkyl ester having an alkyl group with 1 to 4 carbon atoms; in particular, at least one selected from the group consisting of a low-molecular alcohol with 1 to 4 carbon atoms, a low-molecular ketone with 3 to 5 carbon atoms, and an acetic acid alkyl ester having an alkyl group with 1 to 4 carbon atoms, the low-molecular alcohol, low-molecular ketone, and acetic acid alkyl ester having a boiling point lower than that of water) is more preferable for allowing drying in a short time and facilitating even more uniform application on the culturing surface. Methanol and ethanol are particularly preferable for their low cost and excellent operability.

One type of these solvents may be used alone, or a combination of two or more types may be used.

Since the solvent has excellent solubility with respect to a temperature-responsive polymer, the temperature-responsive polymer tends not to become insoluble and precipitate even at a temperature equal to or greater than the cloud point (such as room temperature or 37° C.). This eliminates the need to manage the temperature of the temperature-responsive polymer during application of the temperature-responsive polymer, allowing easy preparation of a coated cell culture container.

In the culture container preparation step I, a hydrophilic molecule is preferably included in the temperature-responsive polymer to facilitate self-aggregation of cells. Examples of the hydrophilic molecule include non-ionic, hydrophilic molecules that do not affect the C/A ratio of the temperature-responsive polymer, such as polyethylene glycol (PEG), dimethyl acrylamide (DMAA), glycerin, Triton X, polypropylene glycol, and the like.

In the culture container preparation step I, the content of the temperature-responsive polymer in the temperature-responsive polymer solution is preferably 0.05 mass % to 2.0 mass %, more preferably 0.1 mass % to 1.5 mass %, relative to the temperature-responsive polymer solution (100 mass %) to facilitate uniform coating of the culturing surface by the temperature-responsive polymer.

In the culture container preparation step I, the content of the hydrophilic molecule in the temperature-responsive polymer solution is preferably 0.00001 mass % to 0.00015 mass %, more preferably 0.00003 mass % to 0.0001 mass %, relative to the temperature-responsive polymer (100 mass %) to facilitate self-aggregation of cells.

To facilitate uniform coating of the culturing surface by the temperature-responsive polymer or the temperature-responsive polymer composition, the temperature-responsive polymer solution in the culture container preparation step I preferably does not include water, and the mass ratio of water in the temperature-responsive polymer solution (100 mass %) is more preferably 0.5 mass % or less and even more preferably 0.1 mass % or less.

The mass ratio of water can be measured by a method known to a person skilled in the art, such as gas chromatography or the Karl Fischer method.

In the culture container preparation step I, the temperature-responsive polymer solution may be applied to the entire culturing surface or to a portion of the culturing surface. When the temperature-responsive polymer solution is applied to a portion of the culturing surface, one coated culturing surface or a plurality of coated culturing surfaces may be provided on the culturing surface. A cell culture container with a cell non-adhesive culturing surface is preferably used when the temperature-responsive polymer solution is applied to a portion of the culturing surface.

"Cell non-adhesive" refers to adherent cells (for example, fibroblasts, cardiomyocytes, vascular endothelial cells, and the like) either not adhering or tending not to adhere under normal culture conditions.

In the culture container preparation step I, preferred conditions for drying the applied temperature-responsive polymer solution are drying under atmospheric pressure at a temperature of 10° C. to 70° C. for 1 to 3,000 minutes to uniformly coat the culturing surface with the temperature-responsive polymer or the temperature-responsive polymer composition. Quick drying of the applied temperature-responsive polymer solution facilitates uniform coating on the culturing surface with an even distribution of the temperature-responsive polymer or the temperature-responsive polymer composition.

The applied temperature-responsive polymer solution may, for example, be dried by letting the cell culture container stand in an incubator at 37° C.

In the culture container preparation step II, examples of the solvent for dissolving the temperature-responsive polymer or the temperature-responsive polymer composition include water; physiological saline; and buffer solutions such as a phosphate buffer solution, phosphate buffered saline (PBS), and a tris buffer solution.

In the culture container preparation step II, examples of the method of cooling the temperature-responsive polymer aqueous solution include placing the temperature-responsive polymer aqueous solution in a refrigerator at approximately 4° C. and cooling to a temperature at or below the cloud point.

In the culture container preparation step II, examples of the method of casting the temperature-responsive polymer aqueous solution onto the culturing surface include a method of tilting the culturing surface of the cell culture container to spread the temperature-responsive polymer aqueous solution that has a temperature at or below the cloud point and a method of spreading the temperature-responsive polymer aqueous solution using a spatula.

In the culture container preparation step II, examples of the method of heating the cast temperature-responsive polymer aqueous solution to above the cloud point include a method of letting the cell culture container after the casting step stand in an incubator at 37° C.

Examples of the cell culture container include commercially available multiwell plates, dishes, flasks, and the like. Examples of the material of the cell culture container include polystyrene, polyethylene terephthalate (PET), polypropylene, polybutene, polyethylene, polycarbonate, and glass. Among these, polystyrene and polyethylene terephthalate (PET) are preferable for being easy to mold precisely, for allowing adoption of various sterilization methods, and for being suitable for microscope observation by virtue of being transparent.

Cell adhesion treatment or the like may be applied to the culturing surface of the cell culture container, or the surface may be untreated. The culturing surface may be coated, processed, or the like to adjust the cell adhesiveness.

The planar shape of the culturing surface is not restricted and may, for example, be a substantially rectangular shape or other substantially polygonal shape, a substantially circular shape, or the like. Among these, a substantially circular shape is preferred to facilitate obtaining a more homogeneous cell structure.

The bottom shape of the culturing surface (the cross-sectional shape of the bottom) is not restricted, and examples include a flat bottom, round bottom, and uneven bottom. Among these, a flat bottom or a slightly curved concave bottom is preferable to facilitate obtaining a more homogeneous, spheroidal cell structure.

The area of the culturing surface of the cell culture container is preferably 200 $mm^2$ or less, more preferably 75 $mm^2$ or less, and even more preferably 32 $mm^2$ or less, from the perspective of supplying oxygen to the cardiomyocytes. The lower limit on the area of the culturing surface of the cell culture container is not restricted, and any commercially available size may be used.

The area of each coated culturing surface (the area of each portion coated with a temperature-responsive polymer or a temperature-responsive polymer composition) is preferably 200 $mm^2$ or less, more preferably 75 $mm^2$ or less, and even more preferably 32 $mm^2$ or less, from the perspective of supplying oxygen to the cardiomyocytes.

In the coated cell culture container, the amount of temperature-responsive polymer per unit area of the coated culturing surface is preferably 0.1 $ng/mm^2$ to 10.0 $ng/mm^2$ and more preferably 0.5 $ng/mm^2$ to 5.0 $ng/mm^2$. Adopting these ranges facilitates achievement of the effect of easier formation of an aggregated cell structure.

The zeta potential of the coated culturing surface in the coated cell culture container is preferably 0 mV to 50 mV, more preferably 0 mV to 35 mV, and even more preferably 10 mV to 25 mV. A zeta potential of 0 mV or more facilitates adhesion of negatively charged cells. A zeta potential of 50 mV or less can reduce cytotoxicity.

Furthermore, setting the zeta potential in the aforementioned ranges further facilitates production of an aggregated (pellet-like) cell structure by simply culturing cells under appropriate culture conditions. The reason is that setting the surface zeta potential within the aforementioned ranges is inferred to provide the coated culturing surface with a weak positive charge that does not trigger cytotoxicity, to ensure rapid adhesion of the seeded cells, to improve cell activity and encourage secretion of extracellular matrix, and also to appropriately inhibit cell migration, strengthening the bond between cells. The zeta potential refers to the value calculated with the Smoluchowski equation by measurement using a zeta potential meter (for example, model "ELSZ" by Otsuka Electronics Co.) with a particle (zeta potential: −5 mV to +5 mV) in which polystyrene latex is coated with hydroxypropyl cellulose as a reference monitor particle.

The contact angle of water relative to the coated culturing surface is preferably 50° to 90°, more preferably 60° to 80°, and even more preferably 620 to 780 to increase the effects of Aspect (VI). The contact angle of water relative to the coated culturing surface refers to the average contact angle measured in accordance with JIS R3257 at any number of points on the coated culturing surface.

(Seeding Step)

The seeding step is a step of seeding cardiomyocytes and fibroblasts in the coated cell culture container at a ratio of 200 to 300 fibroblasts per 100 cardiomyocytes. The cells may all be mixed and seeded at once or seeded a portion at a time. Each type of cell may also be seeded at once or seeded a portion at a time.

The cells seeded on the coated culturing surface of the coated cell culture container include at least cardiomyocytes and fibroblasts.

Cardiomyocytes, myocardial stem cells, and iPS cells, ES cells, or the like in the differentiation induction stage are preferred as the aforementioned cardiomyocytes to facilitate obtaining a cell structure in which cardiomyocytes and fibroblasts are more homogenously dispersed.

One type of cardiomyocytes may be used alone, or a combination of two or more types may be used.

Examples of the fibroblasts include myocardial fibroblasts, subcutaneous adipose, fascia, synovium, and periosteal-derived mesenchymal stem cells. Among these, myocardial fibroblasts and subcutaneous adipose-derived mesenchymal stem cells are preferred to facilitate obtaining a cell structure in which cardiomyocytes and fibroblasts are more homogenously dispersed.

One type of fibroblasts may be used alone, or a combination of two or more types may be used.

In the seeding step, vascular endothelial cells or vascular stromal cells may be also be seeded. One type of these cells may be used alone, or a combination of two or more types may be used.

In the seeding step, immune system cells may also be seeded.

Examples of the immune system cells include macrophages, T cells such as CD4+ T cells, and monocytes. Among these, inclusion of macrophages and/or T cells is preferred to facilitate obtaining a cell structure even closer to tissue that has suffered heart disease such as cardiac failure.

One type of these immune system cells may be used alone, or a combination of two or more types may be used.

In the seeding step, the number of fibroblasts per 100 cardiomyocytes is 200 to 300, preferably 200 to 250, and more preferably 200 to 230. Setting the number of fibroblasts per 100 cardiomyocytes to be 200 or more facilitates curling of the mixed cells to form an aggregated cell structure, and setting the number to be 300 or less allows a cell structure closer to tissue that has suffered heart disease such as cardiac failure to be obtained.

In the seeding step, the ratio of cardiomyocytes among all of the seeded cells is preferably 25% to 50% of all of the seeded cells (100%), more preferably 25% to 30%, to obtain a cell structure closer to tissue that has suffered heart disease such as cardiac failure.

In the seeding step, the number of vascular endothelial cells per 100 cardiomyocytes is preferably 5 to 50, more preferably 10 to 30, to obtain a cell structure closer to tissue that has suffered heart disease such as cardiac failure.

In the seeding step, the number of immune system cells per 100 cardiomyocytes is preferably 5 to 50, more preferably 10 to 30, to obtain a cell structure closer to tissue that has suffered heart disease such as cardiac failure.

In the seeding step, the density of all of the seeded cells on the coated culturing surface is preferably a confluency of 90% to 100% relative to the surface area of the coated culturing surface, more preferably a confluency of 95% to 100%, and even more preferably a confluency of 99% to 100%. Setting the density of seeded cells within the aforementioned ranges prevents the cells from each forming colonies, allowing the cells to aggregate and form a cell structure while remaining homogeneously dispersed. Furthermore, the seeded cells do not grow easily if the cell density is high, allowing formation of an aggregated cell structure before cells grow. Hence, a cell structure including cells in the same ratio as the seeded cells can be formed. The difference in growth rates of cells also has little effect. Since the properties of seeded cells may change when the cells grow, impeding cell growth allows formation of a cell structure including cells with the same properties as at the time of seeding.

While the density of all of the seeded cells on the coated culturing surface depends on the type of cell, a density of 20 cells/mm$^2$ to 15,000 cells/mm$^2$ is preferred. For example, when seeding by adding 1.0 mL of cell fluid to a 24 well cell culture plate with a coated culturing surface area of 200 mm$^2$, the density is preferably $4\times10^4$ cells/mL to $30\times10^4$ cells/mL. Live cells are seeded.

The coated cell culture container may be left to stand in an incubator at 37° C. and subsequently removed and placed on a clean bench at room temperature, for example, with cell seeding then being performed.

Cells are preferably seeded after being diluted in a medium. The medium for dilution may be any medium in which cells can be cultured.

(Culturing Step)

The culturing step is a step of culturing the seeded cells to obtain an aggregated cell structure.

It is known that cardiomyocytes necrotize in tissue that has suffered myocarditis, the necrotic cardiomyocytes are replaced by excessive growth of fibroblasts, and moreover, many inflammatory immune cells infiltrate. To reproduce, in a test tube, myocarditis tissue into which immune system cells have infiltrated, it is desirable to produce a cell structure that includes cardiomyocytes and fibroblasts and into which immune system cells, which are suspended cells, have infiltrated. However, this is difficult with a known hanging drop method or low-adhesion culture dish, which require 1 to 2 weeks to produce cell structures.

In the manufacturing method of Embodiment (VI), immune system cells may be further added to the coated cell culture container in the culturing step. The timing at which immune system cells are added is preferably during or after the aforementioned seeding step (simultaneous with or after cell seeding) and before a cell structure is obtained. The timing is more preferably when or after seeded cells adhere to the coated culturing surface and form a sheet-like cell structure (see (iii) of FIG. 39) and before the sheet-like cell structure starts to aggregate towards the central portion of the coated culturing surface and the edge separates from the coated culturing surface and starts to warp, forming a cell structure with a warped edge. In other words, the immune system cells may be seeded during the seeding step or added after the seeding step.

Specifically, the immune system cells are added simultaneous with or after cell seeding, preferably within 48 hours after seeding of cells (for example, after the cells that are seeded last).

Adding the immune system cells at the aforementioned timing allows the immune system cells, which are suspended cells, to precipitate due to gravity. When cells adhered to the coated culturing surface aggregate like a drawstring bag, the immune system cells are incorporated inside, allowing formation of a cell structure that includes immune system cells on the inside. A cell structure even closer to heart disease model tissue that has suffered myocarditis, cardiac failure, or the like can thus be obtained (see FIG. 39).

The conditions for culturing the seeded cells may, for example, be the use of a typical cell incubator at 37° C. The cells are preferably cultured continuously until forming an aggregated cell structure. Specifically, the cells are preferably cultured for 10 hours to 96 hours and more preferably for 15 hours to 50 hours.

Surprisingly, even when mixing, seeding, and culturing adherent cells (such as cardiomyocytes) and suspended cells (such as immune system cells), the manufacturing method of a cell structure of Embodiment (VI) allows a cell structure to be obtained by seeding and culturing the adherent cells and the suspended cells simultaneously using a medium suitable for the adherent cells being used or a medium suitable for the suspended cells being used (preferably a medium suitable for the adherent cells), without the need for preparation of a special medium.

Mixed cells including the cardiomyocytes and the fibroblasts, which adhere to the coated culturing surface and are cultured, self-aggregate to form an aggregated cell structure. The resulting cell structure includes living cells inside the aggregated structure.

The cell structure preferably has, for example, an outer diameter of 30 µm to 200 µm, more preferably 40 µm to 150 µm, and even more preferably 50 µm to 100 µm, to obtain a beating cell structure that includes living cardiomyocytes on the inside.

The cell structure obtainable with the manufacturing method of a cell structure of Embodiment (VI) is a heart disease model reproducing tissue that has suffered heart disease such as cardiac failure and can be used for purposes including research on heart disease, such as myocardial infarction, cardiac failure, and myocarditis; development of drugs for heart disease; and development of treatment for heart disease.

An example manufacturing method of a cell structure of Embodiment (VI) is described below with reference to FIGS. 38 and 39.

FIG. 38 illustrates an example manufacturing method of a cell structure that includes cardiomyocytes and fibroblasts.

A temperature-responsive polymer is applied to a culturing surface of a cell culture container to coat the culturing surface, thereby preparing a coated cell culture container having a coated culturing surface (see (i) and (ii) of FIG. 38). Subsequently, mixed cells composed of cardiomyocytes and fibroblasts and diluted with medium are added to the coated culturing surface to seed the mixed cells (see (ii) of FIG. 38). The seeded mixed cells adhere to the entire coated culturing surface (see (iii) of FIG. 38). In this example, the density of the mixed cells is 100% confluency (see (iii) of FIG. 38). Subsequently, the mixed cells adhered to the coated culturing surface start to aggregate towards the central portion of the coated culturing surface, and the edge separates from the coated culturing surface and starts to warp, yielding a cell structure with a warped edge (see (iv) of FIG. 38). The cells then continue to aggregate to form an aggregated cell structure, which floats from the coated culturing surface (see (v) of FIG. 38).

FIG. 39 illustrates an example manufacturing method of a cell structure that includes cardiomyocytes, fibroblasts, and immune system cells (suspended cells) such as macrophages.

A temperature-responsive polymer is applied to a culturing surface of a cell culture container to coat the culturing surface, thereby preparing a coated cell culture container having a coated culturing surface (see (i) and (ii) of FIG. 39). Subsequently, mixed cells composed of cardiomyocytes and fibroblasts and diluted with medium are added to the coated culturing surface to seed the mixed cells (see (ii) of FIG. 39). The seeded mixed cells adhere to the entire coated culturing surface to form a sheet-like (single layer) cell structure (see (iii) of FIG. 39). In this example, the density of the mixed cells is 100% confluency (see (iii) of FIG. 39).

After the cardiomyocytes and fibroblasts form the sheet-like cell structure, immune system cells such as macrophages are added ((iv) of FIG. 39). Subsequently, the mixed cells adhered to the coated culturing surface start to aggregate towards the central portion of the coated culturing surface, and the edge separates from the coated culturing surface and starts to warp, yielding a cell structure with a warped edge (see (v) of FIG. 39). At this time, the cell structure incorporates the immune system cells that are adhered to the sheet-like cell structure or are suspended in the culture dish. The cells then continue to aggregate to form an aggregated cell structure that includes cardiomyocytes, fibroblasts, and immune system cells. The cell structure then floats from the coated culturing surface (see (vi) of FIG. 39).

[[Aspect (VII)]]
[Manufacturing Method of a Cell Structure]

A manufacturing method of a cell structure of Aspect (VII) includes the successive steps of a production step of producing a temperature-responsive polymer or a temperature-responsive polymer composition, a culture container preparation step of coating a culturing surface of a cell culture container with the temperature-responsive polymer or the temperature-responsive polymer composition to prepare a coated cell culture container, a seeding step of seeding hepatocytes and fibroblasts in a ratio of 10 to 50 fibroblasts per 100 hepatocytes in the coated cell culture container, and a culturing step of culturing the seeded cells to obtain an aggregated cell structure.

In the present disclosure, the coated portion, on the culturing surface of the cell culture container, coated with the temperature-responsive polymer or the temperature-responsive polymer composition is also referred to as a "coated culturing surface". The coated cell culture container is a cell culture container with the coated culturing surface. The entire culturing surface of the coated cell culture container may be the coated culturing surface, or a portion of the culturing surface may be the coated culturing surface. The culturing surface may have one coated culturing surface or a plurality of coated culturing surfaces.

A spheroidal cell structure including hepatocytes and fibroblasts can be formed over a long time of 1 to 2 weeks using a well-known U-shaped low-adhesion culture dish or the hanging drop method. Production is time consuming, however, leading to problems such as difficulty coculturing cells whose growth rates, adhesiveness to the culturing surface, and suitable culture conditions differ.

We discovered the surprising fact that seeding hepatocytes and fibroblasts in a coated cell culture container in which the culturing surface is coated with a temperature-responsive polymer or a temperature-responsive polymer composition allows easy formation of a cell structure imitating tissue that has suffered hepatic failure or the like.

The manufacturing method of a cell structure of Embodiment (VII) allows hepatocytes and fibroblasts to aggregate while maintaining a state of homogeneous dispersion and allows reproduction of tissue, in a state close to a state of existence in a living organism, that includes hepatocytes and fibroblasts and that has suffered hepatic failure.

Since hepatocytes and fibroblasts have different growth rates, adhesiveness to the culturing surface, and suitable culture conditions, it is extremely difficult to form a cell structure including hepatocytes and fibroblasts with a known method of forming a cell structure by culturing for a long time. The manufacturing method of a cell structure of Embodiment (VII) uses a coated cell culture container in which the adhesiveness between the coated culturing surface and the cells is in an appropriate range and therefore does not require cells to be grown. For example, hepatocytes and fibroblasts aggregate and roll up in a short period of time, such as within 24 hours after seeding, thereby easily allowing formation of an aggregated cell structure that includes hepatocytes and fibroblasts.

(Production Step)

Examples of the production step of producing the temperature-responsive polymer and the temperature-responsive polymer composition used in a cell culture container of Embodiment (VII) include a step similar to the production step in Aspect (I), and a similar step is preferred.

In Embodiment (VII), the temperature-responsive polymer and the temperature-responsive polymer composition used in the manufacturing method are preferably (A) to further facilitate obtaining an aggregated cell structure that includes hepatocytes and fibroblasts.

The production step of producing a mixture containing 2-N,N-dimethylaminoethyl methacrylate (DMAEMA) in Embodiment (VII) is also referred to as a mixture production step.

(Culture Container Preparation Step)

In the manufacturing method of an embodiment of Aspect (VII), the culture container preparation step is a step of coating a culturing surface of a cell culture container with the temperature-responsive polymer or the temperature-responsive polymer composition to prepare a coated cell culture container.

The culture container preparation step may, for example, be a step of dissolving a temperature-responsive polymer or a temperature-responsive polymer composition in a solvent to form a temperature-responsive polymer solution, applying the solution onto the culturing surface of a cell culture container, and drying to prepare a coated cell culture container (culture container preparation step I). The culture container preparation step may instead be a step of cooling an aqueous solution including a temperature-responsive polymer or a temperature-responsive polymer composition (temperature-responsive polymer aqueous solution) to the cloud point of the temperature-responsive polymer or below, casting the cooled temperature-responsive polymer aqueous solution onto the culturing surface of a cell culture container, and heating to a temperature above the cloud point to prepare a coated cell culture container (culture container preparation step II).

Examples of the solvent in the temperature-responsive polymer solution in the culture container preparation step I include water; physiological saline; buffer solutions; alcohols such as methanol, ethanol, n-propyl alcohol, isopropyl alcohol, 1-butanol, isobutyl alcohol, 2-butanol, t-butyl alcohol, 1-pentanol, 2-pentanol, 3-pentanol, 2-methyl-1-butanol, 3-methyl-1-butanol, 2-methyl-2-butanol, 3-methyl-2-butanol, 2,2-dimethyl-1-propanol, 1-pentanol, 2-pentanol, 3-pentanol, 2-methyl-1-butanol, 3-methyl-1-butanol, 2-methyl-2-butanol, 3-methyl-2-butanol, 2,2-dimethyl-1-propanol, 1-hexanol, 2-methyl-2-pentanol, allyl alcohol, benzyl alcohol, and salicyl alcohol; ketones such as acetone, ethyl methyl ketone, diethyl ketone, methyl propyl ketone, methyl isobutyl ketone, methyl vinyl ketone, cyclohexanone, 2-methyl cyclopentanone, acetophenone, benzophenone, and isophorone; esters such as methyl acetate, ethyl acetate, propyl acetate, isopropyl acetate, n-butyl acetate, isobutyl acetate, sec-butyl acetate, tert-butyl acetate, vinyl acetate, methyl formate, ethyl formate, propyl formate, esters of the aforementioned alcohols and phosphoric acid, and esters of the aforementioned alcohols and carbonic acid; chloroform; benzene; toluene; diethyl ether; and dichloromethane.

Among these, water; alcohols such as methanol, ethanol, n-propyl alcohol, isopropyl alcohol, 2-butanol, t-butyl alcohol, and allyl alcohol; ketones such as acetone, ethyl methyl ketone, diethyl ketone, and methyl vinyl ketone; esters such as methyl acetate, ethyl acetate, isopropyl acetate, tert-butyl acetate, and vinyl acetate; chloroform; benzene; toluene; diethyl ether; and dichloromethane are preferred for facilitating uniform coating of the culturing surface and for having excellent solubility of temperature-responsive polymers. An organic solvent with a low boiling point (such as at least one selected from the group consisting of a low-molecular alcohol with 1 to 4 carbon atoms, a low-molecular ketone with 3 to 5 carbon atoms, and an acetic acid alkyl ester having an alkyl group with 1 to 4 carbon atoms; in particular, at least one selected from the group consisting of a low-molecular alcohol with 1 to 4 carbon atoms, a low-molecular ketone with 3 to 5 carbon atoms, and an acetic acid alkyl ester having an alkyl group with 1 to 4 carbon atoms, the low-molecular alcohol, low-molecular ketone, and acetic acid alkyl ester having a boiling point lower than that of water) is more preferable for allowing drying in a short time and facilitating even more uniform application on the culturing surface. Methanol and ethanol are particularly preferable for their low cost and excellent operability.

One type of these solvents may be used alone, or a combination of two or more types may be used.

Since the solvent has excellent solubility with respect to a temperature-responsive polymer, the temperature-responsive polymer tends not to become insoluble and precipitate even at a temperature equal to or greater than the cloud point (such as room temperature or 37° C.). This eliminates the need to manage the temperature of the temperature-responsive polymer during application of the temperature-responsive polymer, allowing easy preparation of a coated cell culture container.

In the culture container preparation step I, a hydrophilic molecule is preferably included in the temperature-responsive polymer to facilitate self-aggregation of cells. Examples of the hydrophilic molecule include non-ionic, hydrophilic molecules that do not affect the C/A ratio of the temperature-responsive polymer, such as polyethylene glycol (PEG), dimethyl acrylamide (DMAA), glycerin, Triton X, polypropylene glycol, and the like.

In the culture container preparation step I, the content of the temperature-responsive polymer in the temperature-responsive polymer solution is preferably 0.01 mass % to 3.0 mass %, more preferably 0.25 mass % to 2.5 mass %, relative to the temperature-responsive polymer solution (100 mass %) to facilitate uniform coating of the culturing surface by the temperature-responsive polymer.

In the culture container preparation step I, the content of the hydrophilic molecule in the temperature-responsive polymer solution is preferably 0.00001 mass % to 0.00015 mass %, more preferably 0.00003 mass % to 0.0001 mass %, relative to the temperature-responsive polymer (100 mass %) to facilitate self-aggregation of cells.

To facilitate uniform coating of the culturing surface by the temperature-responsive polymer or the temperature-responsive polymer composition, the temperature-responsive polymer solution in the culture container preparation step I preferably does not include water, and the mass ratio of water in the temperature-responsive polymer solution (100 mass %) is more preferably 0.5 mass % or less and even more preferably 0.1 mass % or less.

The mass ratio of water can be measured by a method known to a person skilled in the art, such as gas chromatography or the Karl Fischer method.

In the culture container preparation step I, the temperature-responsive polymer solution may be applied to the entire culturing surface or to a portion of the culturing surface. When the temperature-responsive polymer solution is applied to a portion of the culturing surface, one coated culturing surface or a plurality of coated culturing surfaces may be provided on the culturing surface. A cell culture container with a cell non-adhesive culturing surface is preferably used when the temperature-responsive polymer solution is applied to a portion of the culturing surface.

"Cell non-adhesive" refers to adherent cells (for example, fibroblasts, hepatocytes, vascular endothelial cells, and the like) either not adhering or tending not to adhere under normal culture conditions.

In the culture container preparation step I, preferred conditions for drying the applied temperature-responsive polymer solution are drying under atmospheric pressure at a temperature of 10° C. to 70° C. for 1 to 3,000 minutes to uniformly coat the culturing surface with the temperature-responsive polymer or the temperature-responsive polymer composition. Quick drying of the applied temperature-responsive polymer solution facilitates uniform coating on the culturing surface with an even distribution of the temperature-responsive polymer or the temperature-responsive polymer composition.

The applied temperature-responsive polymer solution may, for example, be dried by letting the cell culture container stand in an incubator at 37° C.

In the culture container preparation step II, examples of the solvent for dissolving the temperature-responsive polymer or the temperature-responsive polymer composition include water; physiological saline; and buffer solutions such as a phosphate buffer solution, phosphate buffered saline (PBS), and a tris buffer solution.

In the culture container preparation step II, examples of the method of cooling the temperature-responsive polymer aqueous solution include placing the temperature-responsive polymer aqueous solution in a refrigerator at approximately 4° C. and cooling to a temperature at or below the cloud point.

In the culture container preparation step II, examples of the method of casting the temperature-responsive polymer aqueous solution onto the culturing surface include a method of tilting the culturing surface of the cell culture container to spread the temperature-responsive polymer aqueous solution that has a temperature at or below the cloud point and a method of spreading the temperature-responsive polymer aqueous solution using a spatula.

In the culture container preparation step II, examples of the method of heating the cast temperature-responsive polymer aqueous solution to above the cloud point include a method of letting the cell culture container after the casting step stand in an incubator at 37° C.

Examples of the cell culture container include commercially available multiwell plates, dishes, flasks, and the like. Examples of the material of the cell culture container include polystyrene, polyethylene terephthalate (PET), polypropylene, polybutene, polyethylene, polycarbonate, and glass. Among these, polystyrene and polyethylene terephthalate (PET) are preferable for being easy to mold precisely, for allowing adoption of various sterilization methods, and for being suitable for microscope observation by virtue of being transparent.

Cell adhesion treatment or the like may be applied to the culturing surface of the cell culture container, or the surface may be untreated. The culturing surface may be coated, processed, or the like to adjust the cell adhesiveness.

The planar shape of the culturing surface is not restricted and may, for example, be a substantially rectangular shape or other substantially polygonal shape, a substantially circular shape, or the like. Among these, a substantially circular shape is preferred to facilitate obtaining a more homogeneous cell structure.

The bottom shape of the culturing surface (the cross-sectional shape of the bottom) is not restricted, and examples include a flat bottom, round bottom, and uneven bottom. Among these, a flat bottom or a slightly curved concave bottom is preferable to facilitate obtaining a more homogeneous, spheroidal cell structure.

The area of the culturing surface of the cell culture container is preferably 32 $mm^2$ or less, more preferably 10 $mm^2$ or less, and even more preferably 8 $mm^2$ or less, to further facilitate manufacturing of an aggregated cell structure. The lower limit on the area of the culturing surface of the cell culture container is not restricted, and any commercially available size may be used.

The area of each coated culturing surface (the area of each portion coated with a temperature-responsive polymer or a temperature-responsive polymer composition) is preferably 32 $mm^2$ or less, more preferably 10 $mm^2$ or less, and even more preferably 8 $mm^2$ or less, to further facilitate manufacturing of an aggregated cell structure.

In the coated cell culture container, the amount of temperature-responsive polymer per unit area of the coated culturing surface is preferably 0.15 $ng/mm^2$ to 15.0 $ng/mm^2$ and more preferably 1.0 $ng/mm^2$ to 5.0 $ng/mm^2$. Adopting these ranges facilitates achievement of the effect of easier formation of an aggregated cell structure.

The zeta potential of the coated culturing surface in the coated cell culture container is preferably 0 mV to 50 mV, more preferably 0 mV to 35 mV, and even more preferably 10 mV to 25 mV. A zeta potential of 0 mV or more facilitates adhesion of negatively charged cells. A zeta potential of 50 mV or less can reduce cytotoxicity.

Furthermore, setting the zeta potential in the aforementioned ranges further facilitates production of an aggregated (pellet-like) cell structure by simply culturing cells under appropriate culture conditions. The reason is that setting the surface zeta potential within the aforementioned ranges is inferred to provide the coated culturing surface with a weak positive charge that does not trigger cytotoxicity, to ensure rapid adhesion of the seeded cells, to improve cell activity and encourage secretion of extracellular matrix, and also to appropriately inhibit cell migration, strengthening the bond between cells.

The zeta potential refers to the value calculated with the Smoluchowski equation by measurement using a zeta potential meter (for example, model "ELSZ" by Otsuka Electronics Co.) with a particle (zeta potential: −5 mV to +5 mV) in which polystyrene latex is coated with hydroxypropyl cellulose as a reference monitor particle.

The contact angle of water relative to the coated culturing surface is preferably 50° to 90°, more preferably 60° to 80°, and even more preferably 62° to 78° to increase the effects of Aspect (VII). The contact angle of water relative to the coated culturing surface refers to the average contact angle measured in accordance with JIS R3257 at any number of points on the coated culturing surface.

(Seeding Step)

The seeding step is a step of seeding hepatocytes and fibroblasts in a ratio of 10 to 50 fibroblasts per 100 hepatocytes in the coated cell culture container. The cells may all be mixed and seeded at once or seeded a portion at a time. Each type of cell may also be seeded at once or seeded a portion at a time.

The cells seeded on the coated culturing surface of the coated cell culture container include at least hepatocytes and fibroblasts.

The hepatocytes that are used may, for example, be primary cells collected from a living organism, hepatocytes derived from iPS cells or ES cells, or hepatoma cells such as HepG2 cells or HepRA cells. Among these, HepG2 cells and HepRA cells are preferred for having average hepatocyte functions, such as a transporter function, metabolic activity, and albumin production, and for ease of obtaining a cell structure with a homogeneous dispersion of hepatocytes and fibroblasts.

One type of the hepatocytes may be used alone, or a combination of two or more types may be used.

Examples of the fibroblasts include subcutaneous tissue-derived fibroblasts, synovium, dental pulp, bone marrow, and subcutaneous adipose-derived mesenchymal stem cells. Among these, subcutaneous adipose-derived mesenchymal stem cells are preferred for having immunological tolerance and having little effect on cocultured cells, for being highly adhesive, and for facilitating production of a cell structure with a more uniform dispersion of hepatocytes and fibroblasts.

One type of fibroblasts may be used alone, or a combination of two or more types may be used.

In the seeding step, vascular endothelial cells may also be seeded.

One type of vascular endothelial cells may be used alone, or a combination of two or more types may be used.

In the seeding step, adipocytes may also be seeded. Examples of the adipocytes include adipose tissue-derived adherent adipocytes.

One type of adipocytes may be used alone, or a combination of two or more types may be used.

In the seeding step, immune system cells may also be seeded. The immune system cells preferably include at least one selected from the group consisting of monocytes, granulocytes, lymphocytes, and macrophages to facilitate obtaining a cell structure even closer to tissue that has suffered hepatic failure.

One type of these immune system cells may be used alone, or a combination of two or more types may be used.

In the seeding step, the number of fibroblasts per 100 hepatocytes is 10 to 50, preferably 10 to 45. Setting the number of fibroblasts per 100 hepatocytes to be 10 or more facilitates curling of the mixed cells to form an aggregated cell structure, and setting the number to be 50 or less allows a cell structure closer to tissue that has suffered hepatic failure to be obtained.

In the seeding step, the ratio of hepatocytes among all of the seeded cells is preferably 50% to 95% of all of the seeded cells (100%) to obtain a cell structure closer to tissue that has suffered hepatic failure.

In the seeding step, the number of vascular endothelial cells per 100 hepatocytes is preferably 10 to 100 to obtain a cell structure closer to tissue that has suffered hepatic failure.

In the seeding step, the number of adipocytes per 100 hepatocytes is preferably 10 to 100, and more preferably 50, to obtain a cell structure closer to tissue that has suffered hepatic failure.

The number of adipocytes per 100 fibroblasts is preferably 100 to 500 to obtain a cell structure closer to tissue that has suffered hepatic failure.

Among these ranges, adipocytes are preferably included at a ratio of 50 adipocytes per 100 hepatocytes and 100 to 500 adipocytes per 100 fibroblasts.

In the seeding step, the number of immune system cells per 100 hepatocytes is preferably 10 to 100 to obtain a cell structure closer to tissue that has suffered hepatic failure.

In the seeding step, the density of seeded cells on the coated culturing surface is preferably a confluency of 90% to 100% relative to the surface area of the coated culturing surface, more preferably a confluency of 95% to 100%, and even more preferably a confluency of 99% to 100%. Setting the density of seeded cells within the aforementioned ranges prevents the cells from each forming colonies, allowing the cells to aggregate and form a cell structure while remaining homogeneously dispersed. Furthermore, the seeded mixed cells do not grow easily if the cell density is high, allowing formation of an aggregated cell structure before cells grow. Hence, a cell structure including cells in the same ratio as the seeded mixed cells can be formed. The difference in growth rates of cells also has little effect. Since the properties of seeded cells may change when the cells grow, impeding cell growth allows formation of a cell structure including cells with the same properties as at the time of seeding.

While the density of the seeded cells on the coated culturing surface depends on the type of cell, a density of 20 cells/mm$^2$ to 15,000 cells/mm$^2$ is preferred. For example, when seeding by adding 1.0 mL of cell fluid to a 24 well cell culture plate with a coated culturing surface area of 200 mm$^2$, the density is preferably $4 \times 10^4$ cells/mL to $30 \times 10^4$ cells/mL. Live cells are seeded.

The coated cell culture container may be left to stand in an incubator at 37° C. and subsequently removed and placed on a clean bench at room temperature, for example, with cell seeding then being performed.

Cells are preferably seeded after being diluted in a medium. The medium for dilution may be any medium in which cells can be cultured.

(Culturing Step)

The culturing step is a step of culturing the seeded cells to obtain an aggregated cell structure.

It is known that in tissue that has suffered hepatic failure, fibroblasts grow excessively, and additionally many inflammatory immune cells may be present. To reproduce, in a test tube, hepatic failure tissue including immune system cells, it is desirable to produce a cell structure that includes hepatocytes and fibroblasts and also immune system cells, which are suspended cells. However, this is difficult with a known hanging drop method or low-adhesion culture dish, which require 1 to 2 weeks to produce cell structures. Apart from different growth rates and different compositions of the optimal medium, the reasons for this difficulty include a high probability of the mixed macrophages differentiating into fibroblasts during a long culturing period.

In the manufacturing method of Embodiment (VII), immune system cells may be further added to the coated cell culture container in the culturing step. The timing at which immune system cells are added is preferably during or after the aforementioned seeding step (simultaneous with or after cell seeding) and before a cell structure is obtained. The timing is more preferably when or after seeded cells adhere to the coated culturing surface and form a sheet-like cell structure (see (iii) of FIG. 41) and before the sheet-like cell structure starts to aggregate towards the central portion of the coated culturing surface and the edge separates from the coated culturing surface and starts to warp, forming a cell structure with a warped edge. In other words, the immune system cells may be seeded during the seeding step or added after the seeding step.

Specifically, the immune system cells are added simultaneous with or after cell seeding, preferably within 48 hours after seeding of cells (for example, after the cells that are seeded last).

Adding the immune system cells at the aforementioned timing allows the immune system cells, which are suspended cells, to precipitate due to gravity. When cells adhered to the coated culturing surface aggregate like a drawstring bag, the immune system cells are incorporated inside, allowing formation of a cell structure that includes immune system cells on the inside. A cell structure even closer to hepatic failure model tissue can thus be obtained (see FIG. 41).

The conditions for culturing the seeded mixed cells may, for example, be the use of a typical cell incubator at 37° C. The cells are preferably cultured continuously until forming an aggregated cell structure. Specifically, the cells are preferably cultured for 5 hours to 96 hours and more preferably for 9 hours to 50 hours.

Surprisingly, even when mixing, seeding, and culturing adherent cells (such as hepatocytes) and suspended cells (such as immune system cells), the manufacturing method of a cell structure of Embodiment (VII) allows a cell structure to be obtained by seeding and culturing the adherent cells and the suspended cells simultaneously using a medium suitable for the adherent cells being used or a medium suitable for the suspended cells being used (preferably a medium suitable for the adherent cells), without the need for preparation of a special medium.

Mixed cells including the hepatocytes and the fibroblasts, which adhere to the coated culturing surface and are cultured, self-aggregate to form an aggregated cell structure. The resulting cell structure includes living cells inside the aggregated structure.

The cell structure preferably has, for example, an outer diameter of 50 μm to 2,500 μm, more preferably 50 μm to 500 μm, and even more preferably 50 μm to 150 μm, to obtain a cell structure with a homogeneous distribution of hepatocytes and fibroblasts.

The cell structure obtainable with the manufacturing method of a cell structure of Embodiment (VII) is a hepatic failure model reproducing tissue that has suffered hepatic failure and can be used for purposes including research on hepatic failure and liver regeneration, development of drugs for hepatic failure, and development of treatment for hepatic failure.

An example manufacturing method of a cell structure of Embodiment (VII) is described below with reference to FIGS. 40 and 41.

FIG. 40 illustrates an example manufacturing method of a cell structure that includes hepatocytes and fibroblasts.

A temperature-responsive polymer is applied to a culturing surface of a cell culture container to coat the culturing surface, thereby preparing a coated cell culture container having a coated culturing surface (see (i) and (ii) of FIG. 40). Subsequently, mixed cells composed of hepatocytes and fibroblasts and diluted with medium are added to the coated culturing surface to seed the mixed cells (see (ii) of FIG. 40). The seeded mixed cells adhere to the entire coated culturing surface (see (iii) of FIG. 40). In this example, the density of the mixed cells is 100% confluency (see (iii) of FIG. 40). Subsequently, the mixed cells adhered to the coated culturing surface start to aggregate towards the central portion of the coated culturing surface, and the edge separates from the coated culturing surface and starts to warp, yielding a cell structure with a warped edge (see (iv) of FIG. 40). The cells then continue to aggregate to form an aggregated cell structure, which floats from the coated culturing surface (see (v) of FIG. 40).

FIG. 41 illustrates an example manufacturing method of a cell structure that includes hepatocytes, fibroblasts, and immune system cells (suspended cells) such as macrophages.

A temperature-responsive polymer is applied to a culturing surface of a cell culture container to coat the culturing surface, thereby preparing a coated cell culture container having a coated culturing surface (see (i) and (ii) of FIG. 41). Subsequently, mixed cells composed of hepatocytes and fibroblasts and diluted with medium are added to the coated culturing surface to seed the mixed cells (see (ii) of FIG. 41). The seeded mixed cells adhere to the entire coated culturing surface to form a sheet-like (single layer) cell structure (see (iii) of FIG. 41). In this example, the density of the mixed cells is 100% confluency (see (iii) of FIG. 41).

After the hepatocytes and fibroblasts form the sheet-like cell structure, immune system cells such as macrophages are added ((iv) of FIG. 41). Subsequently, the mixed cells adhered to the coated culturing surface start to aggregate towards the central portion of the coated culturing surface, and the edge separates from the coated culturing surface and starts to warp, yielding a cell structure with a warped edge (see (v) of FIG. 41). At this time, the cell structure incorporates the immune system cells that are adhered to the sheet-like cell structure or are suspended in the culture dish. The cells then continue to aggregate to form an aggregated cell structure that includes hepatocytes, fibroblasts, and immune system cells. The cell structure then floats from the coated culturing surface (see (vi) of FIG. 41).

EXAMPLES

The present disclosure is described below in greater detail with reference to examples, but the present disclosure is in no way limited by these examples.

Examples of Aspect (I)

In the following tests, commercially available reagents were used without further purification, unless otherwise noted.

(Test I-A) Production of Temperature-Responsive Polymer

First, 10.0 g of 2-N,N-dimethylaminoethyl methacrylate (DMAEMA) and 5,000 μL of water were added to a 50 mL capacity transparent vial made of soft glass, and the vial was stirred using a magnetic stirrer. The mixture (liquid) was then purged with Gi-grade, highly pure (purity: 99.99995%) nitrogen gas for 10 minutes (flow rate: 2.0 L/min) to deoxygenize the mixture. The DMAEMA that was used included 0.5 weight % of methylhydroquinone (MEHQ), which is a polymerization inhibitor.

Subsequently, this reactant was polymerized by irradiation with ultraviolet light for 22 hours using a round, black fluorescent lamp (model FCL20BL, 18 W, by NEC Corporation). The reactant became viscous 5 hours later and hardened 15 hours later. A polymer was thus obtained as a reaction product. This reaction product was dissolved in 2-propanol, and the solution was transferred to a dialysis tube. Dialysis was performed for 72 hours to purify the reaction product.

The solution including the reaction product was filtered with a 0.2 μm cellulose mixed-ester filter (model 25AS020 by Toyo Roshi Kaisha), and the resulting filtrate was freeze dried to obtain an intramolecular ion complex-type temperature-responsive polymer (6.8 g yield, 68% conversion ratio). The number-average molecular weight (Mn) of this polymer was measured using a GPC (model LC-10vp series by Shimadzu Corporation) with polyethylene glycol (TSK series by Shodex) as a standard substance and was determined to be Mn=100,000 (Mw/Mn=10.0).

(Test I-B) Preparation of Coated Culturing Surface (Test I-B-1) Preparation of Coated Culturing Surface Using a Masking Sheet A ϕ35 mm low cell-adsorption plate (PrimeSurface® by SUMILON) was used as a cell culture container.

A sheet (thickness of 1.0 mm) of silicone material (K-125 by Tigers Polymer Corporation) modified with a hydrophilic group was prepared, and a cutout that was donut-shaped in plan view (outer diameter (ϕo) of 8 mm, inner diameter (ϕi) of 4 mm, and width of 2 mm) was formed in the central portion of the sheet. This sheet with a donut-shaped hole was used as a masking sheet.

The masking sheet was laid on the culturing surface of the plate, 22.5 μL of an aqueous solution of the above-described polymer produced in Test I-A (concentration: 3 ng/μL) was added at room temperature, and the aqueous solution was then dried at 45° C. for 3 hours. After drying, the silicone sheet was peeled off.

(Test I-B-2) Preparation of Coated Culturing Surface Using a Cell Non-Adhesive Sheet A ϕ35 mm low cell-adsorption plate (PrimeSurface® by SUMILON) was used as a cell culture container.

A sheet of silicone material modified with a hydrophilic group was prepared, and a cutout that was donut-shaped in plan view (outer diameter (ϕo) of 8 mm, inner diameter (ϕi) of 4 mm or 3 mm, and width of 2 mm or 2.5 mm) was formed in the central portion of the sheet. This sheet with a donut-shaped hole was used as a pad.

Next, 22.5 μL of an aqueous solution of the aforementioned polymer produced in Test I-A (concentration: 3 ng/μL) was added at room temperature, and the aqueous solution was then dried at 45° C. for 3 hours. After drying, the pad was laid on the coated culturing surface.

The surface zeta potential of the coated culturing surface was measured using a zeta potential meter (model ELSZ by Otsuka Electronics Co.) and a cell unit for flat plate samples. During the measurement, a quartz cell was used as the cell, a particle (zeta potential: −5 mV to +5 mV) in which polystyrene latex (particle size: approximately 500 nm) was coated with hydroxypropyl cellulose (Mw=30,000) was used as a reference monitor particle, and a 10 mM sodium chloride aqueous solution at pH=7 and 37° C. was used as a solvent. The zeta potential was calculated with the Smoluchowski equation.

The resulting zeta potential of the surface of the first coated region coated with a temperature-responsive polymer was +20 mV. As is well known to a person skilled in the art, the measured value of the zeta potential exhibits a variation of approximately ±10%.

The contact angle of water relative to the first coated region of a cell culture plate was measured as 700±10° using a contact angle meter (DMs-400, by Kyowa Interface Science Co.) in conformity with JIS R3257.

(Test I-C) Seeding and Culturing of Cells (Test I-C-1) (Reference Example I)

The cell culture container prepared in Test I-B-1 was used.

GFP recombinant rat chondrocyte A (Rat Chondrocyte-A (GFP)) was suspended in a growth medium (RPMI-1640+ 10% fetal bovine serum (FBS)+10 ng/μL FGF-2; DMEM: by Gibco; FBS: lot number 715929 by Biological Industries; FGF-2: catalog number 400-29 by PeproTech) to produce a cell suspension.

The cell suspension was added to the plate at room temperature to yield a cell density of at least $1.0 \times 10^5$ cells/cm$^2$.

These cells were then cultured in a cell culture incubator at 37° C. and 5% $CO_2$.

Approximately 15 hours after the start of culturing, the chondrocytes started to aggregate from the coated culturing surface and formed a donut-shaped (ringed) cell structure by 24 hours after the start of culturing.

Three hours after the start of culturing, the medium was exchanged with a redifferentiation medium (Dulbecco's Modified Eagle Medium (DMEM)+10% fetal bovine serum (FBS)+10 ng/μL recombinant rat TGF-β1 (Rat TGF-β1 recombinant)+50 μg/mL ascorbic acid diphosphate; DMEM: model 11965 by Gibco; FBS: lot number 715929 by Bio-Rad; recombinant rat TGF-β1: catalog number 100-21 by PeproTech; ascorbic acid diphosphate: catalog number 196-01252 by Wako Pure Chemical Industries).

After the medium exchange, the cells were cultured continually for another 21 hours.

As described above, seeding and culturing was performed once in the absence of a cell mass in Test I-C-1 (Reference Example I).

Figure 7:
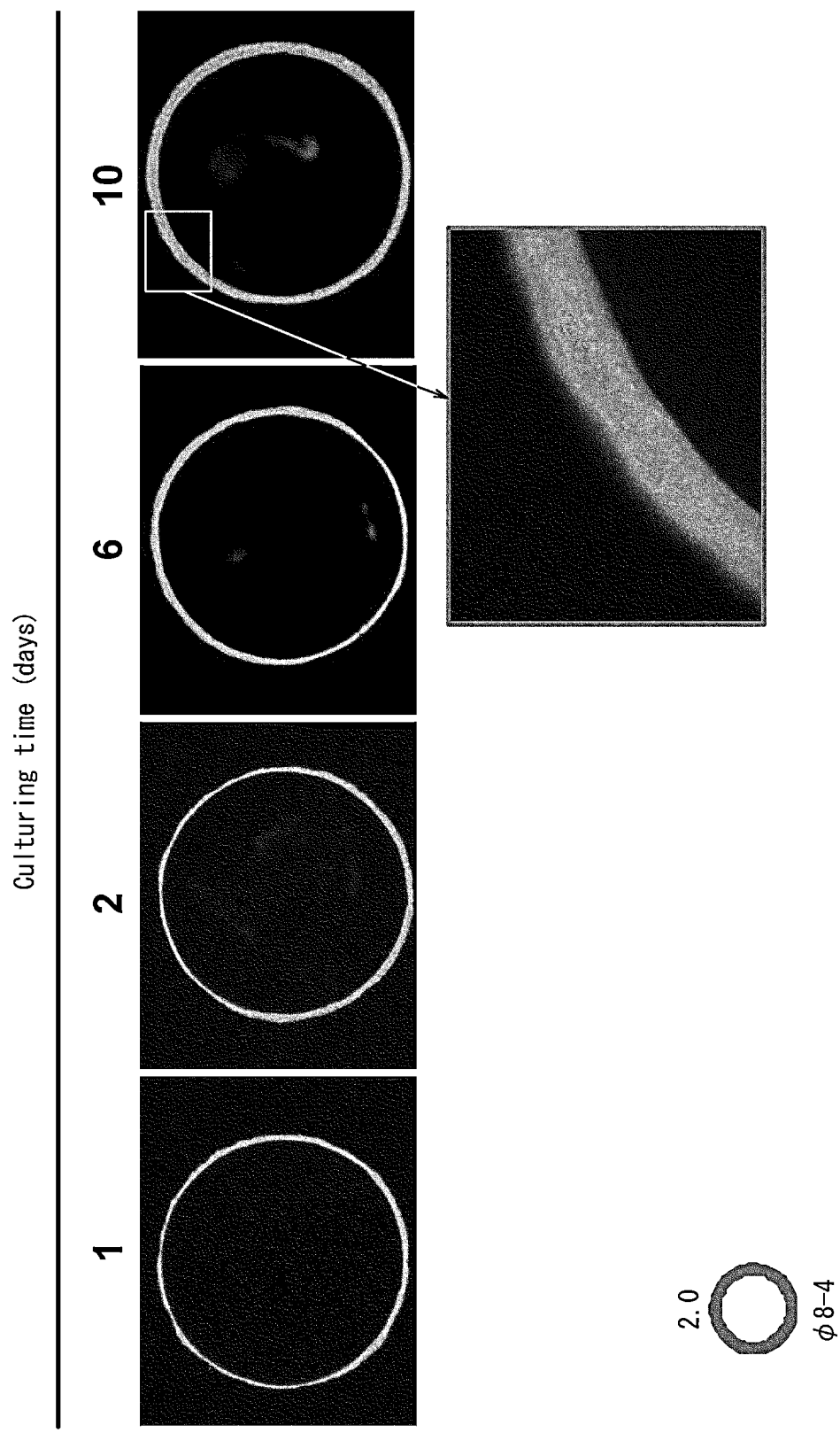
FIG. 7 contains photographs taken when using a fluorescence microscope to observe the state of a cell structure 24 hours (1 day), 2 days, 6 days, and 10 days after the start of culturing in Test I-C-1 (Reference Example I) of Embodiment (I); in particular, the lower portion illustrates a partial enlargement of the photograph of the cell structure after 10 days.

FIG. 7 contains photographs taken when using a fluorescence microscope to observe the state of a cell structure 24 hours (1 day), 2 days, 6 days, and 10 days after the start of culturing in Test I-C-1 (Reference Example I). In particular, the lower portion of FIG. 7 illustrates a partial enlargement of the photograph of the cell structure after 10 days.

It is clear from the photographs in FIG. 7 that the cells constituting the resulting cell structure have a cartilage-like circular cell form.

Figure 8:
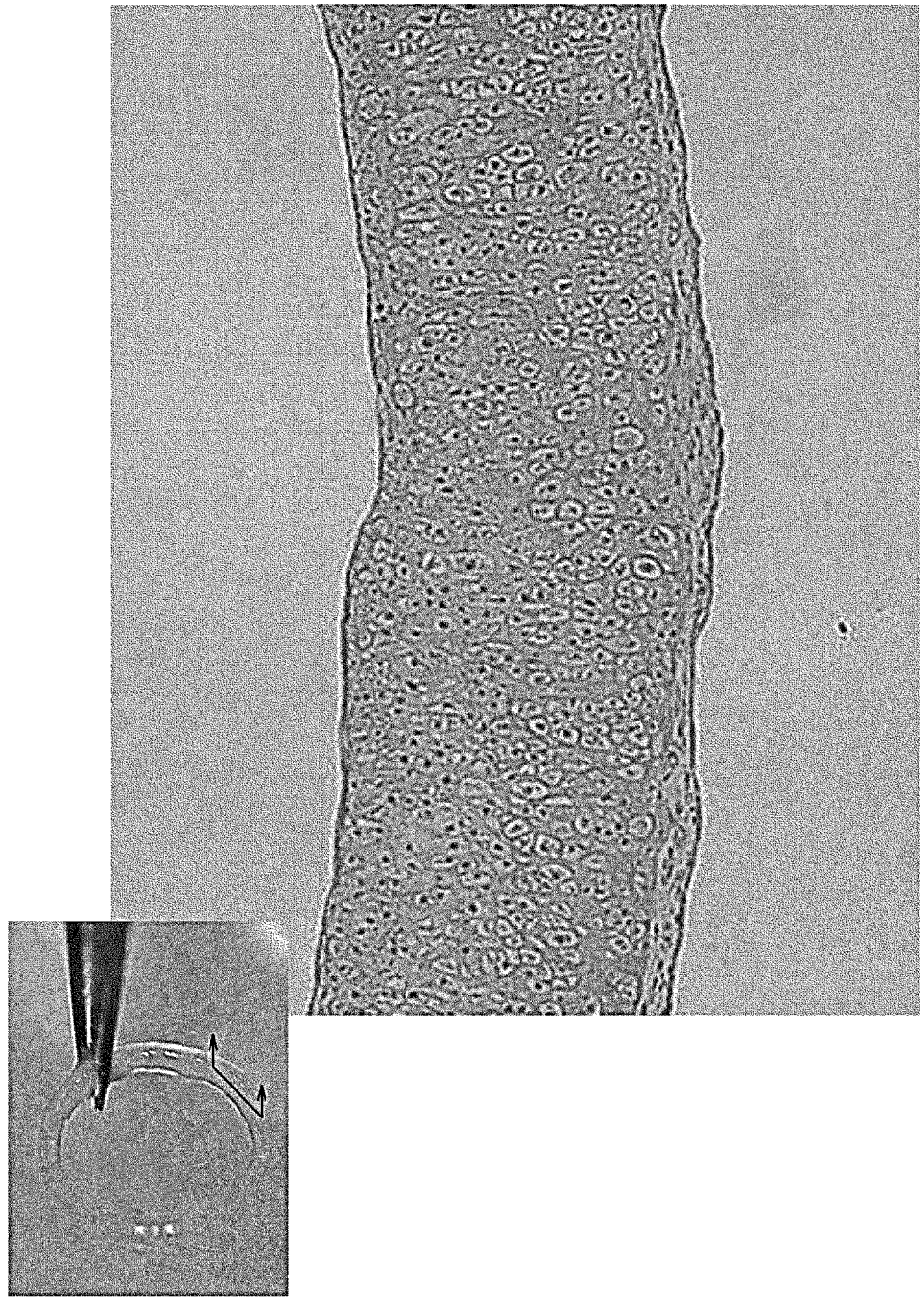
FIG. 8 is a photograph taken after cutting a cross-section of the cell structure obtained in Test I-C-1 (Reference Example I) of Embodiment (I) along the short-axis.

FIG. 8 is a photograph taken after cutting a cross-section of the cell structure obtained in Test I-C-1 (Reference Example I) along the short-axis.

It is clear from the photograph in FIG. 8 that the cells constituting the resulting cell structure have a unique cartilage cavity structure forming a rounded, pupa-like chamber, that extracellular matrix such as chondroitin and collagen is present in the portion with no surrounding nucleus, and that the cell structure forms cartilage-like tissue.

(Test I-C-2)

The cell culture container prepared in Test I-B-2 was used.

GFP recombinant rat chondrocyte A (Rat Chondrocyte-A (GFP)) was suspended in a growth medium (RPMI-1640+ 10% fetal bovine serum (FBS)+10 ng/μL FGF-2; DMEM: by Gibco; FBS: lot number 715929 by Bio-Rad; FGF-2: catalog number 400-29 by PeproTech) to produce a cell suspension.

The cell suspension was added to the plate at room temperature to yield a cell density of at least $1.0 \times 10^5$ cells/cm$^2$.

These cells were then cultured in a cell culture incubator at 37° C. and 5% $CO_2$.

Fifteen hours after the start of culturing, the chondrocytes started to aggregate from the coated culturing surface and formed a donut-shaped (ringed) cell structure by 24 hours after the start of culturing. The cell structure precipitated and rested on the widthwise central portion of the bottom of the recess in the pad.

Three to five hours after the start of culturing, the medium was exchanged with a redifferentiation medium (Dulbecco's Modified Eagle Medium (DMEM)+10% fetal bovine serum (FBS)+10 ng/μL recombinant rat TGF-β1 (Rat TGF-β1 recombinant)+50 μg/mL ascorbic acid diphosphate; DMEM: model 11965 by Gibco; FBS: lot number 715929 by Bio-Rad; recombinant rat TGF-β1: catalog number 100-21 by PeproTech; ascorbic acid diphosphate: catalog number 196-01252 by Wako Pure Chemical Industries). After the medium exchange, the cells were cultured continually for another 24 hours.

After returning the medium to a growth medium, a cell suspension was added in the presence of a cell structure at room temperature to yield a cell density of at least $1.0 \times 10^5$ cells/cm$^2$.

These cells were then cultured in a cell culture incubator at 37° C. and 5% $CO_2$.

Figure 9:
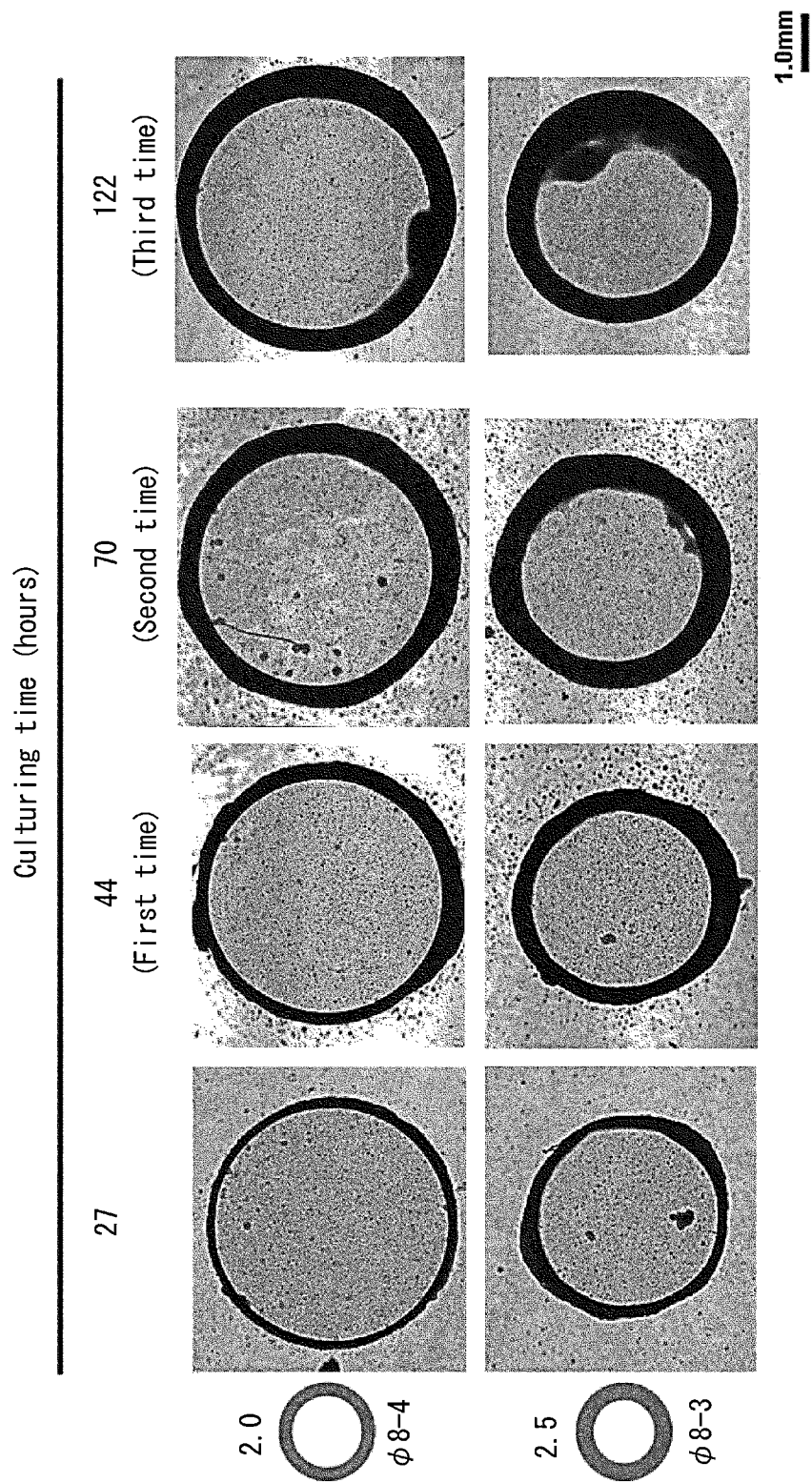
FIG. 9 contains photographs taken when using a fluorescence microscope to observe the state of a cell structure 27 hours, 44 hours, 70 hours, and 122 hours after the start of culturing in Test I-C-2 of Embodiment (I); the upper portion illustrates the state of the cell structure when using a pad with a 2 mm wide donut-shaped cutout, and the lower portion illustrates the state of the cell structure when using a pad with a 2.5 mm wide donut-shaped cutout.

Fifteen hours after the start of culturing, the seeded chondrocytes started to aggregate from the coated culturing surface, aggregating to enclose the donut-shaped (ringed) cell structure and form a larger donut-shaped (ringed) cell structure. The cell structure precipitated and rested on the widthwise central portion of the bottom of the recess in the pad. FIG. 9 illustrates the state of the cell structure 27 hours after the start of culturing.

The above seeding and culturing in the presence of a cell structure was repeated 3 times. FIG. 9 illustrates the state of the cell structure after 1, 2, and 3 repetitions.

FIG. 9 contains photographs taken when using a fluorescence microscope to observe the state of a cell structure 27 hours, 44 hours, 70 hours, and 122 hours after the start of culturing in Test I-C-2. The upper portion illustrates the state of the cell structure when using a pad with a 2 mm wide donut-shaped cutout, and the lower portion illustrates the state of the cell structure when using a pad with a 2.5 mm wide donut-shaped cutout.

It is clear from the photographs in FIG. 9 that the size of the donut-shaped (ringed) chondrocyte mass was greater after seeding and culturing of new cells.

(Test I-C-3)

The cell culture container prepared in Test I-B-2 was used.

Adipose-derived mesenchymal stem cells (adipose-derived vascular stromal cells (ADSC)) of a GFP recombinant Lewis rat were suspended in a growth medium (Dulbecco's Modified Eagle Medium (DMEM)+10% fetal bovine serum (FBS); DMEM: model 11965 by Gibco; FBS: lot number 715929 by Bio-Rad) to produce a cell suspension.

The cell suspension was added to the plate at room temperature to yield a cell density of at least $1.0 \times 10^5$ cells/cm$^2$.

These cells were then cultured in a cell culture incubator at 37° C. and 5% $CO_2$.

Six hours after the start of culturing, the chondrocytes started to aggregate from the coated culturing surface and formed a donut-shaped (ringed) cell structure by 8 hours after the start of culturing. The cell structure precipitated and rested on the widthwise central portion of the bottom of the recess in the pad.

One and a half hours after the start of culturing, the medium was exchanged with a cartilage differentiation medium (Dulbecco's Modified Eagle Medium (DMEM)+ 10% fetal bovine serum (FBS)+1% ITS Premix+50 μg/mL ascorbic acid diphosphate+10 ng/μL recombinant rat TGF-β1 (Rat TGF-β1 recombinant)+10 M dexamethasone; DMEM: model 11965 by Gibco; FBS: lot number 715929 by Bio-Rad; ITS Premix: catalog number 354341 by BD Biosciences; ascorbic acid diphosphate: catalog number 196-01252 by Wako Pure Chemical Industries; recombinant rat TGF-β1: catalog number 100-21 by PeproTech; dexamethasone: catalog number 047-18863 by Wako Pure Chemical Industries).

After the medium exchange, the cells were cultured continually for another 24 hours.

After returning the medium to a growth medium, a cell suspension was added in the presence of a cell structure at room temperature to yield a cell density of at least $1.0 \times 10^5$ cells/cm$^2$ These cells were then cultured in a cell culture incubator at 37° C. and 5% $CO_2$.

Figure 10:
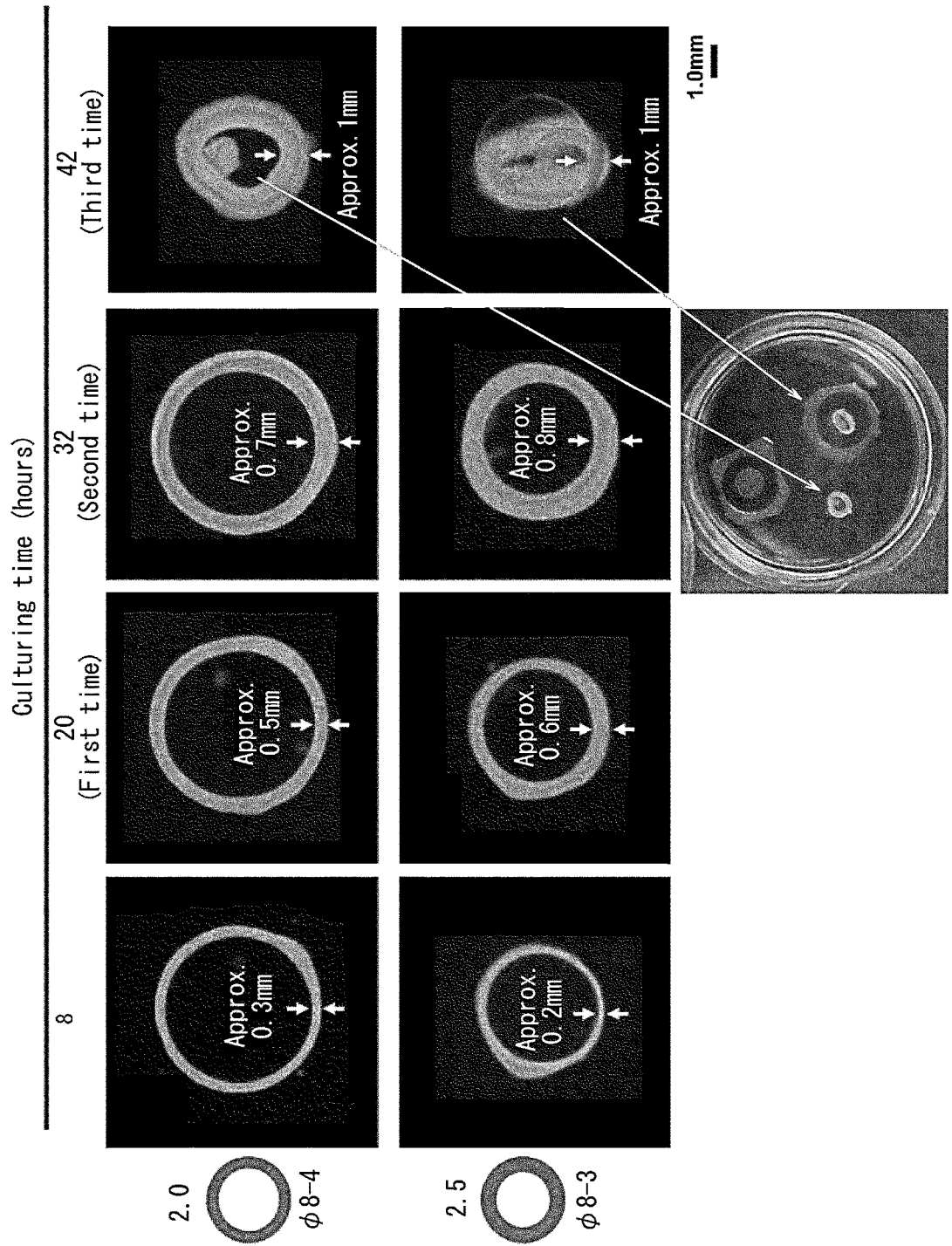
FIG. 10 contains photographs taken when using a fluorescence microscope to observe the state of a cell structure 8 hours, 20 hours, 32 hours, and 42 hours after the start of culturing in Test I-C-3 of Embodiment (I); the upper portion illustrates the state of the cell structure when using a pad with a 2 mm wide donut-shaped cutout, the lower portion illustrates the state of the cell structure when using a pad with a 2.5 mm wide donut-shaped cutout, and the lowermost portion is a photograph taken when using a stereomicroscope to observe the state of the cell structure after 42 hours.

Six hours after the start of culturing, the seeded chondrocytes started to aggregate from the coated culturing surface, aggregating to enclose the donut-shaped (ringed) cell structure and form a larger donut-shaped (ringed) cell structure. FIG. 10 illustrates the state of the cell structure 8 hours after the start of culturing.

The above seeding and culturing in the presence of a cell structure was repeated 3 times. FIG. 10 illustrates the state of the cell structure after 1, 2, and 3 repetitions.

FIG. 10 contains photographs taken when using a fluorescence microscope to observe the state of a cell structure 8 hours, 20 hours, 32 hours, and 42 hours after the start of culturing in Test I-C-3. The upper portion illustrates the state of the cell structure when using a pad with a 2 mm wide donut-shaped cutout, and the lower portion illustrates the state of the cell structure when using a pad with a 2.5 mm wide donut-shaped cutout. The lowermost portion is a photograph taken when using a stereomicroscope to observe the state of the cell structure after 42 hours.

It is clear from the photographs in FIG. 10 that the size of the donut-shaped (ringed) chondrocyte mass was greater after seeding and culturing of new cells.

In particular, it is clear that after repeating the seeding and culturing 3 times (42 hours after the start of culturing), the donut-shaped (ringed) chondrocyte mass protruded outside of the recess in the pad.

A graft material (not illustrated) was successfully produced by performing the seeding and culturing step one more time using ADSC cells, which are mesenchymal cells, on the donut-shaped (ringed) chondrocyte mass obtained in Test I-C-2 and Test I-C-3.

(Test I-D) Production of Composite Material

As a tubular structure, a biotube (outer diameter: 3 mm; inner diameter: 2 mm; length: 20 mm) having collagen as the principal component (see, for example, the method disclosed in the Examples of JP2004261260A) was prepared. A silicone rod-like structure (cylindrical; length: 20 mm; outer diameter: 1.8 mm) was prepared as a core material (see (i) of FIG. 6).

Next, the rod-like structure was inserted into the hollow portion of the biotube from one end to the other (see (ii) of FIG. 6).

Four of the donut-shaped chondrocyte masses produced in Test I-C-2 were fitted onto the biotube with a gap of approximately 1 mm between each chondrocyte mass to produce a composite body (see (iii) of FIG. 6).

Three minutes after completion of fitting, culturing of the composite body in a cell culture incubator at 37° C. and 5% $CO_2$ was started. Thereafter, the composite body was cultured for 21 days. By 21 days after the start of culturing, the biotube and the chondrocyte mass were integrated to produce a composite material (see (iv) of FIG. 6).

Figure 11A:
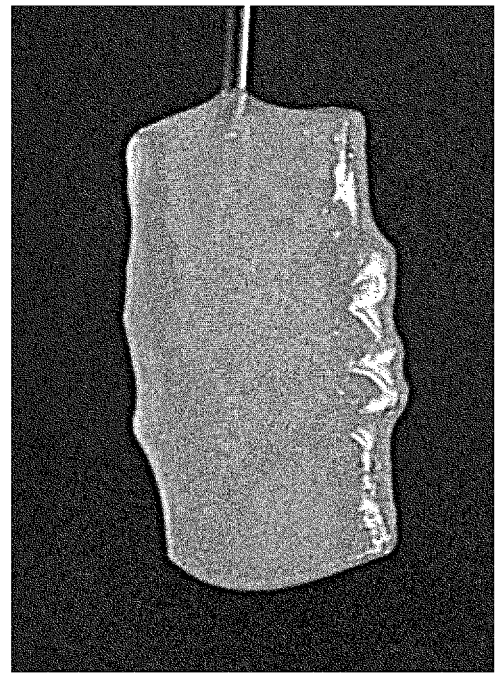
FIG. 11A is a photograph taken when observing the state of a composite material with the naked eye 6 days after the start of culturing in Test I-D of Embodiment (I), and FIG.

FIG. 11A is a photograph taken when observing the state of the composite material with the naked eye 6 days after the start of culturing in Test I-D.

Figure 11B:
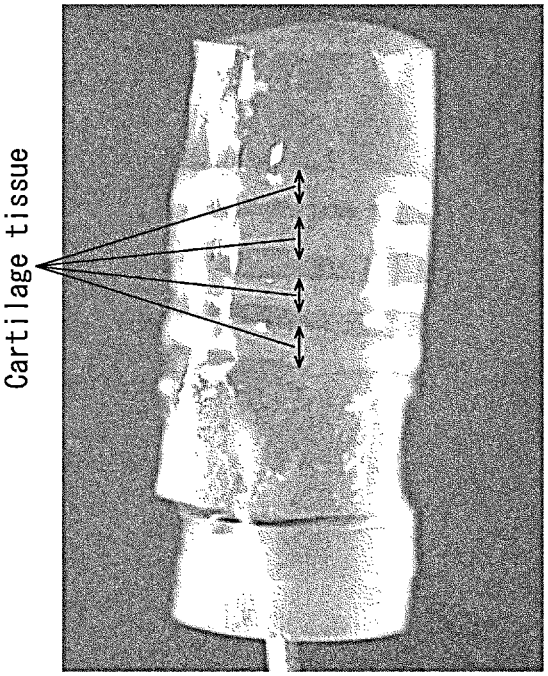

FIG. 11B is a photograph taken when observing the state of the composite material with the naked eye 21 days after the start of culturing in Test I-D.

FIG. 12 is an enlargement of a photograph taken when observing the state of a portion of the composite material with the naked eye 21 days after the start of culturing in Test I-D.

As illustrated in FIG. 12, cartilage tissue was formed on the outer surface of the biotube.

The interval between chondrocyte masses that was approximately 1 mm when the composite body was produced was approximately 1 mm.

FIGS. 13A to 13D are photographs taken when observing, with the naked eye, the state of the composite material produced in Test I-D when manipulating the composite material with tweezers. FIG. 13A illustrates the outer peripheral surface without manipulation, FIG. 13B illustrates the luminal surface without manipulation, FIG. 13C illustrates the state when the entire material is crushed, and FIG. 13D illustrates the state when pulling towards a portion of the side surface.

It is clear from FIGS. 13A to 13D that the composite material had sufficient mechanical strength to withstand the aforementioned normal operations, and that the cartilage tissue also remained firmly adhered to the biotube.

FIGS. 14A to 14D are photographs taken when using a microscope to observe the state of a composite material produced in Test I-D when subjecting the composite material to a hematoxylin and eosin stain (H&E stain). FIG. 14A is an exterior photograph of the composite material, FIG. 14B is a cross-sectional view of the composite material in a plane along the A-A line in FIG. 14A, and FIGS. 14C and 14D are partial enlargements of the photograph in FIG. 14B.

The portions stained pink in FIGS. 14C and 14D (indicated by solid arrows in the figures) are collagen, and the portions stained violet are cells. It is clear from these figures that the collagen fibers of the biotube and the extracellular matrix of the chondrocyte are integrated.

Examples of Aspect (II)

Aspect (II) is described below in greater detail with reference to examples, but the present disclosure is in no way limited by these examples.

(Production of Temperature-Responsive Polymer)

First, 10.0 g of 2-N,N-dimethylaminoethyl methacrylate (DMAEMA) and 5 mL of water were added to a 50 mL capacity transparent vial made of soft glass, and the vial was stirred using a magnetic stirrer. The mixture (liquid) was then purged with Gi-grade, highly pure (purity: 99.99995%) nitrogen gas for 10 minutes (flow rate: 2.0 L/min) to deoxygenize the mixture. The DMAEMA that was used included 0.5 mass % of methylhydroquinone (MEHQ), which is a polymerization inhibitor.

Subsequently, this reactant was polymerized by irradiation with ultraviolet light for 22 hours using a round, black fluorescent lamp (model FCL20BL, 18 W, by NEC Corporation). The reactant became viscous 5 hours later and hardened 15 hours later. A polymer was thus obtained as a reaction product. This reaction product was dissolved in 2-propanol, and the solution was transferred to a dialysis tube. Dialysis was performed for 72 hours to purify the reaction product.

The solution including the reaction product was filtered with a 0.2 μm cellulose mixed-ester filter (model 25AS020 by Toyo Roshi Kaisha), and the resulting filtrate was freeze dried to obtain a temperature-responsive (homo)polymer (6.8 g yield, 68% conversion ratio). The number-average molecular weight (Mn) of this polymer was measured using a GPC (model LC-10vp series by Shimadzu Corporation) with polyethylene glycol (TSK series by Shodex) as a standard substance and was determined to be $Mn=1.0\times10^5$ g/mol (Mw/Mn=10.0).

The nuclear magnetic resonance (NMR) spectrum of the above-described temperature-responsive polymer was measured using a nuclear magnetic resonance apparatus (model Gemini-300 by Varian) with heavy water ($D_2O$) as a standard substance. A representative peak is indicated below.

$^1$H-NMR (in $D_2O$) δ 0.8-1.2 (br, —$CH_2$—C($CH_3$)—), 1.6-2.0 (br, —$CH_2$—C($CH_3$)—), 2.2-2.4 (br, —N($CH_3$)$_2$), 2.5-2.7 (br, —$CH_2$—N($CH_3$)$_2$), 4.0-4.2 (br, —O—$CH_2$—).

Here, from the number of protons A in the methyl group (δ 0.8-1.2) of the main chain (3 per monomer molecule in the case of a DMAEMA homopolymer) and the number of methyl protons B in the dimethylamino group (δ 2.2-2.4) of the side chain (6 per monomer molecule in the case of a DMAEMA homopolymer), the ratio was calculated between the number of functional groups that are amino groups in the side chain and the number of functional groups that are carboxyl groups in the side chain produced by a hydrolysis reaction, which proceeds simultaneously with the polymerization reaction, of an ester bond of the side chain.

The resulting ratio was 94:6 in the case of the above-described temperature-responsive polymer. Converting into the C/A ratio for an ion complex in a two-component mixed system that includes a cationic polymer and an anionic polymer yields a C/A ratio of 15.6.

The cloud point of the above-described temperature-responsive polymer was measured with the following method.

A 3% aqueous solution of the temperature-responsive polymer was produced, and the absorbance of the aqueous solution at 660 nm was measured between 20° C. and 40° C.

Between 20° C. and 30° C., the aqueous solution was transparent, with an absorbance of nearly 0. Starting around 31° C., however, the aqueous solution became cloudy, and the absorbance increased suddenly at 32° C. The temperature-responsive polymer was thus confirmed to have a cloud point of approximately 32° C.

Once the temperature-responsive polymer was increased in temperature to 37° C., the polymer aqueous solution was suspended with good responsiveness. Subsequently, the entire aqueous solution hardened. When maintained at room temperature (25° C.), the hardened product retained its hard state for several tens of hours. Subsequently, the hardened product gradually dissolved, changing into a homogeneous aqueous solution. Upon being cooled to 4° C., the hardened polymer rapidly dissolved. Repeating the aforementioned operation to raise and lower the temperature caused no change in responsiveness, thereby confirming that the polymer reversibly underwent phase transitions.

(Manufacturing of Coated Cell Culture Container)

The above-described temperature-responsive polymers were dissolved in pure water to produce temperature-responsive polymer solutions. The concentration of the temperature-responsive polymer in each temperature-responsive polymer solution was adjusted as follows: temperature-responsive polymer a, 0.125 ng/μL; temperature-responsive polymer b, 0.25 ng/μL; temperature-responsive polymer c, 0.5 ng/μL; temperature-responsive polymer d, 1.0 ng/μL.

Next, 25 μL of the temperature-responsive polymers a to d was added to the wells of 384-well plates (PrimeSurface®, MS-9384U, by Sumitomo Bakelite Co.).

The applied temperature-responsive polymer aqueous solution was then dried by leaving the plates in an incubator (40° C.) for 6 hours to prepare coated cell culture containers a to d having the coated region A.

The above-described temperature-responsive polymers were dissolved in physiological saline to produce temperature-responsive polymer solutions. The concentration of the temperature-responsive polymer in each temperature-responsive polymer solution was adjusted as follows: temperature-responsive polymer e, 6 ng/μL; temperature-responsive polymer f, 12 ng/μL; temperature-responsive polymer g, 24 ng/μL.

Next, 25 μL of the temperature-responsive polymers e to g was added to the wells of 384-well plates (PrimeSurface®, MS-9384U, by Sumitomo Bakelite Co.). The wells of the plates had a rounded bottom with a radius of curvature (average) R of approximately 1.6 mm and had a maximum width L of approximately 2.5 mm.

The plates were left in an incubator (37° C.) for 3 hours to prepare coated cell culture containers e to g having the coated region A. In the coated cell culture containers e to g, the temperature-responsive polymer solution added to the wells was not dried.

The above-described temperature-responsive polymers were dissolved in pure water to produce temperature-responsive polymer solutions. The concentration of the temperature-responsive polymer in each temperature-responsive polymer solution was adjusted as follows: temperature-responsive polymer h, 0.9 pg/μL; temperature-responsive polymer i, 1.8 pg/μL; temperature-responsive polymer j, 7.5 pg/μL; temperature-responsive polymer k, 15 pg/μL; temperature-responsive polymer l, 31 pg/μL; temperature-responsive polymer m, 67 pg/μL; temperature-responsive polymer n, 125 pg/μL; and temperature-responsive polymer o, 500 pg/μL.

Next, 2.5 μL of the temperature-responsive polymers h to o was added to the wells of 384-well plates (PrimeSurface®, MS-9384U, by Sumitomo Bakelite Co.).

The applied temperature-responsive polymer aqueous solution was then dried by leaving the plates in an incubator (40° C.) for 6 hours to prepare coated cell culture containers h to o having the coated region A.

Next, 25 μL of physiological saline was added to the wells of a 384-well plate (PrimeSurface®, MS-9384U, by Sumitomo Bakelite Co.).

The plate was then left for 3 hours in an incubator (37° C.) to prepare a cell culture container p. The cell culture container p was a cell culture container not coated by a temperature-responsive polymer.

[Culture Method of Epithelial Cells]

Examples II-1 to II-35

Human hepatoma cells (number "HepG2-500" by Cosmo Bio) were mixed into a medium (DMAEM+10% FBS (lot number 715929 by Gibco)) to produce cell solutions at the following concentrations: $0.5 \times 10^3$ cells/50 μL (cell solution I), $1.0 \times 10^3$ cells/50 μL (cell solution II), $2.0 \times 10^3$ cells/50 μL (cell solution III), $4.0 \times 10^3$ cells/50 μL (cell solution IV), and $8.0 \times 10^3$ cells/50 μL (cell solution V).

Next, 50 μL of the cell solutions I to V was added to the wells of the coated cell culture containers a to g to seed cells. Table 1 lists the combination of coated cell culture container and cell solution in each Example.

Subsequently, cells were cultured for 24 hours in a cell incubator (37° C., 5% $CO_2$). The cells were then observed with a microscope (ECLIPSE-Ti by Nikon Corporation).

Examples II-36 to II-75

Human hepatoma cells (number "HepG2-500" by Cosmo Bio) were mixed into a medium (DMAEM+10% FBS (lot number 715929 by Gibco)) to produce cell solutions at the following concentrations: $0.5 \times 10^3$ cells/25 μL (cell solution VI), $1.0 \times 10^3$ cells/25 μL (cell solution VII), $2.0 \times 10^3$ cells/25 μL (cell solution VIII), $4.0 \times 10^3$ cells/25 μL (cell solution IX), and $8.0 \times 10^3$ cells/25 μL (cell solution X).

Next, 25 μL of the cell solutions VI to X was added to the wells of the coated cell culture containers h to o to seed cells. Table 1 lists the combination of coated cell culture container and cell solution in each Example.

Subsequently, cells were cultured for 24 hours in a cell incubator (37° C., 5% $CO_2$). The cells were then observed with a microscope (ECLIPSE-Ti by Nikon Corporation).

Comparative Examples II-1 to II-5

Fifty μL of the cell solutions I to V was added to the wells of the coated cell culture container p to seed cells. Table 1 lists the combination of coated cell culture container and cell solution in each Comparative Example. Subsequently, cells were cultured for 24 hours in a cell incubator (37° C., 5% $CO_2$). The cells were then observed with a microscope (ECLIPSE-Ti by Nikon Corporation).

[Manufacturing Method of a Cell Structure]

Examples II-76 to II-80

Fifty μL of the cell solutions I to V was added to the wells of the coated cell culture container e to seed cells. Table 2 lists the combination of coated cell culture container and cell solution in each Example.

Subsequently, cells were cultured for 24 hours in a cell incubator (37° C., 5% $CO_2$) and observed with a microscope (ECLIPSE-Ti by Nikon Corporation). It was confirmed that an aggregated cell structure was formed at the bottom of all of the wells. The below-described evaluation of peeling resistance of the cell structure was also performed. Table 2 lists the results.

Examples II-81 to II-100

Twenty-five μL of the cell solutions VI to X was added to the wells of the coated cell culture containers h to k to seed cells. Table 2 lists the combination of coated cell culture container and cell solution in each Example.

Subsequently, cells were cultured for 24 hours in a cell incubator (37° C., 5% $CO_2$) and observed with a microscope (ECLIPSE-Ti by Nikon Corporation). It was confirmed that an aggregated cell structure was formed at the bottom of all of the wells. The below-described evaluation of peeling resistance of the cell structure was also performed. Table 2 lists the results.

Comparative Examples II-6 to II-10

Fifty μL of the cell solutions I to V was added to the wells of the coated cell culture container p to seed cells. Table 2 lists the combination of cell culture container and cell solution in each Comparative Example.

Subsequently, cells were cultured for 24 hours in a cell incubator (37° C., 5% $CO_2$) and observed with a microscope (ECLIPSE-Ti by Nikon Corporation).

HepG2 aggregated at the bottom without adhering to the culturing surface. The aggregated cell structure was not adhered to the bottom, and the cell structure moved when the plate was simply shaken. In some cases, the cell structure collapsed when pipetting was performed, perhaps because of the low secretion of extracellular matrix.

[Evaluation]
(Adhesion of Cells to Coated Region)

The HepG2 cells cultured in Examples II-1 to II-75 and Comparative Examples II-1 to II-5 were observed with a microscope (ECLIPSE-Ti by Nikon Corporation). The case of the HepG2 cells adhering to the coated region and being culturable was evaluated as good (G), and the case of HepG2 not adhering to the coated region was evaluated as poor (P).

(Appearance of Cell Structure)

The cell structures obtained in Examples II-76 to II-100 and Comparative Examples II-6 to II-10 were observed with a microscope (ECLIPSE-Ti by Nikon Corporation). Subsequently, pipetting was performed forcefully using a pipettor ("Reference" by Eppendorf), and the cell structures were observed again. The appearance of the cell structures was then evaluated with the following criteria.

G (good): an aggregated cell structure was formed, and the cell structure did not collapse even when subjected to forceful pipetting.

P (poor): an aggregated cell structure was formed but collapsed when subjected to forceful pipetting.

(Peeling Resistance of Cell Structure)

The cell structures obtained in Examples II-76 to II-100 and Comparative Examples II-6 to II-10 were repeatedly subjected to manual pipetting using a pipettor ("Reference" by Eppendorf), and the number of times until the cell structures peeled off from the culturing surface was counted.

E (excellent): the cell structure did not peel off even when subjected to pipetting more than 10 times.

G (good): the cell structure peeled off when subjected to pipetting 2 to 10 times.

F (fair): the cell structure peeled off when subjected to pipetting once.

P (poor): the cell structure was not adhered to the culturing surface.

TABLE 1

| | Coated Cell Culture Container | | Cell Solution | | | |
|---|---|---|---|---|---|---|
| | Type | Temperature-Responsive Polymer Concentration (pg/mm$^2$) | Type | Added Amount (μL) | Number of Cells per Well | Evaluation Adhesion of Cells |
| Example II-1 | a | 372.0 | I | 50 | $0.5 \times 10^3$ | G |
| Example II-2 | a | 372.0 | II | 50 | $1.0 \times 10^3$ | G |
| Example II-3 | a | 372.0 | III | 50 | $2.0 \times 10^3$ | G |
| Example II-4 | a | 372.0 | IV | 50 | $4.0 \times 10^3$ | G |
| Example II-5 | a | 372.0 | V | 50 | $8.0 \times 10^3$ | G |
| Example II-6 | b | 744.0 | I | 50 | $0.5 \times 10^3$ | G |
| Example II-7 | b | 744.0 | II | 50 | $1.0 \times 10^3$ | G |
| Example II-8 | b | 744.0 | III | 50 | $2.0 \times 10^3$ | G |
| Example II-9 | b | 744.0 | IV | 50 | $4.0 \times 10^3$ | G |
| Example II-10 | b | 744.0 | V | 50 | $8.0 \times 10^3$ | G |
| Example II-11 | c | 1488.1 | I | 50 | $0.5 \times 10^3$ | G |
| Example II-12 | c | 1488.1 | II | 50 | $1.0 \times 10^3$ | G |
| Example II-13 | c | 1488.1 | III | 50 | $2.0 \times 10^3$ | G |
| Example II-14 | c | 1488.1 | IV | 50 | $4.0 \times 10^3$ | G |
| Example II-15 | c | 1488.1 | V | 50 | $8.0 \times 10^3$ | G |
| Example II-16 | d | 2976.2 | I | 50 | $0.5 \times 10^3$ | G |
| Example II-17 | d | 2976.2 | II | 50 | $1.0 \times 10^3$ | G |
| Example II-18 | d | 2976.2 | III | 50 | $2.0 \times 10^3$ | G |
| Example II-19 | d | 2976.2 | IV | 50 | $4.0 \times 10^3$ | G |
| Example II-20 | d | 2976.2 | V | 50 | $8.0 \times 10^3$ | G |
| Example II-21 | e | 17857.1 | I | 50 | $0.5 \times 10^3$ | G |
| Example II-22 | e | 17857.1 | II | 50 | $1.0 \times 10^3$ | G |
| Example II-23 | e | 17857.1 | III | 50 | $2.0 \times 10^3$ | G |
| Example II-24 | e | 17857.1 | IV | 50 | $4.0 \times 10^3$ | G |
| Example II-25 | e | 17857.1 | V | 50 | $8.0 \times 10^3$ | G |
| Example II-26 | f | 35714.3 | I | 50 | $0.5 \times 10^3$ | G |
| Example II-27 | f | 35714.3 | II | 50 | $1.0 \times 10^3$ | G |
| Example II-28 | f | 35714.3 | III | 50 | $2.0 \times 10^3$ | G |
| Example II-29 | f | 35714.3 | IV | 50 | $4.0 \times 10^3$ | G |
| Example II-30 | f | 35714.3 | V | 50 | $8.0 \times 10^3$ | G |
| Example II-31 | g | 71428.6 | I | 50 | $0.5 \times 10^3$ | G |
| Example II-32 | g | 71428.6 | II | 50 | $1.0 \times 10^3$ | G |
| Example II-33 | g | 71428.6 | III | 50 | $2.0 \times 10^3$ | G |
| Example II-34 | g | 71428.6 | IV | 50 | $4.0 \times 10^3$ | G |
| Example II-35 | g | 71428.6 | V | 50 | $8.0 \times 10^3$ | G |
| Example II-36 | h | 0.27 | VI | 25 | $0.5 \times 10^3$ | G |
| Example II-37 | h | 0.27 | VII | 25 | $1.0 \times 10^3$ | G |
| Example II-38 | h | 0.27 | VIII | 25 | $2.0 \times 10^3$ | G |
| Example II-39 | h | 0.27 | IX | 25 | $4.0 \times 10^3$ | G |
| Example II-40 | h | 0.27 | X | 25 | $8.0 \times 10^3$ | G |
| Example II-41 | i | 0.54 | VI | 25 | $0.5 \times 10^3$ | G |
| Example II-42 | i | 0.54 | VII | 25 | $1.0 \times 10^3$ | G |
| Example II-43 | i | 0.54 | VIII | 25 | $2.0 \times 10^3$ | G |

TABLE 1-continued

| | Coated Cell Culture Container | | Cell Solution | | | Evaluation |
|---|---|---|---|---|---|---|
| | | Temperature-Responsive Polymer Concentration (pg/mm²) | | | Number of Cells per Well | Adhesion of Cells |
| | Type | | Type | Added Amount (µL) | | |
| Example II-44 | i | 0.54 | IX | 25 | 4.0 × 10³ | G |
| Example II-45 | i | 0.54 | X | 25 | 8.0 × 10³ | G |
| Example II-46 | j | 2.2 | VI | 25 | 0.5 × 10³ | G |
| Example II-47 | j | 2.2 | VII | 25 | 1.0 × 10³ | G |
| Example II-48 | j | 2.2 | VIII | 25 | 2.0 × 10³ | G |
| Example II-49 | j | 2.2 | IX | 25 | 4.0 × 10³ | G |
| Example II-50 | j | 2.2 | X | 25 | 8.0 × 10³ | G |
| Example II-51 | k | 4.5 | VI | 25 | 0.5 × 10³ | G |
| Example II-52 | k | 4.5 | VII | 25 | 1.0 × 10³ | G |
| Example II-53 | k | 4.5 | VIII | 25 | 2.0 × 10³ | G |
| Example II-54 | k | 4.5 | IX | 25 | 4.0 × 10³ | G |
| Example II-55 | k | 4.5 | X | 25 | 8.0 × 10³ | G |
| Example II-56 | l | 9.2 | VI | 25 | 0.5 × 10³ | G |
| Example II-57 | l | 9.2 | VII | 25 | 1.0 × 10³ | G |
| Example II-58 | l | 9.2 | VIII | 25 | 2.0 × 10³ | G |
| Example II-59 | l | 9.2 | IX | 25 | 4.0 × 10³ | G |
| Example II-60 | l | 9.2 | X | 25 | 8.0 × 10³ | G |
| Example II-61 | m | 19.9 | VI | 25 | 0.5 × 10³ | G |
| Example II-62 | m | 19.9 | VII | 25 | 1.0 × 10³ | G |
| Example II-63 | m | 19.9 | VIII | 25 | 2.0 × 10³ | G |
| Example II-64 | m | 19.9 | IX | 25 | 4.0 × 10³ | G |
| Example II-65 | m | 19.9 | X | 25 | 8.0 × 10³ | G |
| Example II-66 | n | 37.2 | VI | 25 | 0.5 × 10³ | G |
| Example II-67 | n | 37.2 | VII | 25 | 1.0 × 10³ | G |
| Example II-68 | n | 37.2 | VIII | 25 | 2.0 × 10³ | G |
| Example II-69 | n | 37.2 | IX | 25 | 4.0 × 10³ | G |
| Example II-70 | n | 37.2 | X | 25 | 8.0 × 10³ | G |
| Example II-71 | o | 148.8 | VI | 25 | 0.5 × 10³ | G |
| Example II-72 | o | 148.8 | VII | 25 | 1.0 × 10³ | G |
| Example II-73 | o | 148.8 | VIII | 25 | 2.0 × 10³ | G |
| Example II-74 | o | 148.8 | IX | 25 | 4.0 × 10³ | G |
| Example II-75 | o | 148.8 | X | 25 | 8.0 × 10³ | G |
| Comparative Example II-1 | p | 0 | I | 50 | 0.5 × 10³ | P |
| Comparative Example II-2 | p | 0 | II | 50 | 1.0 × 10³ | P |
| Comparative Example II-3 | p | 0 | III | 50 | 2.0 × 10³ | P |
| Comparative Example II-4 | p | 0 | IV | 50 | 4.0 × 10³ | P |
| Comparative Example II-5 | p | 0 | V | 50 | 8.0 × 10³ | P |

TABLE 2

| | Coated Cell Culture Container | | Cell Solution | | | Evaluation | |
|---|---|---|---|---|---|---|---|
| | | Temperature-Responsive Polymer Concentration (pg/mm²) | | Added Amount (µL) | Number of Cells per Well | Appearance of Cell Structure | Peeling Resistance of Cell Structure |
| | Type | | Type | | | | |
| Example II-76 | e | 17857.1 | I | 50 | 0.5 × 10³ | G | F |
| Example II-77 | e | 17857.1 | II | 50 | 1.0 × 10³ | G | F |
| Example II-78 | e | 17857.1 | III | 50 | 2.0 × 10³ | G | F |
| Example II-79 | e | 17857.1 | IV | 50 | 4.0 × 10³ | G | F |
| Example II-80 | e | 17857.1 | V | 50 | 8.0 × 10³ | G | F |
| Example II-81 | h | 0.27 | VI | 25 | 0.5 × 10³ | G | F |
| Example II-82 | h | 0.27 | VII | 25 | 1.0 × 10³ | G | F |
| Example II-83 | h | 0.27 | VIII | 25 | 2.0 × 10³ | G | F |
| Example II-84 | h | 0.27 | IX | 25 | 4.0 × 10³ | G | F |
| Example II-85 | h | 0.27 | X | 25 | 8.0 × 10³ | G | F |
| Example II-86 | i | 0.54 | VI | 25 | 0.5 × 10³ | G | F |
| Example II-87 | i | 0.54 | VII | 25 | 1.0 × 10³ | G | F |
| Example II-88 | i | 0.54 | VIII | 25 | 2.0 × 10³ | G | F |

TABLE 2-continued

| | Coated Cell Culture Container | | Cell Solution | | Evaluation | |
|---|---|---|---|---|---|---|
| | Type | Temperature-Responsive Polymer Concentration (pg/mm$^2$) | Type | Added Amount (μL) | Number of Cells per Well | Appearance of Cell Structure | Peeling Resistance of Cell Structure |
| Example II-89 | i | 0.54 | IX | 25 | $4.0 \times 10^3$ | G | F |
| Example II-90 | i | 0.54 | X | 25 | $8.0 \times 10^3$ | G | F |
| Example II-91 | j | 2.2 | VI | 25 | $0.5 \times 10^3$ | G | G |
| Example II-92 | j | 2.2 | VII | 25 | $1.0 \times 10^3$ | G | G |
| Example II-93 | j | 2.2 | VIII | 25 | $2.0 \times 10^3$ | G | G |
| Example II-94 | j | 2.2 | IX | 25 | $4.0 \times 10^3$ | G | G |
| Example II-95 | j | 2.2 | X | 25 | $8.0 \times 10^3$ | G | G |
| Example II-96 | k | 4.5 | VI | 25 | $0.5 \times 10^3$ | G | E |
| Example II-97 | k | 4.5 | VII | 25 | $1.0 \times 10^3$ | G | E |
| Example II-98 | k | 4.5 | VIII | 25 | $2.0 \times 10^3$ | G | E |
| Example II-99 | k | 4.5 | IX | 25 | $4.0 \times 10^3$ | G | E |
| Example II-100 | k | 4.5 | X | 25 | $8.0 \times 10^3$ | G | E |
| Comparative Example II-6 | p | 0 | I | 50 | $0.5 \times 10^3$ | P | P |
| Comparative Example II-7 | p | 0 | II | 50 | $1.0 \times 10^3$ | P | P |
| Comparative Example II-8 | p | 0 | III | 50 | $2.0 \times 10^3$ | p | p |
| Comparative Example II-9 | p | 0 | IV | 50 | $4.0 \times 10^3$ | P | P |
| Comparative Example II-10 | p | 0 | V | 50 | $8.0 \times 10^3$ | P | P |

[Epithelial-Mesenchymal Transition Inducer]

Example II-101

Human hepatoma cells (number "HepG2-500" by Cosmo Bio) were mixed into a medium (DMAEM+10% FBS (lot number 715929 by Gibco)) to produce a cell solution at a concentration of $4.0 \times 10^3$ cells/25 μL.

A 0.5 μL droplet of the above-described temperature-responsive polymer d (1.0 ng/μL) was spotted onto the central portion of the wells of a 24-well plate ("Sumilon cell tight", MS-9024X, by Sumitomo Bakelite Co.) using a micropipettor (Digifit by Sibata Scientific Technology).

The applied temperature-responsive polymer aqueous solution was then dried by leaving the plate in an incubator (37° C.) for 3 hours to prepare a coated cell culture container q having the coated region A.

Next, 1,000 μL of the cell solution I was added to the wells of the coated cell culture container q to seed cells. Subsequently, cells were cultured for 96 hours in a cell incubator (37° C., 5% $CO_2$). The cells were then observed with a microscope (ECLIPSE-Ti by Nikon Corporation).

(Transition from Epithelial Cells to Stromal Cells)

The HepG2 cells cultured in Example II-101 were observed with a microscope (ECLIPSE-Ti by Nikon Corporation). The adhesion state of the HepG2 cells adhered to the coated region was evaluated to judge whether transition from epithelial cells to stromal cells had occurred.

TABLE 3

| | Coated Cell Culture Container | | Cell Solution | | | Evaluation | |
|---|---|---|---|---|---|---|---|
| | Type | Temperature-Responsive Polymer Concentration (pg/mm$^2$) | Type | Added Amount (μL) | Number of Cells per Well | Transition from Epithelial Cells to Stromal Cells | FIG. |
| Example II-101 | q | 2.8 | I | 1000 | $1.0 \times 10^4$ | cells in coated region: confluent cells in non-coated region: scattered (isolated) like cobblestones | FIG. 17 |

FIG. 17 is a photograph illustrating the state when culturing epithelial cells for 96 hours on a temperature-responsive polymer or a temperature-responsive polymer composition used in the present disclosure. In FIG. 17, the portion surrounded by the dashed line indicates a coated region A, the arrow with a black outline indicates cells adhered to and growing in the coated region A, and the solid black arrows indicate cells adhered to and growing in the non-coated region.

It is clear from FIG. 17 that after culturing for 96 hours, the cells cultured in the coated region A were confluent and had a fibroblast-like form, whereas the cells cultured in the non-coated region were scattered (isolated) like cobblestones and maintained the characteristics of epithelial cells. These results indicate that the temperature-responsive polymer or the temperature-responsive polymer composition used in the present disclosure has the effect of epithelial-stromal transition.

Examples of Aspect (III)

Aspect (III) is described below in greater detail with reference to examples, but the present disclosure is in no way limited by these examples.

Example III-1

(Manufacturing of Production Apparatus of Three-Dimensional Tissue Body)

A stainless-steel tube (by Fuji Filter Manufacturing Co., 3ϕ) with a meshed surface was used as a shaft, and "Prime-Surface®" (number MS-9024X, by Sumitomo Bakelite Co.) was used as a culturing surface, a portion of the culturing surface being cut out to form a through hole (approximately 3 mm diameter), to manufacture an apparatus in which the culturing surface and the shaft are in contact. The culturing surface was substantially circular, with an outer diameter of approximately 25 mm. The apparatus was shaped as in FIG. 18.

First, 10.0 g of 2-N,N-dimethylaminoethyl methacrylate (DMAEMA) and 5 mL of water were added to a 50 mL capacity transparent vial made of soft glass, and the vial was stirred using a magnetic stirrer. The mixture (liquid) was then purged with Gi-grade, highly pure (purity: 99.99995%) nitrogen gas for 10 minutes (flow rate: 2.0 L/min) to deoxygenize the mixture. The DMAEMA that was used included 0.5 mass % of methylhydroquinone (MEHQ), which is a polymerization inhibitor.

Subsequently, this reactant was polymerized by irradiation with ultraviolet light for 22 hours using a round, black fluorescent lamp (model FCL20BL, 18 W, by NEC Corporation). The reactant became viscous 5 hours later and hardened 15 hours later. A polymer was thus obtained as a reaction product. This reaction product was dissolved in 2-propanol, and the solution was transferred to a dialysis tube. Dialysis was performed for 72 hours to purify the reaction product.

The solution including the reaction product was filtered with a 0.2 μm cellulose mixed-ester filter (model 25AS020 by Toyo Roshi Kaisha), and the resulting filtrate was freeze dried to obtain a temperature-responsive (homo)polymer (6.8 g yield, 68% conversion ratio). The number-average molecular weight (Mn) of this polymer was measured using a GPC (model LC-10vp series by Shimadzu Corporation) with polyethylene glycol (TSK series by Shodex) as a standard substance and was determined to be $Mn=1.0\times10^5$ g/mol (Mw/Mn=10.0).

The nuclear magnetic resonance (NMR) spectrum of the above-described temperature-responsive polymer was measured using a nuclear magnetic resonance apparatus (model Gemini-300 by Varian) with heavy water ($D_2O$) as a standard substance. A representative peak is indicated below.

$^1$H-NMR (in $D_2O$) δ 0.8-1.2 (br, —$CH_2$—C($CH_3$)—), 1.6-2.0 (br, —$CH_2$—C($CH_3$)—), 2.2-2.4 (br, —N($CH_3)_2$), 2.5-2.7 (br, —$CH_2$—N($CH_3)_2$), 4.0-4.2 (br, —O—$CH_2$—).

Here, from the number of protons A in the methyl group (δ 0.8-1.2) of the main chain (3 per monomer molecule in the case of a DMAEMA homopolymer) and the number of methyl protons B in the dimethylamino group (δ 2.2-2.4) of the side chain (6 per monomer molecule in the case of a DMAEMA homopolymer), the ratio was calculated between the number of functional groups that are amino groups in the side chain and the number of functional groups that are carboxyl groups in the side chain produced by a hydrolysis reaction, which proceeds simultaneously with the polymerization reaction, of an ester bond of the side chain.

The resulting ratio was 94:6 in the case of the above-described temperature-responsive polymer. Converting into the C/A ratio for an ion complex in a two-component mixed system that includes a cationic polymer and an anionic polymer yields a C/A ratio of 15.6.

The cloud point of the above-described temperature-responsive polymer was measured with the following method.

A 3% aqueous solution of the temperature-responsive polymer was produced, and the absorbance of the aqueous solution at 660 nm was measured between 20° C. and 40° C.

Between 20° C. and 30° C., the aqueous solution was transparent, with an absorbance of nearly 0. Starting around 31° C., however, the aqueous solution became cloudy, and the absorbance increased suddenly at 32° C. The temperature-responsive polymer was thus confirmed to have a cloud point of approximately 32° C.

Once the temperature-responsive polymer was increased in temperature to 37° C., the polymer aqueous solution was suspended with good responsiveness. Subsequently, the entire aqueous solution hardened. When maintained at room temperature (25° C.), the hardened product retained its hard state for several tens of hours. Subsequently, the hardened product gradually dissolved, changing into a homogeneous aqueous solution. Upon being cooled to 4° C., the hardened polymer rapidly dissolved. Repeating the aforementioned operation to raise and lower the temperature caused no change in responsiveness, thereby confirming that the polymer reversibly underwent phase transitions.

The above-described temperature-responsive polymer was dissolved in pure water to produce a temperature-responsive polymer solution (final concentration 15 ng/μL). This solution was applied to the entire culturing surface of the above-described apparatus, and the applied temperature-responsive polymer aqueous solution was then dried by leaving the apparatus in an incubator (40° C.) for 1 hour to prepare a production apparatus, of a three-dimensional tissue body, having a coated culturing surface.

Example III-2

A stainless-steel tube (by Fuji Filter Manufacturing Co., 3ϕ) with a meshed surface was used as a shaft, and "Prime-Surface®" (number MS-9024X, by Sumitomo Bakelite Co.) was used as a culturing surface, a portion of the culturing surface being cut out to form a through hole (approximately 3.2 mm diameter), to manufacture an apparatus with a gap between the culturing surface and the shaft. The culturing surface was substantially circular, with an outer diameter of approximately 25 mm. The gap between the culturing surface and the shaft was 0.2 mm. The apparatus was shaped as in FIG. 20.

As in Example III-1, the culturing surface was coated with a temperature-responsive polymer to prepare a production apparatus, of a three-dimensional tissue body, having a coated culturing surface.

Example III-3

(Production of Ringed Three-Dimensional Tissue Body)

The production apparatus of a three-dimensional tissue body manufactured in Example III-1 was placed in a conical tube (product code "2345-050" by Iwaki & Co) with an inner diameter of 30 mm and immersed in a medium (DMEM+10% FBS (lot number 715929 by Biological Industries)+50 µg/mL of ascorbic acid diphosphate (catalog number 196-1252 by Wako Pure Chemical Industries)). Subsequently, adipose-derived mesenchymal stem cells (ADSC) of a GFP recombinant Lewis rat were mixed into a medium, similar to the medium in which the production apparatus was immersed, to produce a cell suspension. Next, 2 mL of the cell suspension at $60\times10^5$ cells/mL was added to seed cells.

The cells were then cultured for 24 hours in a cell incubator (37° C., 5% $CO_2$), and obtainment of a ringed three-dimensional tissue body wound around the shaft was confirmed.

The resulting ringed three-dimensional tissue body was nearly identical to the one in FIG. 23. The resulting ringed three-dimensional tissue body had ADSC as the principal component.

Example III-4

(Production of Ringed Three-Dimensional Tissue Body)

Except for using the production apparatus of a three-dimensional tissue body produced in Example III-2, a ringed three-dimensional tissue body was produced in a way similar to Example III-3. The aggregated cells jumped over the gap between the culturing surface and the shaft, and obtainment of a ringed three-dimensional tissue body wound around the shaft was confirmed.

FIG. 23 illustrates the ringed three-dimensional tissue body obtained in Example III-4. The resulting ringed three-dimensional tissue body had ADSC as the principal component.

Example III-5

(Production of Luminal Three-Dimensional Tissue Body)

The production apparatus of a three-dimensional tissue body manufactured in Example III-1 was placed in a conical tube (product code "2345-050" by Iwaki & Co) with an inner diameter of 30 mm and immersed in a medium (RPMI-1640+10% FBS (lot number 715929 by Biological Industries)+10 ng/µL rat TGF-β1 recombinant (catalog number 100-21 by PeproTech)+50 µg/mL of ascorbic acid diphosphate (catalog number 196-01252 by Wako Pure Chemical Industries). Subsequently, chondrocytes collected from the knee joint of a GFP recombinant Lewis rat with a conventional method were mixed into a medium, similar to the medium in which the production apparatus was immersed, to produce a cell suspension. Next, 2 mL of the cell suspension at $60\times10^5$ cells/mL was added to seed cells, and the cells were cultured for 48 hours in a cell incubator (37° C., 5% $CO_2$). Obtainment of a ringed three-dimensional tissue body wound around the shaft was confirmed.

Subsequently, the culturing surface was moved downward 0.5 mm in the extending direction of the shaft, another 2 mL of the cell suspension was added to seed cells again, and the cells were cultured for 48 hours in a cell incubator (37° C., 5% $CO_2$) (second cell seeding and culturing). Seeding and culturing of cells in the same way were continuously repeated a total of 9 times.

Obtainment of a luminal three-dimensional tissue body in which 9 ringed three-dimensional tissue bodies were connected and adhered to each other was confirmed.

FIG. 24 illustrates the luminal three-dimensional tissue body obtained in Example III-5. Note that FIG. 24 is a photograph taken after replacing the stainless-steel tube shaft with a silicone resin tube.

Example III-6

(Production of Luminal Three-Dimensional Tissue Body)

Except for using the production apparatus of a three-dimensional tissue body manufactured in Example III-2 and moving the culturing surface upward 0.2 mm in the extending direction of the shaft, a luminal three-dimensional tissue body was produced in a way similar to Example III-5. Obtainment of a luminal three-dimensional tissue body in which 9 ringed three-dimensional tissue bodies were connected and adhered to each other was confirmed.

The resulting luminal three-dimensional tissue body was nearly identical to the one in FIG. 24.

Example III-7

(Manufacturing of Production Apparatus, of Three-Dimensional Tissue Body, with a Plurality of Culturing Surfaces)

A stainless-steel tube (by Fuji Filter Manufacturing Co., 3ϕ) with a meshed surface was used as a shaft, and "PrimeSurface®" (number MS-9024X, by Sumitomo Bakelite Co.) was used as a culturing surface, a portion of the culturing surface being cut out to form a through hole (approximately 3.2 mm diameter), to manufacture an apparatus with 9 culturing surfaces and a gap between the culturing surfaces and the shaft. All of the culturing surfaces were substantially circular, with an outer diameter of approximately 24 mm. The gap between the culturing surfaces and the shaft was 0.2 mm. The apparatus was shaped as in FIG. 25, except with nine culturing surfaces and one shaft passed through the through holes of the nine culturing surfaces. As in Example III-1, the culturing surfaces were all coated with a temperature-responsive polymer to prepare a production apparatus, of a three-dimensional tissue body, having coated culturing surfaces.

The gap between culturing surfaces was 1 mm.

Example III-8

(Production of Luminal Three-Dimensional Tissue Body)

The production apparatus of a three-dimensional tissue body manufactured in Example III-7 was placed in a conical tube (product code "2345-050" by Iwaki & Co) with an inner diameter of 30 mm and immersed in a medium (DMEM+10% FBS (lot number 715929 by Biological Industries)). Subsequently, rat subcutaneous adipose-derived mesenchymal stem cells were mixed into a medium, similar to the medium in which the production apparatus was immersed, to produce a cell suspension. Next, 2 mL of the cell suspension at $60\times10^6$ cells/mL was added to seed cells on each coated culturing surface, and the cells were cultured for 48 hours in a cell incubator (37° C., 5% $CO_2$). Obtainment from each coated culturing surface of a ringed three-dimensional tissue body wound around the shaft was confirmed.

Subsequently, culturing was further continued for 48 hours, after which obtainment of a luminal three-dimensional tissue body, in which 9 ringed three-dimensional tissue bodies formed from the coated culturing surfaces were connected and adhered to each other, was confirmed.

FIG. 27A illustrates the luminal three-dimensional tissue body obtained in Example III-8 (photograph after 3.8% glutaraldehyde fixation), and FIG. 27B illustrates an HE stain section image.

Example III-9

(Synthetic Blood Vessel)

Cells were seeded by mixing vascular endothelial cells, derived from umbilical cord blood and labeled with a red fluorescent label using a cell linker kit, in a medium (DMEM+10% FBS (lot number 715929 by Biological Industries) and adding 1 mL at a time at a concentration of $60 \times 10^5$ cells/mL to the nine culturing surfaces of the production apparatus of a three-dimensional tissue body manufactured in Example III-7. The apparatus was placed in a conical tube (product code "2345-050" by Iwaki & Co) with an inner diameter of 30 mm and immersed in a medium (DMEM+10% FBS (lot number 715929 by Biological Industries)). The cells were then cultured for 48 hours in a cell incubator (37° C., 5% $CO_2$). Obtainment of a ringed three-dimensional tissue body of vascular endothelial cells wound around the shaft was confirmed.

Subsequently, GFP knock-in rat subcutaneous adipose-derived mesenchymal stem cells were mixed into a medium, similar to the medium in which the production apparatus was immersed, to produce a mesenchymal stem cell suspension. Ten mL at $60 \times 10^5$ cells/mL was added to seed cells, and the cells were cultured for 48 hours in a cell incubator (37° C., 5% $CO_2$). Obtainment of a luminal three-dimensional tissue body (synthetic blood vessel) in which 9 ringed three-dimensional tissue bodies were connected and adhered to each other, the tissue bodies having a two-layer structure with a layer of mesenchymal stem cells surrounding a layer of vascular endothelial cells, was confirmed.

FIG. 28 illustrates a fluorescence microscope image of the synthetic blood vessel obtained in Example III-9.

Example III-10

(Synthetic Blood Trachea)

The production apparatus of a three-dimensional tissue body manufactured in Example III-1 was placed in a conical tube (product code "2345-050" by Iwaki & Co) with an inner diameter of 30 mm and immersed in a medium (DMEM+10% FBS (lot number 715929 by Biological Industries)+50 µg/mL of ascorbic acid diphosphate (catalog number 196-1252 by Wako Pure Chemical Industries)).

Subsequently, beagle knee joint-derived chondrocytes were mixed into a medium, similar to the medium in which the production apparatus was immersed, to produce a chondrocyte suspension. Two mL of the chondrocyte suspension at $60 \times 10^5$ cells/mL was then added to seed cells, and the cells were cultured for 48 hours in a cell incubator (37° C., 5% $CO_2$). Obtainment of a ringed three-dimensional tissue body of chondrocytes wound around the shaft was confirmed.

Subsequently, the culturing surface was moved downward 0.5 mm in the extending direction of the shaft, and 2 mL of a fibroblast suspension ($60 \times 10^5$ cells/mL), produced by mixing rat adipose-derived mesenchymal stem cells (ADSC) into a similar medium as the medium in which the production apparatus was immersed, was added to seed cells again. The cells were cultured for 48 hours in a cell incubator (37° C., 5% $CO_2$) (second cell seeding and culturing).

Chondrocytes and mesenchymal stem cells were used alternately. Obtainment of a luminal three-dimensional tissue body (synthetic trachea) in which 6 ringed three-dimensional tissue bodies were connected and adhered to each other was confirmed.

FIG. 29 illustrates the synthetic trachea obtained in Example III-10. Note that FIG. 29 is a photograph taken after replacing the stainless-steel tube shaft with a silicone resin tube.

Example III-11

(Three-Dimensional Tissue Body Having Protein as Principal Component)

The production apparatus of a three-dimensional tissue body manufactured in Example III-1 was placed in a conical tube (product code "2345-050" by Iwaki & Co) with an inner diameter of 30 mm and immersed in a medium (DMEM+10% FBS (lot number 715929 by Biological Industries)+50 µg/mL of ascorbic acid diphosphate (catalog number 196-1252 by Wako Pure Chemical Industries)).

Subsequently, rat adipose-derived mesenchymal stem cells (ADSC) were mixed into a medium, similar to the medium in which the production apparatus was immersed, to produce a cell suspension. Next, 2 mL of the cell suspension at $60 \times 10^5$ cells/mL was added to seed cells, and the cells were cultured for 48 hours in a cell incubator (37° C., 5% $CO_2$). Obtainment of a ringed three-dimensional tissue body wound around the shaft was confirmed.

Subsequently, the culturing surface was moved downward 0.5 mm in the extending direction of the shaft, another 2 mL of the cell suspension was added to seed cells again, and the cells were cultured for 48 hours in a cell incubator (37° C., 5% $CO_2$) (second cell seeding and culturing).

Seeding and culturing of cells in the same way was continuously repeated a total of 6 times.

Obtainment of a luminal three-dimensional tissue body in which 6 ringed three-dimensional tissue bodies were connected and adhered to each other was confirmed.

Subsequently, the obtained luminal three-dimensional tissue body was treated with sodium dodecyl sulfate and ethanol and then treated with 3.8% glutaraldehyde to kill the cells in the three-dimensional tissue body. Obtainment of a luminal three-dimensional tissue body having protein as the principal component was confirmed.

FIG. 30 illustrates the three-dimensional tissue body, obtained in Example III-11, having protein as the principal component.

Examples of Aspect (IV)

Aspect (IV) is described below in greater detail with reference to examples, but the present disclosure is in no way limited by these examples.

In the following tests, commercially available reagents were used without further purification, unless otherwise noted.

Example IV-A1

(Test IV-A1) Manufacturing of Polymer

First, 10.0 g of 2-N,N-dimethylaminoethyl methacrylate (DMAEMA) and 5 mL of water were added to a 50 mL capacity transparent vial made of soft glass, and the vial was stirred using a magnetic stirrer. The mixture (liquid) was then purged with Gi-grade, highly pure (purity: 99.99995%) nitrogen gas for 10 minutes (flow rate: 2.0 L/min) to deoxygenize the mixture. The DMAEMA that was used included 0.5 mass % of methylhydroquinone (MEHQ), which is a polymerization inhibitor.

Subsequently, this reactant was polymerized by irradiation with ultraviolet light for 22 hours using a round, black fluorescent lamp (model FCL20BL, 18 W, by NEC Corporation). The reactant became viscous 5 hours later and hardened 15 hours later. A polymer was thus obtained as a reaction product. This reaction product was dissolved in 2-propanol, and the solution was transferred to a dialysis tube. Dialysis was performed for 72 hours to purify the reaction product.

The solution including the reaction product was filtered with a 0.2 μm cellulose mixed-ester filter (model 25AS020 by Toyo Roshi Kaisha), and the resulting filtrate was freeze dried to obtain a temperature-responsive (homo)polymer (6.8 g yield, 68% conversion ratio). The number-average molecular weight (Mn) of this polymer was measured using a GPC (model LC-10vp series by Shimadzu Corporation) with polyethylene glycol (TSK series by Shodex) as a standard substance and was determined to be $Mn=1.0\times10^5$ g/mol (Mw/Mn=10.0) (Example Polymer 1).

The nuclear magnetic resonance (NMR) spectrum of the above-described temperature-responsive polymer was measured using a nuclear magnetic resonance apparatus (model Gemini-300 by Varian) with heavy water ($D_2O$) as a standard substance. A representative peak is indicated below.

$^1$H-NMR (in $D_2O$) δ 0.8-1.2 (br, —$CH_2$—$C(CH_3)$—), 1.6-2.0 (br, —$CH_2$—$C(CH_3)$—), 2.2-2.4 (br, —$N(CH_3)_2$), 2.5-2.7 (br, —$CH_2$—$N(CH_3)_2$), 4.0-4.2 (br, —O—$CH_2$—).

Here, from the number of protons A in the methyl group (δ 0.8-1.2) of the main chain (3 per monomer molecule in the case of a DMAEMA homopolymer) and the number of methyl protons B in the dimethylamino group (δ 2.2-2.4) of the side chain (6 per monomer molecule in the case of a DMAEMA homopolymer), the ratio was calculated between the number of functional groups that are amino groups in the side chain and the number of functional groups that are carboxyl groups in the side chain produced by a hydrolysis reaction, which proceeds simultaneously with the polymerization reaction, of an ester bond of the side chain.

The resulting ratio was 94:6 in the case of the above-described temperature-responsive polymer. Converting into the C/A ratio for an ion complex in a two-component mixed system that includes a cationic polymer and an anionic polymer yields a C/A ratio of 15.6.

A 3% aqueous solution of Example Polymer 1 was produced, and the absorbance of the aqueous solution at 660 nm was measured between 20° C. and 40° C.

Between 20° C. and 30° C., the aqueous solution was transparent, with an absorbance of nearly 0. Starting around 31° C., however, the aqueous solution became cloudy, and the absorbance increased suddenly at 32° C. The aforementioned polymer was thus confirmed to have a cloud point of approximately 32° C.

Once the Example Polymer was increased in temperature to 37° C., the polymer aqueous solution was suspended with good responsiveness. Subsequently, the entire aqueous solution hardened. When maintained at room temperature (25° C.), the hardened product retained its hard state for several tens of hours. Subsequently, the hardened product gradually dissolved, changing into a homogeneous aqueous solution. Upon being cooled to 4° C., the hardened polymer rapidly dissolved. Repeating the aforementioned operation to raise and lower the temperature caused no change in responsiveness, thereby confirming that the polymer reversibly underwent phase transitions.

(Test IV-A2) Manufacturing of Cell Structure

In Example IV-A1, a cell structure was manufactured using a culturing surface produced by application and drying.

A 35 mm polystyrene cell culture plate (model 3000-035-MYP by Iwaki & Co., Ltd, bottom area of 9 cm$^2$ per well) was used as a cell culture container.

Next, 40 μL of a temperature-responsive polymer aqueous solution (concentration: 15 μg/mL) cooled to the cloud point or below was applied over the entire culturing surface.

The applied aqueous solution of temperature-responsive polymer was dried by leaving the cell culture plate on a clean bench.

A coated region that was coated with the temperature-responsive polymer was thus provided on the culturing surface of the cell culture plate.

(Test IV-A3) Measurement of Zeta Potential

The surface zeta potential of the coated region, which was provided on a small piece of a cell culture plate with a procedure similar to the procedure for Test IV-A2, was measured using a zeta potential meter (model ELSZ by Otsuka Electronics Co., Ltd) and a cell unit for flat plate samples.

Specifically, a sample of the small piece was tightly adhered to the bottom surface of a quartz cell, and a monitor particle suspension was injected into the cell. Here, particles (zeta potential: −5 mV to +5 mV) yielded by coating polystyrene latex (particle size: approximately 500 nm) with hydroxypropyl cellulose (Mw=30,000) were used as standard monitoring particles. A 10 mM sodium chloride aqueous solution at pH=7 and 37° C. was used as a solvent. The zeta potential was calculated using the Smoluchowski equation.

The zeta potential of the surface of a small piece of non-coated cell culture plate was −68 mV, which is a value known to a person skilled in the art as the zeta potential of a solid surface of a typical thermoplastic resin.

In contrast, the zeta potential of the surface of the small piece of cell culture plate coated with a temperature-responsive polymer was +20 mV.

As a person skilled in the art knows, the measured value of the zeta potential of a solid surface exhibits approximately ±10% variation with current techniques. Variation is also present in the coating operation itself during the step of producing the sample. Hence, the aforementioned measurement of the zeta potential may have a certain error.

(Test IV-A4) Measurement of Contact Angle

The contact angle of water relative to the coated region of the cell culture plate was measured as 700±10° using a contact angle meter (DMs-400, by Kyowa Interface Science Co.) in conformity with JIS R3257.

(Test IV-A5) Cell Culture

Here, 3.0×10$^5$ cells/mL of mesenchymal adipose stem cells, derived from rat subcutaneous fat and tagged with GFP, were suspended in a complete medium (Dulbecco's Modified Eagle Medium (DMEM)+10% fetal bovine serum (FBS); DMEM: model 11995-065 by Gibco; FCS: lot number 928696, by Invitrogen) to produce a cell suspension.

Droplets of the cell suspension were spotted with a pipettor in 100 locations (see (iv) of FIG. 31) while appropriately selecting between amounts of 0.5 μL, 2 μL, 4 μL, and 20 μL. The shape of the droplets was nearly a true circle, and the diameter of the droplets was 1 mm in the case of 0.5 μL, 2 mm in the case of 2 μL, 3 mm in the case of 4 μL, and 5.5 mm in the case of 20 μL. The gap between any two droplets was 200 μm or more. The ratio of the bottom area of the droplet to the area of the coated region was approximately 75%.

The seeded adipose stem cells derived from rat subcutaneous fat were cultured for 8 hours in a cell culture incubator at 37° C. in a 5% $CO_2$ atmosphere.

At 0 hours after the start of culturing (immediately after spotting), the adipose stem cells were adhered to the entire coated region (see (v) of FIG. 31).

At 2 hours after the start of culturing, the cells located near the periphery of the coated region spontaneously started to peel off.

From 3 hours to 6 hours after the start of culturing, spontaneous detachment of cells progressed slowly from the periphery of the coated region towards the center of the coated region.

At 8 hours after the start of culturing, cell structures having a spheroidal structure finally formed from the cultures in the coated regions, the cell structures being equal in number to the number of coated regions (see FIG. (vi) of FIG. 31).

The formed spheroidal cell structures uniformly had a nearly spherical shape with a desired size in accordance with the amount of the droplet.

Examples IV-A2 to IV-A5

In Example IV-A2, an experiment was performed in a way similar to Example IV-A1, except for changing the surface zeta potential of the coated region from +20 mV to +15 mV by adjusting the conditions for manufacturing the polymer. Cell structures with a spheroidal structure and a uniform shape of a desired size were obtained, as in Example IV-A1.

In Example IV-A3, an experiment was performed in a way similar to Example IV-A1, except for changing the surface zeta potential of the coated region from +20 mV to +35 mV by adjusting the conditions for manufacturing the polymer. Cell structures with a spheroidal structure and a uniform shape of a desired size were obtained, as in Example IV-A1.

In Example IV-A4, an experiment was performed in a way similar to Example IV-A1, except for changing the contact angle of water relative to the coated region from 70°±10° to 65°±7° by adjusting the conditions for manufacturing the polymer. Cell structures with a spheroidal structure and a uniform shape of a desired size were obtained, as in Example IV-A1.

In Example IV-A5, an experiment was performed in a way similar to Example IV-A1, except for changing the contact angle of water relative to the coated region from 70°±10° to 75°±5° by adjusting the conditions for manufacturing the polymer. Cell structures with a spheroidal structure and a uniform shape of a desired size were obtained, as in Example IV-A1.

Example IV-B1

(Test IV-B1) Production of Culturing Surface
A precision glass plate produced by Matsunami Glass Ind., MICRO COVER GLASS (30 mm×40 mm×0.15 mm thick) was washed with diethyl ether and dried. The washing was intended to remove foreign materials and an oil component that prevents glass plates from sticking together.

(Test IV-B1-1) <Case of Entire Culturing Surface being Coated with Polymer>
Vinyltrimethoxysilane was dissolved in a 4% acetic acid aqueous solution and adjusted to a final concentration of 0.5% or 2.0%. This silane compound solution was cast over the entire surface of the glass and drained to yield a solution thickness of approximately 0.1 μm. The glass plate was left to stand for 72 hours in a 25° C. sealed desiccator increased to a humidity of 84% with a saturated solution of potassium chloride. After washing with RO water, the glass was treated for 10 minutes at 100° C. to evaporate moisture and was then further washed with RO water and 2-propanol. It was confirmed with IR analysis that vinyl groups derived from the silane coupling agent Vinyltrimethoxysilane were fixed to the glass surface.

A solution with a mixture of 10 g of 2-(N,N-Dimethylaminoethyl)methacrylate and 5 g of RO was bubbled for 10 minutes with nitrogen gas. The glass plate, with introduced vinyl groups, produced in (1) above was placed in a 100 mm diameter Petri dish, 10 mL of a monomer aqueous solution deoxygenated by nitrogen gas bubbling was added to soak the glass plate, and the Petri dish was sealed to form a nitrogen atmosphere inside. A 375 nm black light was irradiated from the bottom of the Petri dish for 10 hours, and the glass plate was washed with RO water and 2-propanol and dried to yield a cell culture container (1).

The correlation between the droplet amount and the droplet diameter in the cell culture container (1) produced in Test IV-B1-1 was investigated.

With a pipettor, 0.5 μL to 50 μL droplets of a rat subcutaneous adipose-derived mesenchymal stem cell suspension (cell density: $3.0×10^5$ cells/mL, complete medium (Dulbecco's Modified Eagle Medium (DMEM)+10% fetal bovine serum (FBS) solution; DMEM: model 11995-065 by Gibco; FCS: lot number 928696, by Invitrogen)) were spotted on the glass plate surface to which the copolymer was fixed. The diameter of the droplets was then measured from a projection image of the bottom. The droplet amount and the droplet diameter did not have a first order correlation over the entire range of the droplet amounts of 0.5 μL to 50 μL, as illustrated in FIG. 33A.

On the other hand, dividing into a 0.5 μL to 5.0 μL range and a 5.0 μL to 50 μL range, as illustrated in FIGS. 33A and 33C, revealed a linear correlation in each region and suggested that the droplet diameter can be controlled by the droplet amount.

FIGS. 33A to 33C illustrate the results of investigating the correlation between the amount of a droplet and the diameter of the droplet on the culturing surface in an example.

(Test IV-B1-2) <Case of Coating a Plurality of Locations on the Culturing Surface with Polymer>
Vinyltrimethoxysilane was dissolved in a 4% acetic acid aqueous solution and adjusted to a final concentration of 2.0%. Twenty droplets of the silane coupling agent solution were spotted 0.5 μL at a time onto a precision glass plate, produced by Matsunami Glass Ind., in four rows and five columns at intervals of 1.2 mm to 12 mm starting from the center of the droplet. The glass plate was left to stand for 72 hours in a 25° C. desiccator increased to a humidity of 84% with a saturated solution of potassium chloride. The droplets were suctioned with a capillary, and the glass plate was washed with water and methanol and dried to yield a cell culture container (2).

As in Test IV-B1-1, graft polymerization was performed. It was confirmed with IR analysis that a copolymer was fixed only onto the droplets (dots) where the silane coupling agent Vinyltrimethoxysilane was spotted.

(Test IV-B2) Manufacturing of Cell Structure
In Example IV-B2, a cell structure was manufactured using a culturing surface produced by graft polymerization.

(Test IV-B2-1)

With a pipettor, 20 droplets of a rat subcutaneous adipose-derived mesenchymal stem cell suspension (cell density: $3.0 \times 10^5$ cells/mL, complete medium (Dulbecco's Modified Eagle Medium (DMEM)+10% fetal bovine serum (FBS) solution; DMEM: model 11995-065 by Gibco; FCS: lot number 928696, by Invitrogen)) were spotted in a range of 0.5 µL to 2.0 µL in four rows and five columns on the glass plate surface, manufactured in Test IV-B1-1, to which the copolymer was fixed. The cells were then cultured in a cell culture incubator (MCO-5C by Sanyo Electric Co.) for 24 hours (37° C., 5% carbon dioxide gas).

Individual cells in the droplet formed a single layer and adhered to the glass surface, and a state of cells accumulating on top of other cells was hardly observed. One hour after spotting of the droplets, all of the cells were adhered to the glass plate and were expanding. After approximately 9 hours of further culturing, cells began to aggregate from the periphery of the droplet towards the center, and after 21 hours, all of the cells had gathered in one place to form a spheroidal mass at the central portion.

After soaking the glass plate in a 0.3% methyl cellulose PBS solution, all of the spheroids could be collected as a solution with suspended spheroids.

Droplets fused when the distance between them was 30 µm or less, possibly due to attraction or the surface tension relative to the air phase. Consequently, a state in which a suspension was cast over the entire glass plate was reached, resulting in cells simultaneously aggregating everywhere.

Examples of Aspect (V)

Aspect (V) is described below in greater detail with reference to examples, but the present disclosure is in no way limited by these examples.

In the following tests, commercially available reagents were used without further purification, unless otherwise noted.

Example V-1

(Test V-A) Production of Temperature-Responsive Polymer

First, 10.0 g of 2-N,N-dimethylaminoethyl methacrylate (DMAEMA) and 5,000 µL of water were added to a 50 mL capacity transparent vial made of soft glass, and the vial was stirred using a magnetic stirrer. The mixture (liquid) was then purged with Gi-grade, highly pure (purity: 99.99995%) nitrogen gas for 10 minutes (flow rate: 2.0 L/min) to deoxygenize the mixture. The DMAEMA that was used included 0.5 weight % of methylhydroquinone (MEHQ), which is a polymerization inhibitor.

Subsequently, this reactant was polymerized by irradiation with ultraviolet light for 22 hours using a round, black fluorescent lamp (model FCL20BL, 18 W, by NEC Corporation). The reactant became viscous 5 hours later and hardened 15 hours later. A polymer was thus obtained as a reaction product. This reaction product was dissolved in 2-propanol, and the solution was transferred to a dialysis tube. Dialysis was performed for 72 hours to purify the reaction product.

The solution including the reaction product was filtered with a 0.2 µm cellulose mixed-ester filter (model 25AS020 by Toyo Roshi Kaisha), and the resulting filtrate was freeze dried to obtain an intramolecular ion complex-type temperature-responsive polymer (6.8 g yield, 68% conversion ratio). The number-average molecular weight (Mn) of this polymer was measured using a GPC (model LC-10vp series by Shimadzu Corporation) with polyethylene glycol (TSK series by Shodex) as a standard substance and was determined to be Mn=100,000 (Mw/Mn=10.0).

The nuclear magnetic resonance (NMR) spectrum of the temperature-responsive polymer was measured using a nuclear magnetic resonance apparatus (model Gemini-300 by Varian) with heavy water ($D_2O$) as a standard substance. The representative peaks common to Example Polymer V-1 are listed below.

$^1$H-NMR (in $D_2O$) δ 0.8-1.2 (br, 3H, —$CH_2$—C($CH_3$)—), 1.6-2.0 (br, 2H, —$CH_2$—C($CH_3$)—), 2.2-2.4 (br, 6H, —N($CH_3$)$_2$), 2.5-2.7 (br, 1.9H, —$CH_2$—N($CH_3$)$_2$), 4.0-4.2 (br, 1.9H, —O—$CH_2$—).

Here, from the number of protons A in the methyl group (δ 0.8-1.2) bonded at the a position (3 in both the case of a DMAEMA unit and the case of a methacrylic acid unit) and the number of methyl protons B in the ethyl group (δ 4.0-4.2) bonded to oxygen in the ester bond of a side chain (2 in the case of a DMAEMA unit and 0 in the case of a methacrylic acid unit), the ratio between the number of functional groups that are amino groups in the side chains of DMAEMA and the number of functional groups that are carboxyl groups in the side chains of methacrylic acid was calculated.

The resulting ratio was 94:6 in the case of the obtained polymer V-1. Converting into the C/A ratio for an ion complex in a two-component mixed system that includes a cationic polymer and an anionic polymer yields a C/A ratio of 15.6.

Furthermore, a 3% aqueous solution of the obtained temperature-responsive polymer was produced, and measuring the absorbance of the aqueous solution at 660 nm between 20° C. and 40° C. yielded a value of approximately 32° C.

(Test V-B) Preparation of First Coated Regions and Second Coated Regions

A φ35 mm low cell-adsorption plate (PrimeSurface® by SUMILON) was used as a cell culture container.

At room temperature, 4.0 µL at a time of the above-described polymer aqueous solution produced in Test V-A (concentration: 15 ng/µL) was spotted onto 6 locations on the culturing surface of the aforementioned plate. The aqueous solution was then dried for 30 minutes at 37° C. to prepare circular first coated regions (area 4.5 mm$^2$).

After drying, 0.2 µL at a time of a fibronectin solution (derived from human plasma) (concentration: 200 ng/µL) (lot number 3353563 by BD Biosciences) was spotted onto 1 of the 6 circular first coated regions, at 2 locations positioned on the edge of the first coated region along a line passing through the center of the first coated region, so as to overlap the first coated region. The solution was then dried at 37° C. for 5 minutes to prepare circular second coated regions (area 0.8 mm$^2$) (see FIG. 37A).

The surface zeta potential of the first coated region was measured using a zeta potential meter (model ELSZ by Otsuka Electronics Co.) and a cell unit for flat plate samples. During the measurement, a quartz cell was used as the cell, a particle (zeta potential: −5 mV to +5 mV) in which polystyrene latex (particle size: approximately 500 nm) was coated with hydroxypropyl cellulose (Mw=30,000) was used as a reference monitor particle, and a 10 mM sodium chloride aqueous solution at pH=7 and 37° C. was used as a solvent. The zeta potential was calculated with the Smoluchowski equation.

The resulting zeta potential of the surface of the first coated region coated with a temperature-responsive polymer was +20 mV. As is well known to a person skilled in the art, the measured value of the zeta potential exhibits a variation of approximately ±10%.

The contact angle of water relative to the first coated region of a cell culture plate was measured as 700±10° using a contact angle meter (DMs-400, by Kyowa Interface Science Co.) in conformity with JIS R3257.

(Test V-C) Seeding and Culturing of Cells

The cell culture container prepared in Test V-B was used.

Adipose-derived mesenchymal stem cells (adipose-derived vascular stromal cells (ADSC)) of a GFP recombinant Lewis rat were suspended in a medium (Dulbecco's Modified Eagle Medium (DMEM)+10% fetal bovine serum (FBS); DMEM: model 11965 by Gibco; FBS: lot number 715929 by Biological Industries) to produce a cell suspension.

The cell suspension was added to the plate at room temperature to yield a cell density of at least $2.5 \times 10^5$ cells/cm$^2$ (95% confluency).

These cells were then cultured for 2 hours in a cell culture incubator at 37° C. and 5% $CO_2$.

At 2 hours after the start of culturing, the medium was exchanged with the above-described medium, and dead cells were removed.

FIG. 37A is a photograph when using a microscope, in Test V-C, to observe the state after 2 hours of culturing ADSC of a GFP recombinant Lewis rat in the first coated region and the second coated regions prepared in Test V-B.

The cells were then further cultured for 18 hours in a cell culture incubator at 37° C. and 5% $CO_2$.

During these 18 hours of culturing, the cells adhered to the first coated region aggregated towards the central portion, whereas the cells adhered to the second coated regions remained adhered to their initial position. The bonding strength of the inter-cell network resulting from maturation of seeded cells exceeded the adhesiveness of cells to the first coated region, leading to cell aggregation. At this time, aggregation and contraction in the long axis direction was limited, whereas aggregation and contraction in the short axis direction was prioritized. Ultimately, a linear cell structure was formed from the 2 cell groups that remained adhered to the second coated regions and the stick-like cell group connecting the 2 cell groups.

FIG. 37A is a photograph when using a microscope, in Test V-C, to observe the state after 20 hours of culturing ADSC of a GFP recombinant Lewis rat in the first coated region and the second coated region prepared in Test V-B.

FIG. 37A is a photograph when observing the cell structure in FIG. 37B at lower magnification.

FIG. 37D is a photograph when using a fluorescence microscope to observe the state of the cell structure indicated by the dashed line in FIG. 37B. It is clear that within the cell structure obtained in Test V-C, the stick-like cell group had a shape such that cells spread in the extending direction of the cell structure, and the stick-like cell group was oriented in the direction of a line connecting the 2 cell groups that remained adhered to the second coated regions.

Example V-2

The cell adhesive substance that was used was changed from a fibronectin solution to laminin (concentration: 50 ng/μL) (by Nippi, Inc.), and a similar test to the above-described Test V-B of Example V-1 was performed. Also, the cells that were used were changed from ADSC of a GFP recombinant Lewis rat to cardiomyocytes (separated from a newborn Lewis rat on the first day after birth with a conventional method), and a similar test to the above-described Test V-C of Example V-1 was performed.

In this case as well, a cell structure with a structure similar to that of the above-described cell structure indicated in FIGS. 37A to 37D was obtained.

TABLE 4

| | | | Example V-1 | Example V-2 |
|---|---|---|---|---|
| Preparation Step | First Coated Region | Shape | circular | circular |
| | | Area (mm$^2$) | 4.5 | 4.5 |
| | Second Coated Regions | Shape | circular | circular |
| | | Area (mm$^2$) | 0.8 | 0.8 |
| | | Number | 2 | 2 |
| | | Cell Adhesive Substance | fibronectin | laminin |
| | | Coated Amount (ng) | 40 | 10 |
| | Cell Non-Adhesive Wall | | none | none |
| Seeding and Culturing Step | Cells | Type | ADSC | cardio-myocytes |
| | | Density (cells/cm$^2$) | $2.5 \times 10^5$ | $2.5 \times 10^5$ |
| Cell Structure | | Shape | spindle | spindle |
| | | Figure | FIGS. 38A to 38D | FIGS. 38A to 38D |

Examples of Aspect (VI)

Aspect (VI) is described below in greater detail with reference to examples, but the present disclosure is in no way limited by these examples.

Example VI-1

First, 10.0 g of 2-N,N-dimethylaminoethyl methacrylate (DMAEMA) and 5 mL of water were added to a 50 mL capacity transparent vial made of soft glass, and the vial was stirred using a magnetic stirrer. The mixture (liquid) was then purged with Gi-grade, highly pure (purity: 99.99995%) nitrogen gas for 10 minutes (flow rate: 2.0 L/min) to deoxygenize the mixture. The DMAEMA that was used included 0.5 mass % of methyl hydroquinone (MEHQ), which is a polymerization inhibitor.

Subsequently, this reactant was polymerized by irradiation with ultraviolet light for 22 hours using a round, black fluorescent lamp (model FCL20BL, 18 W, by NEC Corporation). The reactant became viscous 5 hours later and hardened 15 hours later. A polymer was thus obtained as a reaction product. This reaction product was dissolved in 2-propanol, and the solution was transferred to a dialysis tube. Dialysis was performed for 72 hours to purify the reaction product.

The solution including the reaction product was filtered with a 0.2 μm cellulose mixed-ester filter (model 25AS020 by Toyo Roshi Kaisha), and the resulting filtrate was freeze dried to obtain a temperature-responsive (homo)polymer (6.8 g yield, 68% conversion ratio). The number-average molecular weight (Mn) of this polymer was measured using a GPC (model LC-10vp series by Shimadzu Corporation) with polyethylene glycol (TSK series by Shodex) as a standard substance and was determined to be Mn=$1.0 \times 10^5$ g/mol (Mw/Mn=10.0).

The nuclear magnetic resonance (NMR) spectrum of the above-described temperature-responsive polymer was measured using a nuclear magnetic resonance apparatus (model Gemini-300 by Varian) with heavy water ($D_2O$) as a standard substance. A representative peak is indicated below.

¹H-NMR (in D₂O) δ 0.8-1.2 (br, —CH₂—C(CH₃)—), 1.6-2.0 (br, —CH₂—C(CH₃)—), 2.2-2.4 (br, —N(CH₃)₂), 2.5-2.7 (br, —CH₂—N(CH₃)₂), 4.0-4.2 (br, —O—CH₂—).

Here, from the number of protons A in the methyl group (δ 0.8-1.2) of the main chain (3 per monomer molecule in the case of a DMAEMA homopolymer) and the number of methyl protons B in the dimethylamino group (δ 2.2-2.4) of the side chain (6 per monomer molecule in the case of a DMAEMA homopolymer), the ratio was calculated between the number of functional groups that are amino groups in the side chain and the number of functional groups that are carboxyl groups in the side chain produced by a hydrolysis reaction, which proceeds simultaneously with the polymerization reaction, of an ester bond of the side chain.

The resulting ratio was 94:6 in the case of the above-described temperature-responsive polymer. Converting into the C/A ratio for an ion complex in a two-component mixed system that includes a cationic polymer and an anionic polymer yields a C/A ratio of 15.6.

The cloud point of the above-described temperature-responsive polymer was measured with the following method.

A 3% aqueous solution of the temperature-responsive polymer was produced, and the absorbance of the aqueous solution at 660 nm was measured between 20° C. and 40° C.

Between 20° C. and 30° C., the aqueous solution was transparent, with an absorbance of nearly 0. Starting around 31° C., however, the aqueous solution became cloudy, and the absorbance increased suddenly at 32° C. The temperature-responsive polymer was thus confirmed to have a cloud point of approximately 32° C.

Once the temperature-responsive polymer was increased in temperature to 37° C., the polymer aqueous solution was suspended with good responsiveness. Subsequently, the entire aqueous solution hardened. When maintained at room temperature (25° C.), the hardened product retained its hard state for several tens of hours. Subsequently, the hardened product gradually dissolved, changing into a homogeneous aqueous solution. Upon being cooled to 4° C., the hardened polymer rapidly dissolved. Repeating the aforementioned operation to raise and lower the temperature caused no change in responsiveness, thereby confirming that the polymer reversibly underwent phase transitions.

The above-described temperature-responsive polymer was dissolved in pure water to produce a temperature-responsive polymer solution (final concentration 6 ng/μL). Next, 0.5 μL of the temperature-responsive polymer solution was applied in circles to 10 locations on the culturing surface of a 35 mm dish ("PrimeSurface®", MS-9035X, by Sumitomo Bakelite Co.).

The diameter of the circular coated culturing surface at each location was approximately 2,000 μm, and the distance between coated culturing surfaces was approximately 2,000 μm.

The applied temperature-responsive polymer aqueous solution was then dried by leaving the dish in an incubator (40° C.) for 1 hour to prepare a coated cell culture container having a plurality of coated culturing surfaces.

Mixed cells, in which newborn Lewis rat cardiomyocytes and adipose-derived mesenchymal stem cells (ADSC) of a GFP recombinant Lewis rat were mixed at a ratio of 300 mesenchymal stem cells per 100 cardiomyocytes, were mixed into a medium (SkGM (model CC-3245 by Lonza Co., Ltd.)+10% FBS (lot number 715929 by Gibco)) to produce a 7.2×10⁶ cells/mL mixed cell solution, 5 mL of which was added to a coated cell culture container to seed cells.

Subsequently, cells were cultured for 1 hour in a cell incubator (37° C., 5% $CO_2$), and the medium was exchanged using a new medium. The cells were then further cultured for 48 hours in a cell incubator (37° C., 5% $CO_2$) to obtain an aggregated cell structure.

Example VI-2

Except for mixing newborn Lewis rat cardiomyocytes and adipose-derived mesenchymal stem cells of a GFP recombinant Lewis rat at a ratio of 233 mesenchymal stem cells per 100 cardiomyocytes, an aggregated cell structure was obtained in a way similar to Example VI-1.

Example VI-3

Three types of cells were used: newborn Lewis rat cardiomyocytes as cardiomyocytes, adipose-derived mesenchymal stem cells (ADSC) of a GFP recombinant Lewis rat as mesenchymal stem cells, and macrophages as immune system cells. The macrophages were used after inducing differentiation from monocytes derived from rat bone marrow (number BMM01, melomonocyte culturing kit, by Cosmo Bio).

As the first stage, newborn Lewis rat cardiomyocytes and adipose-derived mesenchymal stem cells of a GFP recombinant Lewis rat were mixed at a ratio of 250 mesenchymal stem cells per 100 cardiomyocytes, the mixed cells were seeded in a way similar to Example VI-1, and after 5 hours, the cells had adhered to form a single layer. The medium was then exchanged. A rat derived macrophage suspension including macrophages was added onto the single layer to adjust the ratio to 5 rat derived macrophages per 100 newborn Lewis rat cardiomyocytes, and static culturing was continued. Other than these differences, operations similar to Example VI-1 were performed.

When a single culture layer composed of cardiomyocytes and mesenchymal stem cells aggregated like a drawstring bag, the macrophages that had precipitated onto the single layer culture layer were incorporated inside the aggregation, and one aggregated cell structure was obtained. No macrophages were confirmed on the exposed culturing surface, and it was confirmed that all of the seeded macrophages were incorporated in the cell aggregation.

Comparative Example VI-1

Except for mixing newborn Lewis rat cardiomyocytes and adipose-derived mesenchymal stem cells of a GFP recombinant Lewis rat at a ratio of 75 mesenchymal stem cells per 100 cardiomyocytes, an aggregated cell structure was obtained in a way similar to Example VI-1.

Comparative Example VI-2

Except for producing a cell solution composed only of newborn Lewis rat cardiomyocytes, without mixing in adipose-derived mesenchymal stem cells of a GFP recombinant Lewis rat, an aggregated cell structure was obtained in a way similar to Example VI-1.

Comparative Example VI-3

Except for mixing newborn Lewis rat cardiomyocytes and adipose-derived mesenchymal stem cells of a GFP recombinant Lewis rat at a ratio of 33 mesenchymal stem cells per 100 cardiomyocytes, an aggregated cell structure was obtained in a way similar to Example VI-1.

Comparative Example VI-4

Except for mixing newborn Lewis rat cardiomyocytes and adipose-derived mesenchymal stem cells of a GFP recombinant Lewis rat at a ratio of 25 mesenchymal stem cells per 100 cardiomyocytes, an aggregated cell structure was obtained in a way similar to Example VI-1.

Comparative Example VI-5

Except for mixing newborn Lewis rat cardiomyocytes and adipose-derived mesenchymal stem cells of a GFP recombinant Lewis rat at a ratio of 100 mesenchymal stem cells per 100 cardiomyocytes, an aggregated cell structure was obtained in a way similar to Example VI-1.

[Evaluation]
(Appearance of Cell Structure)
The aggregated cell structures obtained in the Examples and Comparative Examples were observed with a microscope (ECLIPSE-Ti by Nikon Corporation), and the appearance of the cells was evaluated with the following criteria.
G (good): a spherical aggregated cell structure was obtained on all 10 of the coated culturing surfaces.
P (poor): on one or more of the 10 coated culturing surfaces, the cells that adhered to the coated culturing surface remained as a single layer without aggregating, or a cell structure had a warped edge with a combination of an aggregated portion and an adhered portion not peeled off from the coated culturing surface.
(Occurrence of Beating)
The aggregated cell structures obtained in the Examples and Comparative Examples were observed with a microscope (ECLIPSE-Ti by Nikon Corporation) over a period of 48 hours. The occurrence of beating was then evaluated with the following criteria.
G (good): during the 48-hour observation period, beating was initially confirmed but subsequently stopped being observed.
P (poor): during the 48-hour observation period, beating was confirmed at every observation.

TABLE 5

| | | Example VI-1 | Example VI-2 | Example VI-3 | Comparative Example VI-1 | Comparative Example VI-2 | Comparative Example VI-3 | Comparative Example VI-4 | Comparative Example VI-5 |
|---|---|---|---|---|---|---|---|---|---|
| Culture Container Preparation Step | Cell Culture Container | 35 mm dish | 35 mm dish | 35 mm dish | 35 mm dish | 35 mm dish | 35 mm dish | 35 mm dish | 35 mm dish |
| | Area of Culturing Surface of Cell Culture Container ($mm^2$) | 900 | 900 | 900 | 900 | 900 | 900 | 900 | 900 |
| | Area of Each Coated Culturing Surface ($mm^2$) | 3.14 | 3.14 | 3.14 | 3.14 | 3.14 | 3.14 | 3.14 | 3.14 |
| | Amount of Temperature-Responsive Polymer per Unit Area ($ng/mm^2$) | 0.96 | 0.96 | 0.96 | 0.96 | 0.96 | 0.96 | 0.96 | 0.96 |
| Seeding Step | Number of Fibroblasts per 100 Cardiomyocytes | 300 | 233 | 250 | 75 | 0 | 33 | 25 | 100 |
| | Immune System Cells Added | no | no | yes | no | no | no | no | yes |
| | Number of Immune System Cells per 100 Cardiomyocytes | — | — | 5 | — | — | — | — | — |
| | Percentage of Cardiomyocytes among Total Number of Seeded Cells (%) | 25 | 30 | 28 | 57 | 100 | 75 | 80 | 50 |
| | Percentage of Fibroblasts among Total Number of Seeded Cells (%) | 75 | 70 | 70 | 53 | 0 | 25 | 20 | 50 |
| Culturing Step | Culturing Temperature | 37° C. | 37° C. | 37° C. | 37° C. | 37° C. | 37° C. | 37° C. | 37° C. |
| | Culturing Time (hours) | 48 | 48 | 48 | 48 | 48 | 48 | 48 | 48 |
| Evaluation | Appearance of Cell Structure | G | G | G | G | P | P | P | P |
| | Beating | G | G | G | P | P | P | P | P |

It is clear from Table 5 that the cell structures of the Examples were beating immediately after cell structure formation, but that beating was subsequently not observed. The cell structures of the Examples were thus judged to be useable as a heart disease model. Conversely, the cell structures of the Comparative Examples were observed to be beating throughout the 48-hour observation period and were judged to have a form close to that of a healthy heart.

Examples of Aspect (VII)

Aspect (VII) is described below in greater detail with reference to examples, but the present disclosure is in no way limited by these examples.

Example VII-1

First, 10.0 g of 2-N,N-dimethylaminoethyl methacrylate (DMAEMA) and 5 mL of water were added to a 50 mL capacity transparent vial made of soft glass, and the vial was stirred using a magnetic stirrer. The mixture (liquid) was then purged with Gi-grade, highly pure (purity: 99.99995%) nitrogen gas for 10 minutes (flow rate: 2.0 L/min) to deoxygenize the mixture. The DMAEMA that was used included 0.5 mass % of methylhydroquinone (MEHQ), which is a polymerization inhibitor.

Subsequently, this reactant was polymerized by irradiation with ultraviolet light for 22 hours using a round, black fluorescent lamp (model FCL20BL, 18 W, by NEC Corporation). The reactant became viscous 5 hours later and hardened 15 hours later. A polymer was thus obtained as a reaction product. This reaction product was dissolved in 2-propanol, and the solution was transferred to a dialysis tube. Dialysis was performed for 72 hours to purify the reaction product.

The solution including the reaction product was filtered with a 0.2 μm cellulose mixed-ester filter (model 25AS020 by Toyo Roshi Kaisha), and the resulting filtrate was freeze dried to obtain a temperature-responsive (homo)polymer (6.8 g yield, 68% conversion ratio). The number-average molecular weight (Mn) of this polymer was measured using a GPC (model LC-10vp series by Shimadzu Corporation) with polyethylene glycol (TSK series by Shodex) as a standard substance and was determined to be $Mn=1.0 \times 10^5$ g/mol (Mw/Mn=10.0).

The nuclear magnetic resonance (NMR) spectrum of the above-described temperature-responsive polymer was measured using a nuclear magnetic resonance apparatus (model Gemini-300 by Varian) with heavy water ($D_2O$) as a standard substance. A representative peak is indicated below.

$^1$H-NMR (in $D_2O$) δ 0.8-1.2 (br, —$CH_2$—$C(CH_3)$—), 1.6-2.0 (br, —$CH_2$—$C(CH_3)$—), 2.2-2.4 (br, —$N(CH_3)_2$), 2.5-2.7 (br, —$CH_2$—$N(CH_3)_2$), 4.0-4.2 (br, —O—$CH_2$—).

Here, from the number of protons A in the methyl group (δ 0.8-1.2) of the main chain (3 per monomer molecule in the case of a DMAEMA homopolymer) and the number of methyl protons B in the dimethylamino group (δ 2.2-2.4) of the side chain (6 per monomer molecule in the case of a DMAEMA homopolymer), the ratio was calculated between the number of functional groups that are amino groups in the side chain and the number of functional groups that are carboxyl groups in the side chain produced by a hydrolysis reaction, which proceeds simultaneously with the polymerization reaction, of an ester bond of the side chain.

The resulting ratio was 94:6 in the case of the above-described temperature-responsive polymer. Converting into the C/A ratio for an ion complex in a two-component mixed system that includes a cationic polymer and an anionic polymer yields a C/A ratio of 15.6.

The cloud point of the above-described temperature-responsive polymer was measured with the following method.

A 3% aqueous solution of the temperature-responsive polymer was produced, and the absorbance of the aqueous solution at 660 nm was measured between 20° C. and 40° C.

Between 20° C. and 30° C., the aqueous solution was transparent, with an absorbance of nearly 0. Starting around 31° C., however, the aqueous solution became cloudy, and the absorbance increased suddenly at 32° C. The temperature-responsive polymer was thus confirmed to have a cloud point of approximately 32° C.

Once the temperature-responsive polymer was increased in temperature to 37° C., the polymer aqueous solution was suspended with good responsiveness. Subsequently, the entire aqueous solution hardened. When maintained at room temperature (25° C.), the hardened product retained its hard state for several tens of hours. Subsequently, the hardened product gradually dissolved, changing into a homogeneous aqueous solution. Upon being cooled to 4° C., the hardened polymer rapidly dissolved. Repeating the aforementioned operation to raise and lower the temperature caused no change in responsiveness, thereby confirming that the polymer reversibly underwent phase transitions.

The above-described temperature-responsive polymer was dissolved in pure water to produce a temperature-responsive polymer solution (final concentration 15 ng/μL). Next, 0.5 μL of the temperature-responsive polymer solution was applied in circles to 8 locations on the culturing surface of a 35 mm dish ("PrimeSurface®", MS-9035X, by Sumitomo Bakelite Co.).

The diameter of the circular coated culturing surface at each location was approximately 2,000 μm, and the distance between coated culturing surfaces was approximately 2,500 μm.

The applied temperature-responsive polymer aqueous solution was then dried by leaving the dish in an incubator (37° C.) for 30 minutes to prepare a coated cell culture container having a plurality of coated culturing surfaces.

Human hepatoma cells (number "HepG2-500" by Cosmo Bio) were stained using a PKH26 Red Fluorescent Cell Linker Kit (by Sigma). Mixed cells, in which the stained hepatoma cells and adipose-derived mesenchymal stem cells (ADSC) of a GFP recombinant Lewis rat were mixed at a ratio of 33 mesenchymal stem cells per 100 hepatoma cells, were mixed into a medium (DMAEM+10% FBS (lot number 715929 by Gibco)) to produce a $3.2 \times 10^5$ cells/mL mixed cell suspension, 25 μL of which was added to a coated cell culture container to seed the mixed cells.

Subsequently, cells were cultured for 2 hours in a cell incubator (37° C., 5% $CO_2$), and the medium was exchanged using a new medium. The cells were then further cultured for 48 hours in a cell incubator (37° C., 5% $CO_2$) to obtain an aggregated cell structure.

Example VII-2

Except for mixing human hepatoma cells and adipose-derived mesenchymal stem cells of a GFP recombinant Lewis rat at a ratio of 10 mesenchymal stem cells per 100 hepatoma cells, an aggregated cell structure was obtained in a way similar to Example VII-1.

Example VII-3

Except for mixing human hepatoma cells and adipose-derived mesenchymal stem cells of a GFP recombinant Lewis rat at a ratio of 50 mesenchymal stem cells per 100 hepatoma cells, an aggregated cell structure was obtained in a way similar to Example VII-1.

Example VII-4

Except for mixing human hepatoma cells, adipose-derived mesenchymal stem cells of a GFP recombinant Lewis rat, and adhesive adipocytes derived from Lewis rat adipose at a ratio of 33 mesenchymal stem cells and 33 adhesive adipocytes per 100 hepatoma cells, an aggregated cell structure was obtained in a way similar to Example VII-1.

Example VII-5

As the cells, human hepatoma cells (HepG2) stained in a similar way as in Example VII-1 were used as hepatocytes, adipose-derived mesenchymal stem cells (ADSC) of a GFP recombinant Lewis rat were used as fibroblasts, and macrophages were used as immune system cells. The macrophages were used after inducing differentiation from monocytes derived from rat bone marrow (number BMM01, melomonocyte culturing kit, by Cosmo Bio).

As the first stage, human hepatoma cells and adipose-derived mesenchymal stem cells of a GFP recombinant Lewis rat were mixed at a ratio of 25 mesenchymal stem cells per 100 hepatoma cells, the mixed cells were seeded in a way similar to Example VII-1, and after 5 hours, the cells had adhered to form a single layer. The medium was then exchanged. A macrophage suspension including macrophages was added onto the single layer to adjust the ratio to 5 macrophages per 100 human hepatoma cells, and static culturing was continued. Other than these differences, operations similar to Example VII-1 were performed.

When a single culture layer composed of hepatoma cells and mesenchymal stem cells aggregated like a drawstring bag, the macrophages that had precipitated onto the single culture layer were incorporated inside the aggregation, and one aggregated cell structure was obtained. No macrophages were confirmed on the exposed culturing surface, and it was confirmed that all of the seeded macrophages were incorporated in the cell aggregation.

Comparative Example VII-1

Except for mixing human hepatoma cells and adipose-derived mesenchymal stem cells of a GFP recombinant Lewis rat at a ratio of 300 mesenchymal stem cells per 100 hepatoma cells, an aggregated cell structure was obtained in a way similar to Example VII-1.

Comparative Example VII-2

Except for mixing human hepatoma cells and adipose-derived mesenchymal stem cells of a GFP recombinant Lewis rat at a ratio of 100 mesenchymal stem cells per 100 hepatoma cells, an aggregated cell structure was obtained in a way similar to Example VII-1.

Comparative Example VII-3

Except for producing a cell solution composed only of human hepatoma cells, without mixing in adipose-derived mesenchymal stem cells of a GFP recombinant Lewis rat, an aggregated cell structure was obtained in a way similar to Example VII-1.

Comparative Example VII-4

Except for mixing human hepatoma cells and adipose-derived mesenchymal stem cells of a GFP recombinant Lewis rat at a ratio of 5 mesenchymal stem cells per 100 hepatoma cells, an aggregated cell structure was obtained in a way similar to Example VII-1.

Comparative Example VII-5

Except for mixing human hepatoma cells and adipose-derived mesenchymal stem cells of a GFP recombinant Lewis rat at a ratio of 67 mesenchymal stem cells per 100 hepatoma cells, an aggregated cell structure was obtained in a way similar to Example VII-1.

[Evaluation]
(Appearance of Cell Structure)

The aggregated cell structures obtained in the Examples and Comparative Examples (after 48 hours of culturing) were observed with a microscope (ECLIPSE-Ti by Nikon Corporation), and the appearance of the cells was evaluated with the following criteria.

G (good): a spherical aggregated cell structure was obtained on all 8 of the coated culturing surfaces.

P (poor): on one or more of the 8 coated culturing surfaces, the cells that adhered to the coated culturing surface remained as a single layer without aggregating, or a cell structure had a warped edge with a combination of an aggregated portion and an adhered portion not peeled off from the coated culturing surface.

(Form of Cells in Cell Structure)

The seeded and cultured cells were observed with a microscope (ECLIPSE-Ti by Nikon Corporation) after being cultured for 2 hours, at which point the cells were adhered to the coated culturing surface. The form of the hepatocytes among the adhered cells was evaluated with the following criteria. The seeded hepatocytes (the hepatocytes before adhering to the coated culturing surface) had a cobblestone form in each example.

G (good): many hepatocytes were changed into a form similar to spindle-shaped fibroblasts.

P (poor): no change in form of the hepatocytes was observed.

TABLE 6

| | | Example VII-1 | Example VII-2 | Example VII-3 | Example VII-4 | Example VII-5 | Comparative Example VII-1 | Comparative Example VII-2 | Comparative Example VII-3 | Comparative Example VII-4 | Comparative Example VII-5 |
|---|---|---|---|---|---|---|---|---|---|---|---|
| Culture Container Preparation Step | Cell Culture Container | 35 mm dish | 35 mm dish | 35 mm dish | 35 mm dish | 35 mm dish | 35 mm dish | 35 mm dish | 35 mm dish | 35 mm dish | 35 mm dish |
| | Area of Culturing Surface of Cell Culture Container (mm$^2$) | 900 | 900 | 900 | 900 | 900 | 900 | 900 | 900 | 900 | 900 |

TABLE 6-continued

|  |  | Example VII-1 | Example VII-2 | Example VII-3 | Example VII-4 | Example VII-5 | Comparative Example VII-1 | Comparative Example VII-2 | Comparative Example VII-3 | Comparative Example VII-4 | Comparative Example VII-5 |
|---|---|---|---|---|---|---|---|---|---|---|---|
| | Area of Each Coated Culturing Surface (mm²) | 3.14 | 3.14 | 3.14 | 3.14 | 3.14 | 3.14 | 3.14 | 3.14 | 3.14 | 3.14 |
| Seeding Step | Number of Fibroblasts per 100 Hepatocytes | 33 | 10 | 50 | 33 | 25 | 300 | 100 | 0 | 5 | 67 |
| | Immune System Cells Added | no | no | no | no | yes | no | no | no | no | no |
| | Number of Immune System Cells per 100 Hepatocytes | — | — | — | — | 5 | — | — | — | — | — |
| | Adipocytes Added | no | no | no | yes | no | no | no | no | no | no |
| | Number of Adipocytes per 100 Hepatocytes | — | — | — | 33 | — | — | — | — | — | — |
| | Percentage of Hepatocytes among Total Number of Seeded Cells (%) | 75 | 91 | 67 | 60 | 77 | 25 | 50 | 100 | 95 | 60 |
| | Percentage of Fibroblasts among Total Number of Seeded Cells (%) | 25 | 9 | 33 | 20 | 19 | 75 | 50 | 0 | 5 | 40 |
| Culturing Step | Culturing Temperature | 37° C. | 37° C. | 37° C. | 37° C. | 37° C. | 37° C. | 37° C. | 37° C. | 37° C. | 37° C. |
| | Culturing Time (hours) | 48 | 48 | 48 | 48 | 48 | 48 | 48 | 48 | 48 | 48 |
| Evaluation | Appearance of Cell Structure | G | G | G | G | G | G | G | P | P | G |
| | Form of Cells in Cell Structure | G | G | G | G | G | P | P | P | P | P |

As is clear from Table 6, the hepatocytes changed from a cobblestone form to a fibroblast-like form in the cell structures of the Examples in which hepatocytes and fibroblasts were mixed at a specific ratio. Therefore, the hepatocytes included in the cell structures of the Examples were highly invasive and transformed into highly malignant cancer cells. The cell structures of the Examples were thus judged to be useable as a hepatic failure model. Upon crushing the cell structure of each Example, re-seeding the cells in a culture dish, and observing the form, the hepatocytes had the form of fibroblasts.

On the other hand, the hepatocytes in the cell structures of the Comparative Examples remained in cobblestone form, with no observable change. Upon crushing the cell structure of each Comparative Example, re-seeding the cells in a culture dish, and observing the form, the hepatocytes had a cobblestone form.

INDUSTRIAL APPLICABILITY

The present disclosure can provide a method of efficiently manufacturing a cell mass, a cell structure, or a three-dimensional tissue body.

In particular, Aspect (I) allows easy manufacturing of a chondrocyte mass and a graft material that are useful for treatment of joints, the trachea, the nose, and the like. Aspect (II) allows epithelial cells to be cultured easily, allows a cell structure including epithelial cells to be manufactured easily, and allows culturing of epithelial cells and the manufacturing of cell structures thereof. Aspect (III) allows easy production of a three-dimensional tissue body with a ringed shape, a luminal shape, or the like and also allows easy production of a three-dimensional tissue body with a ringed shape, a luminal shape, or the like. Aspect (IV) allows easy manufacturing of cell structures having a desired size and a well-defined spheroidal shape. Aspect (V) can control the aggregation mode of cells to manufacture cell structures with a desired form. Aspect (VI) allows easy formation of a cell structure that includes cardiomyocytes and fibroblasts and that is useful as a heart disease model. Aspect (VII) allows easy formation of a cell structure that includes hepatocytes and fibroblasts and that is useful as a hepatic failure model.

The invention claimed is:

1. A manufacturing method of a cell structure, the manufacturing method comprising:
   producing a coated region in which a culturing surface is coated with a temperature-responsive polymer or a temperature-responsive polymer composition, forming a droplet of a cell suspension in the coated region, and performing cell culturing in the droplet;
   wherein a surface zeta potential of the coated region is 0 mV to 50 mV.

2. The manufacturing method of a cell structure of claim 1, wherein a contact angle of water relative to the coated region is 50° to 90°.

3. The manufacturing method of a cell structure of claim 1, comprising producing a plurality of the coated regions on the culturing surface.

4. The manufacturing method of a cell structure of claim 1, comprising forming a plurality of the droplets on the coated region.

5. The manufacturing method of a cell structure of claim 1, wherein in each coated region, a bottom area of the droplet is smaller than an area of the coated region.

6. The manufacturing method of a cell structure of claim 1, wherein the number of cells included in the droplet is $3.0 \times 10^5$ cells/mL or less.

7. The manufacturing method of a cell structure of claim 1, wherein the droplet has a diameter of 1 μm to 8 mm.

8. The manufacturing method of a cell structure of claim 1, wherein an amount of the droplet is 0.5 μL to 50 μL.

* * * * *